US010065934B2

(12) United States Patent
Cheng et al.

(10) Patent No.: US 10,065,934 B2
(45) Date of Patent: Sep. 4, 2018

(54) SUBSTITUTED UREA DERIVATIVES AND PHARMACEUTICAL USES THEREOF

(71) Applicant: SUNSHINE LAKE PHARMA CO., LTD., Dongguan, Guangdong (CN)

(72) Inventors: Changchung Cheng, Dongguan (CN); Yingjun Zhang, Dongguan (CN); Bing Liu, Dongguan (CN); Bohua Long, Dongguan (CN); Yu Chen, Dongguan (CN); Zhixin Cheng, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/314,938

(22) PCT Filed: Jul. 16, 2015

(86) PCT No.: PCT/CN2015/084253
§ 371 (c)(1),
(2) Date: Nov. 29, 2016

(87) PCT Pub. No.: WO2016/008433
PCT Pub. Date: Jan. 21, 2016

(65) Prior Publication Data
US 2017/0114032 A1    Apr. 27, 2017

(30) Foreign Application Priority Data

Jul. 17, 2014  (CN) .......................... 2014 1 0342509

(51) Int. Cl.
| | |
|---|---|
| *C07D 261/14* | (2006.01) |
| *C07D 487/04* | (2006.01) |
| *C07D 491/107* | (2006.01) |
| *C07D 413/12* | (2006.01) |
| *C07D 471/04* | (2006.01) |
| *C07D 513/04* | (2006.01) |
| *C07D 519/00* | (2006.01) |
| *A61K 31/5377* | (2006.01) |
| *A61K 31/422* | (2006.01) |
| *A61K 31/4439* | (2006.01) |
| *A61K 31/519* | (2006.01) |
| *A61K 45/06* | (2006.01) |
| *C07D 491/056* | (2006.01) |
| *A61K 31/496* | (2006.01) |
| *A61K 31/454* | (2006.01) |
| *C07D 491/08* | (2006.01) |
| *A61K 31/4545* | (2006.01) |
| *A61K 31/541* | (2006.01) |
| *A61K 31/5025* | (2006.01) |
| *A61K 31/437* | (2006.01) |
| *C07D 513/14* | (2006.01) |

(52) U.S. Cl.
CPC .......... *C07D 261/14* (2013.01); *A61K 31/422* (2013.01); *A61K 31/437* (2013.01); *A61K 31/4439* (2013.01); *A61K 31/454* (2013.01); *A61K 31/4545* (2013.01); *A61K 31/496* (2013.01); *A61K 31/5025* (2013.01); *A61K 31/519* (2013.01); *A61K 31/5377* (2013.01); *A61K 31/541* (2013.01); *A61K 45/06* (2013.01); *C07D 413/12* (2013.01); *C07D 471/04* (2013.01); *C07D 487/04* (2013.01); *C07D 491/056* (2013.01); *C07D 491/08* (2013.01); *C07D 491/107* (2013.01); *C07D 513/04* (2013.01); *C07D 513/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 6,297,381 B1 | 10/2001 | Cirillo et al. |
| 6,863,647 B2 | 3/2005 | Pevarello et al. |
| 7,217,710 B2 | 5/2007 | Adams et al. |
| 7,666,879 B2 | 2/2010 | Barda et al. |
| 7,820,657 B2 | 10/2010 | Bhagwat et al. |
| 8,114,874 B2 | 2/2012 | Zou et al. |
| 8,143,393 B2 | 3/2012 | Dixon et al. |
| 8,278,307 B2 | 10/2012 | Shakespeare et al. |
| 8,461,167 B2 | 6/2013 | Wang et al. |
| 9,216,997 B2 | 12/2015 | Gao |
| 9,296,722 B2 | 3/2016 | Liu |
| 2008/0027076 A1 | 1/2008 | Jones et al. |

(Continued)

FOREIGN PATENT DOCUMENTS

| | | |
|---|---|---|
| WO | 2006082404 A1 | 8/2006 |
| WO | 2009100536 A1 | 8/2009 |
| WO | 2013170770 A | 11/2013 |
| WO | 2015165835 A | 11/2015 |

OTHER PUBLICATIONS

Li, Xingzhou al.,Synthesis and biological evaluation of chromenylurea and chromanylurea derivatives as anti-TNF—a agents that target the p38 MAPK pathway, Molecules, 2014, 19(2): 2004-2028.
Harris, Philip A. al., Discovery of Small Molecule RIP1 Kinase Inhibitors for the Treatment of Pathologies Associated with Necroptosis, ACS Medicinal Chemistry Letters,2013, 4(12): 1238-1243.
Liu, Gang al., Discovery of AC710, a Globally Selective Inhibitor of Platelet-Derived Growth Factor Receptor-Family Kinases, ACS Medicinal Chemistry Letters, 2012, 3(12), 997-1002.
Holladay, Mark W. al., 4-Quinazolinyloxy-diaryl ureas as novel BRAFV600E inhibitors, Bioorganic & Medicinal Chemistry Letters, 2011, 21(18), 5342-5346.
Tan, Zhulin al., Synthesis of p38 MAP kinase inhibitor BIRB 796 and analogs via copper-mediated N-arylation reaction, Tetrahedron Letters, 2010, 51(34), 4547-4551.

(Continued)

*Primary Examiner* — Kamal A Saeed
(74) *Attorney, Agent, or Firm* — Kam W Law

(57) ABSTRACT

Provided herein are novel substituted urea derivatives, and pharmaceutical compositions thereof. Also provided herein are uses of the compounds or pharmaceutical compositions thereof for preventing, managing, treating or lessening a proliferative disease, and modulating the activity of protein kinase.

18 Claims, No Drawings

(56) References Cited

U.S. PATENT DOCUMENTS

2008/0108608 A1  5/2008 Jones et al.
2008/0153838 A1* 6/2008 Jones ................ A61K 31/4427
                                                    514/252.05

OTHER PUBLICATIONS

Chao, Qi al., Identification of N-(5-tert-Butyl-isoxazol-3-yl)-N'-{4-[7-(2-morpholin-4-yl-ethoxy)imidazo[2,1-b][1,3]benzothiazol-2-yl]phenyl}urea Dihydrochloride (AC220), a Uniquely Potent, Selective, and Efficacious FMS-Like Tyrosine Kinase-3 (FLT3) Inhibitor, Medicinal Chemistry, 2009, 52(23), 7808-7816.
Patel, Hitesh K. al., Arylcarboxyamino-substituted diaryl ureas as potent and selective FLT3 inhibitors, Bioorganic & Medicinal Chemistry Letters, 2009 19(17), 5182-5185.
International Search Report of PCT/CN2015/084253.
Written Opinion of PCT/CN2015/084253.

* cited by examiner

SUBSTITUTED UREA DERIVATIVES AND PHARMACEUTICAL USES THEREOF

CROSS-REFERENCE TO RELATED APPLICATIONS

This is a U.S. national stage application of the International Patent Application No. PCT/CN2015/084253, filed Jul. 16, 2015, which claims priorities to Chinese Patent Application No. 201410342509.4, filed Jul. 17, 2014, both of which are incorporated herein by reference in their entirety.

FIELD

The present invention belongs to the pharmaceutical field, and it relates to novel substituted urea derivatives, pharmaceutical compositions thereof and uses thereof for the treatment of FLT3-mediated or FLT3-ITD-induced diseases. The novel substituted urea derivatives and pharmaceutical compositions are useful in treating, ameliorating or preventing a tyrosine kinase activity related disease, or one or more symptoms thereof.

BACKGROUND

Aberrant or excessive activity or dysregulation of activity of receptor protein tyrosine kinase (RPTK) has been observed in many disease states including benign and malignant proliferative disorders as well as inflammatory disorders and immune system disorders that result from inappropriate activation of the immune system to cause, for example, autoimmune diseases. So far, there are about 58 kinds of receptor tyrosine kinases, including VEGF receptors, PDGF receptor (PDGF receptor (PDGFR) family is composed of five kinds of RTK composition: PDGFR-a and -b, c-kit and FLT3), and flk receptor family and so on. These receptors can transduce signals to other tyrosine kinases, such as Src, Raf, Frk, Btk, Csk, Abl, Fes/Fps, Fak, Jak, Ack, etc.

FLT3 plays an important role in the proliferation and differentiation of hematopoietic stem cells, and activating mutation or overexpression of this receptor is found in AML (acute myeloid leukemia) (See, Heinrich, *Mini-Reviews in Medicinal Chemistry*, 2004, 4(3): 255-271, and Kiyoi et al., *Int J Hematol.*, 2005, 82: 85-92, incorporated herein by reference). One study shows the FLT3 inhibtor CEP-701 may be effective in reducing myelin loss in experimental autoimmune encephalomyelitis (EAE), a mouse model for multiple sclerosis (See, Whartenby et al., *PNAS*, 2005, 102: 16741-16746, incorporated herein by reference). A high level of the FLT3 ligand is found in the serum of patients with Langerhans cell histiocytosis and systemic lupus erythematosus, that further means FLT3 signal transduction is implicated in the dysregulation of dendritic cell progenitors in those autoimmune diseases (See, Rolland et al., *J. Immunol.*, 2005, 174:3067-3071, incorporated herein by reference).

Activating internal tandem duplication (ITD) mutations in FLT3 (FLT3-ITD) are detected in approximately 20% of acute myeloid leukemia patients and are associated with a poor prognosis. Research has shown that FLT3-ITD can represent a driver lesion, which has causative role in malignancy pathogenesis, and valid therapeutic target in human AML (See, Catherine et al., *Nature*, 2012, 485: 260-263, incorporated herein by reference). Mutation of FLT3 gene is a frequent event in AML and usually involves internal tandem duplication (ITD) of the juxtamembrane domain coding region or point mutations of the tyrosine kinase domain (TKD). Both FLT3-ITD and FLT3-TKD mutations result in ligand-independent proliferation due to constitutive dimerisation and activation of the FLT3 receptor. High mutant-to-wild type allelic ratios of FLT3-ITD are associated with a very poor prognosis in both adults and children (See, A S Moore et al., *Leukemia*, 2012, 26: 1462-1470, incorporated herein by reference).

bcr-Abl is a tyrosine kinase which inhibits cellular cancerization and immortalization of pH-positive chronic myeloid leukemia (CML) and acute lymphoblastic leukemia (ALL). bcr-Abl protein is the constitutively active, cytoplasmic tyrosine kinase existing in 90% of the patients of chronic myeloid leukemia and 15-30% of the adult patients of acute lymphoblastic leukemia. Many studies have shown that bcr-Abl activation is the need of carcinogenic ability of said chimeric protein.

In recent years, the abnormalities of c-Kit gene, a member of type III receptor tyrosine kinase family in AML, have attracted more attentions. It was found that mutations of c-KIT gene will cause the activation of c-Kit without receptor-ligand binding, thereby the abnormal proliferation of cells occurs, leading to cancer. c-KIT gene mutation in leukemia cell is closely associated with the occurrence of leukemia and the prognosis of therapeutic agent. c-Kit receptor also can be constitutively activated by mutation, leading to abnormal cell proliferation and development, such as mastocytosis (D816V mutation) and other diseases, and various cancers, such as GIST (c-kitΔ27, juxtamembrane deletion).

SUMMARY

Researchers have shown a great interest in developing kinase inhibitors for the treatment of cancer. The present invention provides a novel substituted urea compounds useful for treating, ameliorating or preventing a disease or symptom associated with tyrosine kinase activity, particularly the disease or complications thereof mediated by c-KIT mutation, RET, PDGFR, Bcr-ABL, FLT3 orinduced by FLT3-ITD, and for treating a proliferative disease, particularly blood cancer, especially for treating AML and related complications.

Provided herein are substituted urea derivatives and pharmaceutical compositions thereof used for drug therapy, and a series of substituted urea compounds used for adjusting Abl and FLT3 kinase activities and inhibiting FLT3-ITD, and the uses thereof as therapeutic agents for the treatment of diseases mediated by c-KIT mutation, RET, PDGFR, Bcr-ABL, FLT3 orinduced by FLT3-ITD. The compounds of the present invention show better inhibition activities against the proferation of MV4-11 cell which contains the FLT3/ITD mutation.

In one aspect, provided herein are substituted urea derivatives having Formula (I), or a stereoisomer, a geometric isomer, a tautomer, an N-oxide, a hydrate, a solvate, a metabolite, an ester, a pharmaceutically acceptable salt or a prodrug thereof,

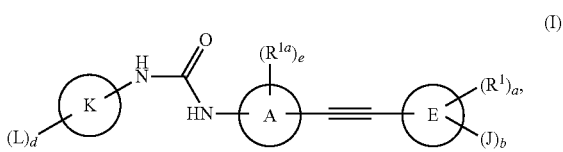

wherein
each of ring A and ring E is independently $C_{6-10}$ aryl or $C_{1-12}$ heteroaryl;

each J is -G-$(CH_2)_n$—$R^2$;

each G is independently —O—, —S(=O)$_t$—, —S—, —C(=O)—, —OC(=O)—, —C(=S)—, —C(=S)—N($R^4$)— or —$(CH_2)_n$—C(=O)—;

each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{1-4}$ alkylamino, $C_{1-4}$ alkyl-C(=O)—NH—, $C_{1-4}$ alkylthio, $C_{3-10}$ cycloalkyl, $C_{2-10}$ heterocyclyl, $C_{1-6}$ alkoxy-$C_{1-6}$-alkyl or $C_{1-4}$ hydroxyalkyl;

each $R^2$ is independently —$NR^3R^{3a}$, cycloalkyl, cycloalkylalkyl, heterocyclylalkyl, heterocyclyl, alkyl-S(=O)$_t$—, hydroxyalkyl, hydroxyalkoxy, aminoalkoxy, haloalkoxy, alkoxyalkyl, alkyl, alkoxy, alkylaminohaloalkoxy, alkylaminoalkoxy, arylalkoxy, arylalkylamino, heteroarylalkoxy, heteroarylalkylamino, heterocyclylalkylamino, heterocyclylalkylaryl, heterocylylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, aryl, arylalkyl, heteroarylalkyl, heteroaryl, bridged heterobicyclyl, spiro heterobicyclyl or fused heterobicyclyl;

each $R^3$ and $R^{3a}$ is independently $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

each $R^4$ is independently H, $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

ring K is 5- to 6-membered heteroaryl;

each L is independently amino, nitro, $C_{1-4}$ alkylthio, $C_{1-6}$ alkyl, $C_{3-10}$ cycloalkyl, $C_{2-10}$ heterocyclyl, $C_{1-4}$ haloalkyl, $C_{1-4}$ alkylamino, hydroxy, F, Cl, Br, I, $C_{1-4}$ alkyl-C(=O)—NH—, $C_{1-4}$ alkoxy, $C_{1-4}$ hydroxyalkyl or cyano;

each a and e is independently 0, 1, 2, 3 or 4;
each n, d and b is independently 1, 2, 3 or 4; and
each t is independently 0, 1 or 2;

wherein optionally each aryl, —$(CH_2)_n$—C(=O)—, alkyl-S(=O)$_t$—, hydroxyalkyl, arylalkyl, heteroarylalkyl, heteroaryl, heterocyclyl, bridged heterobicyclyl, spiro heterobicyclyl, fused heterobicyclyl, alkyl, alkoxy, alkoxyalkyl, haloalkyl, alkylamino, hydroxyalkoxy, aminoalkoxy, haloalkoxy, cycloalkylalkyl, heterocyclylalkyl, alkylaminohaloalkoxy, alkylaminoalkoxy, arylalkoxy, arylalkylamino, heteroarylalkoxy, heteroaryl alkylamino, heterocyclylalkylamino, heterocyclylalkylaryl, heterocyclylalkylheteroaryl, cycloalkyloxy, cycloalkyl amino, heterocyclylalkoxy, carbocyclylalkoxy, carbocyclyl alkyl amino, aryloxyalkoxy, aryloxy, heteroaryloxy, heteroaryloxyalkoxy, heterocycly-loxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkyl amino, spiro heterobicyclylalkyl, spiro heterobicyclylalkoxy, bridged heterobicyclylalkyl, bridged heterobicyclyloxy, bridged heterobicyclylalkoxy, bridged heterobicyclyl alkyl amino, alkyl-C(=O)—NH—, alkylthio and cycloalkyl described in $R^1$, $R^{1a}$, $R^2$, $R^3$, $R^{3a}$, A, E, J, G, L and/or K is independently substituted with one or more $R^{2a}$ which are the same or different, and wherein each $R^{2a}$ is independently H, F, Cl, Br, I, $C_{1-4}$ haloalkyl, $C_{1-4}$ alkyl, $C_{1-4}$ alkylamino, di($C_{1-4}$ alkyl)amino, hydroxy, cyano, nitro, —C(=O)—$NH_2$, carboxy, —S(=O)$_t$O—H, —OS(=O)$_t$—H, —S(=O)$_t$$NH_2$, triazolyl, tetrazolyl, —$(CR^{3b}R^{3c})_n$—$NH_2$, amino, oxo (=O), $C_{1-4}$ alkyl-C(=O)—, benzyl, phenyl, $C_{1-6}$ alkyl-S(=O)$_t$—, $C_{1-6}$ alkoxy-$C_{1-6}$-alkyl, $C_{1-4}$ alkyl-C(=O)—NH—, $C_{1-4}$ alkoxy, $C_{1-4}$ hydroxyalkyl or $C_{1-4}$ alkylthio; and each $R^{3b}$ and $R^{3c}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, provided herein are substituted urea derivatives having Formula (IIa), or a stereoisomer, a geometric isomer, a tautomer, an N-oxide, a hydrate, a solvate, a metabolite, an ester, a pharmaceutically acceptable salt or a prodrug thereof,

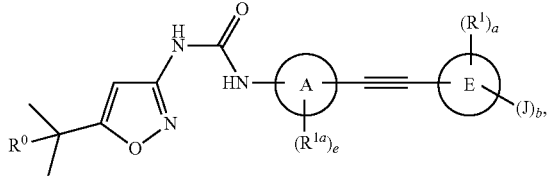

(IIa)

wherein $R^0$ is $C_{2-3}$ alkyl, trifluoromethyl, fluoromethyl, difluoromethyl or hydroxymethyl; and each ring A, ring E, $R^1$, $R^{1a}$, e, b, a and J is as defined herein.

In certain embodiments, provided herein are substituted urea derivatives having Formula (II), or a stereoisomer, a geometric isomer, a tautomer, an N-oxide, a hydrate, a solvate, a metabolite, an ester, a pharmaceutically acceptable salt or a prodrug thereof,

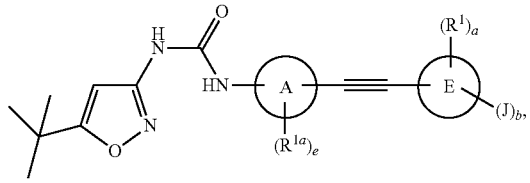

(II)

wherein each ring A, ring E, $R^1$, $R^{1a}$, e, b, a and J is as defined herein.

In certain embodiments, provided herein are substituted urea derivatives having Formula (I), Formula (IIa) or Formula (II), or a stereoisomer, a geometric isomer, a tautomer, an N-oxide, a hydrate, a solvate, a metabolite, an ester, a pharmaceutically acceptable salt or a prodrug thereof, wherein each ring A and ring E is independently one of the following sub-formulae:

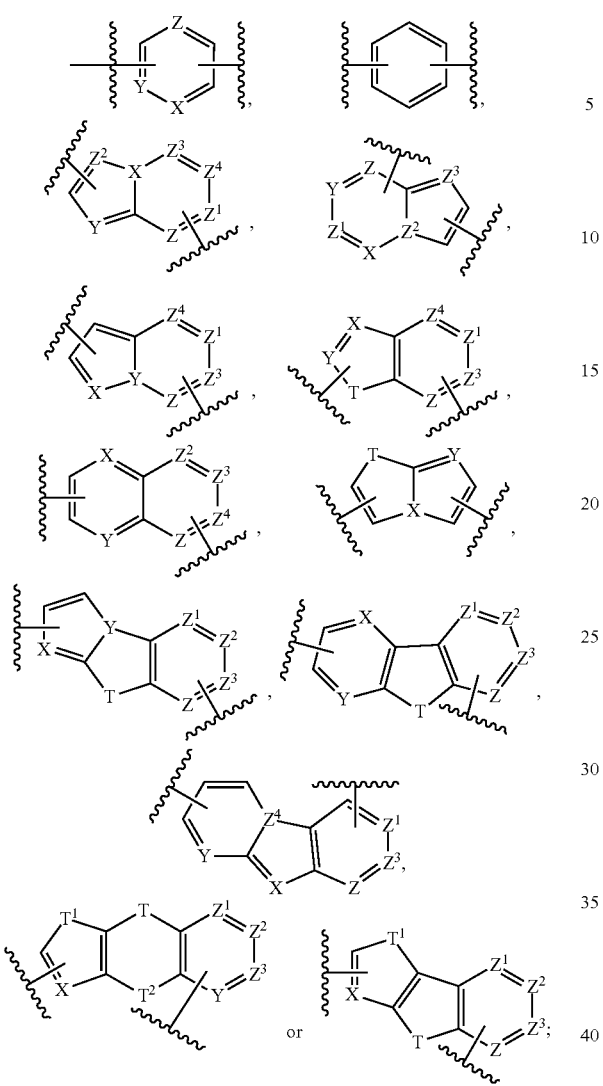

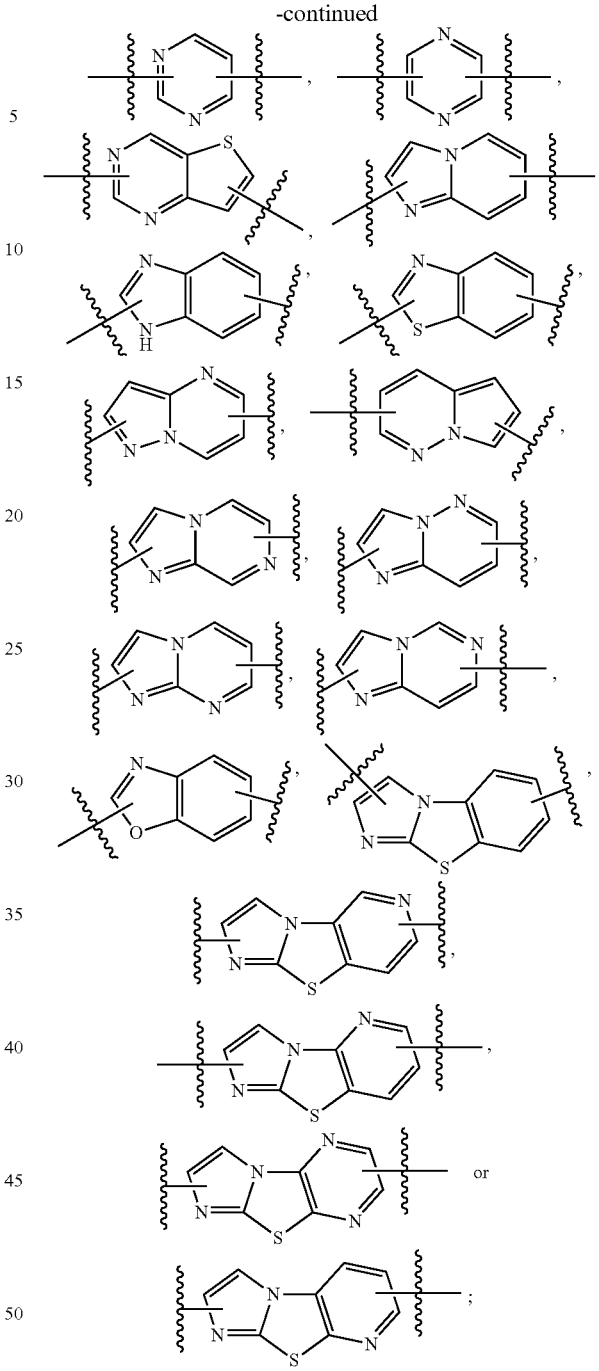

wherein
each X, Y, Z, $Z^1$, $Z^2$, $Z^3$ and $Z^4$ is independently N or CH;
each T, $T^1$ and $T^2$ is independently —O—, —S—, —N($R^4$)— or —CH$_2$—;
each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{1-4}$ alkylamino, $C_{2-10}$ heterocyclyl, $C_{1-6}$ alkoxy-$C_{1-6}$-alkyl or $C_{1-4}$ hydroxyalkyl; and
each $R^4$ is as defined herein.

In certain embodiments, provided herein are substituted urea derivatives having Formula (I), Formula (IIa) or Formula (II), or a stereoisomer, a geometric isomer, a tautomer, an N-oxide, a hydrate, a solvate, a metabolite, an ester, a pharmaceutically acceptable salt or a prodrug thereof,
wherein each ring A and ring E is independently one of the following sub-formulae:

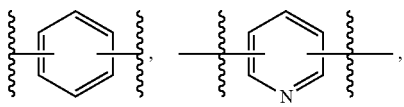

and
each $R^1$ and $R^{1a}$ is independently H, F, Cl, Br, trifluoromethyl, chloroethyl, trifluoroethyl, methyl, ethyl, propyl, isopropyl, dimethylamino, methylamino, diethylamino, ethylamino, hydroxy, cyano, nitro, methoxy, ethoxy, propoxy, cyclopropyl, cyclobutyl, cyclohexyl, cyclopentyl, $C_{2-10}$ heterocyclyl, $C_{1-6}$ alkoxy-$C_{1-6}$-alkyl or $C_{1-4}$ hydroxyalkyl.

In certain embodiments, provided herein are substituted urea derivatives having Formula (I), Formula (IIa) or Formula (II), or a stereoisomer, a geometric isomer, a tautomer, an N-oxide, a hydrate, a solvate, a metabolite, an ester, a pharmaceutically acceptable salt or a prodrug thereof,
each $R^2$ is independently —NR$^3$R$^{3a}$, $C_{3-10}$ cycloalkyl, $C_{3-10}$ cycloalkyl-$C_{1-4}$-alkyl, $C_{2-10}$ heterocyclyl-$C_{1-4}$-alkyl, $C_{1-6}$ alkyl-$S(=O)_t$—, $C_{1-4}$ hydroxyalkyl, $C_{1-4}$ hydroxyalkoxy, $C_{1-4}$ aminoalkoxy, $C_{1-4}$ haloalkoxy, $C_{1-4}$ alkylamino-$C_{1-4}$-haloalkoxy, $C_{1-4}$ alkylamino-$C_{1-4}$-alkoxy, $C_{1-6}$ alkoxy-$C_{1-6}$-alkyl, $C_{1-6}$ alkyl, $C_{1-6}$ alkoxy, $C_{6-10}$ aryl-$C_{1-4}$-alkoxy, $C_{6-10}$ aryl-$C_{1-4}$-alkylamino, $C_{1-9}$ heteroaryl-$C_{1-4}$-alkoxy, $C_{1-9}$ heteroaryl-$C_{1-4}$-alkylamino, $C_{2-10}$ heterocyclyl-$C_{1-4}$-alkylamino, $C_{2-10}$ heterocyclyl-$C_{1-4}$-alkyl-$C_{6-10}$-aryl, $C_{2-10}$ heterocyclyl-$C_{1-4}$-alkyl-$C_{1-9}$-heteroaryl, $C_{3-10}$ cycloalkyloxy, $C_{3-10}$ cycloalkylamino, $C_{2-10}$ heterocyclyl-$C_{1-4}$-alkoxy, $C_{3-10}$ carbocyclyl-$C_{1-4}$-alkoxy, $C_{3-10}$ carbocyclyl-$C_{1-4}$-alkylamino, $C_{6-10}$ aryloxy-$C_{1-4}$-alkoxy, $C_{6-10}$ aryloxy, $C_{1-9}$ heteroaryloxy, $C_{1-9}$ heteroaryloxy-$C_{1-4}$-alkoxy, $C_{2-10}$ heterocyclyloxy-$C_{1-4}$-alkoxy, $C_{3-10}$ carbocyclyloxy-$C_{1-4}$-alkoxy, $C_{2-10}$ heterocyclyloxy, $C_{6-10}$ aryl, $C_{6-10}$ aryl-$C_{1-6}$-alkyl, $C_{1-9}$ heteroaryl-$C_{1-6}$-alkyl, $C_{1-9}$ heteroaryl, $C_{2-10}$ heterocyclyl, $C_{6-12}$ fused bicyclyloxy, $C_{6-12}$ fused bicyclyl-$C_{1-6}$-alkyl, $C_{5-12}$ fused heterobicyclyl-$C_{1-6}$-alkyl, $C_{5-12}$ fused heterobicyclyloxy, $C_{5-12}$ fused heterobicyclylamino, $C_{5-12}$ fused heterobicyclyl-$C_{1-6}$-alkoxy, $C_{5-12}$ fused heterobicyclyl-$C_{1-6}$-alkylamino, $C_{5-12}$ fused heterobicyclyloxy-$C_{1-6}$-alkoxy, $C_{5-12}$ fused heterobicyclyloxy-$C_{1-6}$-alkylamino, $C_{5-12}$ spiro heterobicyclyl-$C_{1-6}$-alkyl, $C_{5-12}$ spiro heterobicyclyl-$C_{1-6}$-alkoxy, $C_{5-12}$ bridged heterobicyclyl-$C_{1-6}$-alkyl, $C_{5-12}$ bridged heterobicyclyloxy, $C_{5-12}$ bridged heterobicyclyl-$C_{1-6}$-alkoxy, $C_{5-12}$ bridged heterobicyclyl-$C_{1-6}$-alkylamino, $C_{5-12}$ bridged heterobicyclyl, $C_{5-12}$ spiro heterobicyclyl or $C_{5-12}$ fused heterobicyclyl; and wherein each $R^2$ is independently substituted with one or more $R^{2a}$ which are the same or different;

each $R^3$ and $R^{3a}$ is independently $C_{1-4}$ alkyl, $C_{3-10}$ cycloalkyl, $C_{2-10}$ heterocycloalkyl, $C_{1-6}$ alkoxy-$C_{1-6}$-alkyl or $C_{1-4}$ hydroxyalkyl; and each $R^{2a}$ is as defined herein.

In certain embodiments, provided herein are substituted urea derivatives having Formula (I), Formula (IIa) or Formula (II), or a stereoisomer, a geometric isomer, a tautomer, an N-oxide, a hydrate, a solvate, a metabolite, an ester, a pharmaceutically acceptable salt or a prodrug thereof, each $R^2$ is independently —$NR^3R^{3a}$, $C_{1-4}$ alkoxy-$C_{1-4}$-alkyl, $C_{1-4}$ alkyl or $C_{1-4}$ hydroxyalkyl, or each $R^2$ is independently one of the following sub-formulae:

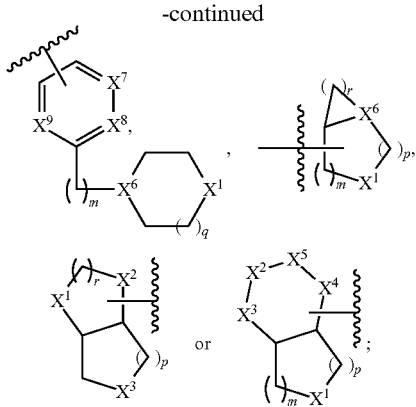

wherein each $X^6$, $X^7$, $X^8$ and $X^9$ is independently N or CH;

each $X^1$, $X^2$, $X^3$, $X^4$ and $X^5$ is independently —$(C(R^{4b})_2)_m$—, —$C(=O)$—, —O—, —$N(R^{4a})$— or —$S(=O)_t$—;

each q, m, p and r is independently 0, 1, 2, 3 or 4;

each t is independently 0, 1 or 2;

wherein each $R^2$ is independently substituted with one or more $R^{2a}$ which are the same or different;

each $R^{4a}$ is independently H, $C_{1-4}$ alkyl, $C_{3-10}$ cycloalkyl, $C_{2-10}$ heterocycloalkyl, $C_{1-6}$ alkoxy-$C_{1-6}$-alkyl, or $C_{1-4}$ hydroxyalkyl;

each $R^{4b}$ is independently H, F, Cl, Br, cyano, nitro, hydroxy, mercapto, amino, carboxy, $C_{1-4}$ alkyl, $C_{3-10}$ cycloalkyl, $C_{1-4}$ haloalkyl, $C_{1-4}$ alkoxy, $C_{1-4}$ alkylamino, —$(CR^{3b}R^{3c})_n$—$NH_2$, —$C(=O)$—$NH_2$, $C_{2-10}$ heterocycloalkyl, $C_{1-6}$ alkoxy-$C_{1-6}$-alkyl or $C_{1-4}$ hydroxyalkyl; and wherein each $R^3$, $R^{3a}$, $R^{3b}$, $R^{3c}$, and $R^{2a}$ is as defined herein.

In certain embodiments, provided herein are substituted urea derivatives having Formula (I), Formula (IIa) or Formula (II), or a stereoisomer, a geometric isomer, a tautomer, an N-oxide, a hydrate, a solvate, a metabolite, an ester, a pharmaceutically acceptable salt or a prodrug thereof, each $R^2$ is independently one of the following sub-formulae:

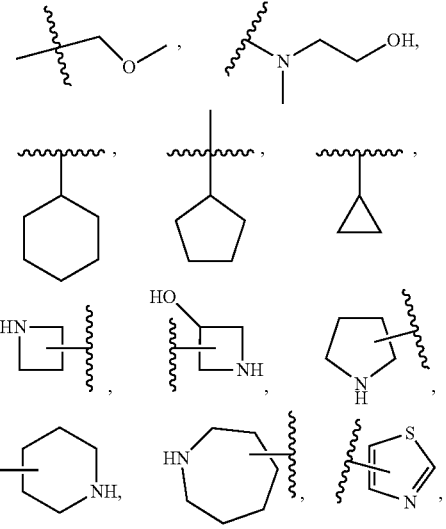

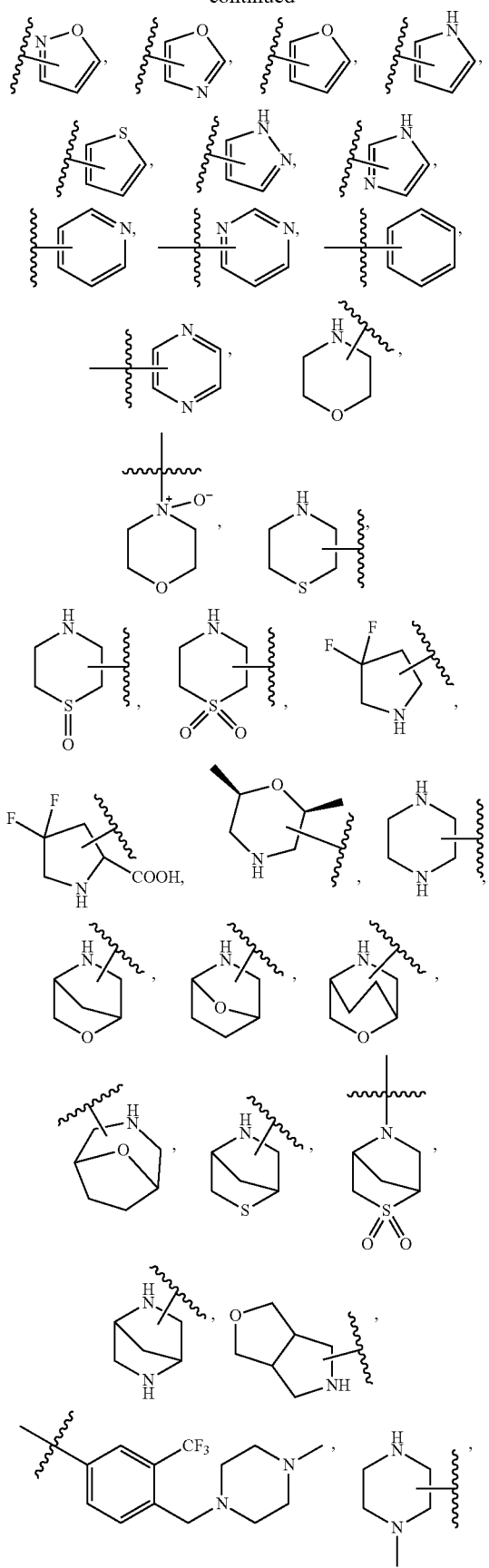
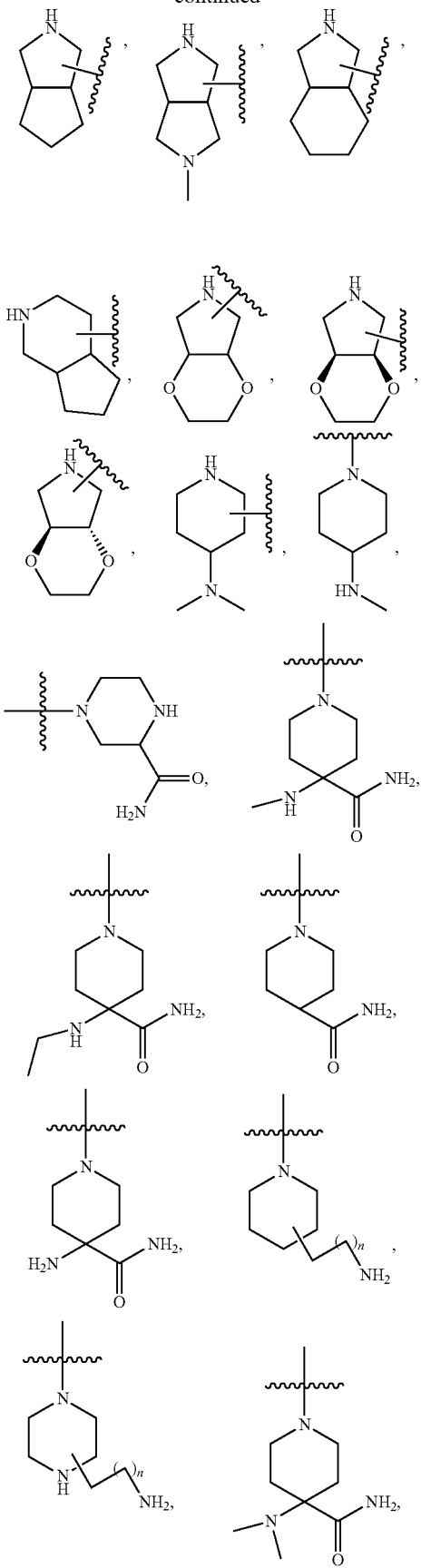

-continued

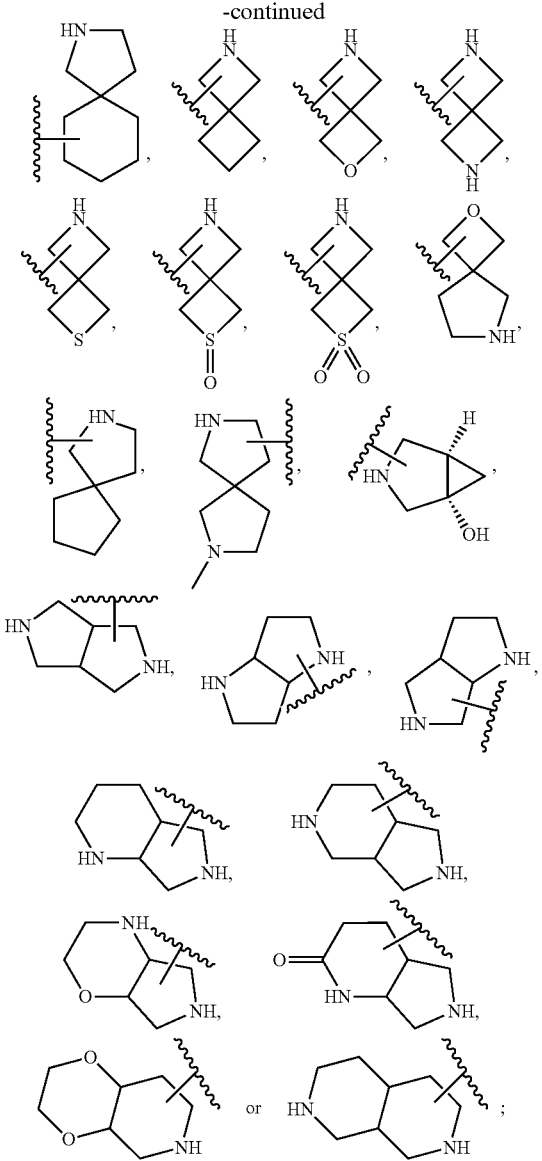

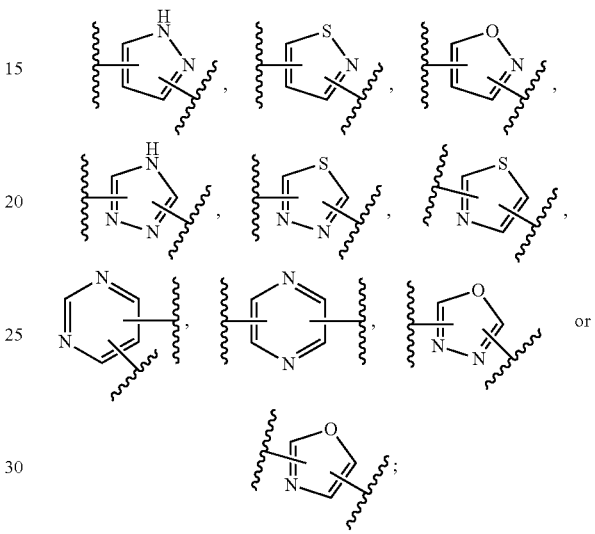

each $R^3$ and $R^{3a}$ is independently methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl;

each $R^4$ and $R^{4a}$ is independently H, methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl;

each $R^{4b}$ is independently H, F, Cl, Br, cyano, nitro, hydroxy, mercapto, amino, carboxy, methyl, ethyl, propyl, isopropyl, tert-butyl, cyclopropyl, cyclopentyl, cyclohexyl, trifluoromethyl, methoxy, $C_{1-4}$ alkylamino, —$(CR^{3b}R^{3c})_n$—$NH_2$, —$C(=O)$—$NH_2$, $C_{2-10}$ heterocycloalkyl, $C_{1-6}$ alkoxy-$C_{1-6}$-alkyl or $C_{1-4}$ hydroxyalkyl;

wherein each sub-formula represented by $R^2$ is independently substituted with one or more $R^{2a}$ which are the same or different; and each $R^{2a}$ is independently H, F, Cl, Br, I, trifluoromethyl, chloroethyl, trifluoroethyl, methyl, ethyl, propyl, isopropyl, dimethylamino, methylamino, diethylamino, ethylamino, hydroxy, cyano, nitro, —C(=O)—NH$_2$, carboxy, —S(=O)$_t$—O—H, —OS(=O)$_t$—H, —S(=O)$_t$NH$_2$, triazolyl, tetrazolyl, —(CH$_2$)—NH$_2$, —(CH$_2$)$_3$—NH$_2$, —(CH(CF$_3$))—NH$_2$, —(CH$_2$)$_2$—NH$_2$, oxo (=O), methyl-C(=O)—, ethyl-C(=O)—, propyl-C(=O)—, benzyl or phenyl.

In certain embodiments, provided herein are substituted urea derivatives having Formula (I), or a stereoisomer, a geometric isomer, a tautomer, an N-oxide, a hydrate, a solvate, a metabolite, an ester, a pharmaceutically acceptable salt or a prodrug thereof, ring K is

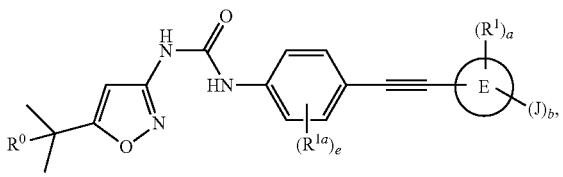

and each L is independently cyclopropyl, cyclobutyl, cyclopentyl, cyclohexyl, $C_{3-6}$ heterocycloalkyl, amino, cyano, nitro, F, Cl, Br, I, trifluoromethyl, 1,1,1-trifluoro-2-methyl-prop-2-yl, methyl, ethyl, butyl, propyl, isopropyl, tert-butyl, $C_{1-4}$ alkylamino, hydroxy, cyano, nitro, $C_{1-4}$ alkyl-C(=O)—NH—, $C_{1-4}$ alkoxy, hydroxymethyl, hydroxyethyl, 1-hydroxy-n-butyl, 2-hydroxy-n-propyl, hydroxy-tert-butyl or $C_{1-4}$ alkylthio.

In certain embodiments, the substituted urea derivatives provided herein having Formula (IIIa), or a stereoisomer, a geometric isomer, a tautomer, an N-oxide, a hydrate, a solvate, a metabolite, an ester, a pharmaceutically acceptable salt or a prodrug thereof, (IIIa)

wherein $R^0$ is $C_{2-3}$ alkyl, trifluoromethyl, fluoromethyl, difluoromethyl or hydroxymethyl; and each $R^{1a}$, $R^1$, J, e, a and b is as defined herein.

In certain embodiments, the substituted urea derivatives provided herein having Formula (III), or a stereoisomer, a geometric isomer, a tautomer, an N-oxide, a hydrate, a solvate, a metabolite, an ester, a pharmaceutically acceptable salt or a prodrug thereof, (III)

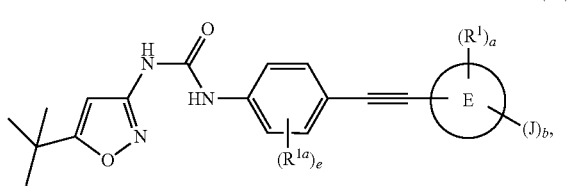

wherein each $R^{1a}$, $R^1$, J, e, a and b is as defined herein.

In other embodiments, the substituted urea derivatives provided herein having Formula (IV), or a stereoisomer, a geometric isomer, a tautomer, an N-oxide, a hydrate, a solvate, a metabolite, an ester, a pharmaceutically acceptable salt or a prodrug thereof, (IV)

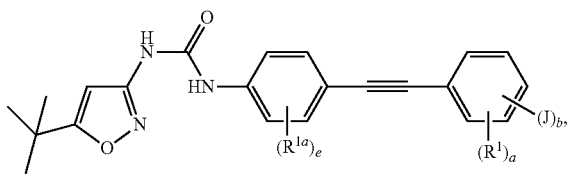

wherein each $R^{1a}$, $R^1$, J, e, a and b is as defined herein.

In other embodiments, the substituted urea derivatives provided herein having Formula (V), or a stereoisomer, a geometric isomer, a tautomer, an N-oxide, a hydrate, a solvate, a metabolite, an ester, a pharmaceutically acceptable salt or a prodrug thereof, (V)

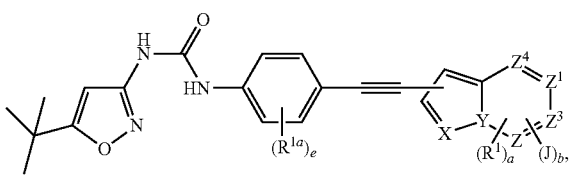

wherein each $R^{1a}$, $R^1$, J, e, a and b is as defined herein; and each of X, Y, Z, $Z^1$, $Z^3$ and $Z^4$ is independently N or CH.

In certain embodiments, the substituted urea derivatives provided herein having Formula (VI), or a stereoisomer, a geometric isomer, a tautomer, an N-oxide, a hydrate, a solvate, a metabolite, an ester, a pharmaceutically acceptable salt or a prodrug thereof, (VI)

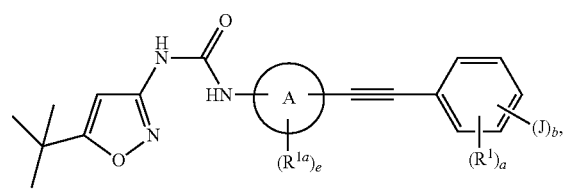

wherein each ring A, $R^{1a}$, $R^1$, J, e, a and b is as defined herein.

In certain embodiments, provided herein are substituted urea derivatives having Formula (VIIa), or a stereoisomer, a geometric isomer, a tautomer, an N-oxide, a hydrate, a solvate, a metabolite, an ester, a pharmaceutically acceptable salt or a prodrug thereof, (VIIa)

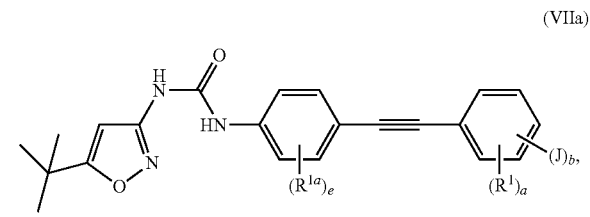

wherein each $R^{1a}$, $R^1$, J, e, a and b is as defined herein; and $R^{00}$ is $C_{1-3}$ alkyl, trifluoromethyl, fluoromethyl, difluoromethyl or hydroxymethyl.

In certain embodiments, provided herein are substituted urea derivatives having Formula (IIIb), or a stereoisomer, a geometric isomer, a tautomer, an N-oxide, a hydrate, a solvate, a metabolite, an ester, a pharmaceutically acceptable salt or a prodrug thereof, (IIIb)

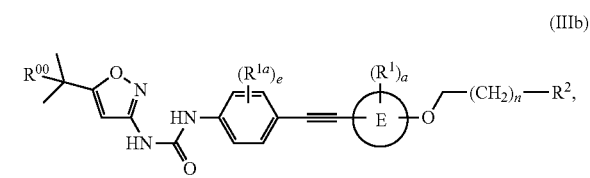

wherein $R^{00}$ is $C_{1-3}$ alkyl, trifluoromethyl, fluoromethyl, difluoromethyl or hydroxymethyl; and each ring E, $R^1$, $R^{1a}$, $R^2$, e, a and n is as defined herein.

In another aspect, provided herein is a pharmaceutical composition comprising the compound disclosed herein.

In certain embodiments, the pharmaceutical composition disclosed herein further comprises at least one of pharmaceutically acceptable carriers, excipients, diluents, adjuvants or vehicles.

In certain embodiments, the pharmaceutical composition disclosed herein further comprises other active agent used for treating a proliferative disease, an autoimmune disease or an inflammatory disease, wherein the other active agent is a chemotherapeutic agent, antiproliferative agent, immunosuppressive agent, immunostimulatory agent, antiinflammatory agent, an agent for treating atherosclerosis, an agent for treating pulmonary fibrosis, CDK4/6-kinase inhibitor, ABL inhibitor, ABL/Scr inhibitor, aurora kinase inhibitor, non-ATP-competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

In certain embodiments, the pharmaceutical composition disclosed herein, wherein the other active agent is chlorambucil, melphalan, cyclophosphamide, ifosfamide, busulfan, carmustine, lomustine, streptozotocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin C, ixabepilone, tamoxifen, flutamide, gonadorelin analogue, megestrol, prednisone, dexamethasone, methylprednisolone, thalidomide, interferon-α, leucovorin calcium, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, quizartinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib or a combination thereof.

In another aspect, provided herein is the use of the compound or the pharmaceutical composition disclosed herein in the manufacture of a medicament for preventing, managing, treating or lessening a proliferative disease, an autoimmune disease or an inflammatory disease in a patient.

In certain embodiments, the use disclosed herein, wherein the proliferative disease is chronic myelogenous leukemia, gastrointestinal stromal tumor, actute promyelocytic leukemia, acute myelomonocytic leukemia, acute monocytic leukemia, acute erythroleukemia, acute megakaryocytic leukemia, minimally differentiated acute myeloid leukemia, acute myelogenous leukemia (AML), mutant chronic myelogenous leukemia (CML), acute lymphocytic leukemia (ALL), leukemia, chronic lymphocytic leukemia, primary macroglobulinemia, monocytic leukemia, leukemoid reaction, aplastic anemia, purpura, secondary benign monoclonal gammopathy, semi-molecular disease, colorectal cancer, stomach cancer, breast cancer, lung cancer, liver cancer, prostate cancer, pancreatic cancer, thyroid cancer, kidney cancer, brain tumor, neck cancer, central nervous system (CNS) cancer, malignant glioma, bone marrow hyperplasia, anemia, atherosclerosis, pulmonary fibrosis, rheumatoid disease, papular mucinosis, Gaucher's disease, amyloidosis, infectious mononucleosis, malignant histiocytosis, lymphoma, cryoglobulinaemia, non-lymphoreticular system tumor, multiple myeloma, granulocytic sarcoma, solitary plasmacytoma, heavy chain disease, light chain disease, malignant lymphoma, osteolytic lesions, lymphoblastoma, non-Hodgkin's lymphoma, sezary's syndrome, infectious mononucleosis syndrome, acute histiocytosis, Hodgkin's lymphoma, hairy cell leukemia, colon cancer, colorectal cancer, gastrointestinal polyposis, small-cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, digestive malignant tumor, non-small cell lung cancer, cervical cancer, testicular tumor, bladder cancer, myeloma or AML related complication.

In other embodiments, the use disclosed herein, wherein the AML related complication is the symptom displayed by the patient, i.e., infection, bleeding, adult respiratory distress syndrome, sarcoidosis, pleural effusion, pulmonary fibrosis, pericardial effusion, cardiac arrhythmia, hypertension, heart failure, acute abdomen, portal hypertension, renal insufficiency, liver and spleen abscesses, anemia, thrombosis, diabetes, diabetes insipidus, electrolyte imbalance, neurological complications, intracranial hemorrhage, necrosis of the femoral head, bone and joint disease, skin lesions, retinal hemorrhage, optic disc edema, conjunctival hyperemia, edema, hypopyon, choroidal infiltration, iris infiltration, vitreous opacities, vision loss, hypopsia, orbital tumor, proptosis, acute glaucoma, chloroma, gingival hyperplasia, oral mucosal lesions, Sweets syndrome, gangrenous pyoderma, arthritis and vasculitis syndrome.

In certain embodiments, the use disclosed herein, wherein the autoimmune disease is leukemia, chronic myelogenous leukemia, gastrointestinal stromal tumor, acute myelogenous leukemia (AML), mutant chronic myelogenous leukemia (CML), acute lymphocytic leukemia (ALL), rheumatoid arthritis, bone and joint pain, central nervous system involvement, lupus, multiple sclerosis, thyroiditis, type I diabetes, sarcoidosis, inflammatory bowel disease, Crohn's disease, systemic lupus or AML related complication.

In certain embodiments, the use disclosed herein, wherein the inflammatory disease is diverticulitis, colitis, pancreatitis, hepatitis, chronic hepatitis, cirrhosis, cholecystitis or chronic inflammation.

In certain embodiments, the use disclosed herein, wherein the disease is a disease mediated by c-KIT mutation, RET, PDGFR, VEGFR, Bcr-ABL, FLT3 or induced by FLT3-ITD.

In one aspect, provided herein is a drug combination comprising the compound or the pharmaceutical composition disclosed herein and one or more other active agents used for the treatment of a proliferative disease, an autoimmune disease or an inflammatory disease.

In certain embodiments, the drug combination disclosed herein, wherein the other active agent is chemotherapeutic agent, antiproliferative agent, immunosuppressive agent, immunostimulatory agent, antiinflammatory agent, CDK4/6-kinase inhibitor, ABL inhibitor, ABL/Scr inhibitor, aurora kinase inhibitor, non-ATP-competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

In certain embodiments, the drug combination disclosed herein, wherein the compound or the pharmaceutical composition disclosed herein is a FLT3 inhibitor or FLT3-ITD inhibitor.

In certain embodiments, the drug combination disclosed herein, wherein the other active agent is a CDK4/6-kinase inhibitor.

In another aspect, provided herein is a method of preventing, managing, treating or lessening a proliferative disease, an autoimmune disease or an inflammatory disease in a patient comprising administering to the patient a therapeutically effective amount of the compound or the pharmaceutical composition disclosed herein.

In certain embodiments, the method disclosed herein, wherein the proliferative disease is chronic myelogenous leukemia, gastrointestinal stromal tumor, acute myelogenous leukemia (AML), mutant chronic myelogenous leukemia (CML), acute lymphocytic leukemia (ALL), leukemia, chronic lymphocytic leukemia, primary macroglobulinemia, monocytic leukemia, leukemoid reaction, aplastic anemia, purpura, secondary benign monoclonal gammopathy, semi-molecular disease, colorectal cancer, stomach cancer, breast cancer, lung cancer, liver cancer, prostate cancer, pancreatic cancer, thyroid cancer, kidney cancer, brain tumor, neck cancer, central nervous system (CNS) cancer, malignant glioma, bone marrow hyperplasia, infectious mononucleosis, malignant histiocytosis, lymphoma, non-lymphoreticular system tumor, multiple myeloma, granulocytic sarcoma, solitary plasmacytoma, malignant lymphoma, osteolytic lesions, lymphoblastoma, non-Hodgkin's lymphoma, infectious mononucleosis syndrome, acute histiocytosis, Hodgkin's lymphoma, colon cancer, colorectal cancer, small-cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, digestive malignant tumor, non-small cell lung cancer, cervical cancer, testicular tumor, bladder cancer, myeloma or AML related complication;

the autoimmune disease is leukemia, chronic myelogenous leukemia, gastrointestinal stromal tumor, acute myelogenous leukemia (AML), mutant chronic myelogenous leukemia (CML), acute lymphocytic leukemia (ALL), rheumatoid arthritis, bone and joint pain, central nervous system involvement, lupus, multiple sclerosis, thyroiditis, type I diabetes, sarcoidosis, inflammatory bowel disease, Crohn's disease, systemic lupus or AML related complication; and the inflammatory disease is diverticulitis, colitis, pancreatitis, hepatitis, chronic hepatitis, cirrhosis, cholecystitis or chronic inflammation.

In certain embodiments, the method disclosed herein, wherein the disease is a disease mediated by c-KIT mutation, RET, PDGFR, VEGFR, Bcr-ABL, FLT3 or induced by FLT3-ITD.

In another aspect, provided herein is the compound or the pharmaceutical composition disclosed herein for use in preventing, managing, treating or lessening a proliferative disease, an autoimmune disease or an inflammatory disease in a patient.

In certain embodiments, the compound or the pharmaceutical composition disclosed herein, wherein the proliferative disease is chronic myelogenous leukemia, gastrointestinal stromal tumor, acute myelogenous leukemia (AML), mutant chronic myelogenous leukemia (CML), acute lymphocytic leukemia (ALL), leukemia, chronic lymphocytic leukemia, primary macroglobulinemia, monocytic leukemia, leukemoid reaction, aplastic anemia, purpura, secondary benign monoclonal gammopathy, semi-molecular disease, colorectal cancer, stomach cancer, breast cancer, lung cancer, liver cancer, prostate cancer, pancreatic cancer, thyroid cancer, kidney cancer, brain tumor, neck cancer, central nervous system (CNS) cancer, malignant glioma, bone marrow hyperplasia, infectious mononucleosis, malignant histiocytosis, lymphoma, non-lymphoreticular system tumor, multiple myeloma, granulocytic sarcoma, solitary plasmacytoma, malignant lymphoma, osteolytic lesions, lymphoblastoma, non-Hodgkin's lymphoma, infectious mononucleosis syndrome, acute histiocytosis, Hodgkin's lymphoma, colon cancer, colorectal cancer, small-cell lung cancer, neuroblastoma, neuroendocrine cell tumor, islet cell tumor, medullary thyroid carcinoma, melanoma, retinoblastoma, uterine cancer, ovarian cancer, head and neck squamous cell carcinoma, digestive malignant tumor, non-small cell lung cancer, cervical cancer, testicular tumor, bladder cancer, myeloma or AML related complication;

the autoimmune disease is leukemia, chronic myelogenous leukemia, gastrointestinal stromal tumor, acute myelogenous leukemia (AML), mutant chronic myelogenous leukemia (CML), acute lymphocytic leukemia (ALL), rheumatoid arthritis, bone and joint pain, central nervous system involvement, lupus, multiple sclerosis, thyroiditis, type I diabetes, sarcoidosis, inflammatory bowel disease, Crohn's disease, systemic lupus or AML related complication; and the inflammatory disease is diverticulitis, colitis, pancreatitis, hepatitis, chronic hepatitis, cirrhosis, cholecystitis or chronic inflammation.

In certain embodiments, the compound or the pharmaceutical composition disclosed herein, wherein the disease is a disease mediated by c-KIT mutation, RET, PDGFR, VEGFR, Bcr-ABL, FLT3 or induced by FLT3-ITD.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope of the invention as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics,* 75th Ed. 1994. Additionally, general principles of organic chemistry are described in Sorrell et al., *"Organic Chemistry"*, University Science Books, Sausalito: 1999, and Smith et al., *"March's Advanced Organic Chemistry"*, John Wiley & Sons, New York: 2007, all of which are incorporated herein by reference in their entireties.

"Stereoisomer" refers to compounds which have identical chemical constitution, but differ with regard to the arrangement of the atoms or groups in space. Stereoisomers include enantiomers, diastereomers, conformers (rotamers), geometric (cis/trans) isomers, atropisomers, and the like.

"Chiral" refers to molecules which have the property of non-superimposability of the mirror image partner, while the term "achiral" refers to molecules which are superimposable on their mirror image partner.

"Racemate" or "racemic mixture" refers to an equimolar mixture of enantiomers which lacks optical activity.

"Enantiomer" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., *McGraw-Hill Dictionary of*

Chemical Terms (1984) McGraw-Hill Book Company, New York and Eliel et al., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972); *Chiral Separation Techniques: A Practical Approach* (Subramanian, G Ed., Wiley-VCH Verlag GmbH & Co. KGaA, Weinheim, Germany, 2007), all of which are incorporated herein by reference.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

"Pharmaceutically acceptable" refers to those compounds, materials, compositions and/or dosage forms which are, within the scope of sound medical judgment, suitable for use in contact with the tissues of patients without excessive toxicity, irritation, allergic response, or with reasonable the benefit/risk ratio relative to said other problems and complications, and effective for their intended use.

Unless otherwise defined herein, for a variable that occurs more than one time in any substituent or in the compound of the invention or any other formulae herein, its definition on each occurrence is independent of its definition at every other occurrence. Combinations of substituents are permissible only if such combinations result in stable compound. Stable compounds are compounds which can be isolated in a useful degree of purity from a reaction mixture.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

As described herein, compounds disclosed herein may optionally be substituted with one or more substituents, such as the compound(s) illustrated by general formula above, or as exemplified by particular classes, subclasses, and species of the invention.

In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "unsubstituted" means the specified group has no substituents.

It will be appreciated that the phrase "optionally substituted" is used interchangeably with the phrase "substituted or unsubstituted", which refers the given structure is unsubstituted or substituted with one or more substituents disclosed herein. Substituents described herein include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroary, alkenyl, alkynyl, heterocyclyl, mercapto, nitro, aryloxy, hydroxyalkoxy, alkanoyl, benzyl, cyclopropyl, phenyl, alkyl-C(=O)—, alkyl-C(=O)—NH—, carboxamido or alkoxyalkyl. Wherein R$^{3b}$, R$^{3c}$, t and n are as defined herein.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" refers to a saturated linear or branched-chain monovalent hydrocarbon group of 1-20 carbon atoms, wherein the alkyl group is independently and optionally substituted with one or more substituents described herein. In some embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms, and in yet other embodiments, the alkyl group contains 1-3 carbon atoms. Further embodiments of the alkyl group include, but are not limited to, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), 2-methylpropyl or isobutyl (i-Bu, —CH$_2$CH(CH$_3$)$_2$), 1-methylpropyl or sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl, n-octyl, and the like. The term "alkyl" or the prefix "alk-" is inclusive of both straight chain and branched saturated carbon chain.

The term "alkynyl" refers to a linear or branched-chain monovalent hydrocarbon group of 2-12 carbon atoms, with at least one site of unsaturation, i.e., a carbon-carbon sp triple bond, wherein the alkynyl group is optionally substituted with one or more substituents described herein. Some non-limiting examples of the alkynyl group include ethynyl

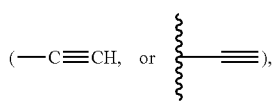

propargyl

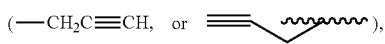

and the like.

The term "alkenyl" refers to a linear or branched-chain monovalent hydrocarbon group of 2-12 carbon atoms, with at least one site of unsaturation, i.e., a carbon-carbon sp$^2$ double bond, wherein the alkenyl group is optionally substituted with one or more substituents described herein, and includes groups having "cis" and "trans" orientations, or alternatively, "E" and "Z" orientations. Some non-limiting examples of the alkenyl group include ethenyl or vinyl (—CH═CH$_2$), allyl (—CH$_2$CH═CH$_2$), and the like.

The term "alkylene" and "alkylene chain" refer to a straight or branched divalent hydrocarbon chain consisting solely of carbon and hydrogen, containing no unsaturation and having 1-8 carbon atoms. Some non-limiting examples of the alkylene group include methylene, ethylene, propylene, n-butylene, and the like. The alkylene chain is attached to the rest of the molecule through any two carbons within the chain.

The term "alkenylene" or "alkenylene chain" refers to a straight or branched divalent unsaturated hydrocarbon chain consisting solely of carbon and hydrogen and having 1-8 carbon atoms, wherein the unsaturated bond exists only as a double bond and the double bond may be located between any two carbon atoms of the chain. Some non-limiting examples of the alkenylene group include ethenylene, 1,3-propenylene, 2-butenylene, and the like. The alkenylene chain is attached to the rest of the molecule through any two carbons within the chain.

The term "alkynylene" or "alkynylene chain" refers to a straight or branched divalent unsaturated hydrocarbon chain consisting solely of carbon and hydrogen and having 1-8 carbon atoms, wherein the unsaturated bond exists only as a triple bond and the triple bond may be located between any two carbon atoms of the chain. Some non-limiting examples of the alkynylene group include ethynylene, 1-propynylene, 2-butynylene, 1-pentynylene 3-pentynylene, and the like. The alkynylene chain is attached to the rest of the molecule through any two carbons within the chain.

The term "halogen" or "halogen atom" refers to fluoro (F), chloro (Cl), bromo (Br) or iodo (I).

The term "alkoxy" refers to an alkyl group, as previously defined, attached to the the rest of molecule via an oxygen atom. Unless otherwise specified, the alkoxy group contains 1-12 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), and the like.

The term "amino" refers to a group having the formula —NH$_2$.

The term "aminoalkyl" refers to a group having the formula R'R"N-alkyl, wherein each of R' and R" is independently hydrogen, alkyl or haloalkyl. Alkyl and amino are as defined herein. Some examples include, but are not limited to, aminoethyl, aminomethyl, aminopropyl and the like.

The term "alkamino" or "alkylamino" refers "N-alkylamino", wherein amino group is substituted with one alkyl group, and wherein the alkyl group is as defined herein. In some embodiments, the alkylamino group is a lower alkylamino group having one $C_{1-6}$ alkyl group attached to nitrogen atom. In other embodiments, the alkylamino group is a lower alkylamino group having 1 to 3 carbon atoms. Some non-limiting examples of the alkylamino group include monoalkylamino such as N-methylamino, N-ethylamino, and the like.

The term "dialkamino" or "di(alkyl)amino" refers "N,N-dialkylamino", wherein amino group is substituted with two alkyl groups, and wherein the alkyl group is as defined herein. In some embodiments, the alkylamino group is a lower alkylamino group having two $C_{1-6}$ alkyl groups attached to nitrogen atom. In other embodiments, the alkylamino group is a lower alkylamino group having two $C_{1-3}$ alkyl groups attached to nitrogen atom. Some non-limiting examples of the dialkamino or di(alkyl)amino group include dialkylamino such as N,N-dimethylamino, N,N-diethylamino, and the like.

The term "alkoxyalkyl" or "alkoxyalkoxy" refers to an alkyl group or alkoxy group substituted with one or more identical or different alkoxy groups, wherein the alkyl group and alkoxy group are as defined herein. Some non-limiting examples of the alkoxyalkyl group and alkoxyalkoxy group include methoxymethyl, ethoxymethyl, methoxypropoxy, methoxymethoxy, and the like.

The term "alkyl-S(=O)$_t$—" refers to —S(=O)$_t$— attached to an alkyl group, wherein the alkyl group is as defined herein, and t is 0, 1 or 2. Some non-limiting examples include methyl-S(=O)$_2$—, ethyl-S(=O)$_2$—, propyl-S(=O)$_2$—, methyl-S(=O)—, ethyl-S(=O)—, propyl-S(=O)—, methyl-S—, ethyl-S—, propyl-S—, and the like.

The term "alkyl-C(=O)—" refers to acyl (—C(=O)—) attached to an alkyl group, wherein the alkyl group is as defined herein. Some non-limiting examples include acetyl (CH$_3$—C(=O)—), propionyl (C$_2$H$_5$—C(=O)—), and the like.

The term "haloalkyl" or "haloalkoxy" refers to an alkyl group or alkoxy group substituted with one or more identical or different halogen atoms, wherein the alkyl group and alkoxy group are as defined herein. Some non-limiting examples of the haloalkyl group and haloalkoxy group include 1,1,1-trifluoro-2-methylprop-2-yl (—C(CH$_3$)$_2$CF$_3$), 1,1-difluoro-2-methylprop-2-yl (—C(CH$_3$)$_2$CHF$_2$), 1-fluoro-2-methylprop-2-yl (—C(CH$_3$)$_2$CH$_2$F), difluoromethyl (—CHF$_2$), trifluoromethyl (—CF$_3$), trifluoromethoxy (—OCF$_3$), 2,2,2-trifluoroethoxy (—OCH$_2$CF$_3$), 2,2,3,3-tetrafluoropropoxy (—OCH$_2$CF$_2$CHF$_2$), and the like.

The term "alkylaminohaloalkoxy" refers to a haloalkoxy group substituted with one or more identical or different alkylamino groups, wherein the alkylamino group and haloalkoxy group are as defined herein. Some non-limiting examples of the alkylaminohaloalkoxy group include methylaminodifluoromethoxy, and the like.

The term "hydroxyalkyl" or "hydroxyalkoxy" refers to an alkyl group or alkoxy group substituted with one or more hydroxy groups, wherein the alkyl group and alkoxy group are as defined herein. Some non-limiting examples of the hydroxyalkyl group and hydroxyalkoxy group include hydroxymethyl, 1-hydroxy-n-butyl, 2-hydroxy-n-propyl, 1-hydroxyethyl, hydroxy-tert-butyl, hydroxypropyl, 1,2-dihydroxypropyl, hydroxymethoxy, 1-hydroxyethoxy, and the like.

The term "aminoalkoxy" or "alkylaminoalkoxy" refers to an alkoxy group substituted with one or more amino groups or alkylamino groups, wherein the alkylamino group and alkoxy group are as defined herein. Some non-limiting examples of the aminoalkoxy group and alkylaminoalkoxy group include aminomethoxy, 1-aminoethoxy, methylaminomethoxy, ethylaminoethoxy, and the like.

The term "aryl" used alone or as part of a larger moiety as in "arylalkyl", "arylalkoxy" or "aryloxyalkyl" refers to monocyclic, bicyclic and tricyclic carbocyclic ring systems. In some embodiments, term "aryl" can be replaced by or used as "arylene". Wherein at least one ring in the "aryl" system is aromatic, and wherein each ring in the system contains 3 to 7 ring members. The term "aryl" may be used interchangeably with the term "aryl ring" or "aromatic ring". Some non-limiting examples of the aryl group include phenyl, naphthyl and anthracene. And the aryl group defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "heteroaryl" or "heteroaryl ring" as used interchangeably herein, used alone or as part of a larger moiety as in "heteroarylalkyl" or "heteroarylalkoxy," which can be replaced by or used as "heteroarylene" in some embodiments, refers to a monocyclic, bicyclic, tricyclic or tetracyclic ring system, wherein the bicyclic heteroaryl, tricyclic heteroaryl or tetracyclic heteroaryl ring system is fused to form a ring. The heteroaryl ring system is aromatic, in which optionally one or more ring atoms are independently selected from heteroatoms (heteroatoms are selected from N, O, P and S, wherein the S or P is optionally substituted with one or more oxo to provide the group SO, SO$_2$, PO or PO$_2$). The heteroaryl system may be attached to the main structure at any heteroatom or carbon atom which results in the creation of a stable compound. The heteroaryl system group may be a 3-7 membered monocyclic ring, a 7-10 membered bicyclic ring or a 10-15 membered tricyclic ring. Bicyclic heteroaryl ring having 7-10 ring atoms can be arranged as a bicyclo[4,5], [5,5], [5,6] or [6,6] system, and tricyclic heteroaryl ring having 10-15 ring atoms can be arranged as a tricyclo[5,5,6], [5,6,6] or [6,5,6] system. And the heteroaryl or heteroaryl ring defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$ NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like. Depending on the structure, the heteroaryl group may be a monoradical or a diradical (i.e., heteroarylene group).

Some non-limiting examples of the heteroaryl system (containing hetereoaryl group, hetereoaryl ring) include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl, benzo[d]thiazol-2-yl, imidazo[1,5-a]pyridin-6-yl, benzimidazolyl, benzoxazolyl, quinoxalinyl, 1,8-naphthyridinyl, benzothienyl, benzothiazolyl, purinyl, quinolinyl (e.g., 2-quinolinyl, 3-quinolinyl and 4-quinolinyl), isoquinolinyl (e.g., 1-isoquinolinyl, 3-isoquinolinyl and 4-isoquinolinyl), benzopyrazolyl, acridinyl, benzindolyl, benzisoxazinyl, benzo[4,6]imidazo[1,2-a]pyridinyl, benzo[d]imidazo[2,1-b]thiazolyl, benzofuryl, benzothiadiazolyl, benzothiazolyl, benzotriazolyl, benzothiopyranyl, benzoxazinyl, benzoxazolyl, benzothiazolyl, β-carbolinyl, carbazolyl, cinnolinyl, dibenzofuryl, imidazopyridyl, imidazothiazolyl, indazolyl, indolizinyl, indolyl, isobenzothianthrenyl, isoindolinyl, isoquinolinyl, isothiazolidinyl, isothiazolyl, naphthyridinyl, decahydroindolyl, decahydroisoindolyl, oxazolidinedionyl, oxazolidinyl, oxazolopyridinyl, oxazolyl, oxiranyl, perimidinyl, phenanthridinyl, phenanthrolinyl, phenarsazinyl, phenazinyl, phenothiazinyl, phenoxazinyl, phthalazinyl, pteridinyl, naphthyridinyl, pyridopyridyl, quinazolinyl, quinoxalinyl, thiophenyl, triazinyl, 2H-pyrrolo[3,4-c]pyridinyl, pyrazolo[2',1':2,3]oxazolo[4,5-c]pyridinyl, imidazo[2',1':2,3]thiazolo[4,5-c]pyridinyl, imidazo[2',1':2,3]thiazolo[4,5-b]pyridinyl, imidazo[2',1':2,3]thiazolo[5,4-b]pyridinyl, pyrazolo[2',1':2,3]thiazolo[4,5-b]pyrazinyl, 1H-benzo[4,5]thieno[2,3-d]imidazolyl, 1-methyl-1H-benzo[4,5]thieno[2,3-d]imidazolyl, imidazo[2',1':2,3]thiazolo[4,5-b]pyrazinyl, imidazo[2',1':2,3]thiazolo[5,4-b]pyridinyl, imidazo[2',1':2,3]thiazolo[4,5-c]pyridinyl, and the like.

The term "carbocyclyl", "cycloaliphatic", "carbocycle" or "cycloalkyl" as used interchangeably herein refers to a monovalent or multivalent, non-aromatic, saturated or partially unsaturated ring consisting solely of carbon and hydrogen atoms and including 3-12 carbon atoms as a monocyclic ring or 7-12 carbon atoms as a bicyclic ring or tricyclic ring. Bicyclic carbocycles having 7-12 ring atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Depending on the structure, the carbocyclyl, cycloaliphatic, carbocycle or cycloalkyl group can be a monoradical or a diradical, i.e., in some embodiments, the carbocyclyl, cycloaliphatic, carbocycle or cycloalkyl group can be replaced by or used as carbocyclylene or cycloalkylene. Some non-limiting examples of the cycloaliphatic group include cycloalkyl, cycloalkenyl and cycloalkynyl. Further examples of the cycloaliphatic group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantly, and the like. The carbocyclyl, cycloaliphatic, carbocycle or cycloalkyl group described herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "heterocyclyl", "heterocycle", "heterocycloaliphatic" or "heterocyclic" as used interchangeably herein refers to a monocyclic, bicyclic, tricyclic or tetracyclic ring system in which one or more ring members are independently selected from heteroatoms and that is completely saturated or that contains one or more units of unsaturation, but which is not aromatic.

Depending on the structure, the heterocyclyl, heterocycle, heterocycloaliphatic or heterocyclic group can be a monoradical or a diradical, i.e., in some embodiments, the heterocyclyl, heterocycle, heterocycloaliphatic or heterocyclic group can be replaced by or used as heterocyclylene. The heterocyclyl system may be attached to the main structure at any heteroatom or carbon atom which results in the creation of a stable compound. One or more hydrogen atoms on the heterocyclic ring are optionally substituted with one or more substituents described herein. In some embodiments, the heterocyclyl, heterocycle, heterocyclylene, heterocycloaliphatic or heterocyclic group is a monocyclic ring having 3-7 ring members (e.g., 1 to 6 carbon atoms and 1 to 3 heteroatoms selected from N, O, P and S, wherein the S or P is optionally substituted with one or more oxo to provide the group SO, SO$_2$, PO or PO$_2$, and the carbon atom can also be optionally substituted with one or more oxo to provide the group —C=O—, with the proviso that when the ring is a 3-membered ring, there is only one heteroatom) or a bicyclic ring having 7-10 ring members (e.g., 4 to 9 carbon atoms and 1 to 3 heteroatoms selected from N, O, P and S, wherein the S or P is optionally substituted with one or more oxo to provide the group SO, SO$_2$, PO or PO$_2$).

In other embodiments, the nitrogen atoms of nitrogen-containing heterocyclic group are oxidated to form nitrogen oxide. For example,

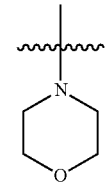 [SMILES: *N1CCOCC1]

is oxidated to form

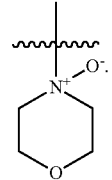

The heterocyclyl may be a carbon radical or heteroatom radical. The heterocyclyl group also includes a group in which the heterocyclyl group is fused with a saturated or partially unsaturated ring or a heterocyclic ring. Some non-limiting examples of the heterocyclyl group include pyrrolidinyl, tetrahydrofuranyl, dihydrofuranyl, tetrahydrothienyl, tetrahydropyranyl, dihydropyranyl, tetrahydrothiopyranyl, piperidinyl, thioxanyl, azetidinyl, oxetanyl, thietanyl, homopiperidinyl, epoxypropyl, azepanyl, oxepanyl, thiepanyl, N-morpholinyl, 2-morpholinyl, 3-morpholinyl, thiomorpholinyl, N-piperazinyl, 2-piperazinyl, 3-piperazinyl, homopiperazinyl, 4-methoxy-piperidin-1-yl, 1,2,3,6-tetrahydropyridin-1-yl, oxazepinyl, diazepinyl, thiazepinyl, 1-pyrrolinyl, 2-pyrrolinyl, 3-pyrrolinyl, dihydroindolyl, 2-indolinyl, 2H-pyranyl, 4H-pyranyl, dioxanyl, 1,3-dioxolanyl, pyrazolinyl, dithianyl, dithiolanyl, dihydrothienyl, pyrazolidinyl, imidazolinyl, imidazolidinyl, 1,2,3,4-tetrahydroisoquinolinyl, 1,1-dioxo-1,2,6-thiadiazin-2-yl, hexahydro-2H-[1,4]dioxin[2,3-c]pyrrolyl, quinolizinyl, 1,1-dioxothiomorpholinyl, 2,3,3a,7a-tetrahydro-1H-isoindolyl, isoindolinyl, 1,2,3,4-tetrahydroquinolyl, N-pyridyl urea, dibenzofuranyl, dihydrobenzoisothiazinyl, dihydrobenzoisoxazinyl, dioxolanyl, dihydropyrazinyl, dihydropyridyl, dihydropyrazolyl, dihydropyrimidinyl, dihydropyrrolyl, 1,4-dithianyl, furanonyl, furyl, imidazolidinyl, imidazolinyl, imidazolyl, imidazopyridyl, imidazothiazolyl, indazolyl, indolinyl, isobenzotetrahydrofuranyl, isobenzotetrahydrothianthrenyl, isobenzothianthrenyl, isobenzodihydropyranyl, isocumarinyl, isoindolinyl, isoindolyl, isoquinolinyl, isothiazolidinyl, isothiazolyl, isoxazolidinyl, isoxazolyl, morpholinyl, decahydroindolyl, decahydroisoindolyl, oxadiazolyl, oxazolidinedionyl, oxazolidinyl, oxazolopyridinyl, oxazolyl, oxiranyl, perimidinyl, phenanthridinyl, phenanthrolinyl, phenarsazinyl, phenazinyl, phenothiazinyl, phenoxazinyl, phthalazinyl, piperazinyl, 4-piperidonyl, purinyl, pyrazinyl, pyrazolidinyl, pyrazolyl, pyridazinyl, pyridyl, pyridopyridyl, pyrimidinyl, pyrrolyl, quinazolinyl, quinolyl, quinoxalinyl, quinuclidinyl, tetrahydroisoquinolinyl, tetrahydrothianthrenyl, tetrazolyl, thiadiazolopyrimidinyl, thiadiazolyl, thiomorpholinyl, thiazolidinyl, thiazolyl, thiophenyl, triazolyl, 1,3,5-trithianyl, and the like. The heterocyclyl group described herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like. Such as 1-methylpyridin-2(1H)-one, cyclohex-2,4-dienone, 2,6-dimethylmorpholinyl, and the like.

The term "fused bicyclic", "fused cyclic", "fused bicyclyl" or "fused cyclyl" refers to a saturated or unsaturated fused ring system, which refers to a bicyclic ring system that is not aromatic and includes at least one non-aromatic ring. Such a system may contain isolated or conjugated unsaturation, but not aromatic or heteroaromatic rings in its core structure (but may have aromatic substitution thereon). Each cyclic ring in the fused bicyclyl can be either a carbocyclic ring or a heteroalicyclic ring. Some non-limiting examples of the fused bicyclic ring system include hexahydro-furo[3,2-b]furanyl, 2,3,3a,4,7,7a-hexahydro-1H-indenyl, 7-azabicyclo[2.2.1]heptyl, fused bicyclo[3.3.0]octyl, fused bicyclo[3.1.0]hexyl, 1,2,3,4,4a,5,8,8a-octahydronaphthyl, and the like. And the fused bicyclyl group defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "fused heterobicyclyl" refers to saturated or unsaturated fused ring system, which refers to a bicyclic ring system that is not aromatic and includes at least one non-aromatic ring. Such a system may contain isolated or conjugated unsaturation, but not aromatic or heteroaromatic rings in its core structure (but may have aromatic substitution thereon).

Depending on the structure, the fused heterobicyclyl group can be a monoradical or a diradical, i.e., in some embodiments, the fused heterobicyclyl group can be replaced by or used as fused heterobicyclylene. And at least one ring in the fused ring system contains one or more heteroatoms. Each ring in the fused ring system contains 3 to 7 ring members and that contains 1 to 6 carbon atoms and 1 to 3 heteroatoms selected from N, O, P and S, wherein the S or P is optionally substituted with one or more oxo to provide the group SO, SO$_2$, PO or PO$_2$, and the carbon atom can also be optionally substituted with one or more oxo to provide the group —C=O—. Some non-limiting examples of the fused heterobicyclyl group include hexahydro-2H-[1,4]dioxin[2,3-c]pyrrolyl, 3-azabicyclo[3.3.0]octyl, 8-azabicyclo[4.3.0]nonyl, 8-azabicyclo[4.3.0]non-3-yl, 3-azabicyclo[4.3.0]non-3-yl, 1,5-dioxa-8-azabicyclo[4.3.0]nonyl, (1R,6S)-2,5-dioxa-8-azabicyclo[4.3.0]nonyl, (1R,6R)-2,5-dioxa-8-azabicyclo[4.3.0]nonyl, isoindolinyl, 1,2,3,4-tetrahydroquinolyl, 3-aza-7-oxabicyclo[3.3.0]octyl, 3,7-diazabicyclo[3.3.0]octyl, 2,6-diazabicyclo[3.3.0]octyl, 2,7-diazabicyclo[3.3.0]octyl, 2,8-diazabicyclo[4.3.0]nonyl, 3,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 2-oxo-3-oxa-8-azabicyclo[4.3.0]nonyl, 3-oxo-2,4,8-triazabicyclo[4.3.0]nonyl, 3-oxo-4-oxa-2,8-diazabicyclo[4.3.0]nonyl, 3-oxo-2,8-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, 5,6-dihydro-4H-pyrrolo[3,4-c]isoxazolyl, [1,2,4]triazolo[4,3-a]piperidyl, 4,5,6,7-tetrahydro-1H-imidazo[4,5-c]pyridinyl, 4,5,6,7-tetrahydrooxazolo[4,5-c]pyridinyl, isoxazolo[4,3-c]piperidinyl, 4,5,6,7-tetrahydroisoxazolo[3,4-c]pyridinyl, [1,2,4]triazolo[4,3-a]piperazinyl, 2-oxo-3-oxa-8-azabicyclo[4.3.0]nonyl, 4,5,6,7-tetrahydro-1H-pyrazolo[4,3-c]pyridinyl, 2-oxa-7-azabicyclo[4.4.0]decyl, 1,5-dioxa-9-azabicyclo[4.4.0]decyl, 4,5,6,7-tetrahydro-2H-pyrazolo[4,3-c]pyridinyl, 3-azabicyclo[4.4.0]decyl, 2-oxa-5,8-diazabicyclo[4.3.0]nonyl, 2,7-diaza-decahydronaphthyl, 2-oxa-8-azabicyclo[4.4.0]decyl, and the like. The fused heterobicyclyl group defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "bridged bicyclyl" refers to a saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon), in which each ring contains 3 to 7 ring members. Some non-limiting examples of the bridged bicyclyl group include bicyclo[2.2.1]heptyl, and the like. The bridged bicyclyl group defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "bridged heterobicyclyl" refers to saturated or unsaturated bridged ring system, which refers to a bicyclic ring system that is not aromatic. Depending on the structure, the bridged heterobicyclyl group can be a monoradical or a diradical, i.e., in some embodiments, the bridged heterobicyclyl group can be replaced by or used as fused heterobicyclylene. Such a system may contain isolated or conjugated unsaturation, but not aromatic or heteroaromatic rings in its core structure (but may have aromatic substitution thereon). And at least one ring in the bridged ring system contains one or more heteroatoms. Each ring in the bridged ring system contains 3 to 7 ring members and that contains 1 to 6 carbon atoms and 1 to 3 heteroatoms selected from N, O, P and S, wherein the S or P is optionally substituted with one or more oxo to provide the group SO or SO$_2$, PO or PO$_2$, and the carbon atom can also be optionally substituted with one or more oxo to provide the group —C=O—. Some non-limiting examples of the bridged heterobicyclyl group include 2-oxa-5-azabicyclo[2.2.1]heptyl, 2-thio-5-azabicyclo[2.2.1]heptyl, 2-oxo-5-azabicyclo[2.2.1]heptyl, 2,5-diazabicyclo[2.2.1]heptyl, and the like. The bridged heterobicyclyl group defined herein may be substituted or unsubstituted, wherein the substituents include, but are not limited to, oxo (=O), fluoro (F), chloro (Cl), bromo (Br), iodo (I), hydroxy, amino, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, alkyl, alkyl-S(=O)$_t$—, haloalkyl, hydroxyalkyl, alkoxy, alkylamino, alkylthio, haloalkoxy, cyano, aryl, heteroaryl, alkenyl, alkynyl, heterocyclyl, mercapto, nitro, aryloxy, hydroxyalkoxy, alkanoyl, benzyl, cyclopropyl, phenyl, alkyl-(C=O)—, alkyl-(C=O)—NH—, carboxamido or alkoxyalkyl, and the like.

The term "cycloalkylalkyl" refers to an alkyl group substituted with one or more cycloalkyl groups, wherein the alkyl group and cycloalkyl group are as defined herein. Some non-limiting examples of the cycloalkylalkyl group include cyclopropylmethyl, cyclohexylmethyl, cyclohexylethyl, and the like.

The term "heterocyclylalkyl" refers to an alkyl group substituted with one or more heterocyclyl groups, wherein the alkyl and heterocyclyl group are as defined herein. Some non-limiting examples of the heterocyclylalkyl group include oxiranylmethyl, morpholinylmethyl, piperidylethyl, and the like.

The term "cycloalkyloxy" or "carbocyclyloxy" refers to an optionally substituted cycloalkyl or carbocyclyl group, as defined herein, attached to an oxygen atom, wherein the oxygen atom serves as the attaching point to the rest of the molecule. Some non-limiting examples of the cycloalkyloxy group include cyclopropyloxy, cyclopentyloxy, cyclohexyloxy, hydroxy-substituted cyclopropyloxy, and the like.

The term "heterocyclylalkylaryl" refers to an aryl group substituted with one or more heterocyclylalkyl groups, wherein the aryl and heterocyclylalkyl are as defined herein. Examples of heterocyclylalkylaryl group include, but are not limited to, N-(4-methylpiperazinyl)-methyl-(3-trifluoromethyl)phenyl, piperazinyl-methyl-phenyl, and the like.

The term "heterocyclylalkylheteroaryl" refers to a hereoaryl group substituted with one or more heterocyclylalkyl groups, wherein the heteroaryl and heterocyclylalkyl are as defined herein. Examples of heterocyclylalkylheteroaryl group include, but are not limited to, N-(4-methylpiperazinyl)-methyl-(3-trifluoromethyl)pyridyl, piperazinylmethyl-pyridyl, and the like.

The term "cycloalkylamino" refers to an amino group substituted with one or two cycloalkyl groups, wherein the cycloalkyl group is as defined herein. Some non-limiting examples of the cycloalkylamino group include cyclopropylamino, cyclopentylamino, cyclohexylamino, hydroxy-substituted cyclopropylamino, dicyclohexylamino, dicyclopropylamino, and the like.

The term "arylalkoxy" refers to an alkoxy group substituted with one or more aryl groups, wherein the aryl group and alkoxy group are as defined herein. Some non-limiting examples of the arylalkoxy group include phenylmethoxy, phenylethoxy, (p-tolyl)methoxy, phenylpropoxy, and the like.

The term "arylalkylamino" refers to an alkylamino group substituted with one or more aryl groups, wherein the aryl group and alkylamino group are as defined herein. Some non-limiting examples of the arylalkylamino group include phenylmethylamino, phenylethylamino, phenylpropylamino, (p-tolyl)methylamino, and the like.

The term "heteroarylalkoxy" refers to an alkoxy group substituted with one or more heteroaryl groups, wherein the heteroaryl group and alkoxy group are as defined herein. Some non-limiting examples of the heteroarylalkoxy group include pyridin-2-ylmethoxy, thiazol-2-yl-ethoxy, imidazol-2-ylethoxy, pyrimidin-2-ylpropoxy, pyrimidin-2-ylmethoxy, and the like.

The term "heteroarylalkylamino" refers to a heteroarylalkyl group which contains a nitrogen atom attached to other groups via the nitrogen atom, wherein the heteroarylalkyl group is as defined herein. Some non-limiting examples of the heteroarylalkylamino group include pyridin-2-ylmethylamino, thiazol-2-ylethylamino, imidazol-2-ylethylamino, pyrimidin-2-ylpropylamino, pyrimidin-2-ylmethyl amino, and the like.

The term "heterocyclylalkoxy" refers to a heterocyclyl-substituted alkoxy group, wherein the oxygen atom serves as the attaching point to the rest of the molecule; the term "heterocyclylalkylamino" refers to a heterocyclyl-substituted alkylamino group, wherein the nitrogen atom serves as the attaching point to the rest of the molecule. Wherein the heterocyclyl, alkoxy and alkylamino group are as defined herein. Some non-limiting examples of the heterocyclylalkoxy group and heterocyclylalkylamino group include morpholin-4-ylethoxy, piperazin-4-ylethoxy, piperidin-4-ylethylamino, and the like.

The term "cycloalkylalkoxy" or "carbocyclylalkoxy" refers to an alkoxy group substituted with one or more cycloalkyl or carbocyclyl groups, wherein the cycloalkyl or carbocyclyl group and alkoxy group are as defined herein. Some non-limiting examples of the cycloalkylalkoxy group or carbocyclylalkoxy group include cyclopropylmethoxy, cyclopropylethoxy, cyclopentylethoxy, cyclohexylethoxy, cyclohexylmethoxy, cyclopropylpropoxy, and the like.

The term "cycloalkylalkylamino" or "carbocyclylalkylamino" refers to an alkylamino group substituted with one or more cycloalkyl or carbocyclyl groups, wherein the cycloalkyl or carbocyclyl group and alkylamino group are as defined herein. Some non-limiting examples of the cycloalkylalkylamino group or carbocyclylalkylaminoinclude cyclopropylmethylamino, cyclopropylethylamino, cyclopentylethylamino, cyclohexylethylamino, cyclohexylmethyl amino, cyclopropylpropylamino, and the like.

The term "aryloxyalkoxy" refers to an alkoxy group substituted with one or more aryloxy groups, wherein the alkoxy group and aryloxy group are as defined herein. Some non-limiting examples of the aryloxyalkoxy group include phenyloxymethoxy, phenyloxyethoxy, phenyloxypropoxy, and the like.

The term "heteroaryloxyalkoxy" refers to an alkoxy group substituted with one or more heteroaryloxy groups, wherein the alkoxy group and heteroaryloxy group are as defined herein. Some non-limiting examples of the heteroaryloxyalkoxy group include pyridinyloxymethoxy, pyrimidinyloxyethoxy, thiazolyloxypropoxy, and the like.

The term "aroxy" or "aryloxy" refers to an optionally substituted aryl group, as defined herein, attached to an oxygen atom, wherein the oxygen atom serves as the attaching point to the rest of the molecule. Some non-limiting examples of the aryloxy group include phenyloxy, methylphenyloxy, ethylphenyloxy, and the like.

The term "heteroaryloxy" refers to an optionally substituted heteroaryl group, as defined herein, attached to an oxygen atom, wherein the oxygen atom serves as the attaching point to the rest of the molecule. Some non-limiting examples of the heteroaryloxy group include pyrid-2-yloxy, thiazol-2-yloxy, imidazol-2-yloxy, pyrimidin-2-yloxy, and the like.

The term "heterocyclyloxyalkoxy" refers to an alkoxy group substituted with one or more heterocyclyloxy groups, wherein the alkoxy group and heterocyclyloxy group are as defined herein. Some non-limiting examples of the heterocyclyloxyalkoxy group include pyrrol-2-yloxymethoxy, pyrrol-3-yloxyethoxy, piperidin-2-yloxyethoxy, piperidin-3-yloxyethoxy, piperazin-2-yloxymethoxy, piperidin-4-yloxyethoxy, and the like.

The term "carbocyclyloxyalkoxy" refers to an alkoxy group substituted with one or more carbocyclyloxy groups, wherein the alkoxy group and carbocyclyloxy group are as defined herein. Some non-limiting examples of the carbocyclyloxyalkoxy group include cyclopropyloxymethoxy, cyclopropyloxyethoxy, cyclopentyloxyethoxy, cyclohexyloxyethoxy, cyclohexen-3-yloxyethoxy, and the like.

The term "heterocyclyloxy" refers to an optionally substituted heterocyclyl group, as defined herein, attached to an oxygen atom, wherein the oxygen atom serves as the attaching point to the rest of the molecule. Some non-limiting examples of the heterocyclyloxy group include pyrrol-2-yloxy, pyrrol-3-yloxy, piperidin-2-yloxy, piperidin-3-yloxy, piperazin-2-yloxy, piperidin-4-yloxy, and the like.

The term "fused bicyclyloxy" refers to an optionally substituted fused bicyclyl group, as defined herein, attached to an oxygen atom, wherein the oxygen atom serves as the attaching point to the rest of the molecule. Some non-limiting examples of the fused bicyclyloxy group include 1,2,3,4,4a,5,8,8a-octahydronaphthyloxy, fused bicyclo[3.3.0]oct-2-yloxy, fused bicyclo[3.1.0]hex-2-yloxy, and the like.

The term "fused heterobicyclyloxy" refers to an optionally substituted fused heterobicyclyl group, as defined herein, attached to an oxygen atom, wherein the oxygen atom serves as the attaching point to the rest of the molecule. Some non-limiting examples of the fused heterobicyclyloxy group include hexahydro-furo[3,2-b]furan-2-yloxy, 7-azabicyclo[2.3.0]hept-2-yloxy, 7-azabicyclo[2.3.0]hept-4-yloxy, and the like.

The term "fused bicyclylamino" refers to an amino group substituted with one or two fused bicyclyl groups, wherein the fused bicyclyl group is as defined herein. Some non-limiting examples of the fused bicyclylamino group include 1,2,3,4,4a,5,8,8a-octahydronaphthylamino, di(1,2,3,4,4a,5,8,8a-octahydronaphthyl)amino, fused bicyclo[3.3.0]octylamino, fused bicyclo[3.1.0]hexylamino, and the like.

The term "fused heterobicyclylamino" refers to an amino group substituted with one or two fused heterobicyclyl groups, wherein the fused heterobicyclyl group is as defined herein. Some non-limiting examples of the fused heterobicyclylamino group include hexahydro-furo[3,2-b]furan-2-ylamino, 7-azabicyclo[2.3.0]hept-2-ylamino, 7-azabicyclo[2.3.0]hept-4-ylamino, and the like.

The term "fused bicyclylalkylamino" refers to an alkylamino group substituted with one or two fused bicyclyl groups, wherein the fused bicyclyl group is as defined herein. Some non-limiting examples of the fused bicyclylalkylamino group include 1,2,3,4,4a,5,8,8a-octahydronaphthylmethylamino, di(1,2,3,4,4a,5,8,8a-octahydronaphthyl)methylamino, fused bicyclo[3.3.0]octylmethylamino, fused bicyclo[3.1.0]hexylmethylamino, and the like.

The term "fused heterobicyclylalkylamino" refers to an alkylamino group substituted with one or two fused heterobicyclyl groups, wherein the fused heterobicyclyl group is as defined herein. Some non-limiting examples of the fused heterobicyclylalkylamino group include hexahydro-furo[3,2-b]furan-2-ylmethylamino, 7-azabicyclo[2.3.0]hept-2-ylmethylamino, 7-azabicyclo[2.3.0]hept-4-ylmethylamino, and the like.

The term "fused bicyclylalkoxy" refers to an alkoxy group substituted with one or more fused bicyclyl groups, wherein the alkoxy group and fused bicyclyl group are as defined herein. Some non-limiting examples of the fused bicyclylalkoxy include 1,2,3,4,4a,5,8,8a-octahydronaphthylmethoxy, 1,2,3,4,4a,5,8,8a-octahydronaphthylethoxy, fused bicyclo[3.3.0]octylethoxy, fused bicyclo[3.1.0]hexylpropoxy, and the like.

The term "fused heterobicyclylalkoxy" refers to an alkoxy group substituted with one or more fused heterobicyclyl groups, wherein the alkoxy group and fused heterobicyclyl group are as defined herein. Some non-limiting examples of the fused heterobicyclylalkoxy group include hexahydro-furo[3,2-b]furan-2-ylpropoxy, 7-azabicyclo[2.2.1]hept-2-ylethoxy, 7-azabicyclo[2.3.0]hept-4-ylpropoxy, hexahydro-furo[3,2-b]furan-2-ylethoxy, 7-azabicyclo[2.3.0]hept-2-ylpropoxy, 7-azabicyclo[2.3.0]hept-4-ylethoxy, and the like.

The term "fused bicyclylalkyl" refers to an alkyl group substituted with one or more fused bicyclyl groups, wherein the alkyl group and fused bicyclyl group are as defined herein. Some non-limiting examples of the fused bicyclylalkyl group include 1,2,3,4,4a,5,8,8a-octahydronaphthylmethyl, 1,2,3,4,4a,5,8,8a-octahydronaphthylethyl, fused bicyclo[3.3.0]octylethyl, fused bicyclo[3.1.0]hexylpropyl, and the like.

The term "fused heterobicyclylalkyl" refers to an alkyl group substituted with one or more fused heterobicyclyl groups, wherein the alkyl group and fused heterobicyclyl group are as defined herein. Some non-limiting examples of the fused heterobicyclylalkyl group include hexahydro-furo[3,2-b]furan-2-ylpropyl, 7-azabicyclo[2.2.1]hept-2-ylethyl, 7-azabicyclo[2.3.0]hept-4-ylpropyl, hexahydro-furo[3,2-b]furan-2-ylethyl, 7-azabicyclo[2.3.0]hept-2-ylpropyl, 7-azabicyclo[2.3.0]hept-4-ylethyl, and the like.

The term "fused heterobicyclyloxyalkoxy" refers to an alkoxy group substituted with one or more fused heterobicyclyloxy groups, wherein the alkoxy group and fused heterobicyclyloxy group are as defined herein. Some non-limiting examples of the fused heterobicyclyloxyalkoxy group include hexahydro-furo[3,2-b]furan-2-yloxypropoxy, 7-azabicyclo[2.2.1]hept-2-yloxyethoxy, 7-azabicyclo[2.3.0]hept-4-yloxypropoxy, hexahydro-furo[3,2-b]furan-2-yloxyethoxy, 7-azabicyclo[2.3.0]hept-2-yloxypropoxy, 7-azabicyclo[2.3.0]hept-4-yloxyethoxy, and the like.

The term "fused heterobicyclyloxyalkylamino" refers to an alkylamino group substituted with one or more fused heterobicyclyloxy groups, wherein the alkylamino group and fused heterobicyclyloxy group are as defined herein. Some non-limiting examples of the fused heterobicyclyloxyalkylamino group include hexahydro-furo[3,2-b]furan-2-yloxypropylamino, 7-azabicyclo[2.2.1]hept-2-yloxyethylamino, 7-azabicyclo[2.3.0]hept-4-yloxypropylamino, hexahydro-furo[3,2-b]furan-2-yloxyethylamino, 7-azabicyclo[2.3.0]hept-2-yloxypropylamino, 7-azabicyclo[2.3.0]hept-4-yloxyethylamino, and the like.

The term "bridged heterobicyclylalkoxy" refers to an alkoxy group substituted with one or more bridged heterobicyclyl groups, wherein the bridged heterobicyclyl group and alkoxy group are as defined herein. Some non-limiting examples of the bridged heterobicyclylalkoxy group include 2-oxa-5-azabicyclo[2.2.1]heptylmethoxy, 2,5-diazabicyclo[2.2.1]heptylethoxy, 2-methyl-2,5-diazabicyclo[2.2.1]heptylpropoxy, and the like.

The term "bridged heterobicyclylalkyl" refers to an alkyl group substituted with one or more bridged heterobicyclyl groups, wherein the bridged heterobicyclyl group and alkyl group are as defined herein. Some non-limiting examples of the bridged heterobicyclylalkyl group include 2-oxa-5-azabicyclo[2.2.1]heptylmethyl, 2,5-diazabicyclo[2.2.1]heptylethyl, 2-methyl-2,5-diazabicyclo[2.2.1]heptylpropyl, and the like.

The term "bridged heterobicyclylalkylamino" refers to an alkylamino group substituted with one or more bridged heterobicyclyl groups, wherein the bridged heterobicyclyl group and alkylamino group are as defined herein. Some non-limiting examples of the bridged heterobicyclylalkylamino group include 2-oxa-5-azabicyclo[2.2.1]heptylmethylamino, 2,5-diazabicyclo[2.2.1]heptylethylamino, 2-methyl-2,5-diazabicyclo[2.2.1]heptylpropylamino, and the like.

The term "bridged heterobicyclyloxy" refers to an optionally substituted bridged heterobicyclyl group, as defined herein, attached to an oxygen atom, wherein the oxygen atom serves as the attaching point to the rest of the molecule. Some non-limiting examples of the bridged heterobicyclyloxy group include 2-methyl-2,5-diazabicyclo[2.2.1]heptyloxy, 2,5-diazabicyclo[2.2.1]heptyloxy, and the like.

The term "arylalkyl" refers to an alkyl group substituted with one or more aryl groups, wherein the alkyl group and aryl group are as defined herein. Some non-limiting examples of the arylalkyl group include phenylethyl, phenylmethyl, (p-tolyl)ethyl, and the like.

The term "heteroarylalkyl" refers to an alkyl group substituted with one or more heteroaryl groups, wherein the alkyl group and heteroaryl group are as defined herein. Some non-limiting examples of the heteroarylalkyl group include pyrid-2-ylethyl, thiazol-2-ylmethyl, imidazol-2-ylethyl, pyrimidin-2-ylpropyl, and the like.

The term "alkylthio" refers to a group in which a linear or branched alkyl group of one to ten carbon atoms is attached to a divalent sulfur atom, wherein the alkyl group is as defined herein. In some embodiments, the alkylthio group is lower alkylthio group having one to three carbon atoms.

Some non-limiting examples of the alkylthio group include methylthio ($CH_3S$—), ethylthio, and the like.

The term "aminoacyl" refers to —$C(=O)NH_2$.

The term "aldehyde" refers to —$C(=O)H$.

The term "alkyl-$C(=O)NH$—" refers to a group in which a linear or branched alkyl group of one to ten carbon atoms is attached to —$C(=O)NH$—, wherein the alkyl group is as defined herein. Some non-limiting examples of the alkyl-$C(=O)NH$— group include acetamido ($CH_3C(=O)NH$—), propionamido ($C_2H_5C(=O)NH$—), and the like.

The term "spirocyclyl", "spirocyclic", "spiro bicyclyl" or "spiro bicyclic" refers to a ring originating from a particular annular carbon of another ring. For example, as depicted in formula y, a saturated bridged ring system (ring B and B') is termed as "fused bicyclic", whereas ring A' and ring B share an atom between the two saturated ring system, which terms as a "spirocyclyl" or "spiro bicyclyl". Each cyclic ring in a spirocyclyl can be either a carbocyclic or a heteroalicyclic. Depending on the structure, the spirocyclyl, spirocyclic, spiro bicyclyl or spiro bicyclic group may be a monoradical or a diradical. i.e., in some embodiments, the spirocyclyl, spirocyclic, spiro bicyclyl or spiro bicyclic group can be replaced by or used as spirocyclylene. Some non-limiting examples of the spiro bicyclyl group include spiro[2.4]hept-5-yl, spiro[4.4]nonyl, and the like.

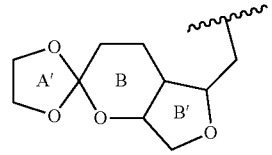

formula (y)

The term "spiro heterobicyclyl" refers to a ring originating from a particular annular carbon of another ring. For example, as depicted by formula (y) above, a saturated bridged ring system (ring B and B') is termed as "fused bicyclic", whereas ring A' and ring B share an atom between the two saturated ring system, which terms as a "spirocyclyl" or "spiro bicyclyl".

Depending on the structure, the spiro heterobicyclyl group may be a monoradical or a diradical. i.e., in some embodiments, the spiro heterobicyclyl group can be replaced by or used as spiro heterobicyclylene. And at least one ring in the system contains one or more heteroatoms, wherein each ring in the system contains 3 to 7 ring members and that contains 1 to 6 carbon atoms and 1 to 3 heteroatoms selected from N, O, P and S, wherein the S or P is optionally substituted with one or more oxo to provide the group $SO$, $SO_2$, $PO$ or $PO_2$, and wherein carbon atom can be oxidized to form —$C(=O)$—. Some non-limiting examples of the spiro heterobicyclyl group include 4-aza-spiro[2.4]hept-5-yl, 4-oxa-spiro[2.4]hept-5-yl, 5-aza-spiro[2.4]hept-5-yl, 7-hydroxy-5-azaspiro[2.4]hept-5-yl, 2-aza-spiro[4.5]decyl, 2-aza-spiro[3.3]heptyl, 2-aza-spiro[4.4]nonyl, 2-methyl-2,6-diaza-spiro[4.5]decyl, 3-aza-spiro[5.4]decyl, and the like.

The term "spiro heterobicyclylalkoxy" refers to an alkoxy group substituted with one or more spiro heterobicyclyl groups, wherein the spiro heterobicyclyl group and alkoxy group are as defined herein. Some non-limiting examples of the spiro heterobicyclylalkoxy group include 4-aza-spiro[2.4]hept-5-yl-methoxy, 4-aza-spiro[2.4]heptan-2-yl-ethoxy, 4-oxa-spiro[2.4]hept-5-yl-ethoxy, 5-aza-spiro[2.4]hept-5-yl-propoxy, and the like.

The term "spiro heterobicyclylalkyl" refers to an alkyl group substituted with one or more spiro heterobicyclyl groups, wherein the spiro heterobicyclyl group and alkyl group are as defined herein. Some non-limiting examples of the spiro heterobicyclylalkyl group include 4-aza-spiro[2.4]hept-5-yl-methyl, 4-aza-spiro[2.4]heptan-2-yl-ethyl, 4-oxa-spiro[2.4]hept-5-yl-ethyl, 5-aza-spiro[2.4]hept-5-yl-propyl, and the like.

"Anti-proliferative agent" refers to anti-metabolites (e.g., 5-fluoro-uracil, methotrexate and fludarabine), antimicrotubule agents (e.g., vinca alkaloids such as vincristine and vinblastine, taxanes such as paclitaxel and docetaxel), alkylating agents (e.g., cyclophosphamide, melphalan, carmustine and nitrosoureas such as bischloroethylnitrosourea and hydroxyurea), platinum agents (e.g., cisplatin, carboplatin, oxaliplatin, JM-216 and Cl-973), anthracyclines (e.g., doxorubicin and daunorubicin), antitumor antibiotics (e.g., mitomycin, idarubicin, doxorubicin and daunorubicin), topoisomerase inhibitors (e.g., etoposide and camptothecin), anti-angiogenesis agents (e.g., bevacizumab), any other cytotoxic agents (estramustine phosphate and prednimustine), hormones or hormone agonists, antagonists, partial agonist or partial antagonists, kinase inhibitors and radiation treatment.

As described herein, a bond drawn from a substituent R to the center of one ring within a ring system represents substitution of the substituent R at any substitutable or reasonable position on the ring. For example, Formula a represents possible substitution of the substituent R in any of the position on ring D or ring B, as shown in Formula b, Formula c, Formula d, Formula e, Formula f, Formula g and Formula h.

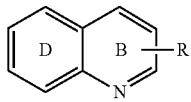

Formula a

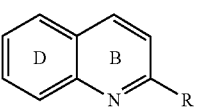

Formula b

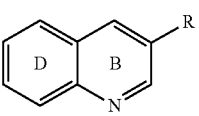

Formula c

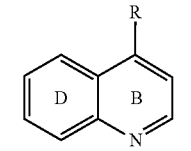

Formula d

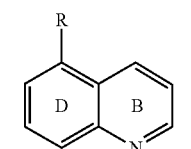

Formula e

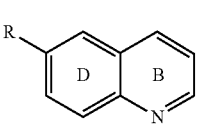

Formula f

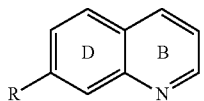

Formula g

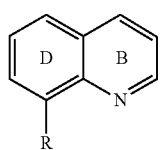

Formula h

As described herein, a bond drawn from a substituent $(R)_n$ to the center of one ring within a ring system represents substitution of n substituents R at any substitutable position on the rings. For example, Formula i represents possible substitution of n substituents R in any of the position on ring D or ring B.

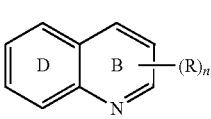

Formula i

As described herein, two attachment points within a ring system C can attach to the rest of the molecule, for example, either E" or E' on ring C as shown in Formula j, can attach to the rest of the molecule and can be used interchangeably with each other.

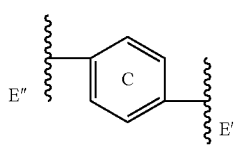

Formula j

As described herein, the attachment point can attach to the rest of the molecule at any attachable position on the rings. For example, Formula k represents attaching at any attachable position on ring D or ring B.

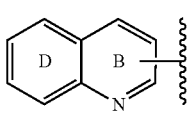

Formula k

As described herein, the attachment points can attach to the rest of the molecule at any attachable position on the rings, meanwhile, the two attachment points can be used interchangeably with each other. For example, Formula m represents attaching at any attachable position on the rings, and the two attachment points can be used interchangeably with each other.

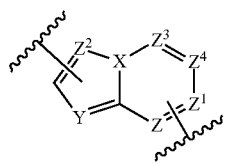

Formula m

Furthermore, what need to be explained is that the phrase "each . . . is independently" and "each of . . . and . . . is independently" in the invention can be used interchangeably herein, unless otherwise specified. It should have a general understanding that it can be expressed both in different groups in which same symbols expressed specific options do not affect each other and the same groups in which same symbols expressed specific options do not affect each other.

Stereochemical definitions and conventions used herein generally follow Parker et al., *McGraw-Hill Dictionary of Chemical Terms* (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

A "hydrate" refers to a compound disclosed herein or a salt thereof, which further includes a stoichiometric or non-stoichiometeric amount of water bound by non-covalent intermolecular forces, and also refers to the complex where the solvent molecule is water.

A "solvate" refers to an association or complex of one or more solvent molecules and a compound disclosed herein. Some non-limiting examples of the solvent that form solvates include water, isopropanol, ethanol, methanol, DMSO, ethyl acetate, acetic acid and ethanolamine.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

An "ester" refers to an in vivo hydrolysable ester of a compound of the Formula (I) to (VIII) containing hydroxy group, for example, a pharmaceutically acceptable ester which is hydrolysed in the human or animal body to produce the parent alcohol. Some non-limiting examples of in vivo hydrolysable ester forming from a compound of the Formula (I) to (VIII) containing hydroxy group include, phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidized to form an N-oxide, where a compound contains several amine functional groups. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid, peroxosulfuric acid) (See, Advanced Organic Chemistiy, by Jerry March, 4th Edition, *Wiley Interscience*, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane. For another example, the amine compound of the present invention can be N-oxidized to form the corresponding N-oxide, such as the synthesis of 4-(3-(4-((4-(3-(5-(1-hydroxy-2-methylpropan-2-yl)isoxazol-3-yl) ureido)phenyl)ethynyl) phenoxy)propyl)morpholine 4-oxide as described in example 88.

Compounds may exist in a number of different geometric isomeric and tautomeric forms and references to compounds of the Formula (I) to (VIII) which include all such forms. For the avoidance of doubt, where a compound can exist in one of several geometric isomeric or tautomeric forms and only one is specifically described or shown, all others are nevertheless embraced by Formula (I) to (VIII).

The term "prodrug" refers to a compound that is transformed in vivo into a compound of Formula (I) to (VIII). Such a transformation can be affected, for example, by hydrolysis of the prodrug form in blood or enzymatic transformation of the prodrug form in blood or tissue to the parent form. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates such as those phosphate compounds derived from the phosphonation of a hydroxy group on the parent compound. A thorough discussion of prodrugs is provided in T. Higuchi and V Stella, Pro-drugs as Novel Delivery Systems, Vol. 14 of the *A.C.S. Symposium Series*, Edward B. Roche, ed., Bioreversible Carriers in Drug Design, *American Pharmaceutical Association and Pergamon Press*, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolite of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including metabolites produced by contacting a compound disclosed herein with a mammal for a sufficient time period.

The compounds disclosed herein are useful in various pharmaceutically acceptable salt forms. The term "pharmaceutically acceptable salt" refers to those salt forms which would be apparent to the pharmaceutical chemist, i.e., those which are substantially nontoxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate. Amine salts include, but are not limited to, N,N'-dibenzylethylenediamine, chloroprocaine, choline, ammonia, diethanolamine and other hydroxyalkylamine, ethylenediamine, N-methylglucamine, procaine, N-benzylphenethylamine, 1-para-chlorobenzyl-2-pyrrolidin-1'-ylmethylbenzimidazole, diethylamine and other alkylamine, piperazine and tris(hydroxymethyl)aminomethane. Alkali earth metal salts include, but are not limited to, barium, calcium and magnesium. Transition metal salts include, but are not limited to, zinc.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethyloxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of the carboxy-protecting group include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfonyl) ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

In the description herein, if there is any discrepancy between a chemical name and chemical structure, the structure preferably controls.

As used herein, the abbreviations for any protective groups, amino acids and other compounds are, unless otherwise indicated, in accord with their common usage, recognized abbreviations, or the IUPAC-IUB Commission on Biochemical Nomenclature (See, Biochem. 1972, 11: 942-944).

As used herein the terms "treatment" of any disease or disorder, in some embodiments, refer to the disease or disorder (i.e., slowing or arresting the development of or alleviate the disease or at least one of the clinical symptoms). In other embodiments, "treating" refers to alleviation or amelioration of at least one physical parameter, including physical parameters of the patient may not be perceived. In other embodiments, "treating" means from the body (e.g., stabilization of a discernible symptom) or physiologically (e.g., stabilization of a physical parameter) or both said modulating the disease or disorder. In other embodiments, "treating" refers to preventing or delaying the onset of the disease or disorder, the onset or worsening.

The term "prevent" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

DESCRIPTION OF COMPOUNDS OF THE INVENTION

Provided herein are substituted urea derivatives and pharmaceutical compositions thereof used for drug therapy, and a series of substituted urea compounds used for modulating the activities of Abl and FLT3 kinases and for inhibiting FLT3-ITD, and the uses thereof as therapeutic agents for the treatment of diseases mediated by Abl, FLT3 or induced by FLT3-ITD.

Because of the potent inhibitory effect on c-KIT, RET, PDGFR, Bcr-ABL, FLT3 or FLT3-ITD protein kinase (these protein kinase triggers diseases induced by abnormal cell proliferation), the novel substituted urea derivatives may be used for preventing or treating the diseases induced by abnormal cell proliferation.

The disorders induced by the abnormal cell proliferation are selected from the group consisting of stomach cancer, lung cancer, liver cancer, colorectal cancer, pancreatic cancer, brain cancer, bone cancer, melanoma, breast cancer, tuberous sclerosis, uterine cancer, cervical cancer, head and neck cancer, esophageal cancer, thyroid cancer, parathyroid cancer, renal cell carcinoma, osteosarcoma, prostate cancer, urinary tract cancer, bladder cancer, blood cancer, lymphoma, psoriasis and fibroadenoma.

Blood cancer is selected from the group consisting of leukemia, multiple myeloma and myelodysplastic syndrome.

Lymphoma is Hodgkin's disease or non-Hodgkin's lymphoma.

In one aspect, provided herein are substituted urea derivatives having Formula (I), or a stereoisomer, a geometric isomer, a tautomer, an N-oxide, a hydrate, a solvate, a metabolite, an ester, a pharmaceutically acceptable salt or a prodrug thereof,

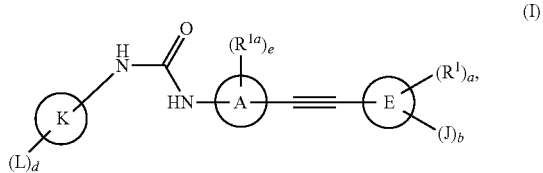

wherein each of ring A and ring E is independently $C_{6-10}$ aryl or $C_{1-12}$ heteroaryl;

each J is -G-$(CH_2)_n$—$R^2$;

each G is independently —O—, —S(=O)$_t$—, —S—, —C(=O)—, —OC(=O)—, —C(=S)—, —C(=S)—N($R^4$)— or —$(CH_2)_n$—C(=O)—;

each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{1-4}$ alkylamino, $C_{1-4}$ alkyl-C(=O)—NH—, $C_{1-4}$ alkylthio, $C_{3-10}$ cycloalkyl, $C_{2-10}$ heterocyclyl, $C_{1-6}$ alkoxy-$C_{1-6}$-alkyl or $C_{1-4}$ hydroxyalkyl;

each $R^2$ is independently —$NR^3R^{3a}$, cycloalkyl, cycloalkylalkyl, heterocyclylalkyl, heterocyclyl, alkyl-S(=O)$_t$—, hydroxyalkyl, hydroxyalkoxy, aminoalkoxy, haloalkoxy, alkoxyalkyl, alkyl, alkoxy, alkylaminohaloalkoxy, alkylaminoalkoxy, arylalkoxy, arylalkylamino, heteroarylalkoxy, heteroarylalkylamino, heterocyclylalkylamino, heterocyclylalkylaryl, heterocylylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, aryl, arylalkyl, heteroarylalkyl, heteroaryl, bridged heterobicyclyl, spiro heterobicyclyl or fused heterobicyclyl;

each $R^3$ and $R^{3a}$ is independently $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

each $R^4$ is independently H, $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

ring K is 5- to 6-membered heteroaryl;

each L is independently amino, nitro, $C_{1-4}$ alkylthio, $C_{1-6}$ alkyl, $C_{3-10}$ cycloalkyl, $C_{2-10}$ heterocyclyl, $C_{1-4}$ haloalkyl, $C_{1-4}$ alkylamino, hydroxy, F, Cl, Br, I, $C_{1-4}$ alkyl-C(=O)—NH—, $C_{1-4}$ alkoxy, $C_{1-4}$ hydroxyalkyl or cyano;

each a and e is independently 0, 1, 2, 3 or 4;

each n, d and b is independently 1, 2, 3 or 4; and each t is independently 0, 1 or 2;

wherein optionally each aryl, —$(CH_2)_n$—C(=O)—, alkyl-S(=O)$_t$—, hydroxyalkyl, arylalkyl, heteroarylalkyl, heteroaryl, heterocyclyl, bridged heterobicyclyl, spiro heterobicyclyl, fused heterobicyclyl, alkyl, alkoxy, alkoxyalkyl, haloalkyl, alkylamino, hydroxyalkoxy, aminoalkoxy, haloalkoxy, cycloalkylalkyl, heterocyclylalkyl, alkylaminohaloalkoxy, alkylaminoalkoxy, arylalkoxy, arylalkylamino, heteroarylalkoxy, heteroaryl alkylamino, heterocyclylalkylamino, heterocyclylalkylaryl, heterocyclylalkylheteroaryl, cycloalkyloxy, cycloalkyl amino, heterocyclylalkoxy, carbocyclylalkoxy, carbocyclyl alkyl amino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkyl amino, spiro heterobicyclylalkyl, spiro heterobicyclylalkoxy, bridged heterobicyclylalkyl, bridged heterobicyclyloxy, bridged heterobicyclylalkoxy, bridged heterobicyclyl alkyl amino, alkyl-C(=O)—NH—, alkylthio and cycloalkyl described in $R^1$, $R^{1a}$, $R^2$, $R^3$, $R^{3a}$, A, E, J, G, L and/or K is independently substituted with one or more $R^{2a}$ which are the same or different, and wherein each $R^{2a}$ is independently H, F, Cl, Br, I, $C_{1-4}$ haloalkyl, $C_{1-4}$ alkyl, $C_{1-4}$ alkylamino, hydroxy, cyano, nitro, —C(=O)—$NH_2$, carboxy, —S(=O)$_t$O—H, —OS(=O)$_t$—H, —S(=O)$_t$$NH_2$, triazolyl, tetrazolyl, —$(CR^{3b}R^{3c})_n$—$NH_2$, amino, oxo (=O), $C_{1-4}$ alkyl-C(=O)—, benzyl, phenyl, $C_{1-6}$ alkyl-S(=O)$_t$—, $C_{1-6}$ alkoxy-$C_{1-6}$-alkyl, $C_{1-4}$ alkyl-C(=O)—NH—, $C_{1-4}$ alkoxy, $C_{1-4}$ hydroxyalkyl or $C_{1-4}$ alkylthio; and each $R^{3b}$ and $R^{3c}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, ring A is $C_{6-10}$ aryl or $C_{1-12}$ heteroaryl.

In certain embodiments, ring E is $C_{6-10}$ aryl or $C_{1-12}$ heteroaryl.

In certain embodiments, each J is -G-$(CH_2)_n$—$R^2$.

each G is independently —O—, —S(=O)$_t$—, —S—, —C(=O)—, —OC(=O)—, —C(=S)—, —C(=S)—N($R^4$)— or —$(CH_2)_n$—C(=O)—;

each $R^2$ is independently —$NR^3R^{3a}$, cycloalkyl, cycloalkylalkyl, heterocyclylalkyl, heterocyclyl, alkyl-S (=O)$_t$—, hydroxyalkyl, hydroxyalkoxy, aminoalkoxy, haloalkoxy, alkoxyalkyl, alkyl, alkoxy, alkylaminohaloalkoxy, alkylaminoalkoxy, arylalkoxy, arylalkylamino, heteroarylalkoxy, heteroarylalkylamino, heterocyclylalkylamino, heterocylylalkylaryl, heterocylylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, aryl, arylalkyl, heteroarylalkyl, heteroaryl, bridged heterobicyclyl, spiro heterobicyclyl or fused heterobicyclyl;

each $R^3$ and $R^{3a}$ is independently $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl; and each $R^4$, t and n is as defined herein.

In certain embodiments, each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{1-4}$ alkylamino, $C_{1-4}$ alkyl-C(=O)—NH—, $C_{1-4}$ alkylthio, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, each $R^4$ is independently H, $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, ring K is 5- to 6-membered heteroaryl.

In certain embodiments, each L is independently amino, nitro, $C_{1-4}$ alkylthio, $C_{1-4}$ alkyl, $C_{3-10}$ cycloalkyl, $C_{2-10}$ heterocyclyl, $C_{1-4}$ haloalkyl, $C_{1-4}$ alkylamino, hydroxy, F, Cl, Br, I, $C_{1-4}$ alkyl-C(=O)—NH—, $C_{1-4}$ alkoxy, $C_{1-4}$ hydroxyalkyl or cyano.

In certain embodiments, each a is independently 0, 1, 2, 3 or 4.

In certain embodiments, each e is independently 0, 1, 2, 3 or 4.

In certain embodiments, each n is independently 1, 2, 3 or 4.

In certain embodiments, each d is independently 1, 2, 3 or 4.

In certain embodiments, each b is independently 1, 2, 3 or 4.

In certain embodiments, each t is independently 0, 1 or 2.

In certain embodiments, each $R^{3b}$ and $R^{3c}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, optionally each aryl, —(CH$_2$)$_n$—C(=O)—, alkyl-S(=O)$_t$—, hydroxyalkyl, arylalkyl, heteroarylalkyl, heteroaryl, heterocyclyl, bridged heterobicyclyl, spiro heterobicyclyl, fused heterobicyclyl, alkyl, alkoxy, alkoxyalkyl, haloalkyl, alkylamino, hydroxyalkoxy, aminoalkoxy, haloalkoxy, cycloalkylalkyl, heterocyclylalkyl, alkylaminohaloalkoxy, alkylaminoalkoxy, arylalkoxy, arylalkylamino, heteroarylalkoxy, heteroarylalkylamino, heterocyclylalkylamino, heterocyclylalkylaryl, heterocyclylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, alkyl-C(=O)—NH—, alkylthio and cycloalkyl described in $R^1$, $R^{1a}$, $R^2$, $R^3$, $R^{3a}$, A, E, J, G, L and/or K is independently substituted with one or more $R^{2a}$ which are the same or different, and wherein each $R^{2a}$ is independently H, F, Cl, Br, I, $C_{1-4}$ haloalkyl, $C_{1-4}$ alkyl, $C_{1-4}$ alkylamino, hydroxy, cyano, nitro, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, amino, oxo (=O), $C_{1-4}$ alkyl-C(=O)—, benzyl, phenyl, $C_{1-6}$ alkyl-S(=O)$_t$—, $C_{1-6}$ alkoxy-$C_{1-6}$-alkyl, $C_{1-4}$ alkyl-C(=O)—NH—, $C_{1-4}$ alkoxy, $C_{1-4}$ hydroxyalkyl or $C_{1-4}$ alkylthio; and each $R^{3b}$ and $R^{3c}$ is as defined herein.

In certain embodiments, provided herein are substituted urea derivatives having Formula (IIa), or a stereoisomer, a geometric isomer, a tautomer, an N-oxide, a hydrate, a solvate, a metabolite, an ester, a pharmaceutically acceptable salt or a prodrug thereof,

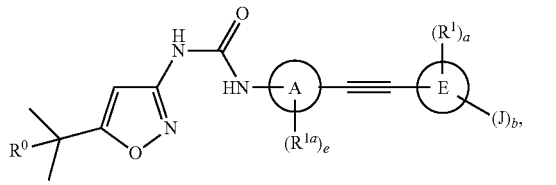

(IIa)

wherein $R^0$ is $C_{2-3}$ alkyl, trifluoromethyl, fluoromethyl, difluoromethyl or hydroxymethyl; and each ring A, ring E, $R^1$, $R^{1a}$, e, b, a and J is as defined herein.

In certain embodiments, $R^0$ is $C_{2-3}$ alkyl, trifluoromethyl, fluoromethyl, difluoromethyl or hydroxymethyl.

In certain embodiments, provided herein are substituted urea derivatives having Formula (II), or a stereoisomer, a geometric isomer, a tautomer, an N-oxide, a hydrate, a solvate, a metabolite, an ester, a pharmaceutically acceptable salt or a prodrug thereof,

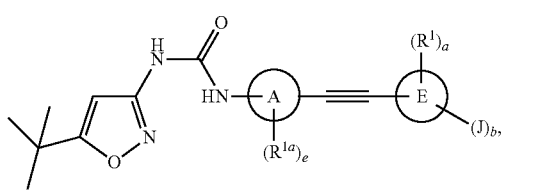

(II)

wherein each ring A, ring E, $R^1$, $R^{1a}$, e, b, a and J is as defined herein.

In certain embodiments, ring A is one of the following sub-formulae:

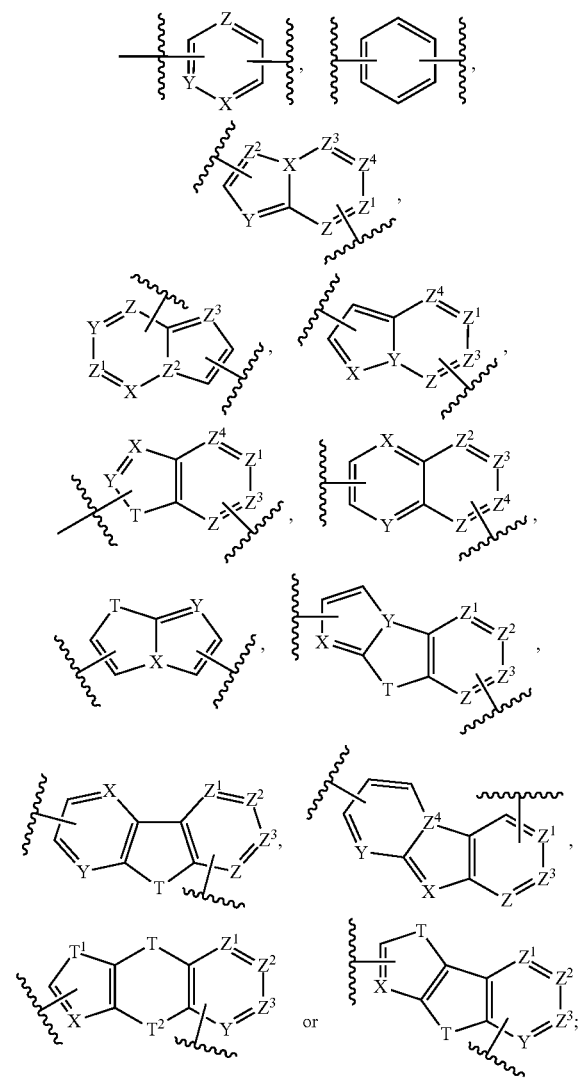

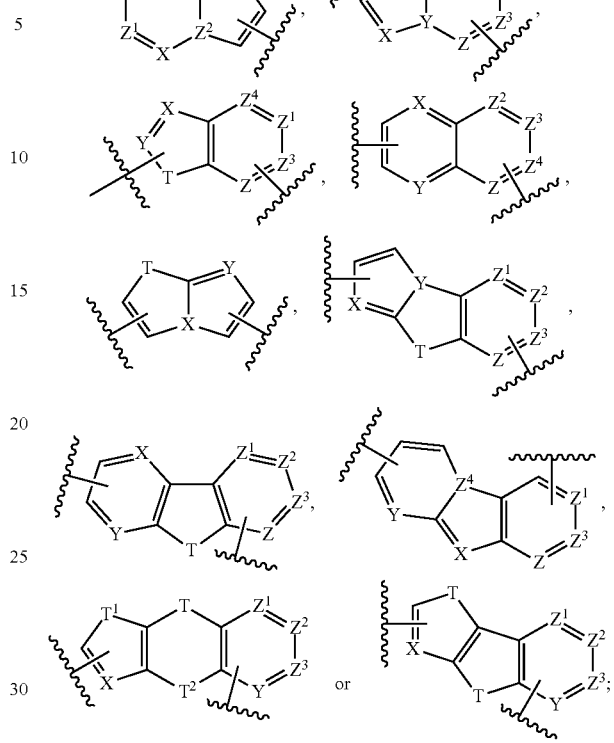

wherein each X, Y, Z, $Z^1$, $Z^2$, $Z^3$ and $Z^4$ is independently N or CH;

each T, $T^1$ and $T^2$ is independently —O—, —S—, —N($R^4$)— or —CH$_2$—; and each $R^4$ is as defined herein.

In certain embodiments, each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{1-4}$ alkylamino, $C_{2-10}$ heterocyclyl, $C_{1-6}$ alkoxy-$C_{1-6}$-alkyl or $C_{1-4}$ hydroxyalkyl.

In certain embodiments, ring A is one of the following sub-formulae:

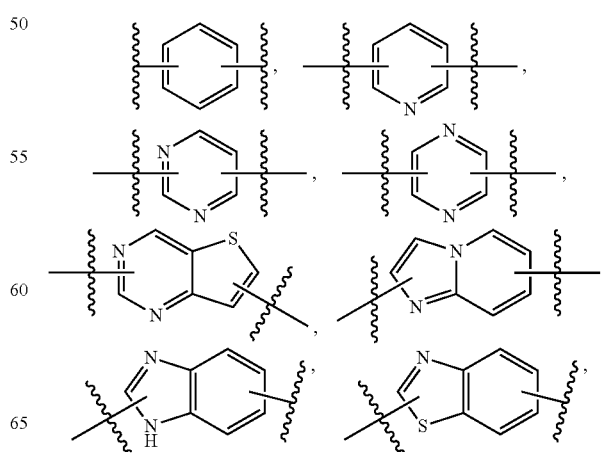

wherein each X, Y, Z, $Z^1$, $Z^2$, $Z^3$ and $Z^4$ is independently N or CH;

each T, $T^1$ and $T^2$ is independently —O—, —S—, —N($R^4$)— or —CH$_2$—; and each $R^4$ is as defined herein.

In certain embodiments, ring E is one of the following sub-formulae:

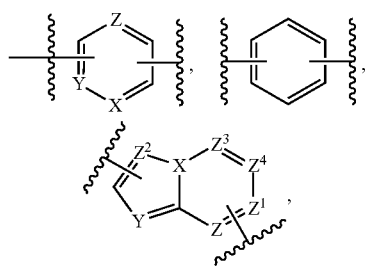

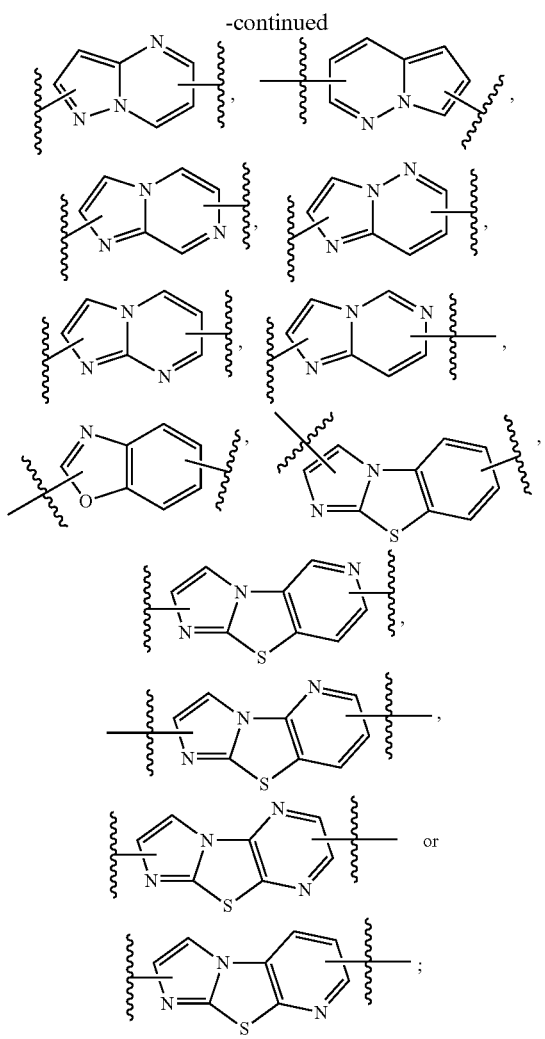

In certain embodiments, ring E is one of the following sub-formulae:

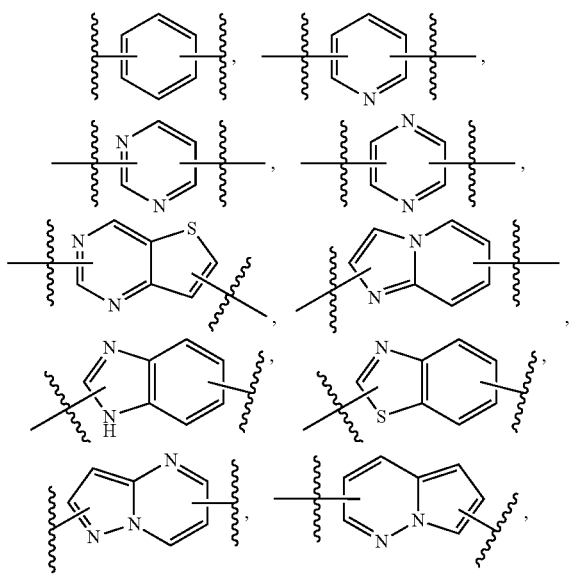

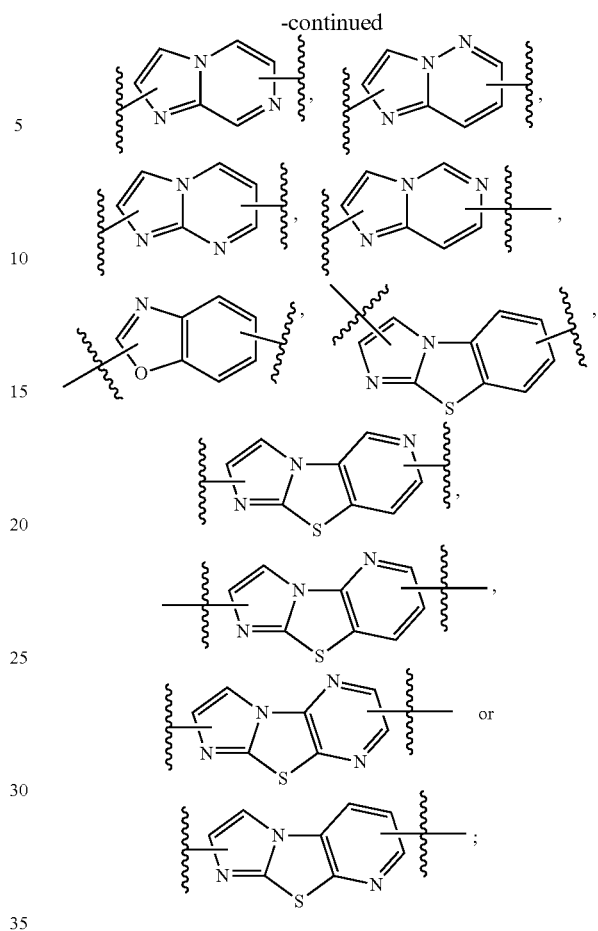

In certain embodiments, each $R^1$ and $R^{1a}$ is independently H, F, Cl, Br, trifluoromethyl, chloroethyl, trifluoroethyl, methyl, ethyl, propyl, isopropyl, dimethylamino, methylamino, diethylamino, ethylamino, hydroxy, cyano, nitro, methoxy, ethoxy, propoxy, cyclopropyl, cyclobutyl, cyclohexyl, cyclopentyl, $C_{2-10}$ heterocyclyl, $C_{1-6}$ alkoxy-$C_{L-6}$-alkyl or $C_{1-4}$ hydroxyalkyl.

In certain embodiments, each $R^2$ is independently —$NR^3R^{3a}$, $C_{3-10}$ cycloalkyl, $C_{3-10}$ cycloalkyl-$C_{1-4}$-alkyl, $C_{2-10}$ heterocyclyl-$C_{1-4}$-alkyl, $C_{1-6}$ alkyl-$S(=O)_t$—, $C_{1-4}$ hydroxyalkyl, $C_{1-4}$hydroxyalkoxy, $C_{1-4}$ aminoalkoxy, $C_{1-4}$ haloalkoxy, $C_{1-4}$ alkylamino-$C_{1-4}$-haloalkoxy, $C_{1-4}$ alkylamino-$C_{1-4}$-alkoxy, $C_{1-6}$ alkoxy-$C_{1-6}$-alkyl, $C_{1-6}$ alkyl, $C_{1-6}$ alkoxy, $C_{6-10}$ aryl-$C_{1-4}$-alkoxy, $C_{6-10}$ aryl-$C_{1-4}$-alkylamino, $C_{1-9}$ heteroaryl-$C_{1-4}$-alkoxy, $C_{1-9}$ heteroaryl-$C_{1-4}$-alkylamino, $C_{2-10}$ heterocyclyl-$C_{1-4}$-alkylamino, $C_{2-10}$ heterocyclyl-$C_{1-4}$-alkyl-$C_{6-10}$-aryl, $C_{2-10}$ heterocyclyl-$C_{1-4}$-alkyl-$C_{1-9}$-heteroaryl, $C_{3-10}$ cycloalkyloxy, $C_{3-10}$ cycloalkylamino, $C_{2-10}$ heterocyclyl-$C_{1-4}$-alkoxy, $C_{3-10}$ carbocyclyl-$C_{1-4}$-alkoxy, $C_{3-10}$ carbocyclyl-$C_{1-4}$-alkylamino, $C_{6-10}$ aryloxy-$C_{1-4}$-alkoxy, $C_{6-10}$ aryloxy, $C_{1-9}$ heteroaryloxy, $C_{1-9}$ heteroaryloxy-$C_{1-4}$-alkoxy, $C_{2-10}$ heterocyclyloxy-$C_{1-4}$-alkoxy, $C_{3-10}$ carbocyclyloxy-$C_{1-4}$-alkoxy, $C_{2-10}$ heterocyclyloxy, $C_{6-10}$ aryl, $C_{6-10}$ aryl-$C_{1-6}$-alkyl, $C_{1-9}$ heteroaryl-$C_{1-6}$-alkyl, $C_{1-9}$ heteroaryl, $C_{2-10}$ heterocyclyl, $C_{6-12}$ fused bicyclyloxy, $C_{6-12}$ fused bicyclyl-$C_{1-6}$-alkyl, $C_{5-12}$ fused heterobicyclyl-$C_{1-6}$-alkyl, $C_{5-12}$ fused heterobicyclyloxy, $C_{5-12}$ fused heterobicyclylamino, $C_{5-12}$ fused heterobicyclyl-$C_{1-6}$-alkoxy, $C_{5-12}$ fused heterobicyclyl-$C_{1-6}$-alkylamino, $C_{5-12}$ fused heterobicyclyloxy-$C_{1-6}$-alkoxy, $C_{5-12}$ fused heterobicyclyloxy-$C_{1-6}$-alkylamino, $C_{5-12}$ spiro heterobicyclyl-$C_{1-6}$-alkyl, $C_{5-12}$ spiro heterobicyclyl-$C_{1-6}$-alkoxy, $C_{5-12}$ bridged heterobicyclyl-$C_{1-6}$-alkyl, $C_{5-12}$ bridged heterobicyclyloxy, $C_{5-12}$ bridged heterobicyclyl-$C_{1-6}$-alkoxy, $C_{5-12}$ bridged heterobicyclyl-$C_{1-6}$-alkylamino, $C_{5-12}$ bridged heterobicyclyl, $C_{5-12}$ spiro heterobicyclyl or $C_{5-12}$ fused heterobicyclyl, and wherein each $R^2$ is independently substituted with one or more $R^{2a}$ which are the same or different; and each $R^3$, $R^{3a}$ and $R^{2a}$ is as defined herein.

In certain embodiments, each $R^{3b}$ and $R^{3c}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{2-10}$ heterocyclyl, $C_{1-6}$ alkoxy-$C_{1-6}$-alkyl or $C_{1-4}$ hydroxyalkyl.

In certain embodiments, each $R^3$ and $R^{3a}$ is independently $C_{1-4}$ alkyl, $C_{3-10}$ cycloalkyl, $C_{2-10}$ heterocycloalkyl, $C_{1-6}$ alkoxy-$C_{1-6}$-alkyl or $C_{1-4}$ hydroxyalkyl.

In certain embodiments, each $R^2$ is independently —$NR^3R^{3a}$, $C_{1-4}$ alkoxy-$C_{1-4}$-alkyl, $C_{1-4}$ alkyl or $C_{1-4}$ hydroxyalkyl, or each $R^2$ is independently one of the following sub-formulae:

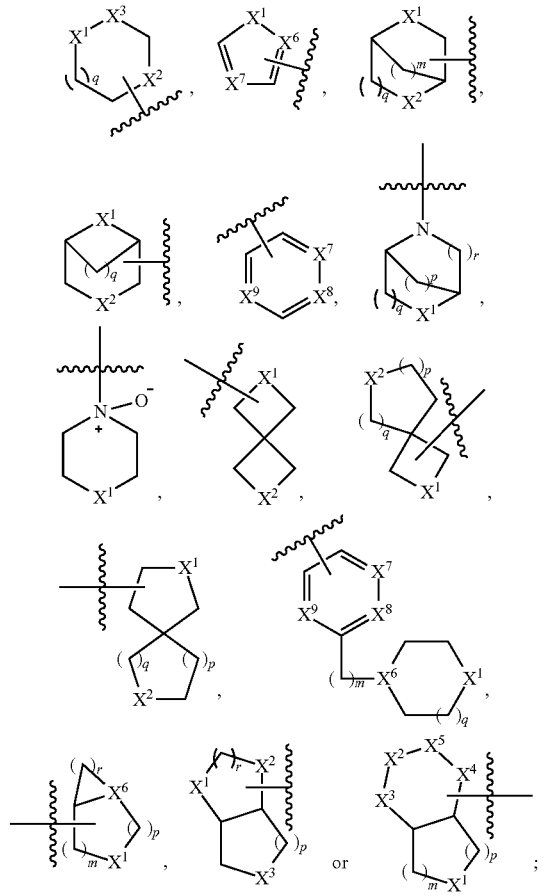

wherein each $X^6$, $X^7$, $X^8$ and $X^9$ is independently N or CH;

each $X^1$, $X^2$, $X^3$, $X^4$ and $X^5$ is independently —$(C(R^{4b})_2)_m$—, —C(=O)—, —O—, —N($R^{4a}$)— or —S(=O)$_t$—;

each q, m, p and r is independently 0, 1, 2, 3 or 4;
each t is independently 0, 1 or 2;
wherein each $R^2$ is independently substituted with one or more $R^{2a}$ which are the same or different; and each $R^{4b}$, $R^{4a}$, $R^3$, $R^{3a}$, $R^{3b}$, $R^{3c}$ and $R^{2a}$ is as defined herein.

In certain embodiments, each $R^{4a}$ is independently H, $C_{1-4}$ alkyl, $C_{3-10}$ cycloalkyl, $C_{2-10}$ heterocycloalkyl, $C_{1-6}$ alkoxy-$C_{1-6}$-alkyl, or $C_{1-4}$ hydroxyalkyl.

In certain embodiments, each $R^{4b}$ is independently H, F, Cl, Br, cyano, nitro, hydroxy, mercapto, amino, carboxy, $C_{1-4}$ alkyl, $C_{3-10}$ cycloalkyl, $C_{1-4}$ haloalkyl, $C_{1-4}$ alkoxy, $C_{1-4}$ alkylamino, —$(CR^{3b}R^{3c})_n$—$NH_2$, —C(=O)—$NH_2$, $C_{2-10}$ heterocycloalkyl, $C_{1-6}$ alkoxy-$C_{1-6}$-alkyl or $C_{1-4}$ hydroxyalkyl; and each $R^{3b}$ and $R^{3c}$ is as defined herein.

In certain embodiments, each $R^2$ is independently one of the following sub-formulae:

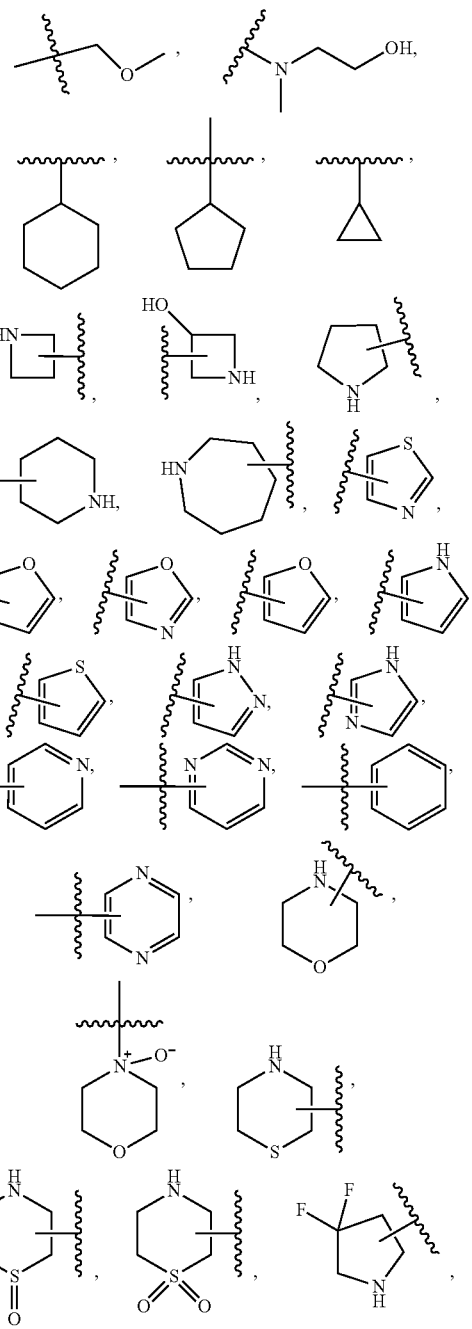

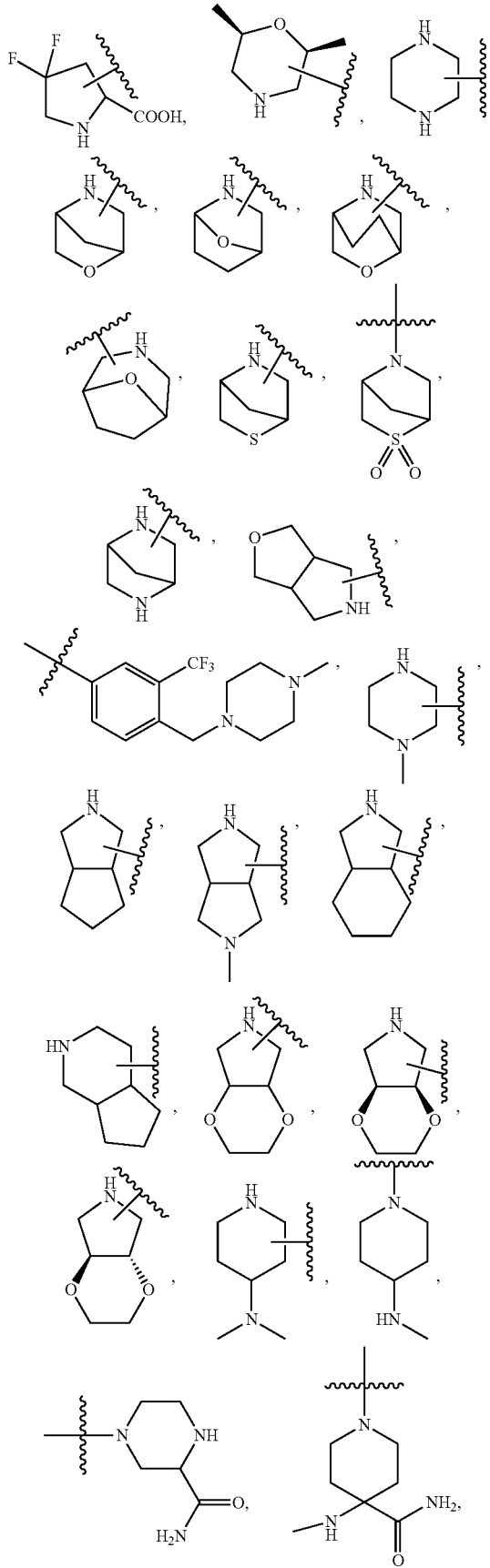

-continued

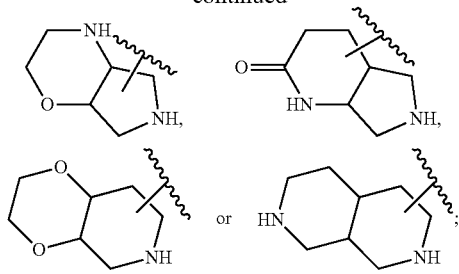

wherein, each sub-formula represented by $R^2$ is independently substituted with one or more $R^{2a}$ which are the same or different; and each n and $R^{2a}$ is as defined herein.

In certain embodiments, each $R^3$ and $R^{3a}$ is independently methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl.

In certain embodiments, each $R^4$ and $R^{4a}$ is independently H, methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl.

In certain embodiments, each $R^{4b}$ is independently H, F, Cl, Br, cyano, nitro, hydroxy, mercapto, amino, carboxy, methyl, ethyl, propyl, isopropyl, tert-butyl, cyclopropyl, cyclopentyl, cyclohexyl, trifluoromethyl, methoxy, $C_{1-4}$ alkylamino, —$(CR^{3b}R^{3c})_n$—$NH_2$, —$C(=O)$—$NH_2$, $C_{2-10}$ heterocycloalkyl, $C_{1-6}$ alkoxy-$C_{1-6}$-alkyl or $C_{1-4}$ hydroxyalkyl;

and each $R^{3b}$, $R^{3c}$, n and $R^{2a}$ is as defined herein.

In certain embodiments, each $R^{2a}$ is independently H, F, Cl, Br, I, trifluoromethyl, chloroethyl, trifluoroethyl, methyl, ethyl, propyl, isopropyl, dimethylamino, methylamino, diethylamino, ethylamino, hydroxy, cyano, nitro, —$C(=O)$—$NH_2$, carboxy, —$S(=O)_tO$—H, —$OS(=O)_t$—H, —$S(=O)_tNH_2$, triazolyl, tetrazolyl, —$(CH_2)$—$NH_2$, —$(CH_2)_3$—$NH_2$, —$(CH(CF_3))$—$NH_2$, —$(CH_2)_2$—$NH_2$, oxo (=O), methyl-$C(=O)$—, ethyl-$C(=O)$—, propyl-$C(=O)$—, benzyl or phenyl; and t is as defined herein.

In certain embodiments, ring K is

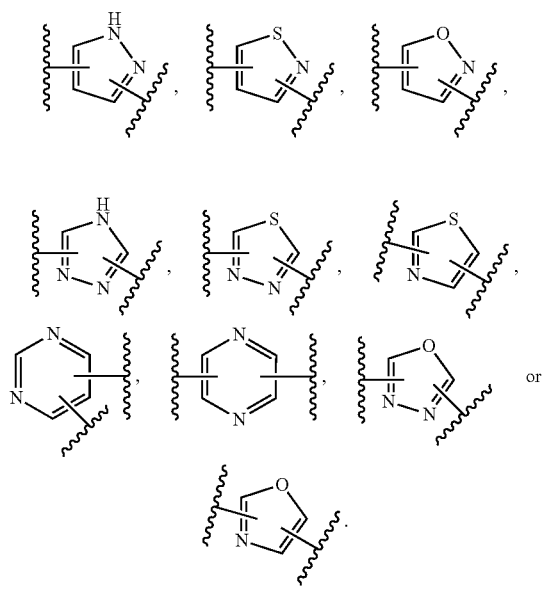

In certain embodiments, each L is independently cyclopropyl, cyclobutyl, cyclopentyl, cyclohexyl, $C_{3-6}$ heterocycloalkyl, amino, cyano, nitro, F, Cl, Br, I, trifluoromethyl, 1,1,1-trifluoro-2-methylprop-2-yl, methyl, ethyl, butyl, propyl, isopropyl, tert-butyl, $C_{1-4}$ alkylamino, hydroxy, cyano, nitro, $C_{1-4}$ alkyl-$C(=O)$—NH—, $C_{1-4}$ alkoxy, hydroxymethyl, hydroxyethyl, 1-hydroxy-n-butyl, 2-hydroxy-n-propyl, 2-hydroxy-i-propyl, hydroxy-tert-butyl or $C_{1-4}$ alkylthio.

In certain embodiments, provided herein are substituted urea derivatives having Formula (IIIa), or a stereoisomer, a geometric isomer, a tautomer, an N-oxide, a hydrate, a solvate, a metabolite, an ester, a pharmaceutically acceptable salt or a prodrug thereof,

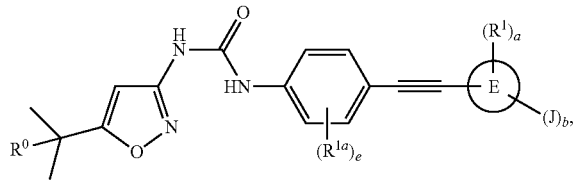

wherein $R^0$ is $C_{2-3}$ alkyl, trifluoromethyl, fluoromethyl, difluoromethyl or hydroxymethyl; and each ring E, $R^{1a}$, $R^1$, J, e, a and b is as defined herein.

In certain embodiments, provided herein are substituted urea derivatives having Formula (III), or a stereoisomer, a geometric isomer, a tautomer, an N-oxide, a hydrate, a solvate, a metabolite, an ester, a pharmaceutically acceptable salt or a prodrug thereof, (III)

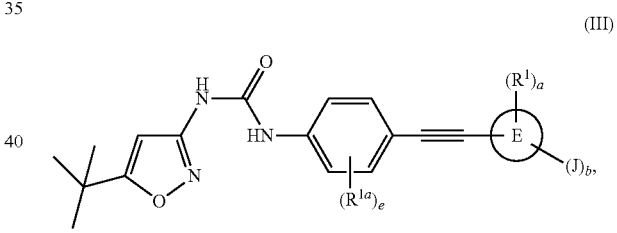

wherein each ring E, $R^{1a}$, $R^1$, J, e, a and b is as defined herein.

In other embodiments, provided herein are substituted urea derivatives having Formula (IIIb), or a stereoisomer, a geometric isomer, a tautomer, an N-oxide, a hydrate, a solvate, a metabolite, an ester, a pharmaceutically acceptable salt or a prodrug thereof, (IIIb)

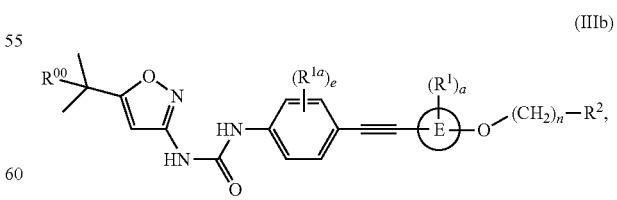

wherein, $R^{00}$ is methyl, $C_{2-3}$ alkyl, trifluoromethyl, fluoromethyl, difluoromethyl or hydroxymethyl; and each ring E, $R^{1a}$, $R^1$, $R^2$, e, a and n is as defined herein.

In other embodiments, provided herein are substituted urea derivatives having Formula Formula (IV), or a stereoisomer, a geometric isomer, a tautomer, an N-oxide, a hydrate, a solvate, a metabolite, an ester, a pharmaceutically acceptable salt or a prodrug thereof, (IV)

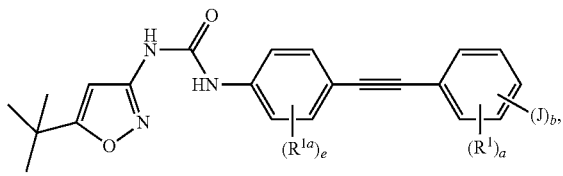

wherein each $R^{1a}$, $R^1$, J, e, a and b is as defined herein.

In other embodiments, provided herein are substituted urea derivatives having Formula (V), or a stereoisomer, a geometric isomer, a tautomer, an N-oxide, a hydrate, a solvate, a metabolite, an ester, a pharmaceutically acceptable salt or a prodrug thereof, (V)

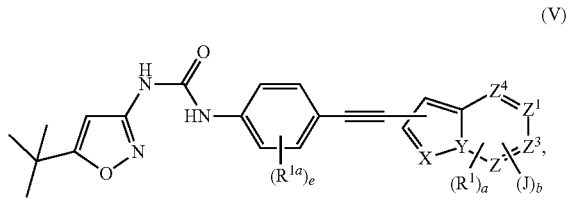

wherein each $R^{1a}$, $R^1$, J, e, a and b is as defined herein; and each of X, Y, Z, $Z^1$, $Z^3$ and $Z^4$ is independently N or CH.

In certain embodiments, provided herein are substituted urea derivatives having Formula (VI), or a stereoisomer, a geometric isomer, a tautomer, an N-oxide, a hydrate, a solvate, a metabolite, an ester, a pharmaceutically acceptable salt or a prodrug thereof, (VI)

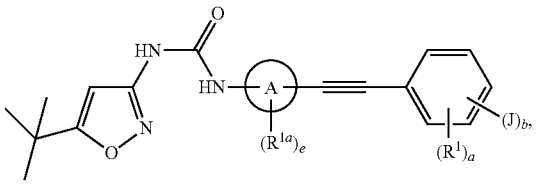

wherein each ring A, $R^{1a}$, $R^1$, J, e, a and b is as defined herein.

In certain embodiments, provided herein are substituted urea derivatives having Formula (VIIa), or a stereoisomer, a geometric isomer, a tautomer, an N-oxide, a hydrate, a solvate, a metabolite, an ester, a pharmaceutically acceptable salt or a prodrug thereof, (VIIa)

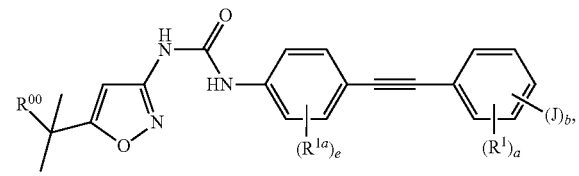

wherein each $R^{1a}$, $R^1$, J, e, a and b is as defined herein; and $R^{00}$ is methyl, $C_{2-3}$ alkyl, trifluoromethyl, fluoromethyl, difluoromethyl or hydroxymethyl.

In one aspect, provided herein is the substituted urea derivative having one of the following structures, or a stereoisomer, a geometric isomer, a tautomer, an N-oxide, a hydrate, a solvate, a metabolite, an ester, a pharmaceutically acceptable salt or a prodrug thereof,

1

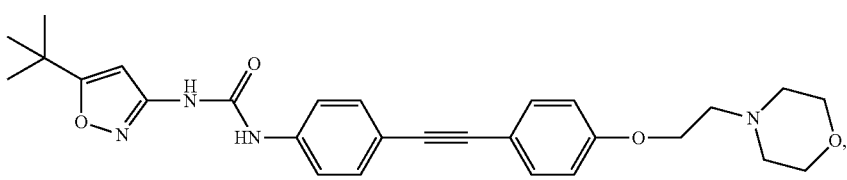

2

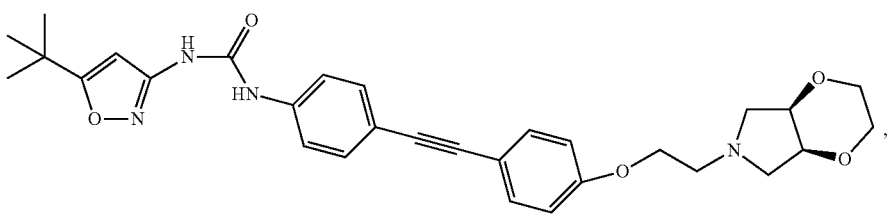

3

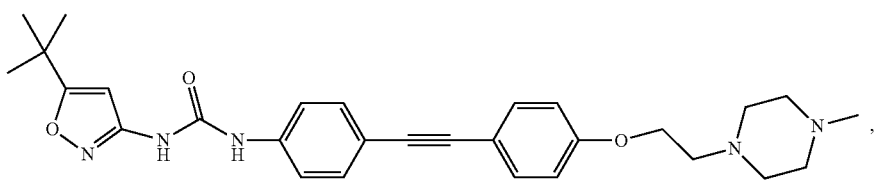

-continued
4
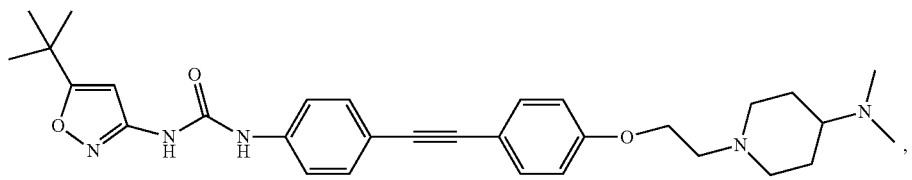
5
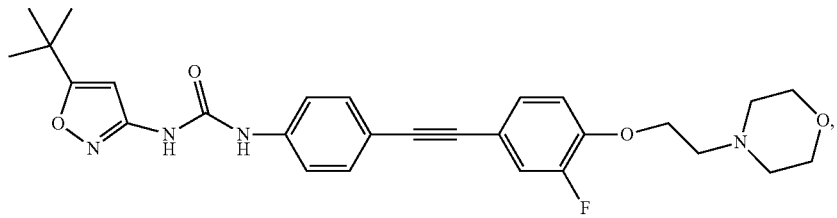
6
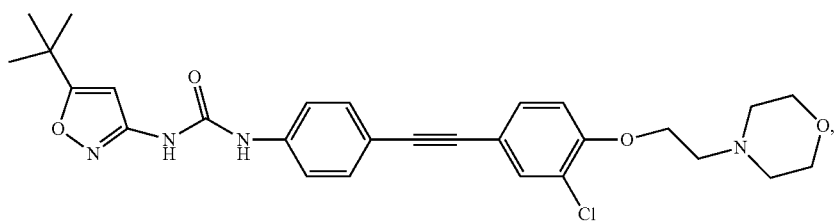
7
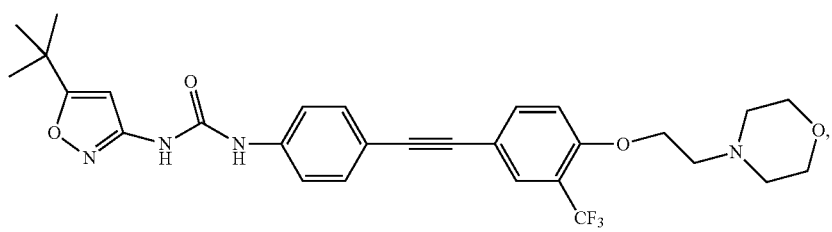
8
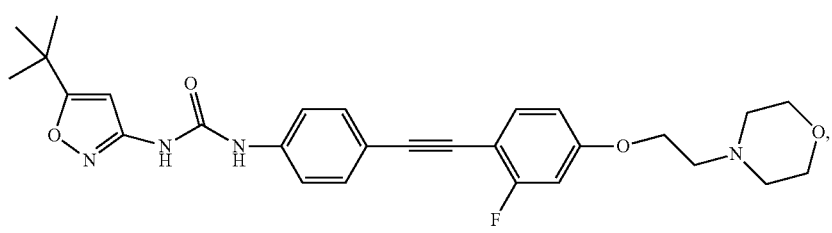
9
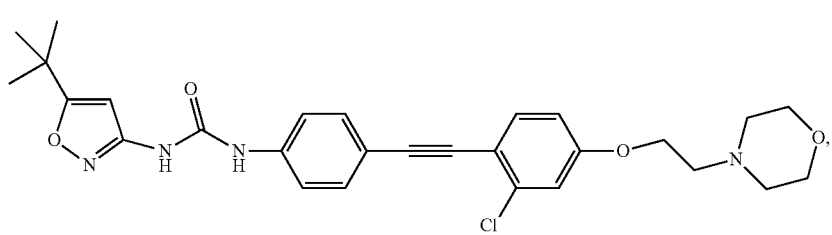
10
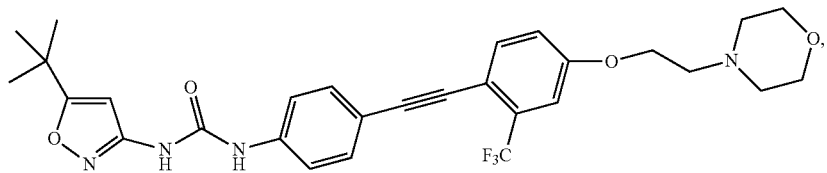

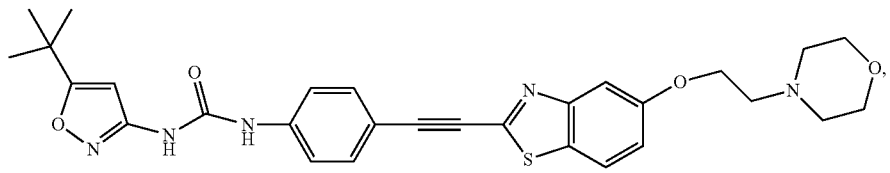
11
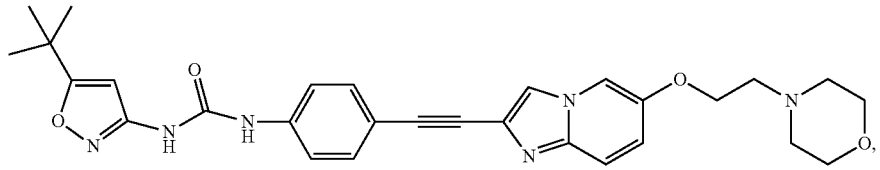
12
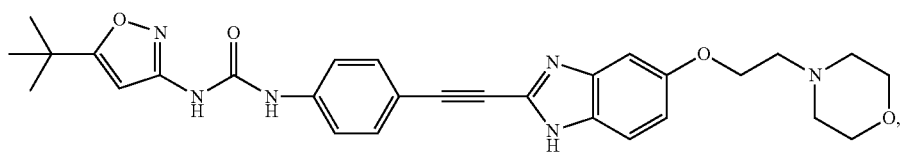
13
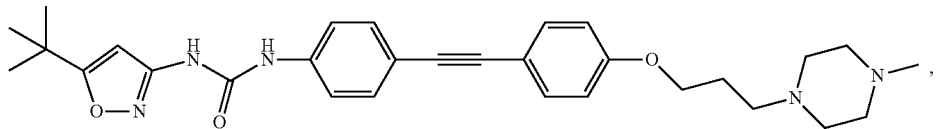
14
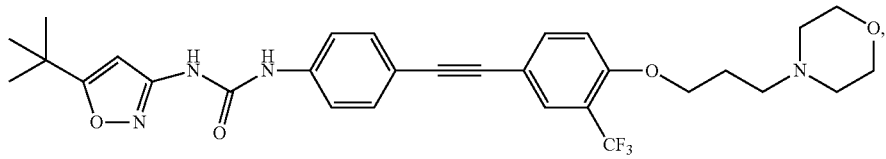
15
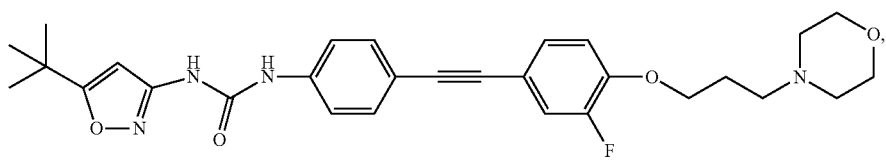
16
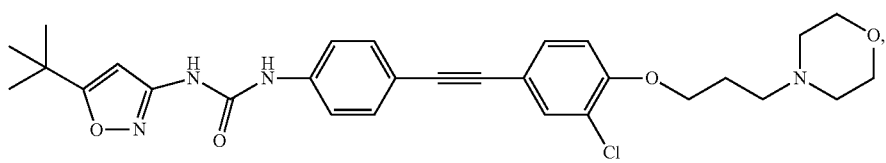
17
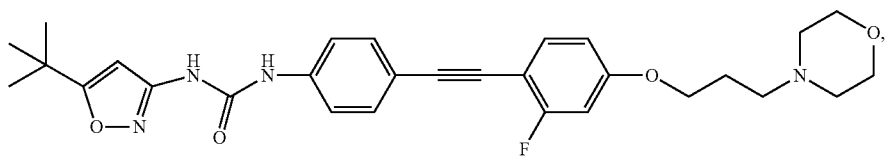
18
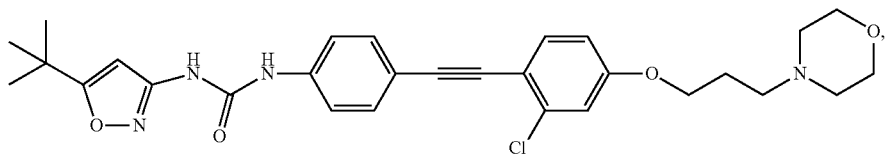
19

-continued
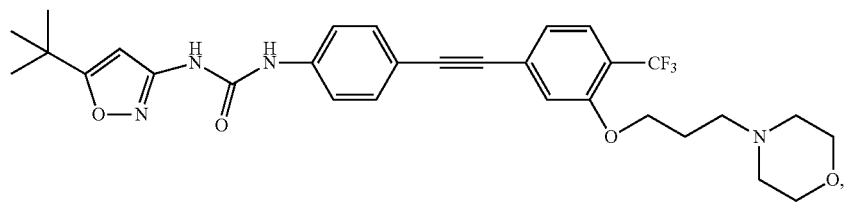
20
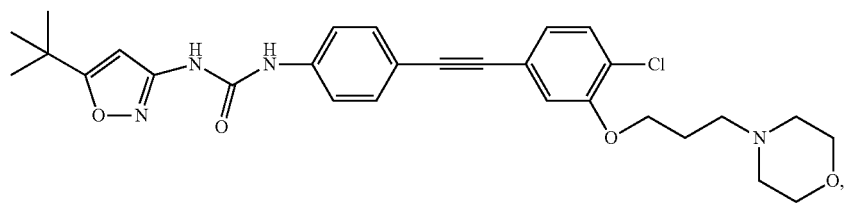
21
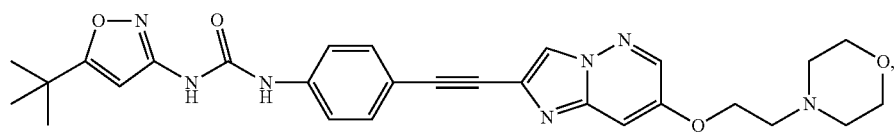
22
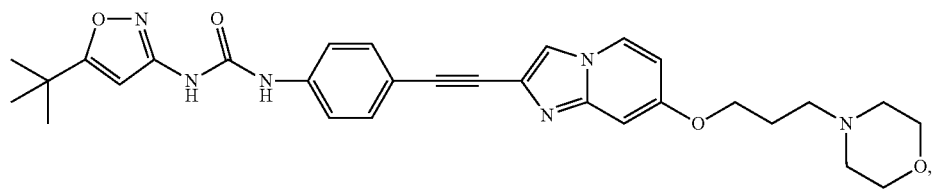
23
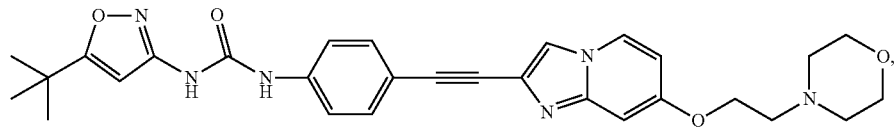
24
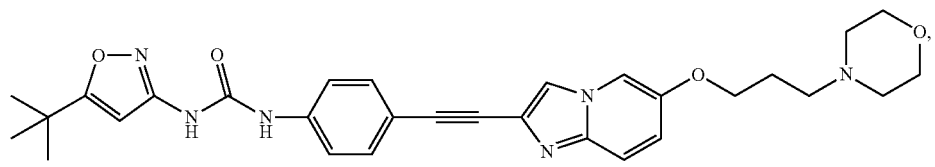
25
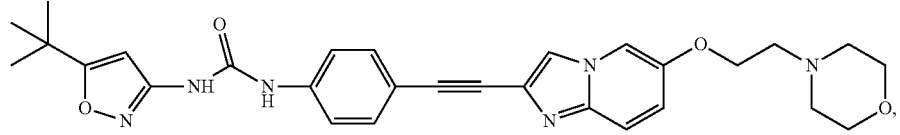
26
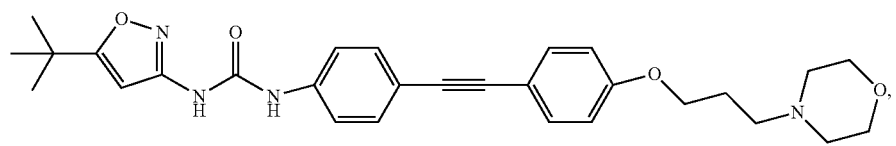
27
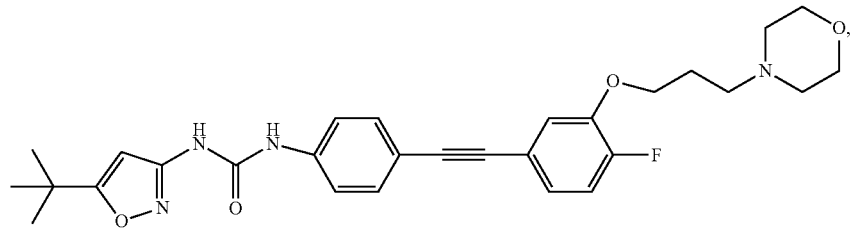
28

29
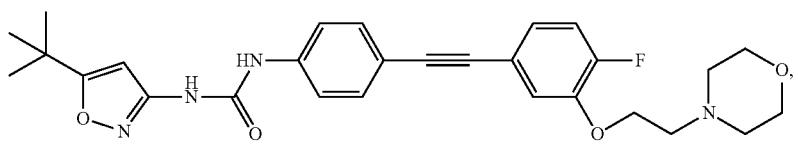
30
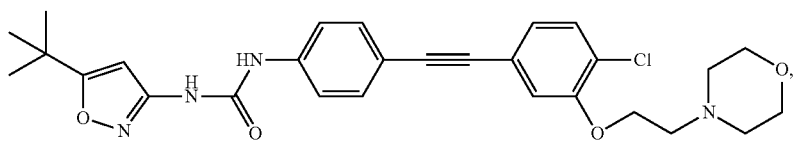
31
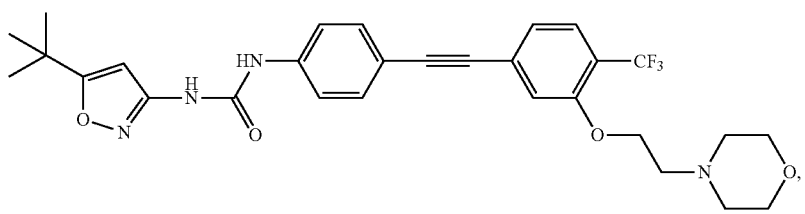
32
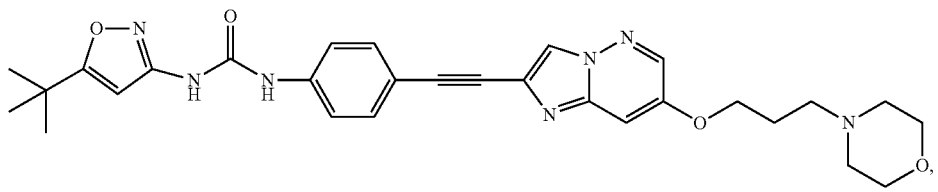
33
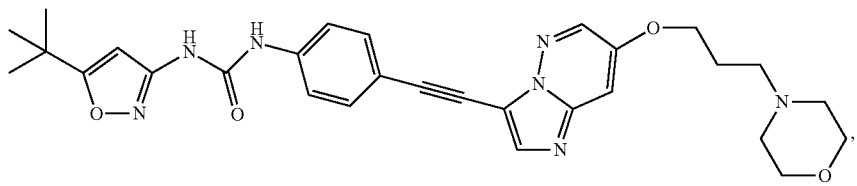
34
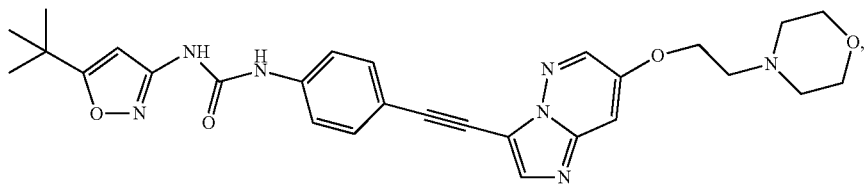
35
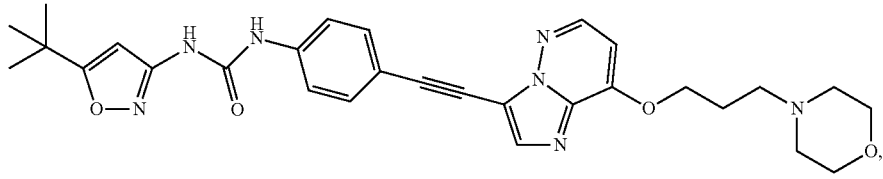
36
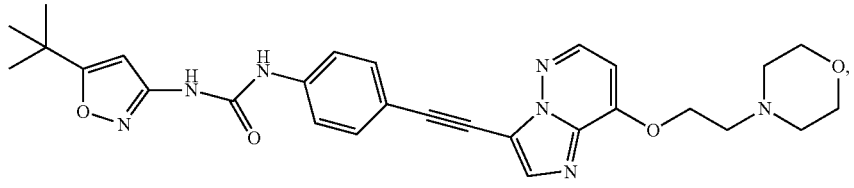

37
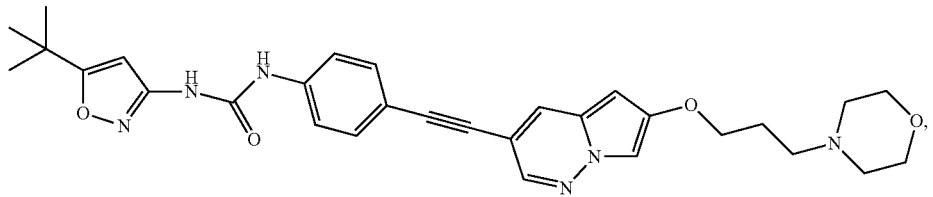
38
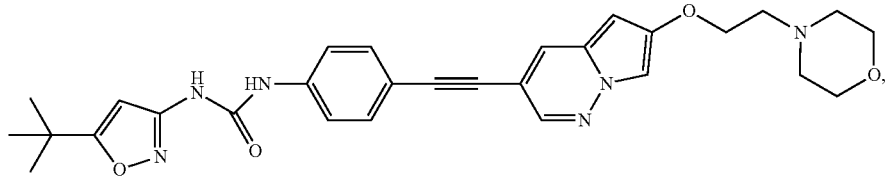
39
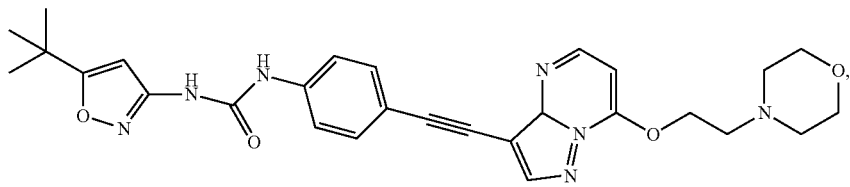
40
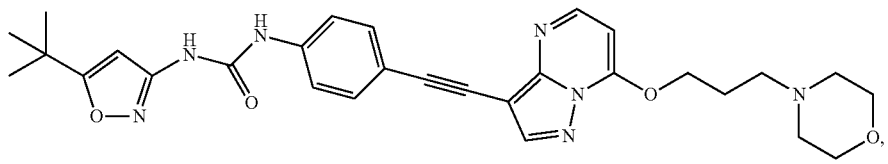
41
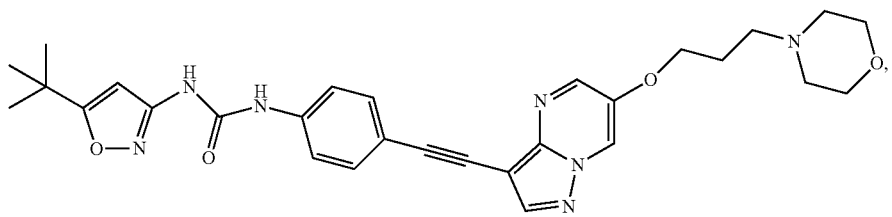
42
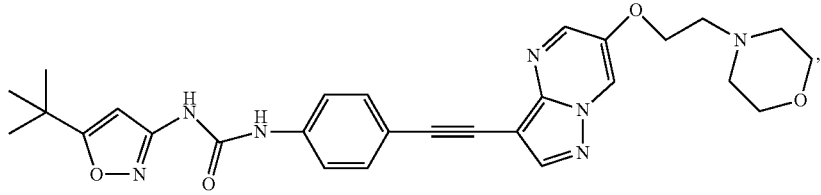
43
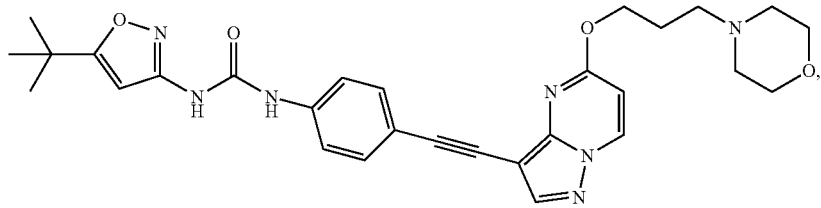

44
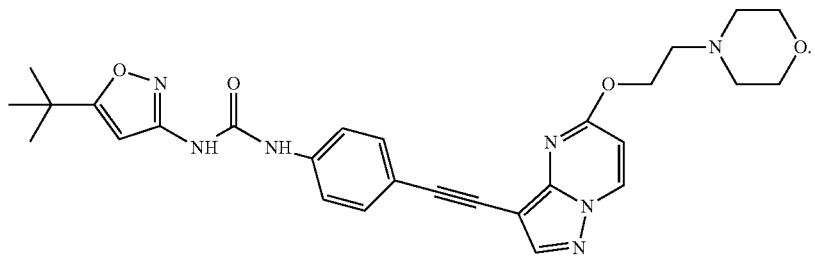
45
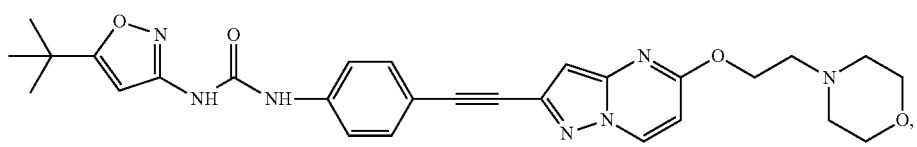
46
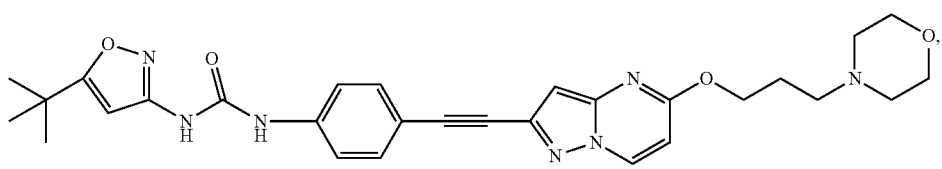
47
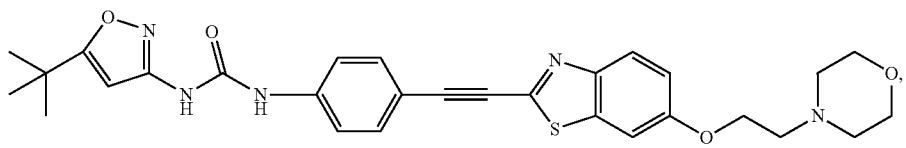
48
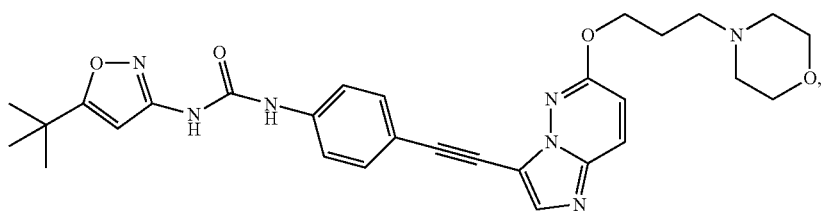
49
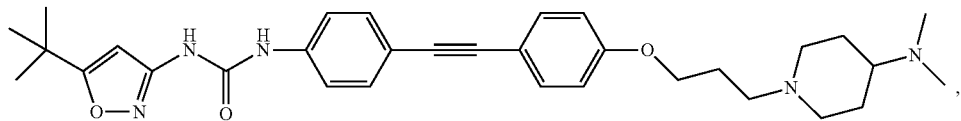
50
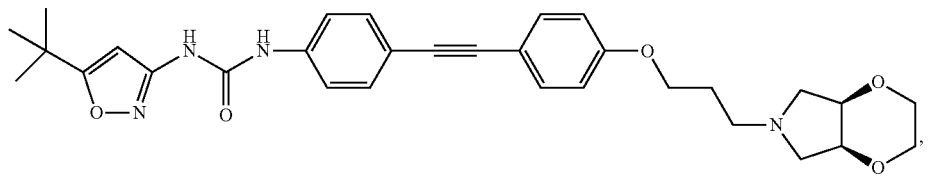
51
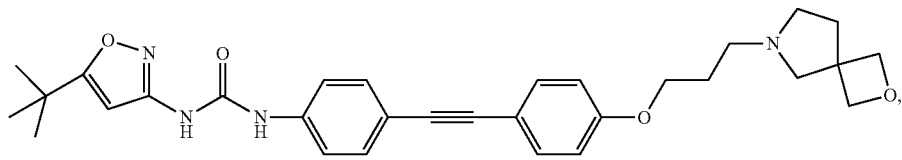
52
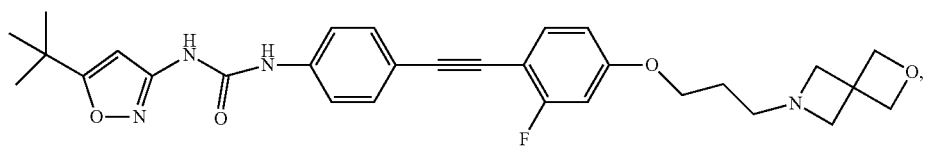

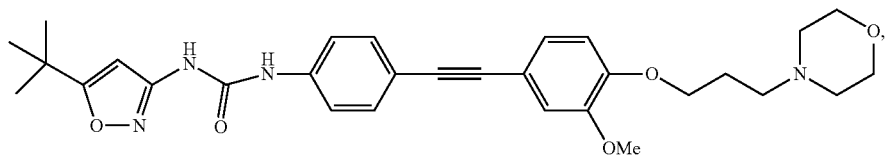
53
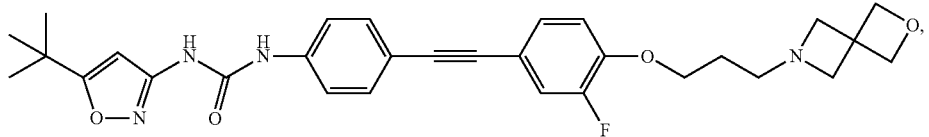
54
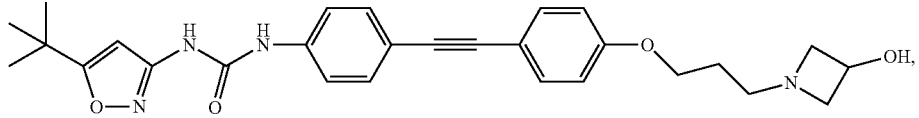
58
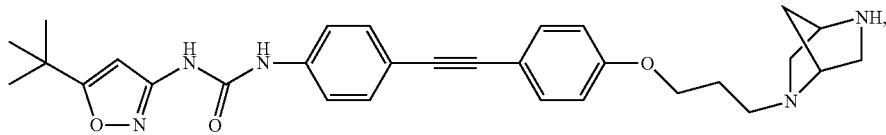
59
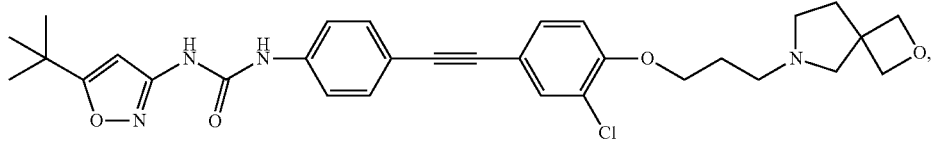
60
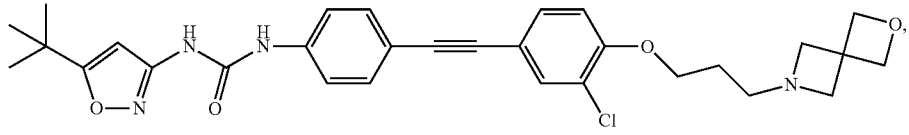
61
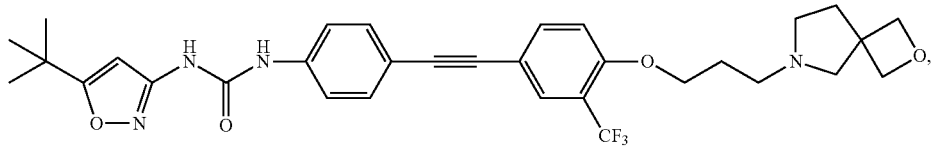
62
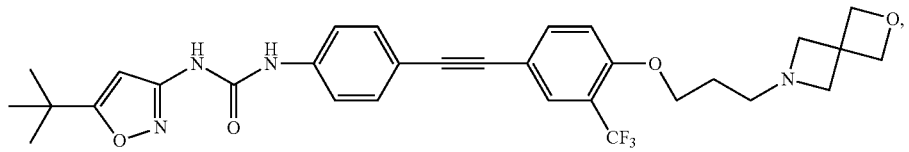
63
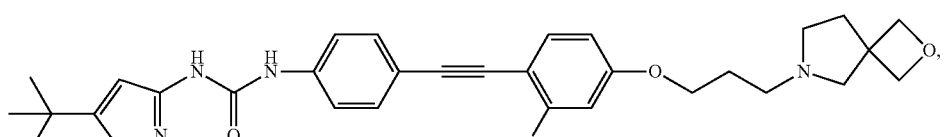
64
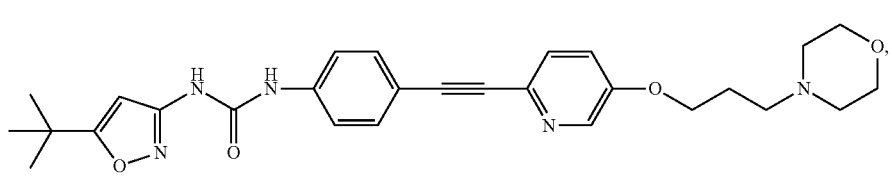
65

66
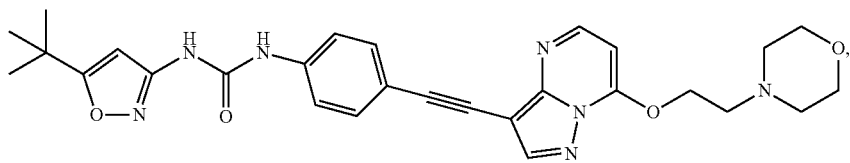
67
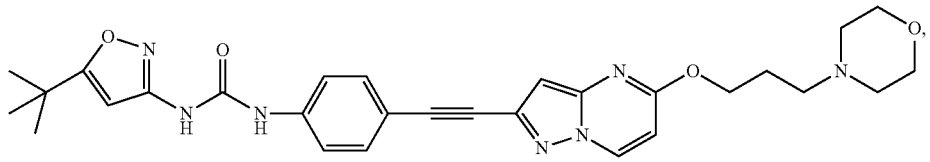
68
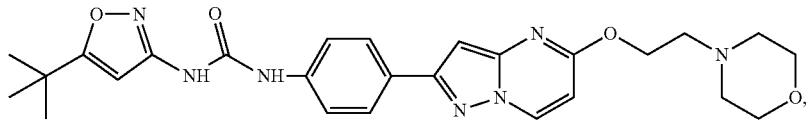
69
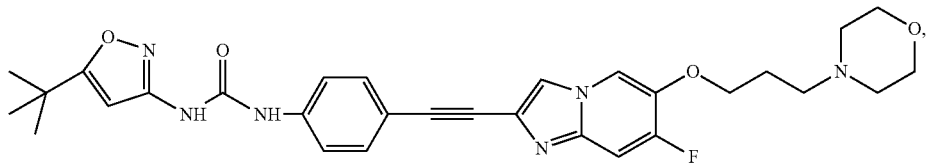
70
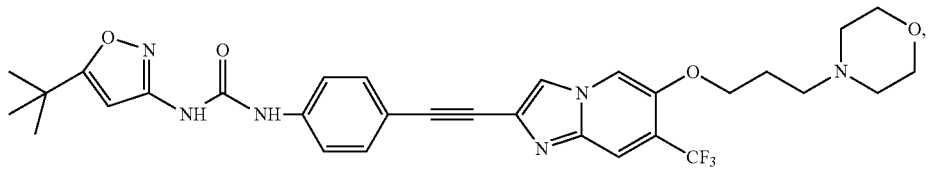
71
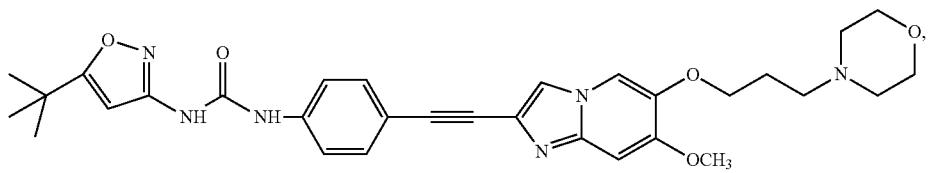
72
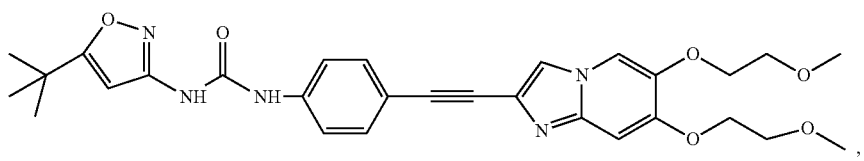
73
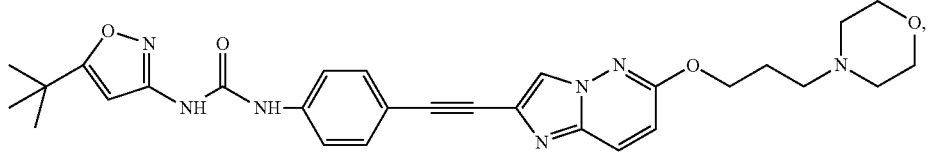
74
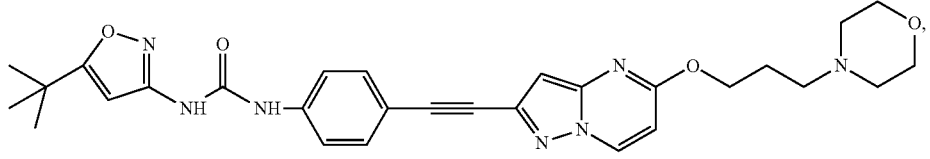

75
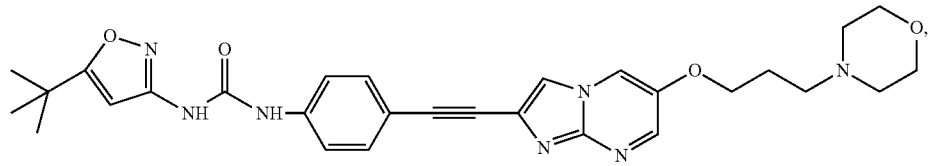
76
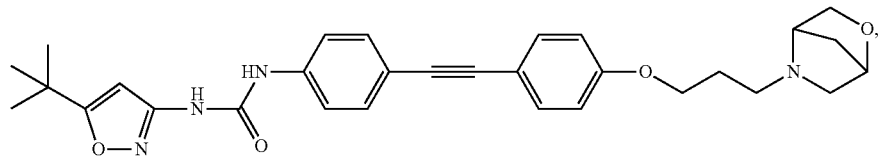
77
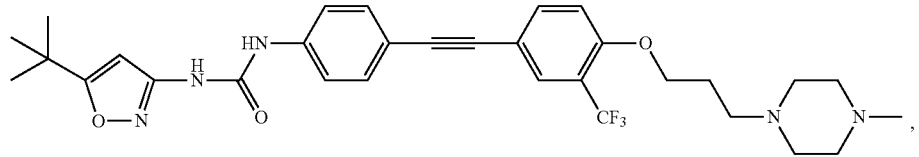
78
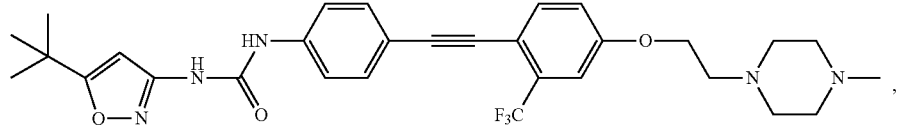
79
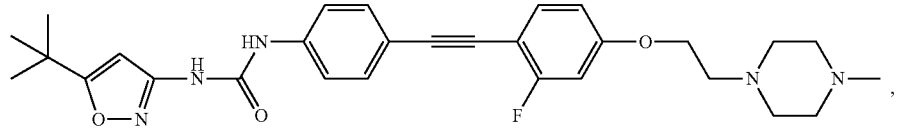
80
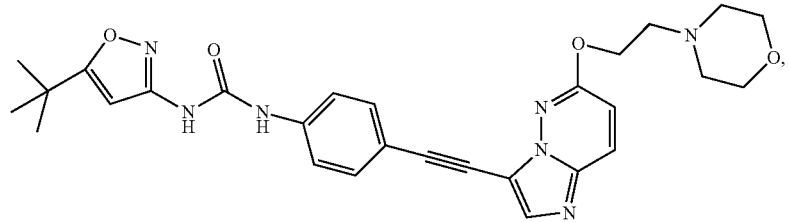
81
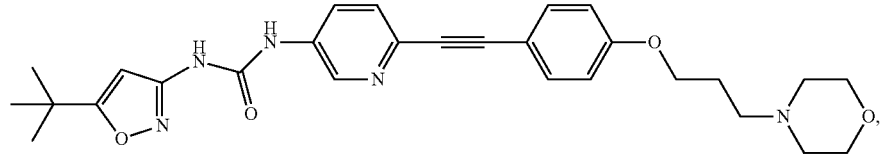
82
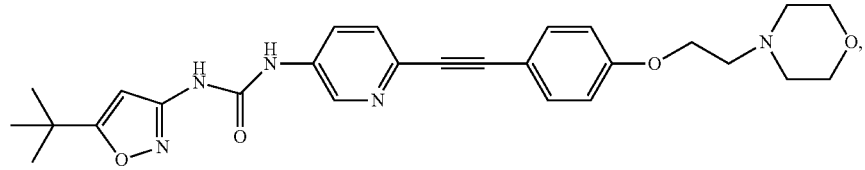
83
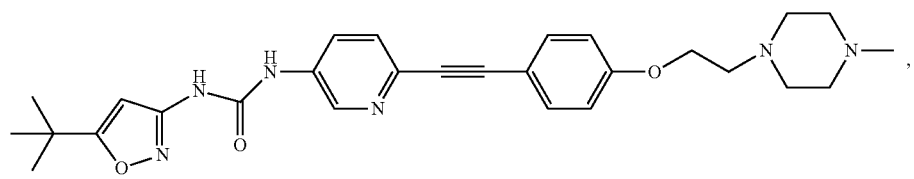

84
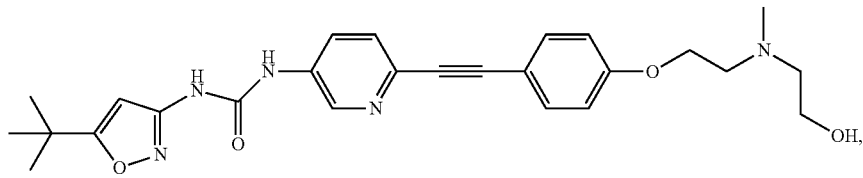
85
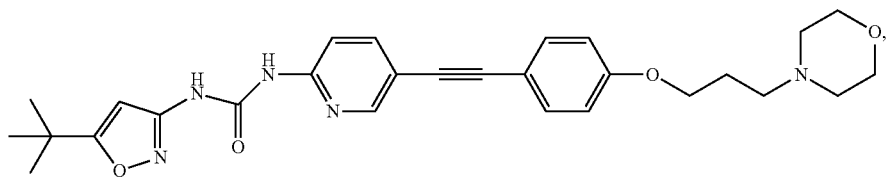
86
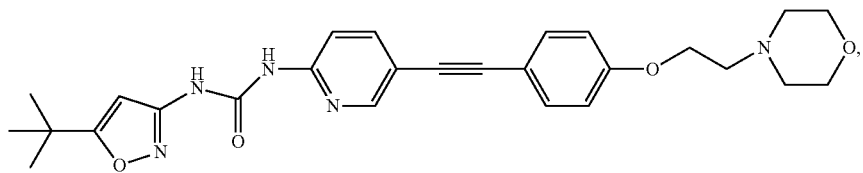
87
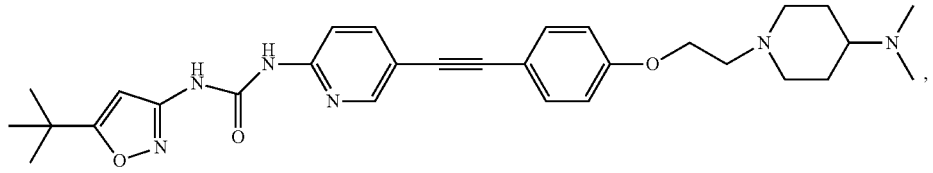
88
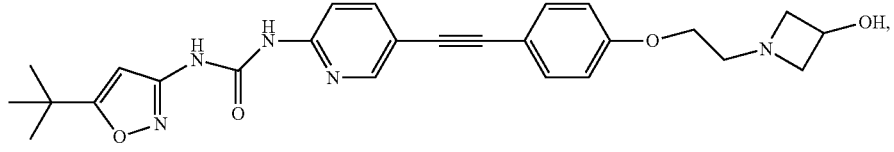
89
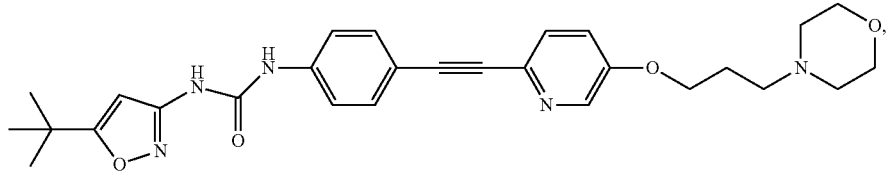
90
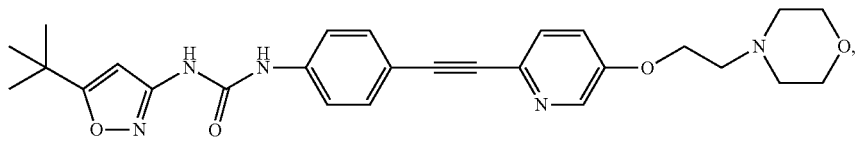
91
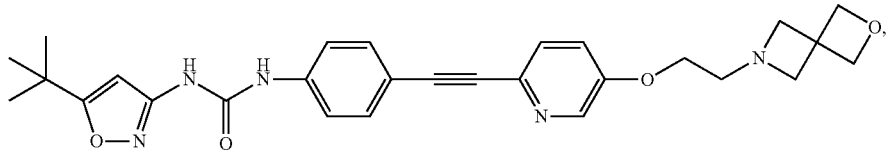
92
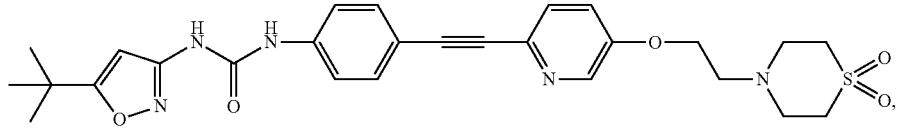

-continued
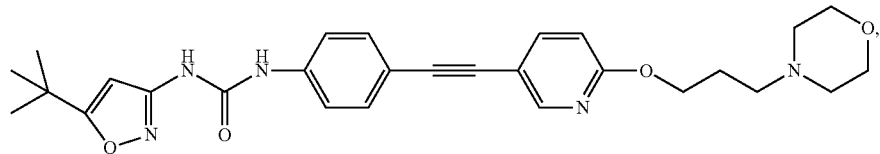
93
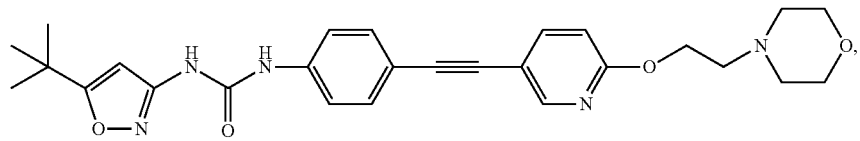
94
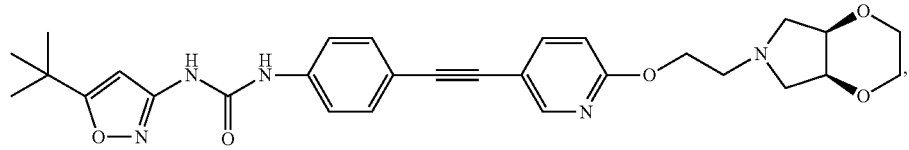
95
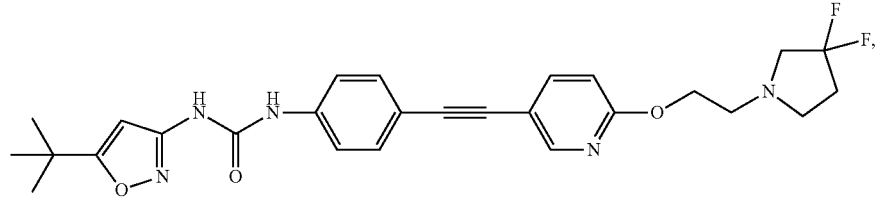
96
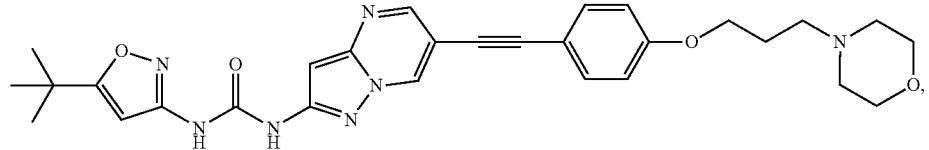
97
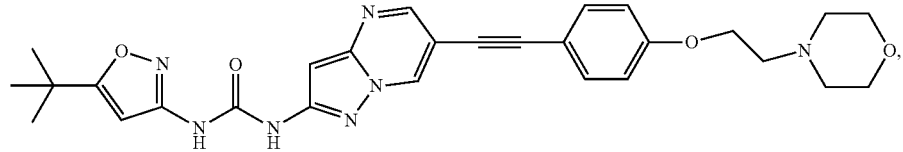
98
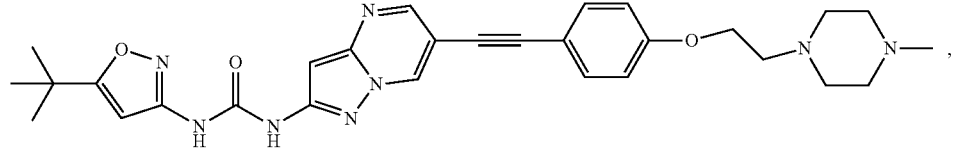
99
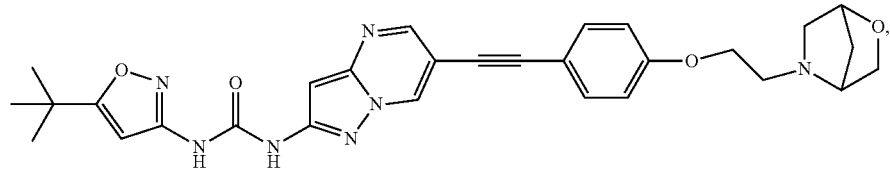
100
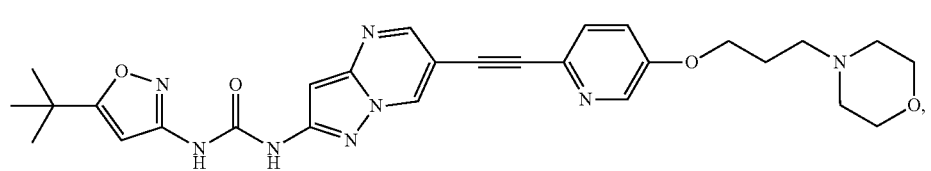
101

-continued
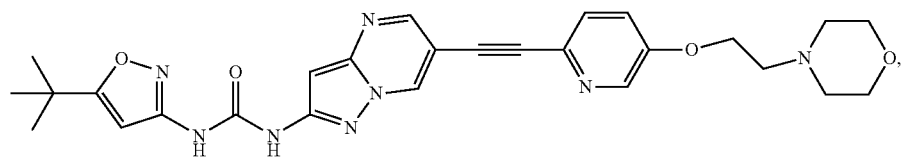
102
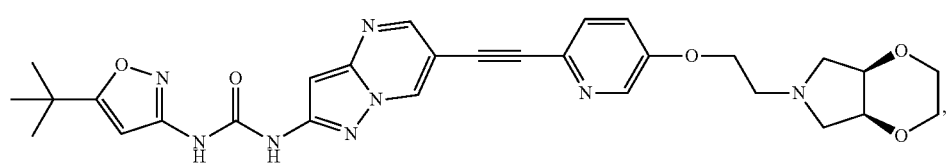
103
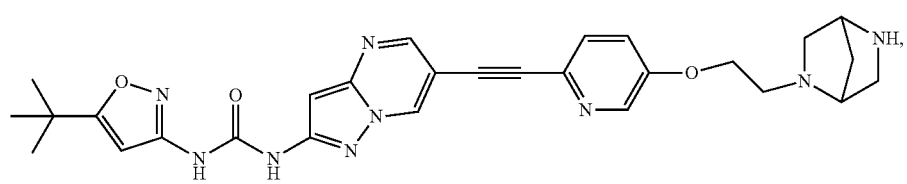
104
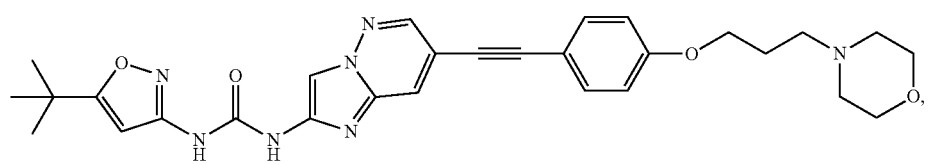
105
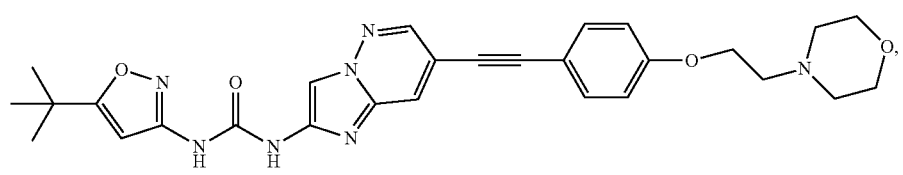
106
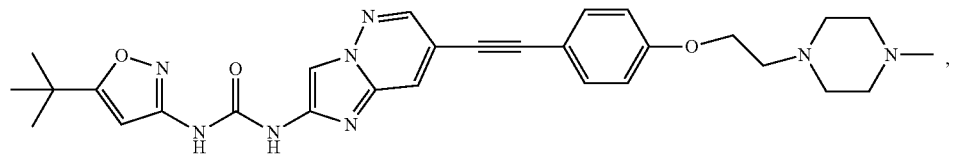
107
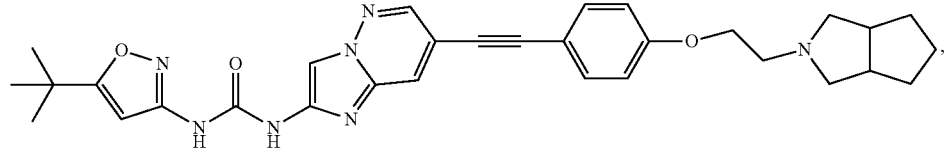
108
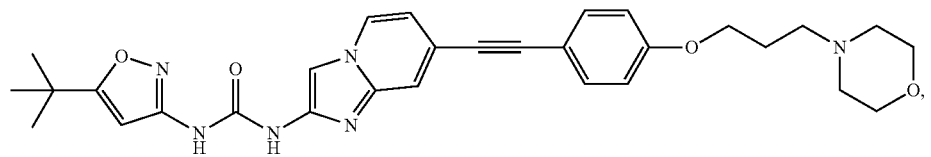
109
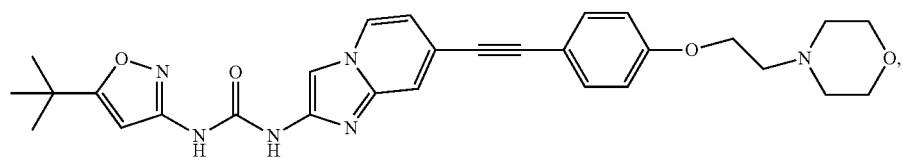
110

111
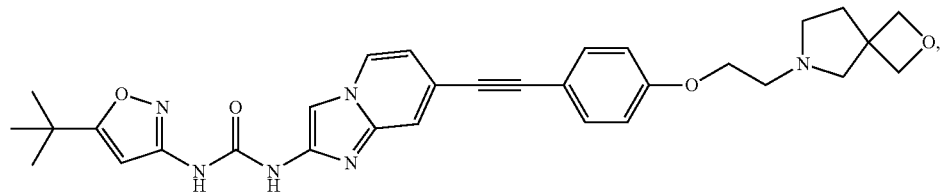
112
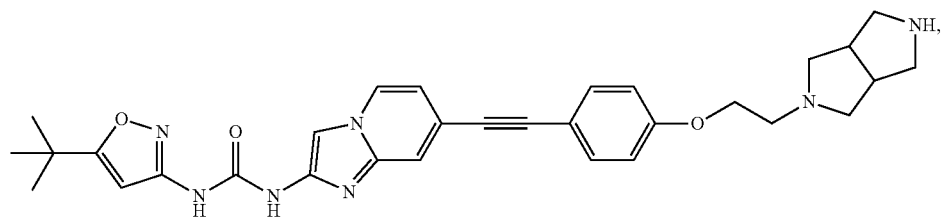
113
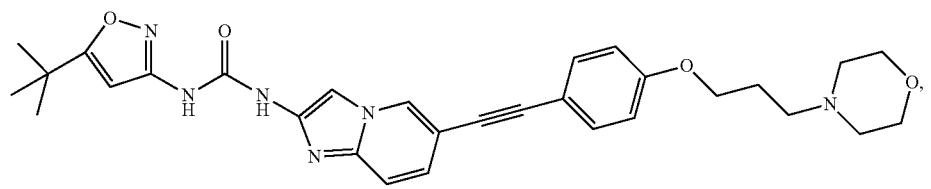
114
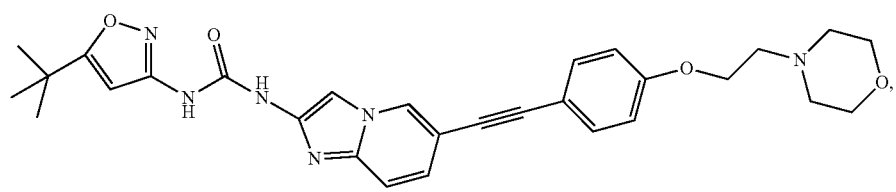
115
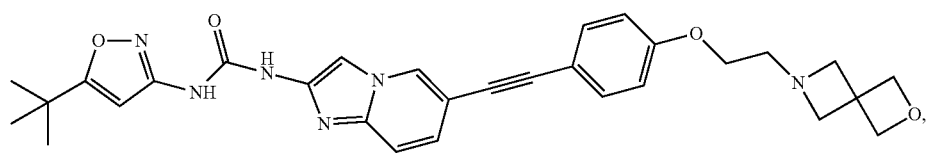
116
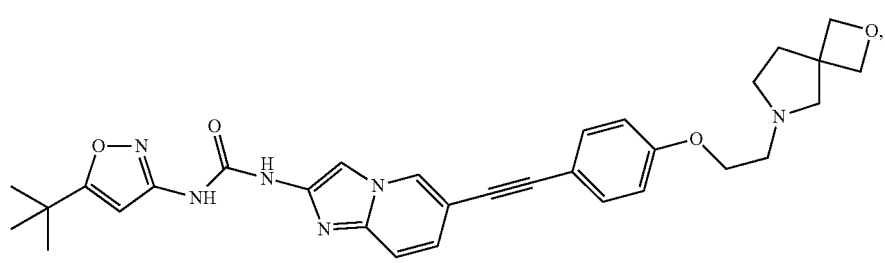
117
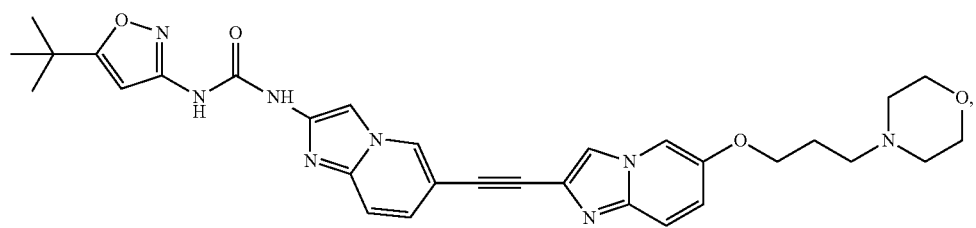

-continued
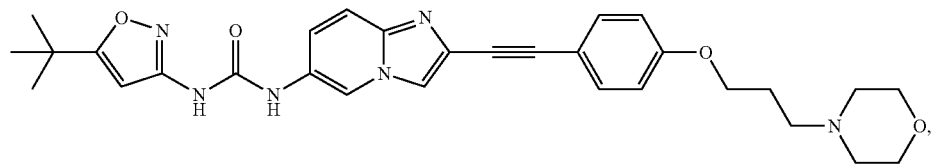
118
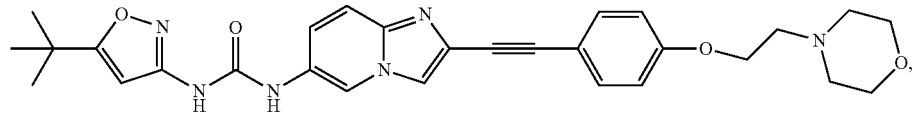
119
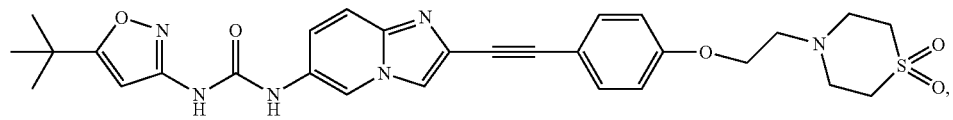
120
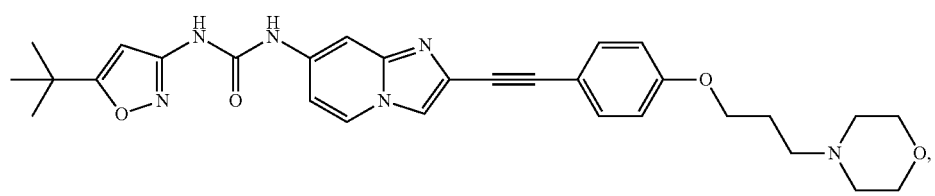
121
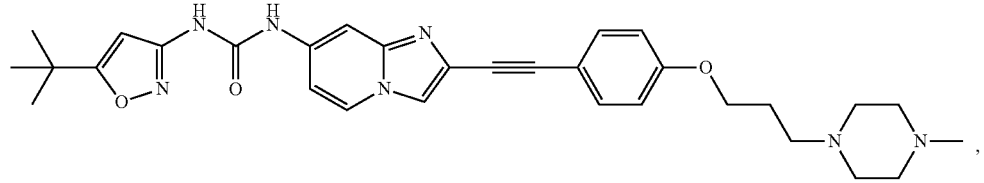
122
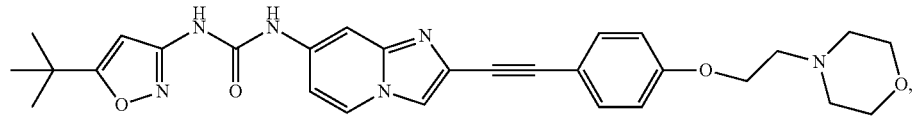
123
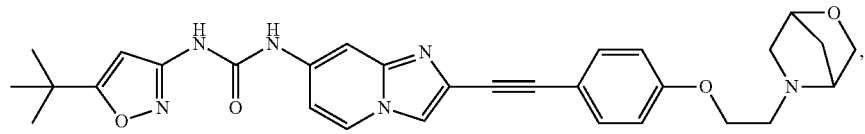
124
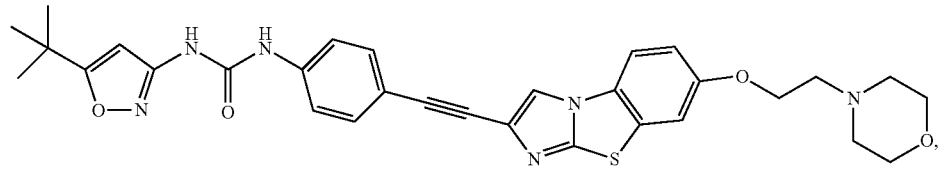
125
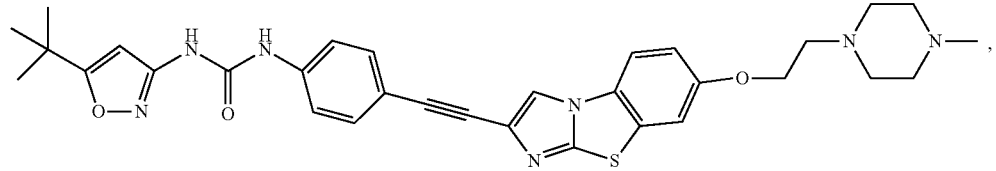
126

127
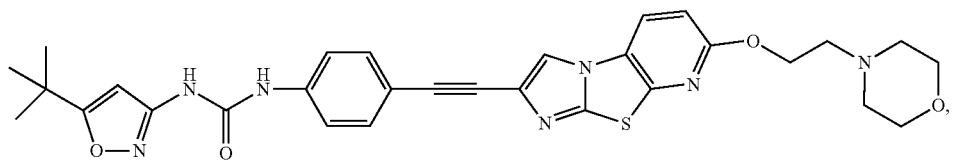
128
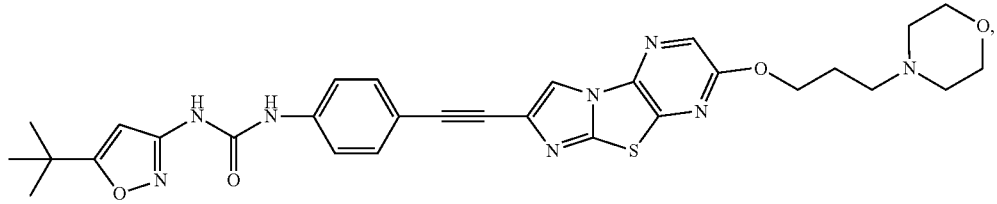
129
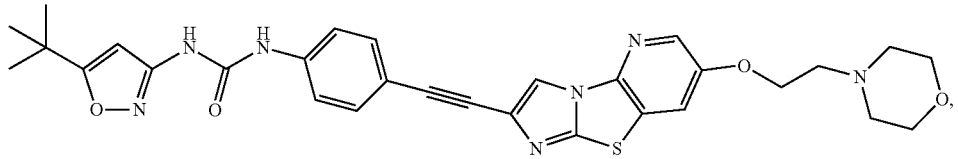
130
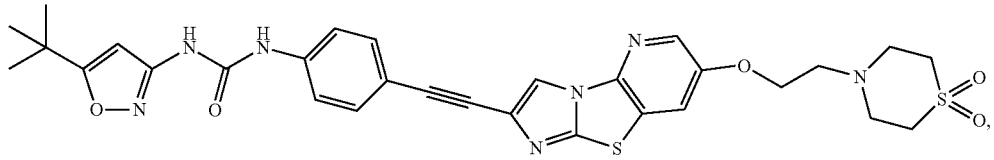
134
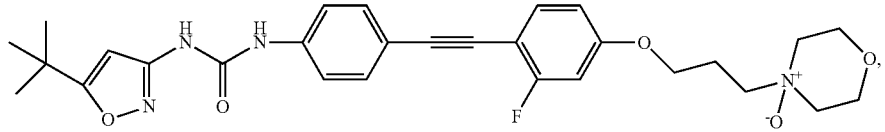
135
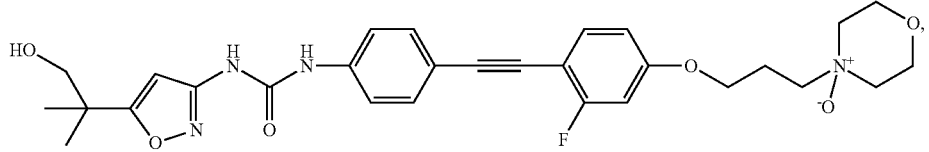
136
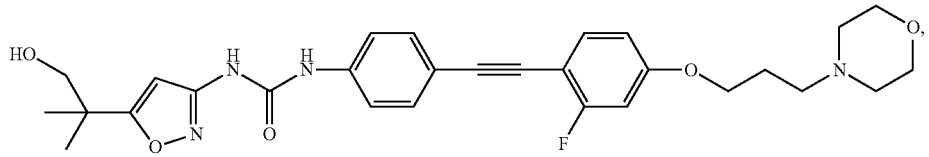
137
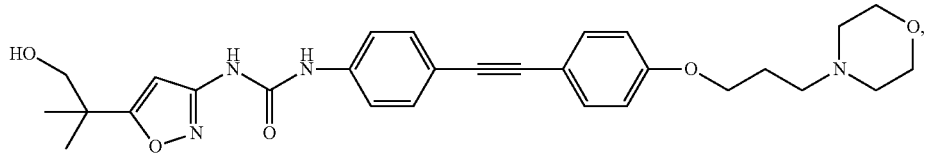
138
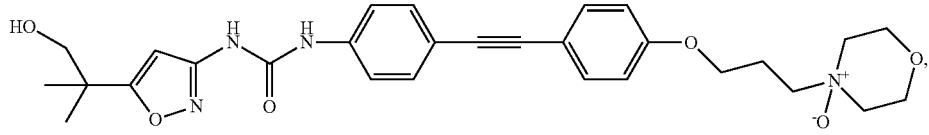

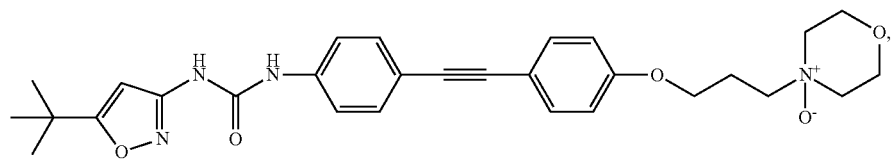
139
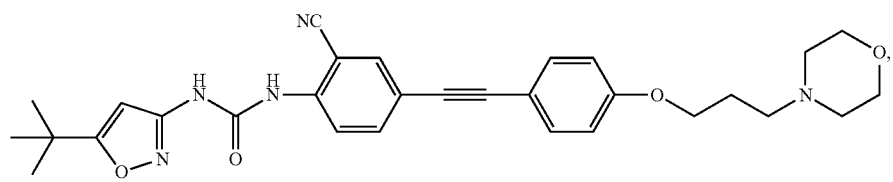
140
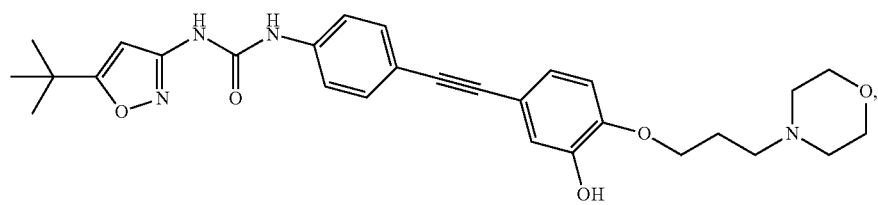
141
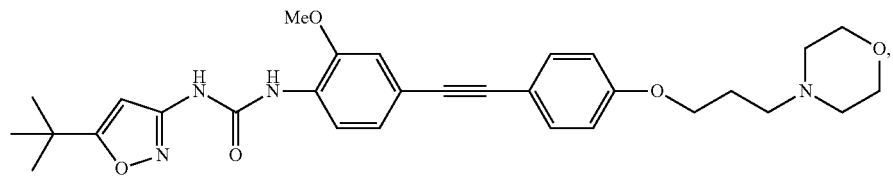
142
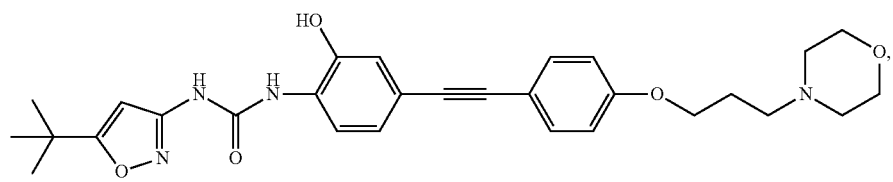
143
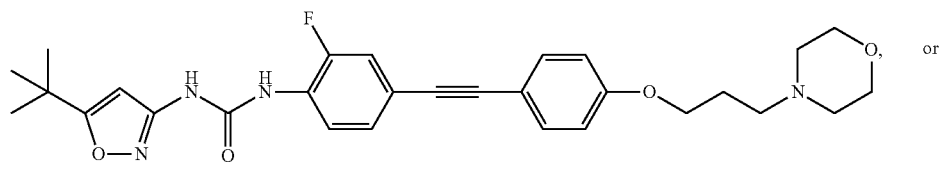
144 or
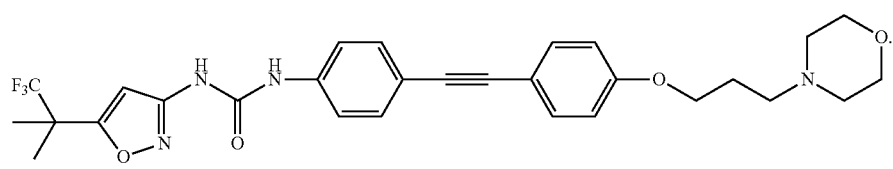
145

In some embodiments, provided herein is the substituted urea derivative having one of the following structures, or a stereoisomer, a geometric isomer, a tautomer, an N-oxide, a hydrate, a solvate, a metabolite, an ester, a pharmaceutically acceptable salt or a prodrug thereof,

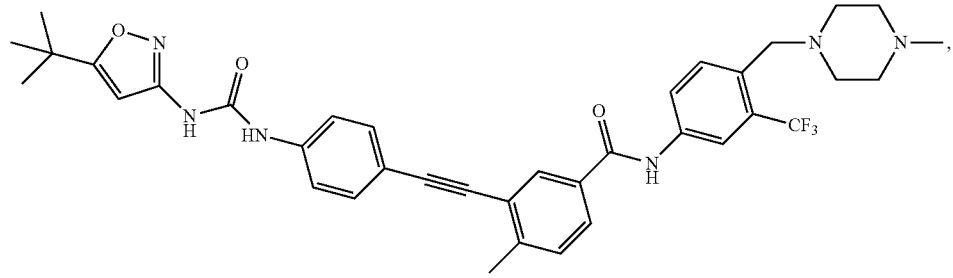

131

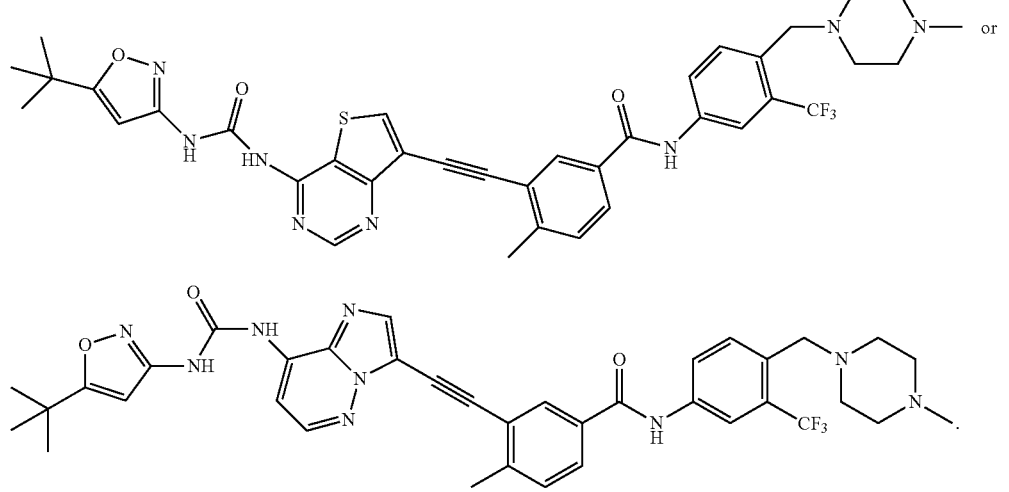

132 or

133

In another aspect, provided herein is the use of the compound or the pharmaceutical composition disclosed herein in the manufacture of a medicament for preventing, managing, treating or lessening a cancer, a tumor, an inflammatory disease, an autoimmune disease or an immune-mediated disease in a patient.

In some embodiments, the use disclosed herein, wherein the cancer, tumour, inflammatory disease, autoimmune disease, or immune-mediated disease is mediated by abnormal activation of B lymphocytes, T lymphocytes, or both.

In some embodiments, the inflammatory disease, autoimmune disease, or immune-mediated disease is arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, lung disease, lung inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, cardiac reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenograft, idiopathic thrombocytopenic purpura (ITP), Parkinson's disease, Alzheimer's disease, diabetes-related disease, inflammation, pelvic inflammatory disease, allergic rhinitis, allergic bronchitis, allergic nasosinusitis, leukemia, lymphoma (lymphioma), B-cell lymphoma, T-cell lymphoma, myeloma, acute lymphoblastic leukemia (ALL), chronic lymphocytic leukemia (CLL), acute myelogenous leukemia (AML), chronic myelogenous leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, follicular lymphoma, sarcoma, epidermoid carcinoma, fibrosarcoma, cervical cancer, stomach cancer, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancer, pancreatic cancer or AML-related complication.

In other embodiments, wherein the disease is an autoimmune disease or an transplantation-induced inflammation, including but not limited to, homograft, graft-versus-host disease, or autoimmune diabetes.

In other embodiments, the use disclosed herein, wherein the AML related complication is the symptom displayed by the patient, i.e., infection, bleeding, adult respiratory distress syndrome, sarcoidosis, pleural effusion, pulmonary fibrosis, pericardial effusion, cardiac arrhythmia, hypertension, heart failure, acute abdomen, portal hypertension, renal insufficiency, liver and spleen abscesses, anemia, thrombosis, diabetes, diabetes insipidus, electrolyte imbalance, neurological complications, intracranial hemorrhage, necrosis of the femoral head, bone and joint disease, skin lesions, retinal hemorrhage, optic disc edema, conjunctival hyperemia, edema, hypopyon, choroidal infiltration, iris infiltration, vitreous opacities, vision loss, hypopsia, orbital tumor, proptosis, acute glaucoma, chloroma, gingival hyperplasia, oral mucosal lesions, Sweets syndrome, gangrenous pyoderma, arthritis and vasculitis syndrome.

In another aspect, provided herein is use of the compound disclosed herein in the manufacture of a medicament for preventing, managing, treating or lessening a proliferative disease, an autoimmune disease or an inflammatory disease in a patient.

In another aspect, provided herein is use of the compound of Formula (I) to (VIII) or the pharmaceutically acceptable salts thereof, in the manufacture of a medicament for the treatment of FLT3 mediated diseases, wherein the use comprises administering a therapeutically effective amount of the compound of Formula (I) to (VIII), or a pharmaceutically acceptable salt, a isomer, a solvate, a hydrate or a prodrug thereof.

In another aspect, the compounds and the compositions provided herein are effective to modulate the activity of the Abl protein tyrosine family.

In some embodiments, the compounds and the compositions provided herein are effective to modulate the activity of the fms-like tyrosine kinase 3 receptor kinase (FLT-3 kinase).

In some embodiments, the compounds and the compositions provided herein are effective to inhibit the activity of the fms-like tyrosine kinase 3 receptor kinase mutation (FLT-3-ITD kinase).

In some embodiments, the compounds and the compositions provided herein are effective to modulate the activity of the Src subfamily, which includes Src, Yes, Fyn, Lyn, Lck, Blk, Hck, Fgr and Yrk.

In some embodiments, the compounds and the compositions provided herein are effective to modulate the activity of one or more kinases selected from the group consisting of sterile 20, sterile 11, sterile, the camk subfamily (calmodulin regulated kinases and related kinases), the AGC subfamily (protein kinase A, protein kinase G and protein kinase C), the CMGC subfamily (CDK, map kinase, glycogen synthetase kinase and clk), the sterile 20 subfamily, Frk, Btk, Csk, AbI, Zap70, Fes, Fps, Fak, Jak and Ack (and their respective subfamilies).

In other embodiments, provided herein are methods of using the disclosed compounds and compositions, or pharmaceutically acceptable salts, solvates, hydrates or prodrugs thereof, for the local or systemic treatment or prophylaxis of human and veterinary diseases, disorders and conditions modulated or otherwise affected via kinase activity.

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention. In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith. The compounds disclosed herein also include salts of the compounds which are not necessarily pharmaceutically acceptable salts, and which may be useful as intermediates for preparing and/or purifying compounds of Formula (I) to (VIII), and/or for separating enantiomers of compounds of Formula (I) to (VIII).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$aryl-$C_{1-4}$-alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

COMPOSITIONS OF COMPOUNDS OF THE INVENTION

According to another aspect, the invention features pharmaceutical compositions that include a compound of Formula (I) to (VIII), a hydrate, a solvate, an isomer, a physiologically/pharmaceutically acceptable salt or a prodrug thereof, a compound listed herein, or a compound named in examples 1-90, and a pharmaceutically acceptable carrier, adjuvant or vehicle. The compositions disclosed herein can be used in the manufacture of a medicament for preventing, managing, treating or lessening a disease mediated by protein kinase. The compositions disclosed herein acting as c-KIT mutation, RET, PDGFR, Bcr-ABL and FLT3 kinase or FLT3-ITD kinase inhibitors are used for preparation of medicaments.

The pharmaceutical compositions disclosed herein may include a compound of Formula (I) to (VIII), and a pharmaceutically acceptable carrier. The compounds of Formula (I) to (VIII) can also be included in pharmaceutical compositions in combination with the second therapeutically active compound.

The second therapeutically active compound disclosed herein may be a chemical therapeutic agent, an anti-proliferative agent, an immunosuppressive agent, an immunostimulatory agent, an anti-inflammatory agent, a CDK4/6 kinase inhibitor, an ABL inhibitors, an ABL/Scr inhibitor, an Aurora kinase inhibitor, a non-ATP-competitive inhibitor of BCR-ABL, a c-KIT mutation inhibitor, a RET inhibitor, a PDGFR inhibitor, a VEGFR inhibitor, a FLT3 inhibitor, a flt3-ITD inhibitor or a combination thereof.

It is known to one of skill in the art that suitable carriers, adjuvants and excipients agents are described in detail in Ansel H. C. et al., *Ansel's Pharmaceutical Dosage Forms and Drug Delivery Systems* (2004) Lippincott, Williams & Wilkins, Philadelphia; Gennaro A. R. et al., *Remington: The*

Science and Practice of Pharmacy (2000) Lippincott, Williams & Wilkins, Philadelphia; and Rowe R. C., Handbook of Pharmaceutical Excipients (2005) Pharmaceutical Press, Chicago.

The pharmaceutical carrier employed can be, for example, a solid, liquid or gas. Examples of solid carriers include lactose, terra alba, sucrose, talc, gelatin, agar, pectin, acacia, magnesium stearate, stearic acid, and the like. Examples of liquid carriers are sugar syrup, peanut oil, olive oil, water, and the like. Examples of gaseous carriers include carbon dioxide, nitrogen, and the like. Similarly, the carrier or diluent may include any time delay material well known to the art, such as glyceryl monostearate or glyceryl stearate, alone or mixed with a wax.

In another aspect, some non-limiting examples of materials which can serve as pharmaceutically acceptable carriers include ion exchanger; aluminum; alumina; aluminum stearate; lecithin; serum protein such as human serum albumin; buffer substance such as phosphate; glycine; sorbic acid; potassium sorbate; partial glyceride mixture of saturated vegetable fatty acid; water; electrolyte such as protamine sulfate, disodium hydrogen phosphate and potassium hydrogen phosphate; salt such as sodium chloride and zinc salt; colloidal silica; magnesium trisilicate; polyvinyl pyrrolidone; polyacrylate; wax; polyethylene-polyoxypropylene-block polymer; wool fat; sugar such as lactose, glucose and sucrose; starch such as corn starch and potato starch; cellulose and its derivative such as sodium carboxymethyl cellulose, ethyl cellulose and cellulose acetate; powdered tragacanth; malt; gelatin; talc; excipients such as cocoa butter and suppository waxes; oil such as peanut oil, cottonseed oil, safflower oil, sesame oil, olive oil, corn oil and soybean oil; glycol such as propylene glycol and polyethylene glycol; ester such as ethyl oleate and ethyl laurate; agar; buffering agent such as magnesium hydroxide and aluminum hydroxide; alginic acid; pyrogen-free water; isotonic saline; Ringer's solution; ethyl alcohol and phosphate buffer solution, as well as other non-toxic compatible lubricant such as sodium lauryl sulfate and magnesium stearate, coloring agent, releasing agent, coating agent, sweetening, flavoring and perfuming agent, preservative and antioxidant.

Pharmaceutical compositions of the invention disclosed herein can be prepared and packaged in bulk form, wherein the pharmaceutical compositions contain a safe and effective amount of extractable compounds of the present invention, and then can be administered to the patient in the form of powder or syrup. Alternatively, the pharmaceutical compositions of the present invention disclosed herein can be prepared and packaged in unit dosage form, wherein each physically discrete unit contains a safe and effective amount of a compound of the present invention. When the compound prepared in unit dosage form, the pharmaceutical compositions of the present invention disclosed herein generally contain, for example, 0.5 mg to 1 g, or 1 mg to 700 mg, or 5 mg to 100 mg of the compounds disclosed herein.

As used herein a "pharmaceutically acceptable excipient" means a pharmaceutically acceptable material, a composition, or a vehicle involved in giving form or consistency to the dosage form or pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be pharmaceutically-acceptable eg of sufficiently high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrating agents, lubricants, glidants, granulating agents, coating agents, wetting agents, solvents, co-solvents, suspending agents, emulsifying agents, sweetening agents, flavoring agents, taste masking agents, coloring agents, anti-caking agents, humectants, chelating agents, plasticizers, adhesion promoters, antioxidants, preservatives, stabilizers, surfactants and buffers. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

Various carriers used for preparing pharmaceutical acceptable composition and their formulations are described in *Remington: The Science and Practice of Pharmacy*, 21st edition, 2005, ed D B Troy, Lippincott Williams & Wilkins, Philadelphia, and *Encyclopedia of Pharmaceutical Technology*, eds J. Swarbrick and J C Boylan, 1988-1999, Marcel Dekker, New, all of which are incorporated herein by reference. Except any carrier due to undesirable biological effects or interacting in a deleterious manner with any of the other ingredients of pharmaceutically acceptable compositions and incompatible with the compound disclosed herein, the other carriers are within the scope of the invention.

Uses

The compounds of Formula (I) to (VIII), or the pharmaceutical compositions thereof disclosed herein are useful in treating conditions characterized by inappropriate FLT3 activity such as proliferative disorders. FLT3 activity increase includes, but is not limited to, enhanced FLT3 activity resulting from increased or denovo expression of FLT3 in cells, increased FLT3 expression or activity, and FLT3 mutations resulting in constitutive activation. The existence of inappropriate or abnormal FLT3 ligand and FLT3 levels or activity can be determined using well-known methods in the art. For example, abnormally high FLT3 levels can be determined using commercially available ELISA kits. FLT3 levels can also be determined using flow cytometric analysis, immunohistochemical analysis and in situ hybridization techniques.

An inappropriate activation of FLT3 can be determined by an increase in one or more of the activities occurring subsequent to FLT3 binding: (1) phosphorylation or autophosphorylation of FLT3; (2) phosphorylation of FLT3 substrates such as Stat5 and Ras; (3) activation of related complexes such as PI3K; (4) activation of adaptor molecules; and (5) cell proliferation. These activities can be readily measured by well-known methods in the art.

The compound of Formula (I) to (VIII), or the pharmaceutical composition disclosed herein is useful in, but not limited to, preventing or treating proliferative diseases, conditions, or disorders in a patient by administering to the patient the compound of Formula (I) to (VIII), or the pharmaceutical composition disclosed herein in an effective amount. Such diseases, conditions, or disorders include cancer, particularly hematopoietic system cancer, metastatic cancer, atherosclerosis, and lung fibrosis.

The compounds or the pharmaceutical compositions disclosed herein are useful for the treatment of neoplasia including cancer and metastatic cancer, including, but not limited to: carcinoma such as cancer of bladder, breast, colon, kidney, liver, lung (including small cell lung cancer), esophageal, gall-bladder, ovary, pancreas, stomach, cervix, thyroid, prostate, and skin (including squamous cell carcinoma); hematopoietic tumors of lymphoid lineage including leukemia, acute lymphocitic leukemia, acute lymphoblastic leukemia, B-cell lymphoma, T-cell lymphoma, Hodgkin's lymphoma, non-Hodgkin's lymphoma, hairy cell leukemia and Burkett's lymphoma; hematopoietic tumors of myeloid lineage including acute and chronic myelogenous leukemias, myelodysplastic syndrome and promyelocytic leukemia; tumors of mesenchymal origin including fibrosarcoma and rhabdomyosarcoma, and other sarcomas, e.g., soft tissue and bone; tumors of the central and peripheral nervous system including astrocytoma, neuroblastoma, glioma and schwannomas; and other tumors including melanoma, seminoma, teratocarcinoma, osteosarcoma, xenoderoma pigmentosum, keratoctanthoma, thyroid follicular cancer and Kaposi's sarcoma.

The compounds or the pharmaceutical compositions disclosed herein are also useful in the manufacture of the medicaments for the treatment of EGFR, EGFR (T790M), BLK, BMX/ETK, BTK, JAK1, JAK2, JAK3, TEC, TXK, FLT3 and FLT3 (D835Y) protein kinase mediated, c-KIT mutation mediated and/or FLT3-ITD mediated diseases like proliferative diseases, autoimmune diseases, kidney diseases, tissue transplant rejection, lupus erythematosis, multiple sclerosis, inflammatory bowel disease, rheumatoid arthritis, AML, arthritis, asthma, and the like.

The compounds or the pharmaceutical compositions disclosed herein are also useful in the manufacture of the medicaments for the treatment of complications of the diseases mediated by EGFR, EGFR (T790M), BLK, BMX/ETK, BTK, JAK1, JAK2, JAK3, TEC, TXK, FLT3 and FLT3 (D835Y) protein kinase mediated, c-KIT mutation and/or FLT3-ITD.

The compounds or the pharmaceutical compositions disclosed herein are also useful in the treatment of diabetic conditions such as diabetic retinopathy and microangiopathy.

The compounds or the pharmaceutical compositions disclosed herein are also useful in the reduction of blood flow in a tumor.

The compounds or the pharmaceutical compositions disclosed herein are also useful in the reduction of metastasis of a tumor.

Besides being useful for human treatment, these compounds or the pharmaceutical compositions are also useful for veterinary treatment of companion animals, exotic animals and farm animals, including mammals, rodents, and the like. In other embodiments, animals include horses, dogs and cats. As used herein, the compounds of Formula (I) to (VIII) disclosed herein include the pharmaceutically acceptable derivatives thereof.

The compounds or the pharmaceutical compositions disclosed herein also are useful in the manufacture of the medicament for inhibiting the growth of a cell that expresses VEGFR or c-Met, which includes contacting the cell with a compound or composition disclosed herein. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell or a leukemia cell.

The compounds or the pharmaceutical compositions disclosed herein also are useful in the manufacture of the medicament for inhibiting VEGFR and/or c-Met kinase activity in a biological sample, which includes contacting the biological sample with a compound or composition disclosed herein. The term "biological sample" as used herein, means a external living organism sample including but not limited to, cell cultures or extracts thereof; biopsied materials obtained from a mammal or extracts thereof; and blood, saliva, urine, feces, semen, tears, or other body liquids or extracts thereof. Inhibition of kinase activity, particularly VEGFR or c-Met kinase activity, in a biological sample is useful for a variety of purposes known to one of skill in the art. Examples of such purposes include, but are not limited to, blood transfusion, organ-transplantation, biological specimen storage and biological assays.

Administration

Where the plural form is used for compounds, salts, pharmaceutical compositions thereof, and the like, this is taken to refer to also a single compound, salt, pharmaceutical composition thereof, and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered in combination with the compound disclosed herein simultaneously or sequentially. In the latter case, administration may be staggered by, for example, 6 hours, 12 hours, 1 day, 2 days, 3 days, 1 week, 2 weeks, 3 weeks, 1 month or 2 months.

Typically a therapeutically effective dosage should produce a serum concentration of active ingredient of from about 0.1 ng/ml to about 50-100 µg/ml. The pharmaceutical compositions disclosed herein should provide a dosage of from about 0.001 mg to about 2000 mg of compound per kilogram of body weight per day. Pharmaceutical dosage unit forms are prepared to provide from about 1 mg to about 1000 mg, and in some embodiments, from about 10 mg to about 500 mg, from about 20 mg to about 250 mg or from about 25 mg to about 100 mg of the essential active ingredient or a combination of essential ingredients per dosage unit form. In some embodiments, pharmaceutical dosage unit forms are prepared to provide about 1 mg, 20 mg, 25 mg, 50 mg, 100 mg, 250 mg, 500 mg, 1000 mg or 2000 mg of the essential active ingredient. In some embodiments, pharmaceutical dosage unit forms are prepared to provide about 50 mg of the essential active ingredient.

The active ingredient of the pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is also to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

An "effective amount" or "effective dose" is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and the general condition of the subject, the severity of the infection, the particular agent, the mode of administration, and the like. A compound or composition can also be administered with one or more other therapeutic agents, as discussed above.

The compounds or the pharmaceutical compositions thereof disclosed herein may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

When administered to a patient for the treatment of cancer, the dosage used can be varied depending upon the type of cancer, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering the compounds of Formula (I) to (VIII) disclosed herein orally or parenterally. The term "parenteral" as used herein includes intravenous, intramuscular or intraperitoneal administration. The subcutaneous and intramuscular forms of parenteral administration are generally preferred. The invention can also be carried out by delivering the compounds of Formula Formula (I) to (VIII) disclosed herein subcutaneously, intranasally, intrarectally, transdermally or intravaginally.

The compounds of Formula (I) to (VIII), or the pharmaceutical compositions disclosed herein may also be administered by inhalation. "Inhalation" is meant intranasal and oral inhalation administration. Appropriate dosage forms for such administration, such as an aerosol formulation or a metered dose inhaler, may be prepared by convention techniques.

Formulation and Administration

The compounds of Formula (I) to (VIII), or the pharmaceutical compositions disclosed herein can be employed to prepare a wide variety of pharmaceutical dosage forms. If a solid dosage is used for oral administration, the preparation can be in the form of a tablet, hard gelatin capsule, lozenge, troche, drop, lotion, and the like. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution. Topical dosage forms are also included. Examples of topical dosage forms are solids, liquids and semi-solids. Solids would include dusting powders, poultices, and the like. Liquids include solutions, suspensions and emulsions. Semi-solids include creams, ointments, gels, and the like.

The amount of a compound of Formula (I) to (VIII), or a pharmaceutical composition thereof disclosed herein used topically will, of course, vary with the compound chosen, the nature and severity of the condition, and can be varied in accordance with the discretion of the physician. A representative, topical dose of a compound of Formula (I) to (VIII), is from as low as about 0.01 mg to as high as about 2.0 g, administered one to four, preferably one to two times daily. The active ingredient may comprise, for topical administration, from about 0.001% to about 10% w/w.

Drops according to the invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98° C.-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine (0.01%). Suitable solvents for the preparation of an oily solution include glycerol, diluted alcohol and propylene glycol.

Lotions according to the invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or oil such as castor oil or arachis oil.

Creams, ointments or pastes according to the invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, coenzyme M, arachis, castor or olive oil; wool fat or its derivatives, or a fatty acid such as stearic or oleic acid together with an alcohol such as propylene glycol or macrogel. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The compounds or the pharmaceutical compositions disclosed herein can also be administered in the form of coating, and suitable coated implantable devices are known in the art. The coatings are typically biocompatible polymeric materials such as a hydrogel polymer, polymethyldisiloxane, polycaprolactone, polyethylene glycol, polylactic acid and mixtures thereof. The coatings may optionally be further covered by a suitable topcoat of fluorosilicone, polysaccharides, polyethylene glycol, phospholipids or combinations thereof to impart controlled release characteristics in the composition. The compounds may also be coated on implantable medical devices, such as beads, or co-formulated with a polymer or other molecule, to provide a "drug depot" thus permitting the drug to be released over a longer time period than administration of an aqueous solution of the drug.

Drug Combination

The present invention provides the combination of one or more compounds or compositions, or a pharmaceutically acceptable derivative thereof with other active drug for the treatment of diseases and conditions described herein.

In practicing the methods, effective amounts of the compounds or compositions containing therapeutically effective concentrations of the compounds, which are formulated for oral, systemic, including parenteral or intravenous delivery, or for local or topical application are administered to an individual exhibiting the symptoms of the disease or disorder to be treated. The amounts are effective to treat, manage or ameliorate the disease or ameliorate or eliminate one or more symptoms of the disease or disorder.

One ordinary skill in the art should understand that the compounds, isomers, prodrugs and pharmaceutically acceptable derivatives thereof disclosed herein, including pharmaceutical compositions and formulations containing these compounds can be widely used in combination therapy for the treatment of the present discomforts and diseases herein.

Accordingly, the compounds, isomers, prodrugs and pharmaceutically acceptable derivatives thereof provided herein are intended for use in combination with other active agents to treat the before mentioned diseases/discomforts of the present invention.

The compounds, compositions or pharmaceutically acceptable derivatives thereof provided herein, may be administered simultaneously with, prior to, or after administration of one or more of the other pharmaceutical active drugs. Other active drugs are particularly useful for the treatment of a proliferative disorder or cancer which plagues subject.

In some embodiments, one or more other active drugs are selected from anticancer agents (such as cell signaling inhibitors, mitotic inhibitors, alkylating agents, anti-metabolites, chimeric (intercalating) anticancer agents, topoisomerase inhibitors, immunotherapeutic agents, or anti-hormonal agents), steroids, methotrexate, leflunomide, anti-TNF-α agents, calcineurin phosphatase (calcineurin) inhibitors, antihistamines, chemotherapeutic agents, antiproliferative agents, immunosuppressive agents, immunostimulatory agents, anti-inflammatory agent, CDK4/6 kinase inhibitor, ABL inhibitors, ABL/Scr inhibitors, aurora kinase inhibitors, non-ATP-competitive inhibitor of BCR-ABL, c-KIT mutation inhibitors, RET inhibitors, PDGFR inhibitors, VEGFR inhibitors, FLT3 inhibitor, FLT3-ITD inhibitor or a combination thereof In some embodiments, one or more other active drugs may be: streptozotocin, oxaliplatin, temozolomide, methotrexate, fluorouracil, gemcitabine, mercaptopurine, vinorelbine, docetaxel, topotecan, irinotecan, trabectedin, dactinomycin, mitomycin C, ixabepilone, gonadorelin analogues, megestrol, prednisone, methylprednisolone, thalidomide, interferon-α, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, busulfan, dipropylamine sulfonester, piposulfan, benzyl tepa, kaposi quinones, uredepa, altretamine, tretamine, triethylenephosphoramide, triethylenethiophosphoramide, trimethylol melamine, chlorambucil, chlornaphazine, cyclophosphamide, estramustine, ifosfamide, mechlorethamine, mechlorethaminoxide, melphalan, new mechlorethamine, phenesterine, prednimustine, trofosfamide, uracil mustard, carmustine, chlorine streptozotocin, fotemustine, lomustine, nimustine, ranimustine, dacarbazine, mannomustine, dibromomannitol, dibromidulcitol, pipobroman, aclacinomycin, actinomycin F(1), anthramycin, azaserine, bleomycin, actinomycin C, carubicin, carzinophilin, chromomycin, actinomycin D, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, dornase alfa, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, ethoglucid, etoposide, flutamide, gallium nitrate, hydroxyurea, interferon-α, interferon-β, interferon-γ, interleukin-2, lentinan, lonidamine, prednisone, dexamethasone, leucovorin, mitoguazone, mitoxantrone, mopidamol, nitracrine, pentostatin, phenamet, pirarubicin, podophyllic acid, 2-ethyl hydrazide, procarbazine, razoxane, sizofiran, spirogermanium, paclitaxel, tamoxifen, teniposide, tenuazonic acid, triaziquone, 2,2',2"-trichlorotriethyl amine, urethane, vinblastine, vincristine, vindesine, deferasirox, cabozantinib, ponatinib, midostaurin, pacritinib, quizartinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib, or a combination thereof.

In some embodiments, when administered in combination, there are two ways: 1) the compound or the pharmaceutical composition of the present invention and other active drug with which can be combined are made as separate formulations, which may be the same or different, and can be administered sequentially or simultaneously; when administered sequentially, the second drug is administered at the time when the first drug has not lost the active effect in vivo; 2) the compound or the pharmaceutical composition of the present invention and other active drug with which can be combined can be made as a single formulation for administering simultaneously.

In some embodiments, also provided herein is a combination therapy used for treating or preventing the symptoms or complications associated with cancer or related diseases, comprising administering to a subject in need of such treatment a compound or a composition of the invention, or a pharmaceutically acceptable derivative thereof, and one or more other active drugs.

In some embodiments, especially provided herein is a drug combination comprising a FLT3 inhibitor or FLT3-ITD inhibitor and CDK4/6 kinase inhibitor. The compound of the invention, or a composition, or a pharmaceutically acceptable derivative thereof, as FLT3 inhibitor or FLT3-ITD inhibitor, may be administered simultaneously with, prior to, or after administration of one or more of other active therapeutic agents. Particularly, other active therapeutic agent is a CDK4/6 kinase inhibitor.

In some embodiments, CDK4/6 kinase inhibitor is deferasirox, palbociclib, abemaciclib, ribociclib, rigosertib sodium, selinexor, roniciclib, AT-7519, seliciclib, alvocidib etc.

General Synthetic Procedures

Generally, the compounds disclosed herein may be prepared by methods described herein, wherein the substituents are as defined for Formula (I) to (VIII) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope of the invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, n-hexane, N,N-dimethylacetamide and N,N-dimethylformamide were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded on a Bruker 400 MHz or 600 MHz nuclear magnetic resonance spectrometer, using $CDCl_3$, DMSO-$d_6$, $CD_3OD$ or acetone-$d_6$ as solvent (reported in ppm), and TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low-resolution mass spectral (MS) data were determined by an Agilent 6120 Series Quadrupole HPLC-M (Zorbax SB-C18, 2.1×30 mm, 3.5 m, 6 min, flow rate: 0.6 mL/min, mobile phase: 5%-95% (1% formic acid in $CH_3CN$) in (1% formic acid in $H_2O$), ESI) with UV detection at 210 nm and 254 nm.

Purities of compounds were assessed by Agilent 1260 pre-HPLC or Calesep pump 250 pre-HPLC (NOVASEP 50/80 mm DAC) with UV detection at 210 nm and 254 nm.

The following abbreviations are used throughout the specification:

MeCN, $CH_3CN$ acetonitrile $Br_2$ bromine $BBr_3$ boron tribromide n-BuLi n-butyllithium t-BuOK potassium tert-butoxide CHCl₃ chloroform CDCl₃ deuterated chloroform CuI cuprous iodide DEAD diethyl azodicarboxylate DMF N,N-dimethylformamide DMAP 4-dimethylaminopyridine DIPEA N,N-diisopropylethylamine DMSO dimethyl sulfoxide DMSO-d₆ dimethyl sulfoxide-d₆

CD₃OD methanol-d, deuterated methanol

Et₃N, TEA triethylamine

H₂ hydrogen

H₂O₂ hydrogen peroxide
K₂CO₃ potassium carbonate

Fe iron

MgSO₄ magnesium sulfate

MeOH, CH₃OH methanol mL, ml milliliter

N₂ nitrogen

PdCl₂(PPh₃)₂ bis(triphenylphosphine)palladium(II) chloride

PPh₃ triphenylphosphine

Pd/C palladium on carbon

MCPBA 3-chloroperoxybenzoic acid

RT, rt room temperature

Rt retention time

SEMCl 2-(trimethylsilyl)ethoxymethyl chloride

NIS N-iodosuccinimide

NBS N-bromosuccinimide

H₂O water

CH₂Cl₂, DCM dichloromethane

EtOAc, EA ethyl acetate

PE petrol ether, petroleum ether

TFA trifluoroacetic acid

Synthesis of Intermediates

Synthesis of Intermediates (9a) and (12a)

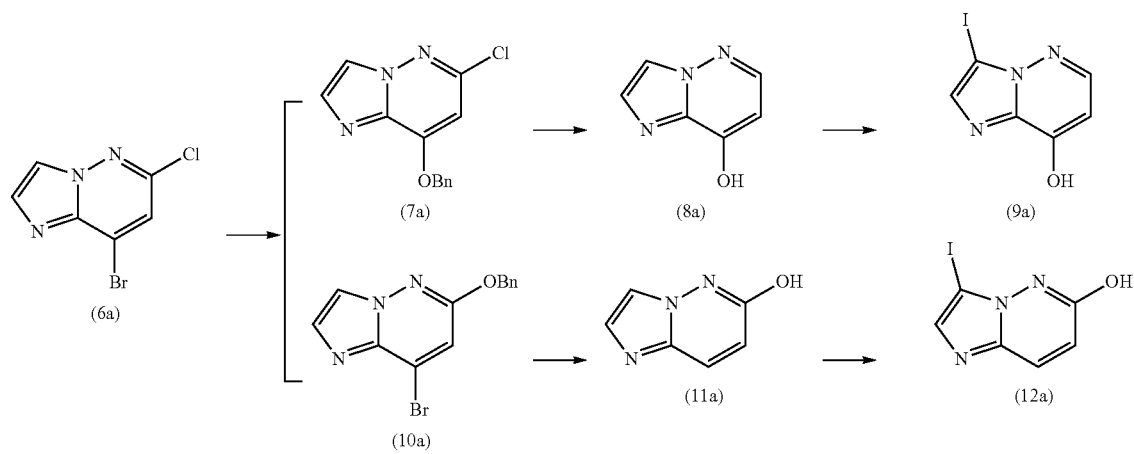

Compound (9a) and (12a) can be prepared from compound (6a) by the following steps. Compound (6a) can react with benzyl alcohol and sodium hydride to form compound (7a) and compound (10a) under a $N_2$ atmosphere in an ice-water bath. After separation and purification of compound (7a) and compound (10a), compound (7a) and compound (10a) can respectively be converted to compound (8a) and compound (11a) by catalytic hydrogenation in the presence of 10% Pd/C under a $H_2$ atmosphere, and then compound (8a) and compound (11a) can respectively react with NIS to form compound (9a) and compound (12a) by iodination.

Synthesis of Intermediate (14a)

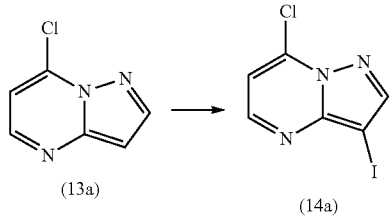 [SMILES: Clc1ccnc2ccnn12 ; Clc1ccnc2c(I)cnn12]

Compound (14a) can be prepared from compound (13a) by the following step. Compound (13a) can react with NIS to form compound (14a).

Synthesis of Intermediate (6b)

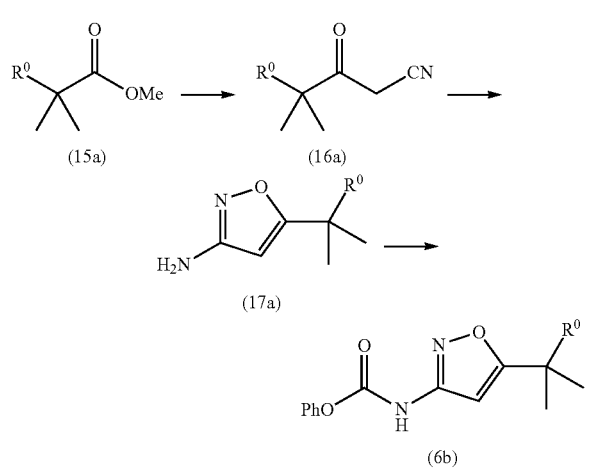

Compound (6b) can be prepared from compound (15a) by the following steps, and wherein each $R^0$ is as defined herein. Compound (15a) can be converted to compound (16a) in acetonitrile in the presence of a strong base. Compound (16a) can react with hydroxylamine hydrochloride to form compound (17a) by ring closing. Compound (17a) can react with phenyl chloroformate to form compound (6b).

Scheme 1 of synthesis of intermediate (5)

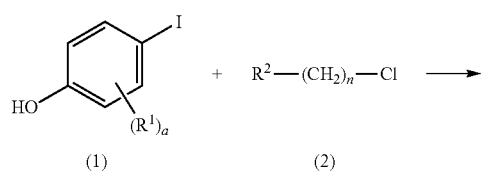

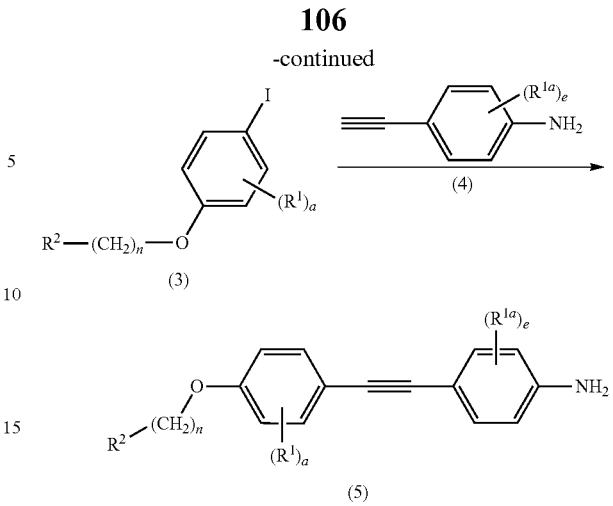

Compound (5) can be prepared by the process illustrated in Scheme 1 of synthesis of intermediate (5), and wherein, each a, e, $R^1$, $R^{1a}$, $R^2$ and n is as defined herein. Compound (1) can react with compound (2) to form compound (3) in the presence of a base. Compound (3) can react with compound (4) to form compound (5) in the presence of a catalyst.

Scheme 2 of synthesis of intermediate (5)

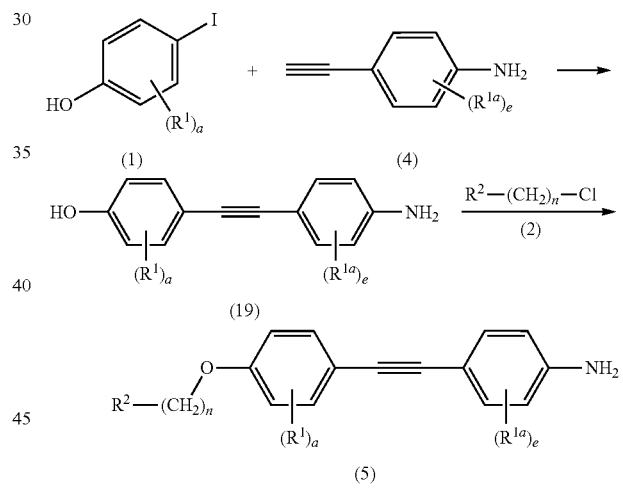

Compound (5) can be prepared by the process illustrated in Scheme 2 of synthesis of intermediate (5), and wherein, each a, e, $R^1$, $R^{1a}$, $R^2$ and n is as defined herein. Compound (1) can react with compound (4) to form compound (19) in the presence of a catalyst. Compound (19) can react with compound (2) to form compound (5) in the presence of a base.

Scheme 3 of synthesis of intermediate (5)

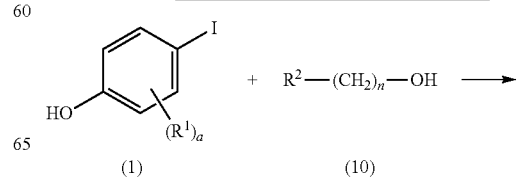

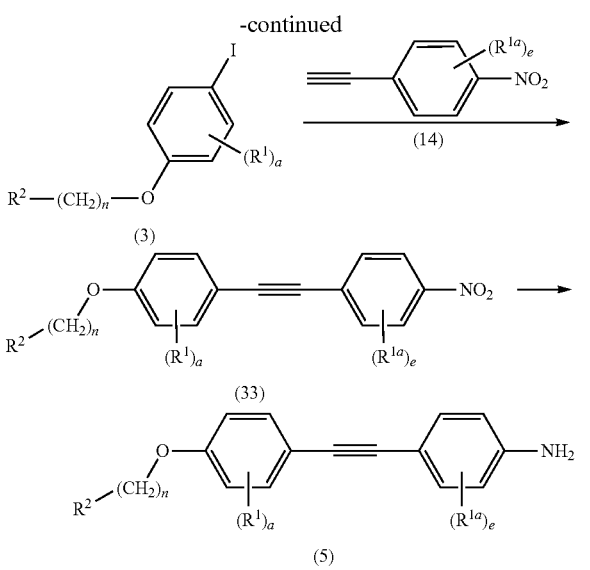

Compound (5) can be prepared by the process illustrated in Scheme 3 of synthesis of intermediate (5), and wherein, each a, e, $R^1$, $R^{1a}$, $R^2$ and n is as defined herein. Compound (1) can react with compound (10) to form compound (3) by Mitsunobu reaction. Compound (3) can react with compound (14) to form compound (33) in the presence of a catalyst. Then compound (33) can be reduced to form compound (5).

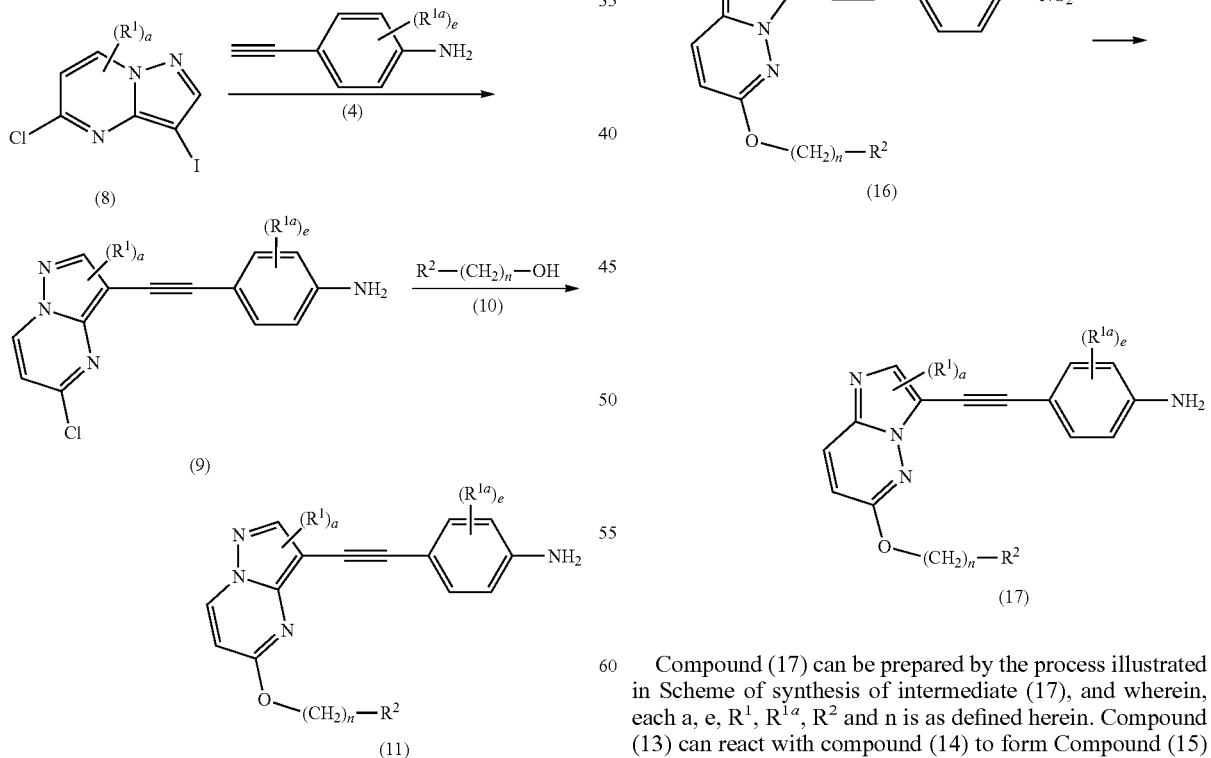

Compound (11) can be prepared by the process illustrated in Scheme of synthesis of intermediate (11), and wherein, each a, e, $R^1$, $R^{1a}$, $R^2$ and n is as defined herein. Compound (8) can react with compound (4) to form compound (9). Compound (9) can react with compound (10) to form compound (11) in the presence of a base.

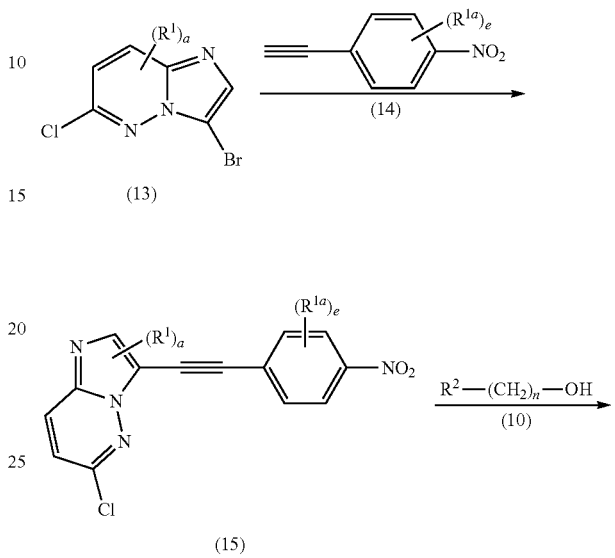

Compound (17) can be prepared by the process illustrated in Scheme of synthesis of intermediate (17), and wherein, each a, e, $R^1$, $R^{1a}$, $R^2$ and n is as defined herein. Compound (13) can react with compound (14) to form Compound (15) in the presence of a palladium catalyst. Compound (15) can react with compound (10) to form compound (16) in the presence of a base, and compound (16) can be reduced to form compound (17).

Scheme of synthesis of intermediate (23)

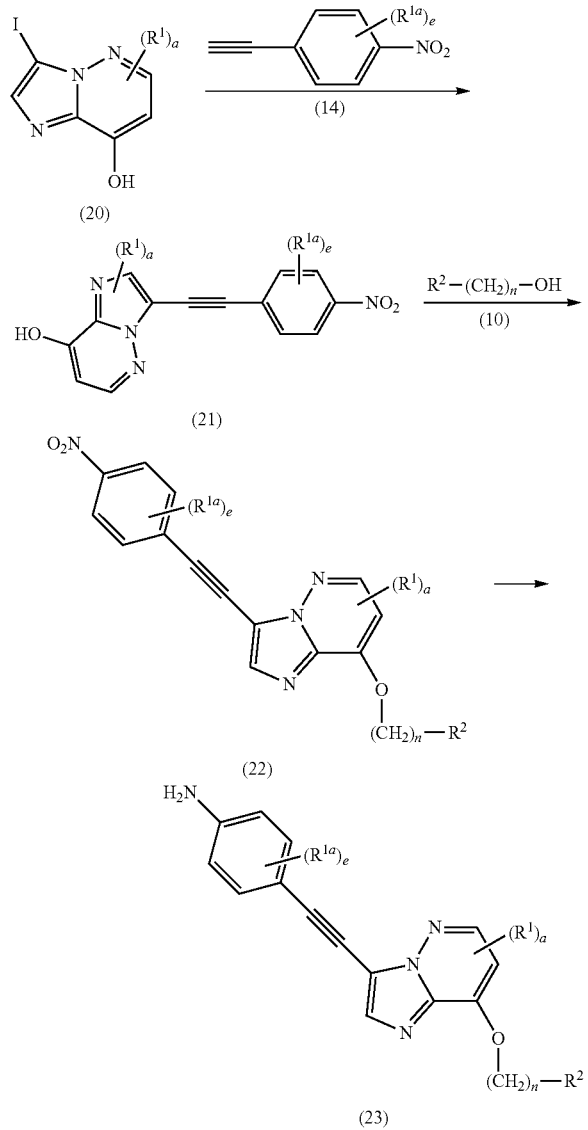

Compound (23) can be prepared by the process illustrated in Scheme of synthesis of intermediate (23), and wherein, each a, e, R¹, R¹ᵃ, R² and n is as defined herein. Compound (20) can react with compound (14) to form compound (21) in the presence of a catalyst. Compound (21) can react with compound (10) to form compound (22) in the presence of a base, and compound (22) can be reduced to form compound (23).

Scheme of synthesis of intermediate (27)

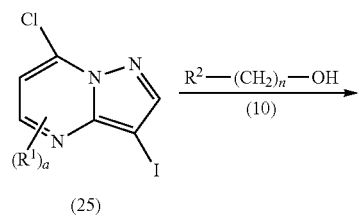

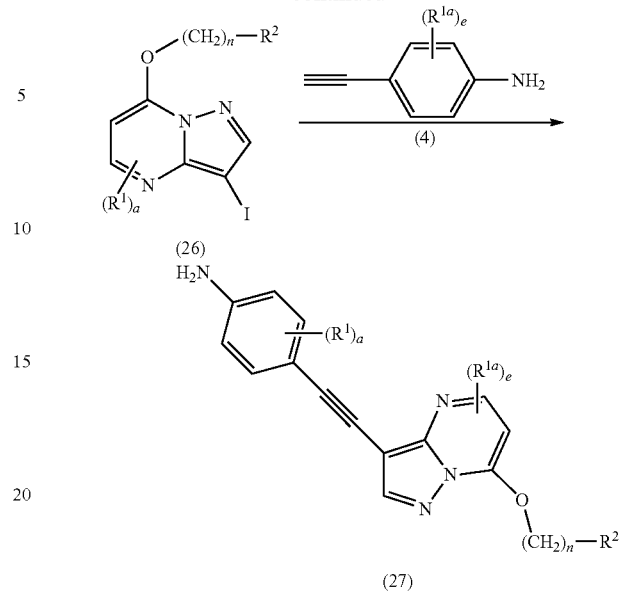

Compound (27) can be prepared by the process illustrated in Scheme of synthesis of intermediate (27), and wherein, each a, e, R¹, R¹ᵃ, R² and n is as defined herein. Compound (25) can react with compound (10) to form Compound (26) in the presence of a base. Compound (26) can react with compound (4) to form compound (27) in the presence of a catalyst.

Scheme of synthesis of intermediate (31)

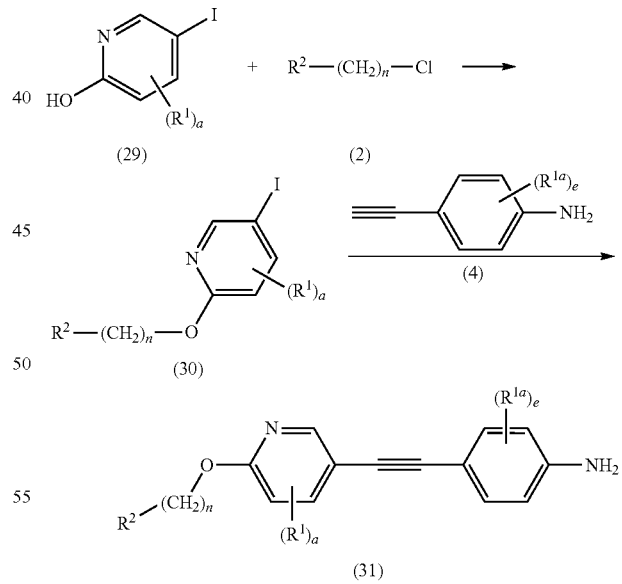

Compound (31) can be prepared by the process illustrated in Scheme of synthesis of intermediate (31), and wherein, each a, e, R¹, R¹ᵃ, R² and n is as defined herein. Compound (29) can react with compound (2) to form compound (30) in the presence of a base. Compound (30) can react with compound (4) to form compound (31) in the presence of a catalyst.

Scheme 1 of synthesis of intermediate (5b)

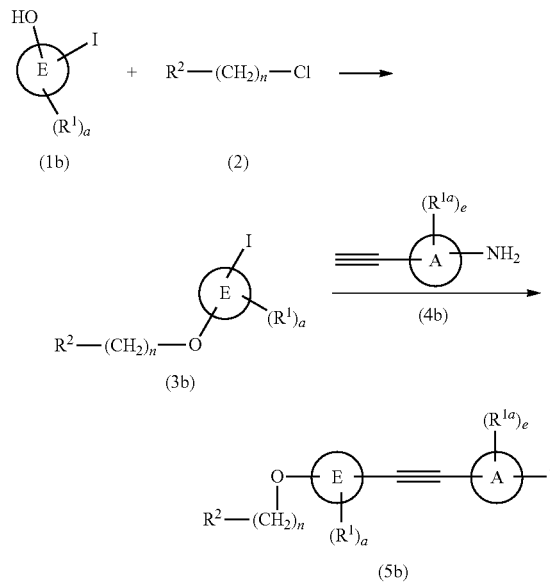

Compound (5b) can be prepared by the process illustrated in Scheme 1 of synthesis of intermediate (5b), and wherein, each ring E, ring A, a, e, $R^1$, $R^{1a}$, $R^2$ and n is as defined herein. Compound (1b) can react with compound (2) to form Compound (3b) in the presence of a base. Compound (3b) can react with compound (4b) to form compound (5b) in the presence of a catalyst.

Scheme 2 of synthesis of intermediate (5b)

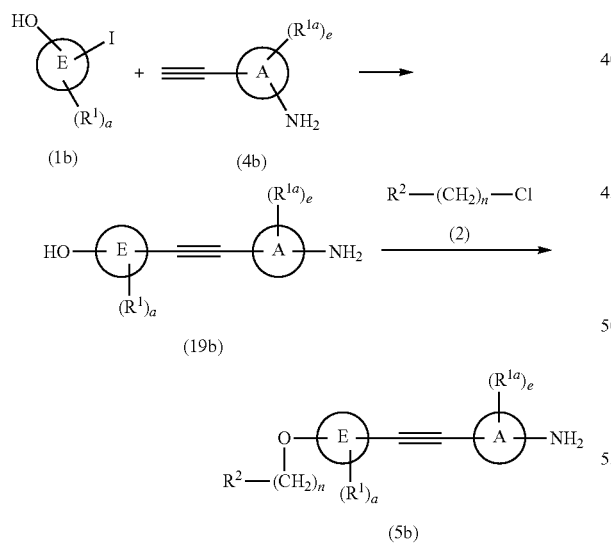

Compound (5b) can be prepared by the process illustrated in Scheme 2 of synthesis of intermediate (5b), and wherein, each ring E, ring A, a, e, $R^1$, $R^{1a}$, $R^2$ and n is as defined herein. Compound (1b) can react with compound (4b) to form compound (19b) in the presence of a catalyst. Compound (19b) can react with compound (2) to form compound (5b) in the presence of a base.

Scheme 3 of synthesis of intermediate (5b)

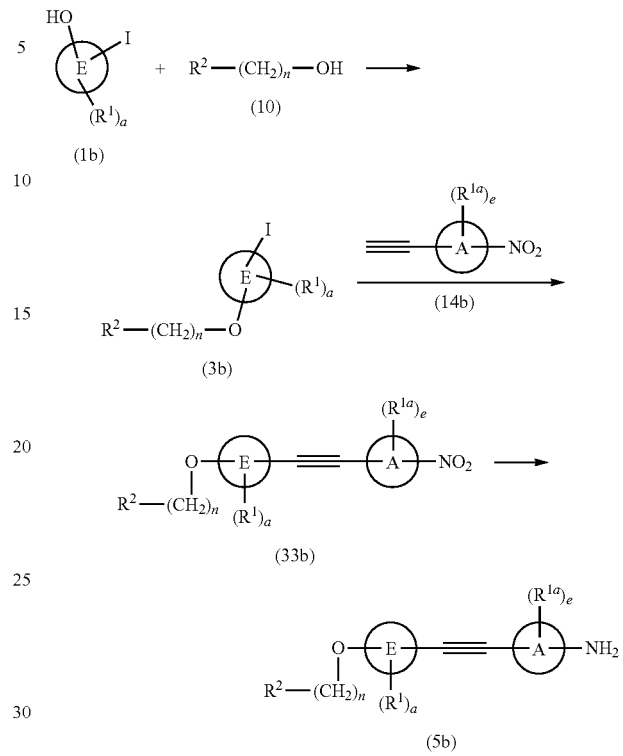

Compound (5b) can be prepared by the process illustrated in Scheme 3 of synthesis of intermediate (5b), and wherein, each ring E, ring A, a, e, $R^1$, $R^{1a}$, $R^2$ and n is as defined herein. Compound (1b) can react with compound (10) to form compound (3b) by Mitsunobu reaction. Compound (3b) can react with compound (14b) to form compound (33b) in the presence of a catalyst, and compound (33b) can be reduced to form compound (5b).

Scheme 4 of synthesis of intermediate (5b)

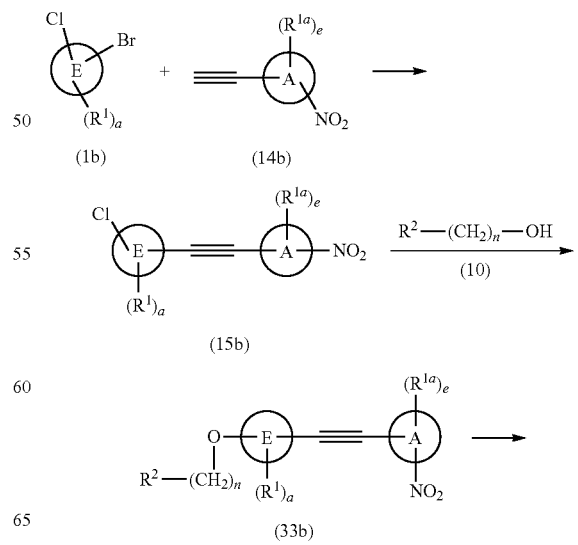

-continued

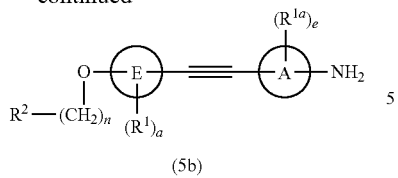

(5b)

Compound (5b) can be prepared by the process illustrated in Scheme 4 of synthesis of intermediate (5b), and wherein, each ring E, ring A, a, e, $R^1$, $R^{1a}$, $R^2$ and n is as defined herein. Compound (1b) can react with compound (14b) to form compound (15b) in the presence of a palladium catalyst. Compound (15b) can react with compound (10) to form compound (33b) in the presence of a base. Compound (33b) can be reduced to form compound (5b).

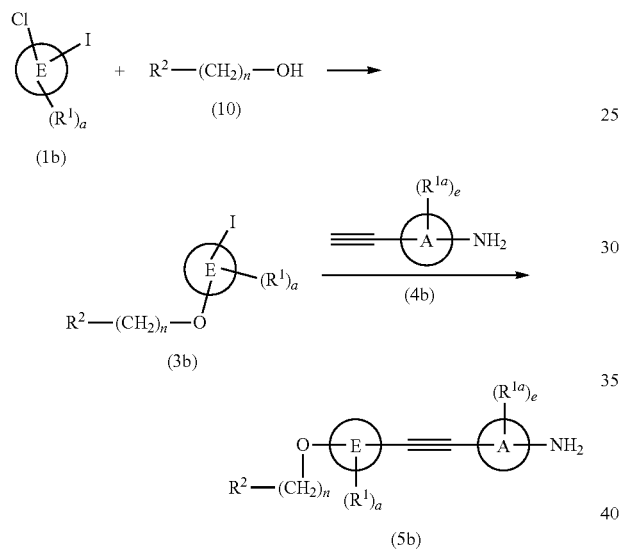

Compound (5b) can be prepared by the process illustrated in Scheme 5 of synthesis of intermediate (5b), and wherein, each ring E, ring A, a, e, $R^1$, $R^{1a}$, $R^2$ and n is as defined herein. Compound (1b) can react with compound (10) to form compound (3b) in the presence of a base. Compound (3b) can react with compound (4b) to form compound (5b) in the presence of a catalyst.

Scheme 6 of synthesis of intermediate (5b)

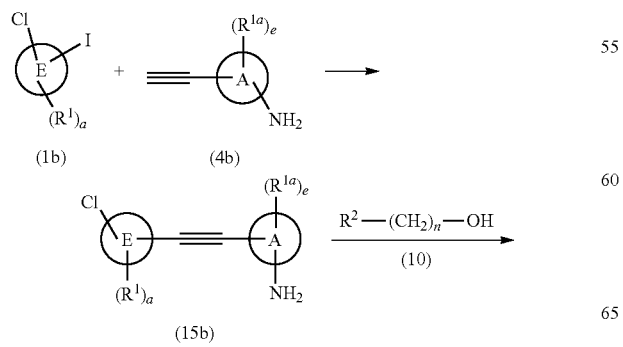

-continued

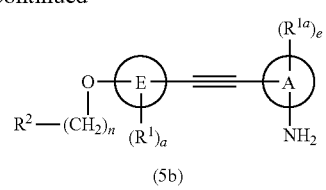

(5b)

Compound (5b) can be prepared by the process illustrated in Scheme 6 of synthesis of intermediate (5b), and wherein, each ring E, ring A, a, e, $R^1$, $R^{1a}$, $R^2$ and n is as defined herein. Compound (1b) can react with compound (4b) to form compound (15b) in the presence of a catalyst. Compound (15b) can react with compound (10) to form compound (5b) in the presence of a base.

Scheme 1

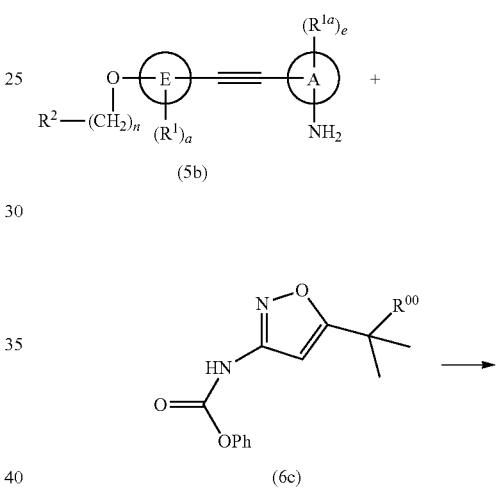

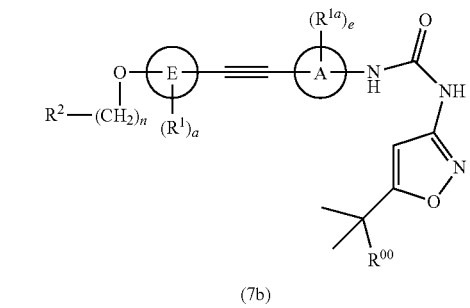

Compound (7b) can be prepared by the process illustrated in Scheme 1, and wherein, each $R^{00}$ is independently methyl or $R^0$, and each ring E, ring A, a, e, $R^1$, $R^{1a}$, $R^2$ and n is as defined herein. Compound (5b) can react with compound (6c) to form the objective compound (7b) in the presence of a base.

Scheme 2

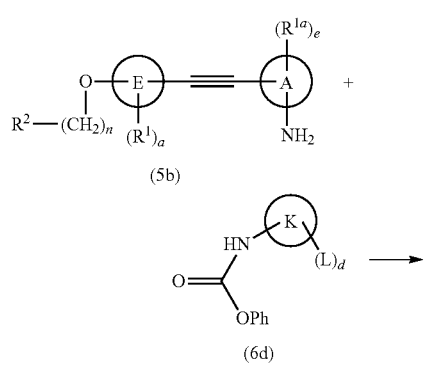

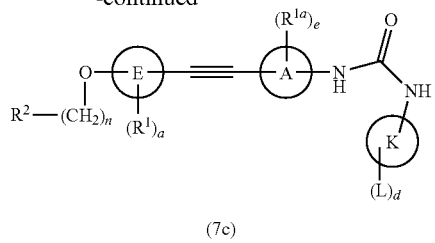

Compound (7c) can be prepared by the process illustrated in Scheme 2, and wherein, each L, n, ring K, ring E, ring A, a, e, $R^1$, $R^{1a}$, $R^2$ and n is as defined herein. Compound (5b) can react with compound (6d) to form the objective compound (7c) in the presence of a base.

Scheme 3

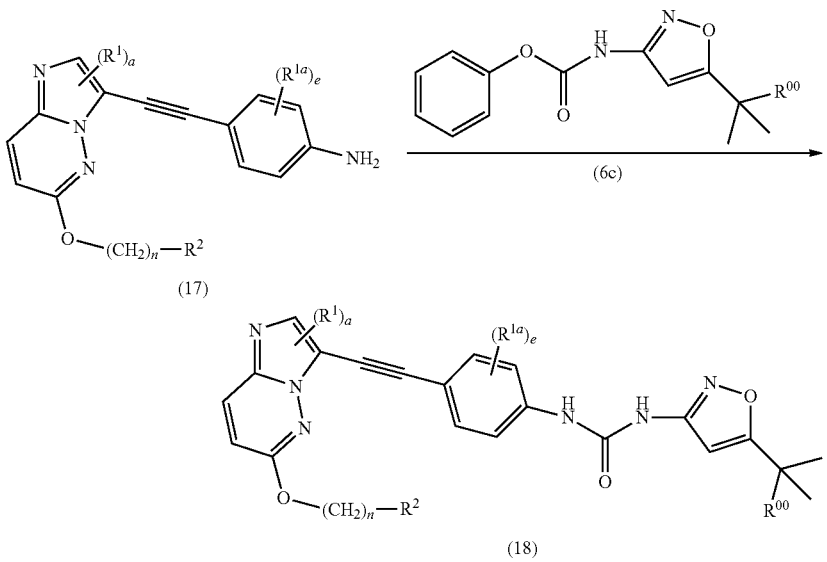

Compound (18) can be prepared by the process illustrated in Scheme 3, and wherein, each $R^0$ is independently methyl or $R^0$, and each $R^0$, a, e, $R^1$, $R^{1a}$, $R^2$ and n is as defined herein. Compound (17) can react with compound (6c) to form the objective compound (18) in the presence of a base.

Scheme 4

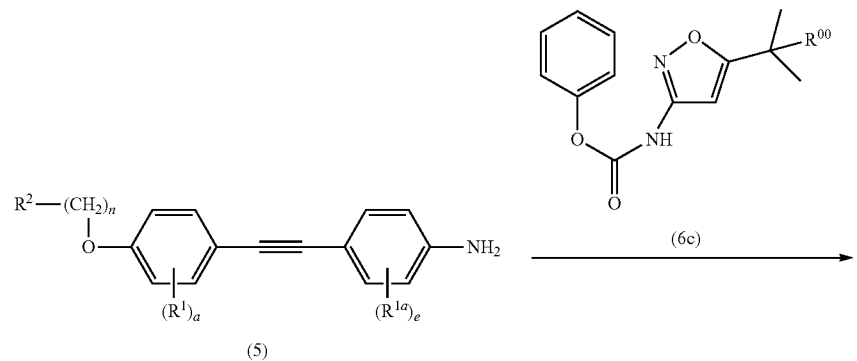

-continued
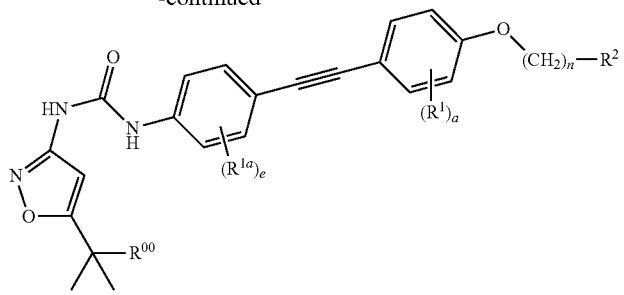
(7)
Compound (7) can be prepared by the process illustrated in Scheme 4, and wherein, each $R^{00}$ is independently methyl or $R^0$, and each $R^0$, a, e, $R^1$, $R^{1a}$, $R^2$ and n is as defined herein. Compound (5) can react with compound (6c) to form the objective compound (7) in the presence of a base.
Scheme 5
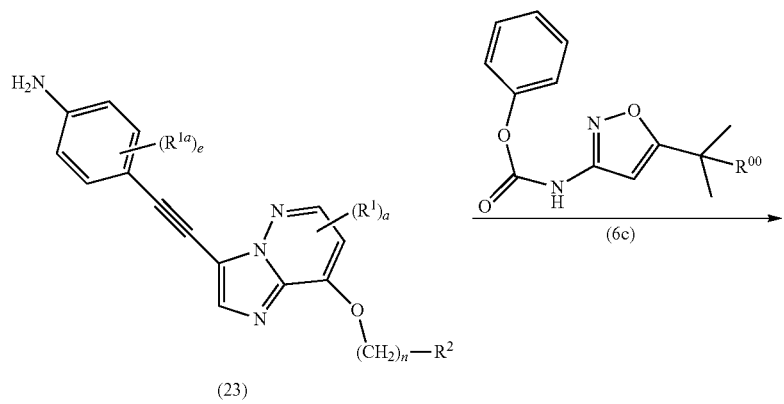
(23)          (6c)
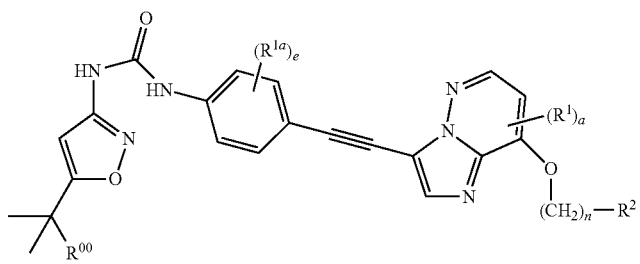
(24)

Compound (24) can be prepared by the process illustrated in Scheme 5, and wherein, each $R^{00}$ is independently methyl or $R^0$, and each $R^0$, a, e, $R^1$, $R^{1a}$, $R^2$ and n is as defined herein. Compound (23) can react with compound (6c) to form the objective compound (24) in the presence of a base.

Scheme 6

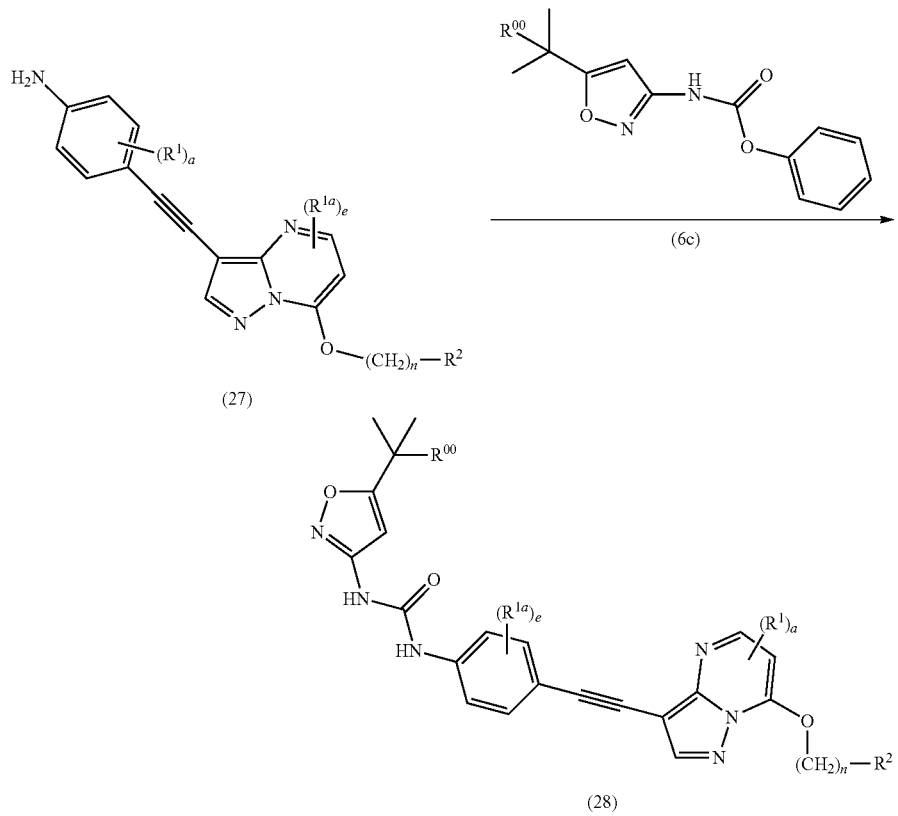

Compound (28) can be prepared by the process illustrated in Scheme 6, and wherein, each $R^{00}$ is independently methyl or $R^0$, and each $R^0$, a, e, $R^1$, $R^{1a}$, $R^2$ and n is as defined herein. Compound (27) can react with compound (6c) to form the objective compound (28) in the presence of a base.

Scheme 7

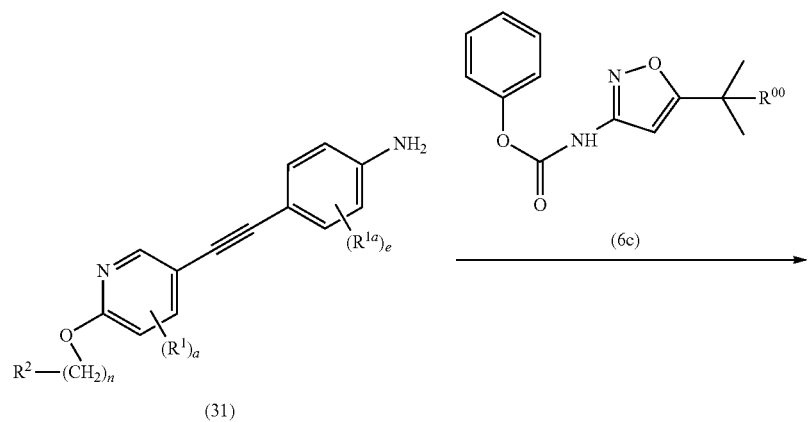

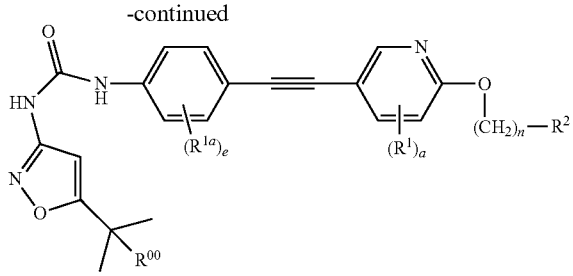

(32)

Compound (32) can be prepared by the process illustrated in Scheme 7, and wherein, each $R^{00}$ is independently methyl or $R^0$, and each $R^0$, a, e, $R^1$, $R^{1a}$, $R^2$ and n is as defined herein. Compound (31) can react with compound (6c) to form the objective compound (32) in the presence of a base.

Scheme 8

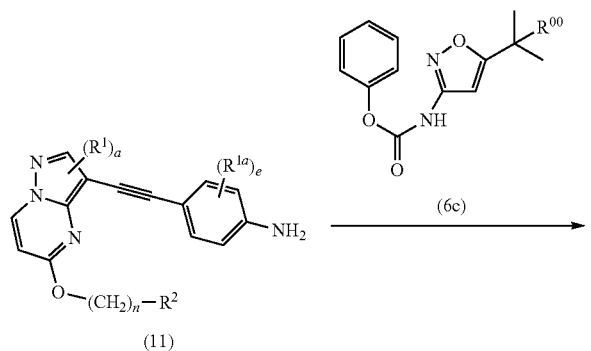

Compound (12) can be prepared by the process illustrated in Scheme 8, and wherein, each $R^{00}$ is independently methyl or $R^0$, and each $R^0$, a, e, $R^1$, $R^{1a}$, $R^2$ and n is as defined herein. Compound (11) can react with compound (6c) to form the objective compound (12) in the presence of a base.

Scheme 9

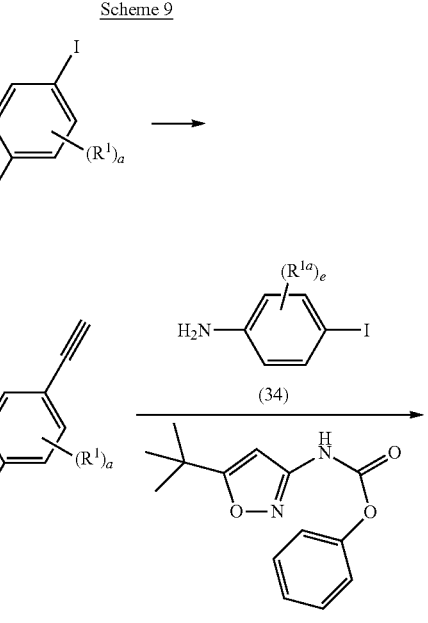

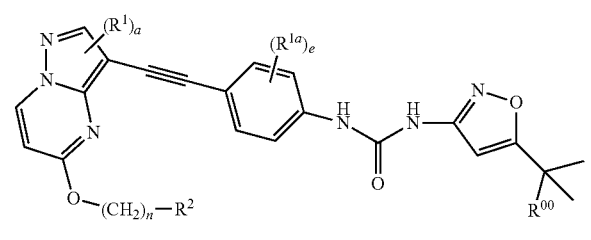

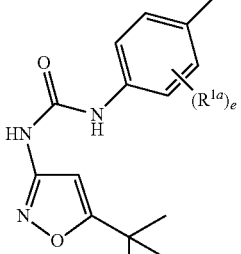

Compound (7) can be prepared by the process illustrated in Scheme 9, and wherein, each a, e, $R^1$, $R^{1a}$, $R^2$ and n is as defined herein. Compound (3) can react with acetonitrile in the presence of a catalyst to form compound (35). Compound (34) can react with compound (35) and compound (6) to form the objective compound (7) by one-pot reaction.

methyl or $R^0$, and each a, e, $R^0$, $R^1$, $R^{1a}$, $R^2$ and n is as defined herein. Compound (5) can react with compound (6c) to form the the objective compound (7a) in the presence of a base.

Scheme 10

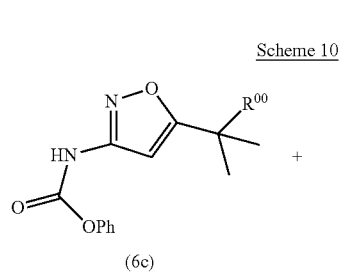

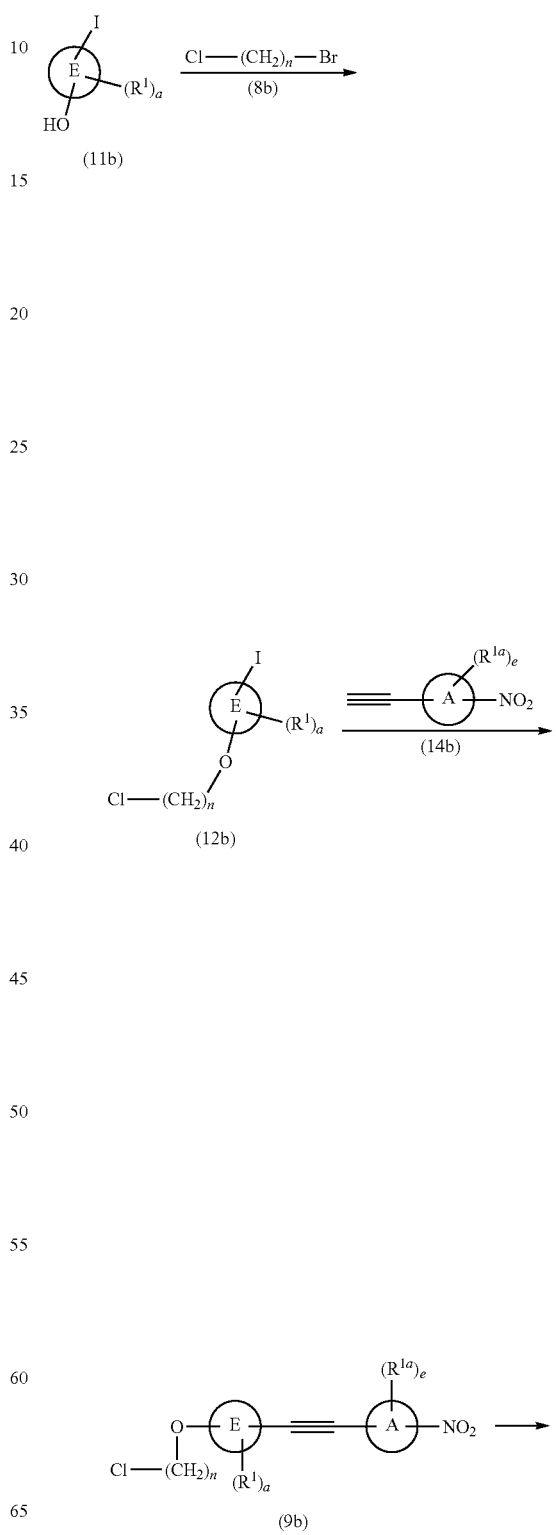

Compound (7a) can be prepared by the process illustrated in Scheme 10, and wherein, each $R^{00}$ is independently -continued

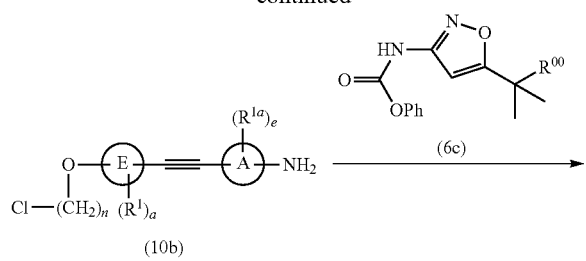

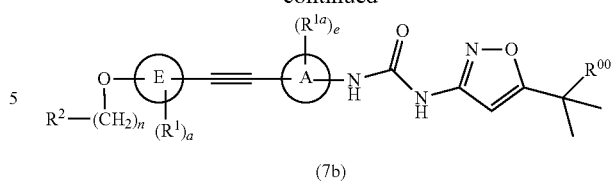

Compound (7b) can be prepared by the process illustrated in Scheme 11, and wherein, each $R^{oo}$ is independently methyl or $R^o$, and each $R^o$, ring E, ring A, a, e, $R^1$, $R^{1a}$, $R^2$ and n is as defined herein. Compound (11b) can react with compound (8b) to form compound (12b) in the presence of a base. Compound (12b) can react with compound (14b) to form compound (9b) in the presence of a catalyst. Compound (9b) can be reduced to form compound (10b). Compound (10b) can react with compound (6c) to form compound (11b) in the presence of a base. Compound (11b) can react with acetonitrile to form the the objective compound (7a) by ring closing in the presence of a base (the base can be but not limited to potassium carbonate).

The objective compounds of schemes 1 to 11 described herein can be oxidated to form the N-oxides thereof.

The following examples are presented to further illustrate the invention. However, these examples should not be used to limit the scope of the invention.

EXAMPLES

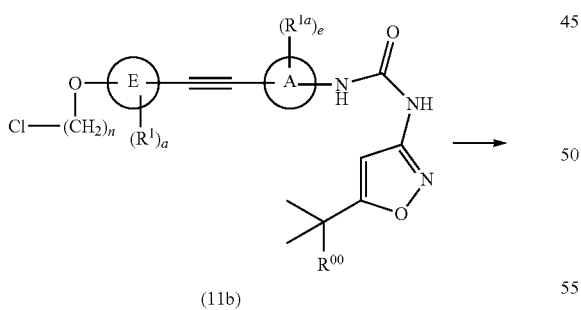

Example 1

1-(5-(tert-Butyl)isoxazol-3-yl)-3-(4-((3-fluoro-4-(3-morpholinopropoxy)phenyl)ethynyl)phenyl)urea

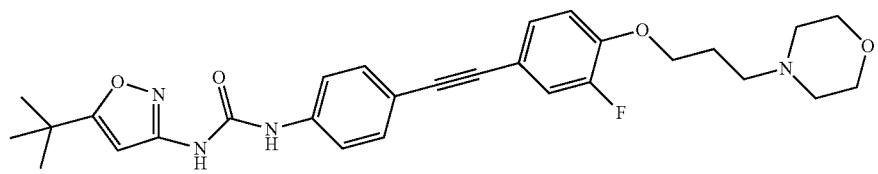 [SMILES: CC(C)(C)c1cc(NC(=O)Nc2ccc(C#Cc3ccc(OCCCN4CCOCC4)c(F)c3)cc2)no1]

Step 1)
4-(3-(2-fluoro-4-iodophenoxy)propyl)morpholine

To a 250 mL one-neck flask were added 2-fluoro-4-iodophenol (5.0 g, 21.0 mmol), 3-chloropropyl morpholine (3.42 g, 20.97 mmol) and acetonitrile (80 mL) in turn, and then potassium carbonate (4.34 g, 31.45 mmol) was added with stirring. After the addition, the reaction mixture was refluxed for 5 hours. The reaction was monitored by TLC until the raw material was consumed completely, and then the reaction mixture was cooled to rt. The resulting mixture was filtered to remove solid and the filtrate was concentrated in vacuo. The residue was dissolved in dichloromethane (80 mL). The organic phase was washed once with saturated aqueous sodium bicarbonate solution (50 mL) and then once with water (50 mL), dried over anhydrous $Na_2SO_4$, filtered. The filtrate was concentrated in vacuo and the residue was purified by silica gel column chromatography (EtOAc/PE (v/v)=2/1) to give the title compound as an off-white solid (5.4 g, 70.4%). The compound was characterized by the following spectroscopic data: MS-ESI: (ESI, pos.ion) m/z: 366.0 $[M+1]^+$.

Step 2) 4-((3-fluoro-4-(3-morpholinopropoxy)phenyl)ethynyl)aniline

To a mixture of 4-(3-(2-fluoro-4-iodophenoxy)propyl) morpholine (1.5 g, 4.11 mmol) in THF (40 mL) were added 4-ethynylaniline (0.96 g, 8.2 mmol), triethylamine (30 mL), $PdCl_2(PPh_3)_2$ (0.12 g, 0.17 mmol) and CuI (32 mg, 0.17 mmol) with stirring in turn. After the addition, the reaction mixture was stirred at rt overnight under a $N_2$ atmosphere. The reaction was monitored by TLC until the raw material was consumed completely, and then the the mixture was filtered. The filter cake was washed with a little THF and the combined filtrates were concentrated in vacuo. The residue was dissolved in dichloromethane (300 mL), and then the mixture was washed once with saturated aqueous sodium bicarbonate solution (100 mL) and once with water (100 mL), and then dried, filtered. The filtrated was concentrated in vacuo. The residue was purified by silica gel column chromatography (EtOAc/PE (v/v)=2/1) to give the title compound as a light yellow solid (1.0 g, 68.7%). The compound was characterized by the following spectroscopic data: MS-ESI: (ESI, pos.ion) m/z: 355.2 $[M+1]^+$.

Step 3) 1-(5-(tert-butyl)isoxazol-3-yl)-3-(4-((3-fluoro-4-(3-morpholinopropoxy)phenyl)ethynyl)phenyl)urea To a mixture of 4-((3-fluoro-4-(3-morpholinopropoxy) phenyl)ethynyl)aniline (0.7 g, 1.98 mmol) in dichloromethane (50 mL) were added phenyl (5-(tert-butyl)isoxazol-3-yl)carbamate (1.29 g, 4.96 mmol) and DMAP (60 mg, 0.49 mmol) with stirring in turn, and then a mixture of triethylamine (0.13 mL, 0.93 mmol) and dichloromethane (2 mL) was added. After the addition, the reaction mixture was refluxed at 45° C. overnight. After the reaction monitored by TLC was completed, the reaction mixture was cooled to rt and the organic phase was washed washed with water (10 mL×1) and saturated aqueous sodium chloride solution (10 mL×1) in turn, and then dried over anhydrous sodium sulfate, filtered. The filtrated was concentrated in vacuo. The residue was purified by silica gel column chromatography ($CH_2Cl_2$/MeOH (v/v)=25/1) to give the title compound as a light yellow solid (468 mg, 45.8%). The compound was characterized by the following spectroscopic data: MS-ESI: (ESI, pos.ion) m/z: 521.2 $[M+1]^+$; and $^1$H NMR (600 MHz, $CDCl_3$) δ: 7.54 (d, J=8.6 Hz, 2H), 7.49 (d, J=8.6 Hz, 2H), 7.25 (dd, J=8.5 Hz, 1.4 Hz, 1H), 7.23 (d, J=1.4 Hz, 1H), 6.93 (d, J=8.5 Hz, 1H), 6.04 (s, 1H), 4.14 (t, J=6.3 Hz, 2H), 3.79 (t, J=4.8 Hz, 4H), 2.63 (m, 6H), 2.08 (m, 2H), 1.38 (s, 9H).

Example 2

1-(5-(tert-Butyl)isoxazol-3-yl)-3-(4-((3-chloro-4-(3-morpholinopropoxy)phenyl)ethynyl) phenyl) urea

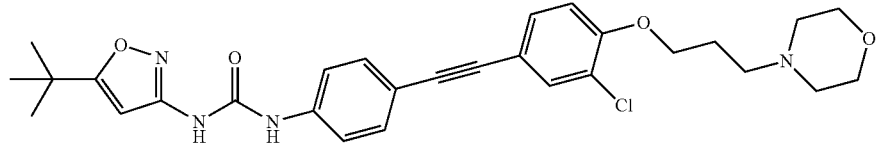

Step 1)
4-(3-(2-chloro-4-iodophenoxy)propyl)morpholine

The title compound was prepared as an off-white solid (2.46 g, 82%) by the procedure described in step 1 of example 1, using 2-chloro-4-iodophenol (2.0 g, 7.88 mmol), 3-chloropropyl morpholine (1.41 g, 8.65 mmol) and potassium carbonate (1.63 g, 11.81 mmol). The compound was characterized by the following spectroscopic data: MS-ESI: (ESI, pos.ion) m/z: 382.0 $[M+1]^+$.

Step 2) 4-((3-chloro-4-(3-morpholinopropoxy)phenyl)ethynyl)aniline

The title compound was prepared as a light yellow solid (1.49 g, 76.8%) by the procedure described in step 2 of example 1, using 4-(3-(2-chloro-4-iodophenoxy)propyl) morpholine (2.0 g, 5.25 mmol), 4-ethynylaniline (1.23 g, 10.51 mmol), triethylamine (3.5 mL), $PdCl_2(PPh_3)_2$ (0.15 g, 0.22 mmol) and CuI (0.04 g, 0.21 mmol). The compound was characterized by the following spectroscopic data: MS-ESI: (ESI, pos.ion) m/z: 371.2 $[M+1]^+$.

Step 3) 1-(5-(tert-butyl)isoxazol-3-yl)-3-(4-((3-chloro-4-(3-morpholinopropoxy)phenyl)ethynyl) phenyl)urea The title compound was prepared as a light yellow solid (146 mg, 14.5%) by the procedure described in step 3 of example 1, using 4-((3-chloro-4-(3-morpholinopropoxy) phenyl)ethynyl)aniline (0.7 g, 1.89 mmol), phenyl (5-(tert-butyl)isoxazol-3-yl)carbamate (1.23 g, 4.73 mmol), DMAP (30 mg, 0.25 mmol) and triethylamine (0.1 mL, 0.72 mmol).

The compound was characterized by the following spectroscopic data: MS-ESI: (ESI, pos.ion) m/z: 537.2 [M+1]$^{+1}$; and $^1$H NMR (600 MHz, CDCl$_3$) δ: 7.53 (d, J=8.4 Hz, 2H), 7.47 (d, J=8.4 Hz, 2H), 7.35 (dd, J=8.5, 1.7 Hz, 1H), 7.15 (s, 1H), 6.86 (d, J=8.5 Hz, 1H), 6.07 (s, 1H), 4.15 (t, J=6.0 Hz, 2H), 3.87 (t, J=4.2 Hz, 4H), 2.79 (m, 6H), 2.17 (m, 2H), 1.37 (s, 9H).

Example 3

1-(5-(tert-Butyl)isoxazol-3-yl)-3-(4-((4-(3-morpholinopropoxy)-3-(trifluoromethyl)phenyl) ethynyl) phenyl)urea

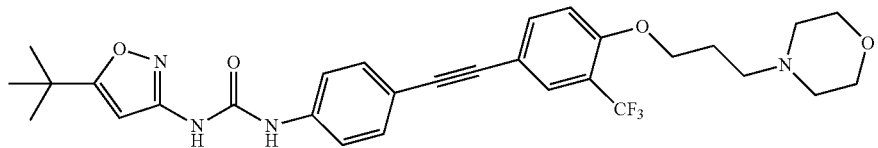 [SMILES: CC(C)(C)c1cc(NC(=O)Nc2ccc(C#Cc3ccc(OCCCN4CCOCC4)c(C(F)(F)F)c3)cc2)no1]

Step 1) 4-(3-(4-iodo-2-(trifluoromethyl)phenoxy) propyl)morpholine

The title compound was prepared as brown oil (3.1 g, 71.76%) by the procedure described in step 1 of example 1, using 2-trifluoromethyl-4-iodophenol (3.0 g, 10.41 mmol), 3-chloropropyl morpholine (1.64 g, 10.02 mmol) and potassium carbonate (2.15 g, 15.55 mmol). The compound was characterized by the following spectroscopic data: MS-ESI: (ESI, pos.ion) m/z: 416.1 [M+1]$^+$.

Step 2) 4-((4-(3-morpholinopropoxy)-3-(trifluoromethyl)phenyl)ethynyl)aniline The title compound was prepared as a yellow solid (1.9 g, 75.04%) by the procedure described in step 2 of example 1, using 4-(3-(2-trifluoromethyl-4-iodophenoxy)propyl)morpholine (2.6 g, 6.26 mmol), 4-ethynylaniline (1.47 g, 12.55 mmol), triethylamine (50 mL), PdCl$_2$(PPh$_3$)$_2$ (0.18 g, 0.26 mmol) and CuI (48 mg, 0.25 mmol). The compound was characterized by the following spectroscopic data: MS-ESI: (ESI, pos.ion) m/z: 405.2 [M+1]$^+$.

Step 3) 1-(5-(tert-butyl)isoxazol-3-yl)-3-(4-((4-(3-morpholinopropoxy)-3-(trifluoromethyl) phenyl) ethynyl)phenyl)urea The title compound was prepared as a light yellow solid (302 mg, 22.5%) by the procedure described in step 3 of example 1, using 4-((3-trifluoromethyl-4-(3-morpholinopropoxy)phenyl)ethynyl)aniline (0.95 g, 2.35 mmol), phenyl (5-(tert-butyl)isoxazol-3-yl)carbamate (1.53 g, 5.88 mmol), DMAP (0.29 g, 2.37 mmol) and triethylamine (0.33 mL, 2.37 mmol). The compound was characterized by the following spectroscopic data: MS-ESI: (ESI, pos.ion) m/z: 571.2 [M+1]$^+$; and $^1$H NMR (400 MHz, CDCl$_3$) δ: 7.74 (d, J=1.6 Hz, 1H), 7.61 (dd, J=8.8, 1.6 Hz, 1H), 7.55 (d, J=8.7 Hz, 2H), 7.49 (d, J=8.7 Hz, 2H), 6.97 (d, J=8.8 Hz, 1H), 6.03 (s, 1H), 4.16 (t, J=6.0 Hz, 2H), 3.77 (m, 4H), 2.61 (m, 6H), 2.07 (m, 2H), 1.38 (s, 9H).

Example 4

1-(5-(tert-Butyl)isoxazol-3-yl)-3-(4-((2-fluoro-4-(3-morpholinopropoxy)phenyl)ethynyl)phenyl) urea

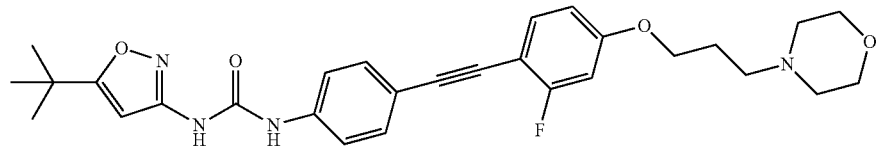 [SMILES: CC(C)(C)c1cc(NC(=O)Nc2ccc(C#Cc3ccc(OCCCN4CCOCC4)cc3F)cc2)no1]

Step 1) 4-(3-(3-fluoro-4-iodophenoxy)propyl)morpholine

The title compound was prepared as brown oil (4.0 g, 65.19%) by the procedure described in step 1 of example 1, using 3-fluoro-4-iodophenol (4.0 g, 16.80 mmol), 3-chloropropyl morpholine (2.74 g, 16.81 mmol) and potassium carbonate (3.48 g, 25.21 mmol). The compound was characterized by the following spectroscopic data: MS-ESI: (ESI, pos.ion) m/z: 366.0 [M+1]$^+$.

Step 2) 4-((2-fluoro-4-(3-morpholinopropoxy)phenyl)ethynyl)aniline

The title compound was prepared as a yellow solid (2.56 g, 77.57%) by the procedure described in step 2 of example 1, using 4-(3-(3-fluoro-4-iodophenoxy)propyl)morpholine (3.4 g, 9.31 mmol), 4-ethynylaniline (2.18 g, 18.63 mmol), triethylamine (40 mL), PdCl$_2$(PPh$_3$)$_2$ (0.26 g, 0.37 mmol) and CuI (71 mg, 0.37 mmol). The compound was characterized by the following spectroscopic data: MS-ESI: (ESI, pos.ion) m/z: 355.2 [M+1]$^+$.

Step 3) 1-(5-(tert-butyl)isoxazol-3-yl)-3-(4-((2-fluoro-4-(3-morpholinopropoxy)phenyl) ethynyl) phenyl)urea The title compound was prepared as a white solid (210 mg, 17.87%) by the procedure described in step 3 of example 1, using 4-((2-fluoro-4-(3-morpholinopropoxy) phenyl)ethynyl)aniline (800 mg, 2.26 mmol), phenyl (5-(tert-butyl)isoxazol-3-yl)carbamate (1.46 g, 5.61 mmol), DMAP (0.27 g, 2.21 mmol) and triethylamine (0.23 g, 2.27 mmol). The compound was characterized by the following spectroscopic data: MS-ESI: (ESI, pos.ion) m/z: 521.2 [M+1]$^+$; and $^1$H NMR (400 MHz, CDCl$_3$) δ: 7.55 (d, J=8.8 Hz, 2H), 7.51 (d, J=8.8 Hz, 2H), 7.41 (t, J=8.4 Hz, 1H), 6.67 (d, J=9.7 Hz, 2H), 5.98 (s, 1H), 4.06 (t, J=6.2 Hz, 2H), 3.81 (s, 4H), 2.63 (m, 6H), 2.07 (m, 2H), 1.38 (s, 9H).

Example 5

1-(5-(tert-Butyl)isoxazol-3-yl)-3-(4-((2-chloro-4-(3-morpholinopropoxy)phenyl)ethynyl) phenyl)urea

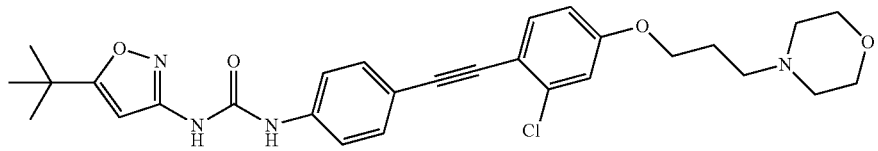 [SMILES: CC(C)(C)c1cc(NC(=O)Nc2ccc(C#Cc3ccc(OCCCN4CCOCC4)cc3Cl)cc2)no1]

Step 1) 4-(3-(3-chloro-4-iodophenoxy)propyl)morpholine

The title compound was prepared as a light yellow solid (3.6 g, 89%) by the procedure described in step 1 of example 1, using 3-chloro-4-iodophenol (2.7 g, 10.63 mmol), 3-chloropropyl morpholine (1.73 g, 10.61 mmol) and potassium carbonate (2.20 g, 15.94 mmol). The compound was characterized by the following spectroscopic data: MS-ESI: (ESI, pos.ion) m/z: 382.0 [M+1]$^+$.

Step 2) 4-((2-chloro-4-(3-morpholinopropoxy)phenyl)ethynyl)aniline

The title compound was prepared as a brown solid (700 mg, 27%) by the procedure described in step 2 of example 1, using 4-(3-(3-chloro-4-iodophenoxy)propyl)morpholine (2.65 g, 6.95 mmol), 4-ethynylaniline (1.62 g, 13.84 mmol), triethylamine (40 mL), PdCl$_2$(PPh$_3$)$_2$ (0.20 g, 0.285 mmol) and CuI (53 mg, 0.28 mmol). The compound was characterized by the following spectroscopic data: MS-ESI: (ESI, pos.ion) m/z: 371.2 [M+1]$^+$.

Step 3) 1-(5-(tert-butyl)isoxazol-3-yl)-3-(4-((2-chloro-4-(3-morpholinopropoxy)phenyl)ethynyl)phenyl)urea The title compound was prepared as a light yellow solid (369 mg, 36.9%) by the procedure described in step 3 of example 1, using 4-((2-chloro-4-(3-morpholinopropoxy)phenyl)ethynyl)aniline (690 mg, 1.86 mmol), phenyl (5-(tert-butyl)isoxazol-3-yl)carbamate (1.21 g, 4.65 mmol), DMAP (0.23 g, 1.88 mmol) and triethylamine (0.26 mL, 1.87 mmol). The compound was characterized by the following spectroscopic data: MS-ESI: (ESI, pos.ion) m/z: 537.2 [M+1]$^+$; and $^1$H NMR (400 MHz, CDCl$_3$) δ: 7.54 (d, J=8.2 Hz, 2H), 7.49 (d, J=8.2 Hz, 2H), 7.39 (d, J=8.0 Hz, 1H), 6.93 (m, 2H), 6.03 (s, 1H), 4.13 (t, J=6.1 Hz, 2H), 3.77 (t, J=4.4 Hz, 4H), 2.68 (m, 6H), 2.12 (m, 2H), 1.37 (s, 9H).

Example 6

1-(5-(tert-Butyl)isoxazol-3-yl)-3-(4-((5-(3-morpholinopropoxy)pyrazolo[1,5-a]pyrimidin-3-yl)ethynyl)phenyl)urea

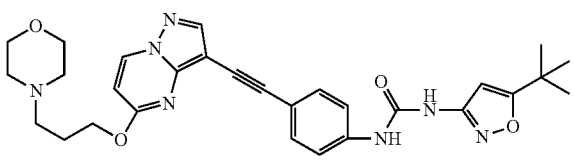 [SMILES: CC(C)(C)c1cc(NC(=O)Nc2ccc(C#Cc3cnn4ccc(OCCCN5CCOCC5)nc34)cc2)no1]

Step 1) 4-((5-chloropyrazolo[1,5-a]pyrimidin-3-yl)ethynyl)aniline

To a mixture of 5-chloro-3-iodopyrazolo[1,5-a]pyrimidine (2.5 g, 8.95 mmol) in THF (70 mL) were added 4-ethynylaniline (2.62 g, 22.4 mmol), Et$_3$N (40 mL), PdCl$_2$(PPh$_3$)$_2$ (650 mg, 0.9 mmol) and CuI (350 mg, 1.8 mmol) with stirring in turn. After the addition, the reation mixture was stirred at rt under a N$_2$ atmosphere. After the reaction monitored by TLC was completed, the resulting mixture was filtered through a Celite pad, and the filter cake was washed with a little THF. The combined filtrates were concentrated in vacuo and the residue was purified by silica gel column chromatography (PE/EtOAc (v/v)=3/2) to give the title compound as a claybank solid (1.98 g, 82.4%). The compound was characterized by the following spectroscopic data: MS-ESI: (ESI, pos.ion) m/z: 269.0 [M+1]$^+$.

Step 2) 4-((5-(3-morpholinopropoxy)pyrazolo[1,5-a]pyrimidin-3-yl)ethynyl)aniline To a mixture of 4-((5-chloropyrazolo[1,5-a]pyrimidin-3-yl)ethynyl)aniline (1.47 g, 5.47 mmol) and N-hydroxypropyl morpholine (1.52 g, 8.15 mmol) in DMF (50 mL) was added cesium carbonate (3.6 g, 10.9 mmol) with stirring. After the addition, the reaction mixture was stirred at 80° C. overnight. The next day, the reaction monitored by TLC was not completed, then to the mixture were added N-hydroxypropyl morpholine (1.0 g) and cesium carbonate (1.5 g), and then the mixture was heated to 90° C. and stirred for 6 hours. Until the raw material was consumed completely, the reaction mixture was cooled to rt, and water (100 mL) and ethyl acetate (200 mL) were added. The organic phase was washed with water (50 mL) and saturated aqueous sodium chloride solution (50 mL) in turn, dried, filtered, and the filtrated was concentrated. The residue was purified by silica gel column chromatography (CH$_2$Cl$_2$/MeOH (v/v)=20/1) to give the title compound as claybank oil (0.42 g, 20%). The compound was characterized by the following spectroscopic data: MS-ESI: (ESI, pos.ion) m/z: 378.1 [M+1]$^+$.

Step 3) 1-(5-(tert-butyl)isoxazol-3-yl)-3-(4-((5-(3-morpholinopropoxy)pyrazolo[1,5-a]pyrimidin-3-yl)ethynyl)phenyl)urea The title compound was prepared as an off-white solid (90 mg, 30%) by the procedure described in step 3 of example 1, using 4-((5-(3-morpholinopropoxy)pyrazolo[1,5-a]pyrimidin-3-yl)ethynyl)aniline (0.21 g, 0.56 mmol) and phenyl (5-(tert-butyl)isoxazol-3-yl)carbamate (0.43 g, 1.6 mmol), DMAP (30 mg, 0.2 mmol) and triethylamine (83 mg, 0.77 mmol). The compound was characterized by the following spectroscopic data: MS-ESI: (ESI, pos.ion) m/z: 544.2 [M+1]$^+$; and $^1$H NMR (400 MHz, CDCl$_3$) δ: 8.41 (d, J=7.2 Hz, 1H), 8.12 (s, 1H), 7.57 (d, J=8.9 Hz, 2H), 7.53 (d, J=8.9 Hz, 2H), 6.37 (d, J=7.2 Hz, 1H), 6.04 (s, 1H), 4.58 (t, J=6.4 Hz, 2H), 3.87 (m, 4H), 2.72 (m, 6H), 2.11 (m, 2H), 1.37 (s, 9H).

Example 7

1-(5-(tert-Butyl)isoxazol-3-yl)-3-(4-((6-(3-morpholinopropoxy)imidazo[1,2-b]pyridazin-3-yl) ethynyl)phenyl)urea

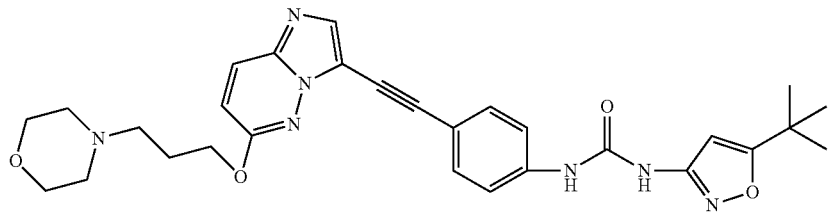 [SMILES: CC(C)(C)c1cc(NC(=O)Nc2ccc(C#Cc3cnc4ccc(OCCCN5CCOCC5)nn34)cc2)no1]

Step 1) 6-chloro-3-((4-nitrophenyl)ethynyl)imidazo[1,2-b]pyridazine

To a 250 mL one-neck flask were added 3-bromo-6-chloroimidazo[1,2-b]pyridazine (3.0 g, 13.0 mmol) and triethylamine (90 mL), and then 4-nitrophenylacetylene (2.29 g, 15.58 mmol), $PdCl_2(PPh_3)_2$ (912 mg, 1.30 mmol), CuI (494 mg, 2.6 mmol) and $PPh_3$ (680 mg, 2.60 mmol) were added with stirring at rt in turn. After the addition, the reaction mixture was refluxed at 95° C. overnight. After the reaction monitored by TLC was completed, the resulting mixture was filtered through a Celite pad, and the filter cake was washed with a little THF. The combined filtrates were concentrated in vacuo and the residue was purified by silica gel column chromatography (PE/EtOAc (v/v)=1/1) to give the title compound as a yellow solid (2.7 g, 70.13%). The compound was characterized by the following spectroscopic data: MS-ESI: (ESI, pos.ion) m/z: 299.1 [M+1]$^+$.

Step 2) 4-(3-((3-((4-nitrophenyl)ethynyl)imidazo[1,2-b]pyridazin-6-yl)oxy)propyl)morpholine A mixture of N-hydroxypropyl morpholine (0.95 g, 6.55 mmol) in anhydrous THF (40 mL) was cooled to 0° C., and t-BuOK (830 mg, 7.41 mmol) was added. After the addition, the reaction mixture was stirred for 20 minutes at rt and then cooled to 0° C. A mixture of 6-chloro-3-((4-nitrophenyl)ethynyl)imidazo[1,2-b]pyridazine (1.1 g, 3.69 mmol) in THF (30 mL) was added and then the reation mixture was warmed to rt and stirred overnight. After the reaction monitored by TLC was completed, water (2.0 mL) was added and the solvent was removed under vacuo. The residue was purified by silica gel column chromatography ($CH_2Cl_2$/MeOH (v/v)=20/1) to give the title compound as a yellow solid (910 mg, 60.67%). The compound was characterized by the following spectroscopic data: MS-ESI: (ESI, pos.ion) m/z: 408.2 [M+1]$^+$.

Step 3) 4-((6-(3-morpholinopropoxy)imidazo[1,2-b]pyridazin-3-yl)ethynyl)aniline To a 250 mL one-neck flask were added 4-(3-((3-((4-nitrophenyl)ethynyl)imidazo[1,2-b]pyridazin-6-yl)oxy)propyl)morpholine (0.91 g, 2.2 mmol), ethyl alcohol (80 mL) and water (20 mL), and zinc power (1.45 g, 22.3 mmol) and ammonium chloride (0.48 g, 9.0 mmol) were added with stirring. After the addition, the reaction mixture was refluxed for 5 hours. After the raw material was consumed completely monitored by TLC, the resulting mixture was filtered immediately while it was hot, and the filter cake was washed with $CH_2Cl_2$ (5 mL). The filtrate was concentrated in vacuo and the residue was purified by silica gel column chromatography ($CH_2Cl_2$/MeOH (v/v)=10/1) to give the title compound as a yellow solid (0.8 mg, 94.9%). The compound was characterized by the following spectroscopic data: MS-ESI: (ESI, pos.ion) m/z: 378.2 [M+1]$^+$.

Step 4) 1-(5-(tert-butyl)isoxazol-3-yl)-3-(4-((6-(3-morpholinopropoxy)imidazo[1,2-b]pyridazin-3-yl)ethynyl)phenyl)urea The title compound was prepared as a light yellow solid (385 mg, 33%) by the procedure described in step 3 of example 1, using 4-((6-(3-morpholinopropoxy)imidazo[1,2-b]pyridazin-3-yl)ethynyl)aniline (0.80 g, 2.1 mmol), phenyl (5-(tert-butyl)isoxazol-3-yl)carbamate (1.15 g, 4.23 mmol), DMAP (0.27 g, 2.1 mmol) and triethylamine (0.3 mL, 2.2 mmol). The compound was characterized by the following spectroscopic data: MS-ESI: (ESI, pos.ion) m/z: 544.2 [M+1]$^+$; and $^1$H NMR (600 MHz, CDCl$_3$) δ: 7.84 (s, 1H), 7.81 (d, J=9.6 Hz, 1H), 7.58 (d, J=8.8 Hz, 2H), 7.55 (d, J=8.8 Hz, 2H), 6.73 (d, J=9.6 Hz, 1H), 6.08 (s, 1H), 4.54 (t, J=6.0 Hz, 2H), 3.76 (t, J=4.4 Hz, 4H), 2.62 (m, 6H), 2.11 (m, 2H), 1.39 (s, 9H).

Example 8

1-(4-((4-(3-(2-Oxa-6-azaspiro[3.4]octan-6-yl)propoxy)-2-fluorophenyl)ethynyl)phenyl)-3-(5-(tert-butyl)isoxazol-3-yl)urea

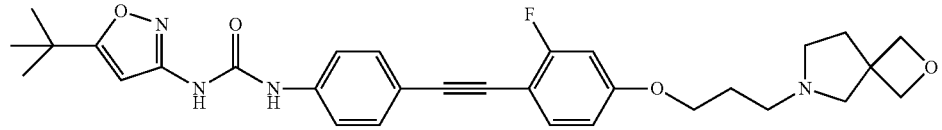 [SMILES: CC(C)(C)c1cc(NC(=O)Nc2ccc(C#Cc3ccc(OCCCN4CCC5(COC5)C4)cc3F)cc2)no1]

Step 1) 4-((4-aminophenyl)ethynyl)-3-fluorophenol

The title compound was prepared as a yellow solid (1.63 g, 57%) by the procedure described in step 1 of example 6, using 3-fluoro-4-iodophenol (3.0 g, 13 mmol), 4-ethynylaniline (2.95 g, 25.2 mmol), triethylamine (40 mL), PdCl$_2$(PPh$_3$)$_2$ (0.36 g, 0.51 mmol) and CuI (0.1 g, 0.51 mmol). The compound was characterized by the following spectroscopic data: MS-ESI: (ESI, pos.ion) m/z: 228.1 [M+1]$^+$.

Step 2) 4-((4-(3-(2-oxa-6-azaspiro[3.4]octan-6-yl)propoxy)-2-fluorophenyl)ethynyl)aniline To a mixture of 4-((4-aminophenyl)ethynyl)-3-fluorophenol (0.38 g, 1.7 mmol) in acetonitrile (30 mL) were added potassium carbonate (0.35 g, 2.5 mmol) and sodium carbonate (28 mg, 0.19 mmol), and then 6-(3-chloropropyl)-2-oxa-6-azaspiro[3.4]octane (0.48 g, 2.5 mmol) was added with stirring. After the addition, the reaction mixture was refluxed at 85° C. overnight. After the reaction monitored by TLC was completed, the resulting mixture was filtered and the filter cake was washed with acetonitrile (10 mL). The combined filtrates were concentrated in vacuo and the residue was purified by silica gel column chromatography (CH$_2$Cl$_2$/MeOH (v/v)=10/1) to give the title compound as a light yellow solid (0.32 g, 50%). The compound was characterized by the following spectroscopic data: MS-ESI: (ESI, pos.ion) m/z: 381.2 [M+1]+.

Step 3) 1-(4-((4-(3-(2-oxa-6-azaspiro[3.4]octan-6-yl)propoxy)-2-fluorophenyl)ethynyl)phenyl)-3-(5-(tert-butyl)isoxazol-3-yl)urea The title compound was prepared as a light yellow solid (140 mg, 31%) by the procedure described in step 3 of example 1, using 4-((4-(3-(2-oxa-6-azaspiro[3.4]octan-6-yl)propoxy)-2-fluorophenyl)ethynyl)aniline (0.31 g, 0.81 mmol), phenyl (5-(tert-butyl)isoxazol-3-yl)carbamate (0.42 g, 1.6 mmol), DMAP (50 mg, 0.41 mmol) and triethylamine (0.12 mL, 0.82 mmol) in acetonitrile (2 mL). The compound was characterized by the following spectroscopic data: MS-ESI: (ESI, pos.ion) m/z: 547.3 [M+1]$^+$; and $^1$H NMR (400 MHz, CDCl$_3$) δ: 7.55 (d, J=8.8 Hz, 2H), 7.51 (d, J=8.8 Hz, 2H), 7.41 (m, 1H), 6.66 (d, J=10.3 Hz, 2H), 5.98 (s, 1H), 4.68 (m, 4H), 4.05 (t, J=6.0 Hz, 2H), 3.03 (s, 2H), 2.76 (m, 4H), 2.28 (t, J=7.2 Hz, 2H), 2.03 (m, 2H), 1.37 (s, 9H).

Example 9

1-(5-(tert-Butyl)isoxazol-3-yl)-3-(4-((8-(2-morpholinoethoxy)imidazo[1,2-b]pyridazin-3-yl) ethynyl)phenyl)urea

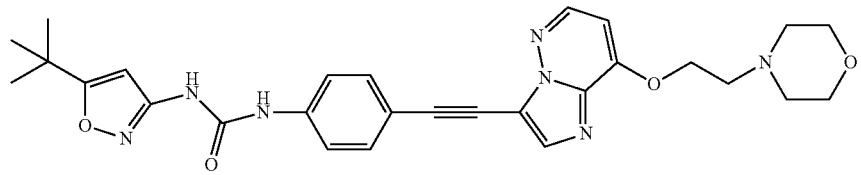 [SMILES: CC(C)(C)c1cc(NC(=O)Nc2ccc(C#Cc3cnc4c(OCCN5CCOCC5)ccnn34)cc2)no1]

Step 1) 8-(benzyloxy)-6-chloroimidazo[1,2-b]pyridazine

To a 0° C. mixture of benzyl alcohol (0.3 mL, 2.98 mmol) in THF (40 mL) was added sodium hydride (0.25 g) in an ice-water bath under a N$_2$ atmosphere. The reaction mixture was stirred for 30 minutes at 0° C., and then a solution of 8-bromo-6-chloroimidazo[1,2-b]pyridazine (462 mg, 1.99 mmol) in THF (50 mL) was added in dropwise. The reaction mixture was warmed to rt slowly and stirred for 1 hour, then quenched with saturated aqueous sodium chloride solution (50 mL) and the resulting mixture was extracted with ethyl acetate (500 mL). The organic phase was washed with water (50 mL) and saturated aqueous sodium chloride solution (50 mL), dried over anhydrous sodium sulfate and concentrated in vacuo. The residue was purified by silica gel column chromatography (EtOAc/PE (v/v)=1/2) to give the title compound as an oil (0.26 g, 50%). The compound was characterized by the following spectroscopic data: MS-ESI: (ESI, pos.ion) m/z: 260.1 [M+1]$^+$.

Step 2) imidazo[1,2-b]pyridazin-8-ol

To a solution of 8-(benzyloxy)-6-chloroimidazo[1,2-b]pyridazine (700 mg, 2.7 mmol) in methanol (60 mL) was added Pd/C catalyst (0.2 g, 10%) under a H$_2$ atmosphere. The reaction mixture was stirred at 40° C. overnight. The reaction was monitored by TLC until the raw material was consumed completely, and then filtered. The filtrate was concentrated in vacuo and dried completely to give the title compound as a gray solid (0.33 g, 91%), which was used directly for the next step. The compound was characterized by the following spectroscopic data: MS-ESI: (ESI, pos.ion) m/z: 136.1 [M+1]$^+$.

Step 3) 3-iodoimidazo[1,2-b]pyridazin-8-ol

To a solution of imidazo[1,2-b]pyridazin-8-ol (300 mg, 2.22 mmol) in chloroform (50 mL) was added NIS (0.55 g, 2.4 mmol). The reaction mixture was stirred at rt for 2 hours and then concentrated in vacuo. The residue was purified by silica gel column chromatography (CH$_2$Cl$_2$/MeOH (v/v)= 10/1) to give the title compound as a white solid (0.45 g, 78%). The compound was characterized by the following spectroscopic data: MS-ESI: (ESI, pos.ion) m/z: 261.9 [M+1]$^+$.

Step 4) 3-((4-nitrophenyl)ethynyl)imidazo[1,2-b]pyridazin-8-ol

To a two-neck flask were added 3-iodoimidazo[1,2-b]pyridazin-8-ol (200 mg, 0.77 mmol), 4-nitrophenylacetylene (0.23 g, 1.53 mmol), CuI (58 mg, 0.31 mmol), PdCl$_2$(PPh$_3$)$_2$ (108 mg, 0.15 mmol) and PPh$_3$ (80 mg, 0.31 mmol) in turn, and then THF (50 mL) and Et$_3$N (0.32 mL, 2.3 mmol) were added under a N$_2$ atmosphere. The mixture was refluxed for 3 hours and then the reaction was monitored by TLC until the raw material was consumed completely. The resulting mixture was concentrated in vacuo and the residue was purified by silica gel column chromatography (CH$_2$Cl$_2$/MeOH (v/v)=10/1) to give the title compound as an oil (160 mg, 75%). The compound was characterized by the following spectroscopic data: MS-ESI: (ESI, pos.ion) m/z: 281.1 [M+1]$^+$.

Step 5) 4-(2-((3-((4-nitrophenyl)ethynyl)imidazo[1,2-b]pyridazin-8-yl)oxy)ethyl)morpholine To a mixture of 3-((4-nitrophenyl)ethynyl)imidazo[1,2-b]pyridazin-8-ol (141 mg, 0.5 mmol) and 4-(2-chloroethyl)morpholine hydrochloride (0.19 g, 1.0 mmol) in DMF (30 mL) was added potassium carbonate (0.7 g, 5.0 mmol). The reaction mixture was heated to 45° C. and stirred overnight. After the reaction monitored by TLC was completed, the reaction mixture was concentrated in vacuo and the residue was purified by silica gel column chromatography (CH$_2$Cl$_2$/MeOH (v/v)=10/1) to give the title compound as an oil (0.15 g, 76%). The compound was characterized by the following spectroscopic data: MS-ESI: (ESI, pos.ion) m/z: 394.1[M+1]$^+$.

Step 6) 4-((8-(2-morpholinoethoxy)imidazo[1,2-b]pyridazin-3-yl)ethynyl)aniline

To a mixture of 4-(2-((3-((4-nitrophenyl)ethynyl)imidazo[1,2-b]pyridazin-8-yl)oxy) ethyl)morpholine (89 mg, 0.23 mmol) in a mixed solution (MeOH/H$_2$O (v/v)=3/1, 16 mL) were added ammonium chloride (0.24 g, 4.5 mmol) and reduced iron power (0.13 g, 2.3 mmol). The reaction mixture was heated to 80° C. and refluxed for 3 hours. After the the reaction monitored by TLC was completed, the resulting mixture was quenched with saturated aqueous sodium bicarbonate solution (50 mL), and the mixture was extracted with ethyl acetate (300 mL). The organic phase was washed with water (50 mL) and saturated aqueous sodium chloride solution (50 mL), dried over anhydrous sodium sulfate. The reaction mixture was concentrated in vacuo and the residue was purified by silica gel column chromatography (CH$_2$Cl$_2$/MeOH (v/v)=10/1) to give the title compound as an oil (75 mg, 91%). The compound was characterized by the following spectroscopic data: MS-ESI: (ESI, pos.ion) m/z: 364.2 [M+1]$^+$.

Step 7) 1-(5-(tert-butyl)isoxazol-3-yl)-3-(4-((8-(2-morpholinoethoxy)imidazo[1,2-b]pyridazin-3-yl)ethynyl)phenyl)urea The title compound was prepared as a white solid (30 mg, 51%) by the procedure described in step 3 of example 1, using 4-((8-(2-morpholinoethoxy)imidazo[1,2-b]pyridazin-3-yl)ethynyl)aniline (40 mg, 0.11 mmol), acetonitrile (30 mL), Et$_3$N (0.3 mL, 2.2 mmol) and phenyl N-(5-(tert-butyl)isoxazol-3-yl)carbamate (0.29 g, 1.1 mmol) in acetonitrile. The compound was characterized by the following spectroscopic data: MS-ESI: (ESI, pos.ion) m/z: 530.2[M+1]$^+$; and $^1$H NMR (400 MHz, CD$_3$OD) δ 8.45 (d, J=5.5 Hz, 1H), 7.88 (s, 1H), 7.56 (s, 4H), 6.82 (d, J=5.6 Hz, 1H), 6.40 (s, 1H), 4.54 (t, J=5.4 Hz, 2H), 3.82-3.67 (m, 4H), 3.11 (t, J=5.3 Hz, 2H), 2.80 (s, 4H), 1.37 (s, 9H).

Example 10

1-(5-(tert-Butyl)isoxazol-3-yl)-3-(4-((6-(2-morpholinoethoxy)imidazo[1,2-b]pyridazin-3-yl) ethynyl) phenyl)urea Step 1) 3-iodoimidazo[1,2-b]pyridazin-6-ol The title compound was prepared as oil (0.45 g, 78%) by the procedure described in step 3 of example 9, using 6-hydroxyimidazo[1,2-b]pyridazine (300 mg, 2.22 mmol) and NIS (0.55 g, 2.4 mmol). The compound was characterized by the following spectroscopic data: MS-ESI: (ESI, pos.ion) m/z: 261.9 [M+1]$^+$.

Step 2) 3-((4-nitrophenyl)ethynyl)imidazo[1,2-b]pyridazin-6-ol

The title compound was prepared as oil (160 mg, 75%) by the procedure described in step 4 of example 9, using 3-iodoimidazo[1,2-b]pyridazin-6-ol (200 mg, 0.77 mmol), 4-nitrophenylacetylene (0.23 g, 1.53 mmol), CuI (58 mg, 0.31 mmol), Pd(PPh$_3$)$_2$Cl$_2$ (108 mg, 0.15 mmol), PPh$_3$ (80 mg, 0.31 mmol), THF (50 mL) and Et$_3$N (0.32 mL, 2.3 mmol). The compound was characterized by the following spectroscopic data: MS-ESI: (ESI, pos.ion) m/z: 281.1[M+1]$^+$.

Step 3) 4-(2-((3-((4-nitrophenyl)ethynyl)imidazo[1,2-b]pyridazin-6-yl)oxy)ethyl)morpholine The title compound was prepared as oil (0.15 g, 75%) by the procedure described in step 5 of example 9, using 3-((4-nitrophenyl)ethynyl)imidazo[1,2-b]pyridazin-6-ol (141 mg, 0.5 mmol), 4-(2-chloroethyl)morpholine hydrochloride (0.19 g, 1.0 mmol) and potassium carbonate (0.7 g, 5.0 mmol). The compound was characterized by the following spectroscopic data: MS-ESI: (ESI, pos.ion) m/z: 394.1 [M+1]$^+$.

Step 4) 4-((6-(2-morpholinoethoxy)imidazo[1,2-b]pyridazin-3-yl)ethynyl)aniline

The title compound was prepared as oil (75 mg, 90%) by the procedure described in step 6 of example 9, using 4-(2-((3-((4-nitrophenyl)ethynyl)imidazo[1,2-b]pyridazin-6-yl)oxy)ethyl)morpholine (89 mg, 0.23 mmol), ammonium chloride (0.24 g, 4.5 mmol) and reduced iron power (0.13 g, 2.3 mmol). The compound was characterized by the following spectroscopic data: MS-ESI: (ESI, pos.ion) m/z: 364.2 [M+1]$^+$.

Step 5) 1-(5-(tert-butyl)isoxazol-3-yl)-3-(4-((6-(2-morpholinoethoxy)imidazo[1,2-b]pyridazin-3-yl)ethynyl)phenyl)urea The title compound was prepared as a white solid (30 mg, 50%) by the procedure described in step 3 of example 1, using 4-((6-(2-morpholinoethoxy)imidazo[1,2-b]pyridazin-3-yl)ethynyl)aniline (40 mg, 0.11 mmol), acetonitrile (30 mL), Et$_3$N (0.3 mL, 2.2 mmol) and phenyl N-(5-(tert-butyl)isoxazol-3-yl)carbamate (0.29 g, 1.1 mmol). The compound was characterized by the following spectroscopic data: MS-ESI: (ESI, pos.ion) m/z: 530.2[M+1]$^+$; and $^1$H NMR (600 MHz, CD$_3$OD) δ 8.22 (d, J=6.2 Hz, 1H), 8.14 (s, 1H), 7.60 (q, J=8.8 Hz, 4H), 6.44 (s, 1H), 6.35 (d, J=6.3 Hz, 1H), 4.98 (t, J=5.9 Hz, 2H), 3.74-3.54 (m, 4H), 2.89 (t, J=6.0 Hz, 2H), 2.58 (m, 4H), 1.38 (s, 9H).

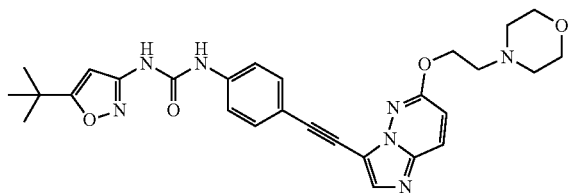 [SMILES: CC(C)(C)c1cc(NC(=O)Nc2ccc(C#Cc3cnc4ccc(OCCN5CCOCC5)nn34)cc2)no1]

Example 11

1-(5-(tert-butyl)isoxazol-3-yl)-3-(4-((4-(3-((4aR,7aS)-tetrahydro-2H-[1,4]dioxino[2,3-c]pyrrol-6(3H)-yl)propoxy)phenyl)ethynyl)phenyl)urea

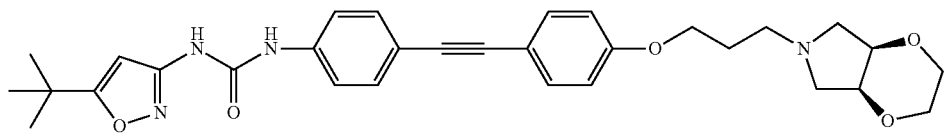 [SMILES: CC(C)(C)c1cc(NC(=O)Nc2ccc(C#Cc3ccc(OCCCN4C[C@@H]5OCCO[C@@H]5C4)cc3)cc2)no1]

Step 1) 4-((4-aminophenyl)ethynyl)phenol

The title compound was prepared as oil (5.4 g, 57%) by the procedure described in step 1 of example 6, using 4-iodophenol (10.0 g, 45.0 mmol), 4-ethynylaniline (10.6 g, 90 mmol), bis(triphenylphosphine)palladium(II) chloride (3.2 g, 4.5 mmol), cuprous iodide (0.86 g, 4.5 mmol), THF (60 mL) and TEA (60 mL). The compound was characterized by the following spectroscopic data: MS-ESI: (ESI, pos.ion) m/z: 210.2 [M+1]+.

Step 2) 4-((4-(3-((4aR,7aS)-tetrahydro-2H-[1,4]dioxino[2,3-c]pyrrol-6(3H)-yl)propoxy) phenyl)ethynyl)aniline The title compound was prepared as a claybank solid (325 mg, 61.7%) by the procedure described in step 2 of example 8, using 4-((4-aminophenyl)ethynyl)phenol (200.0 mg, 0.96 mmol), (4aR,7aS)-6-(3-chloropropyl)hexahydro-2H-[1,4]dioxino[2,3-c]pyrrole (233.7 mg, 1.14 mmol), potassium carbonate (397.4 mg, 2.88 mmol) and potassium iodide (20 mg). The compound was characterized by the following spectroscopic data: MS-ESI: (ESI, pos.ion) m/z: 379.5 [M+1]+.

Step 3) 1-(5-(tert-butyl)isoxazol-3-yl)-3-(4-((4-(3-((4aR,7aS)-tetrahydro-2H-[1,4]dioxino[2,3-c]pyrrol-6(3H)-yl) propoxy) phenyl)ethynyl)phenyl)urea The title compound was prepared as a white solid (25 mg, 18%) by the procedure described in step 3 of example 1, using 4-((4-(3-((4aR,7aS)-tetrahydro-2H-[1,4]dioxino[2,3-c]pyrrol-6(3H)-yl)propoxy)phenyl)ethynyl)aniline (100 mg, 0.60 mmol), dichloromethane (20 mL), phenyl (5-(tert-butyl)isoxazol-3-yl)carbamate (232.8 mg, 0.90 mmol), DMAP (10 mg) and triethylamine (35.1 mg, 0.30 mmol). The compound was characterized by the following spectroscopic data: MS-ESI: (ESI, pos.ion) m/z: 545.2 [M+1]+; and $^1$H NMR (400 MHz, DMSO-$d_6$) δ 9.87 (s, 2H), 7.51 (d, J=8.8 Hz, 2H), 7.44 (m, 4H), 6.96 (d, J=8.9 Hz, 2H), 6.53 (s, 1H), 4.03 (t, J=6.3 Hz, 2H), 3.98 (t, J=4.0 Hz, 2H), 3.73-3.65 (m, 2H), 3.50-3.43 (m, 2H), 2.86-2.80 (m, 4H), 2.68 (dd, J=9.5, 4.5 Hz, 2H), 2.60 (t, J=7.1 Hz, 2H), 1.30 (s, 9H).

Example 12

1-(5-(tert-Butyl)isoxazol-3-yl)-3-(4-((4-(2-(4-methylpiperazin-1-yl)ethoxy)phenyl)ethynyl) phenyl)urea

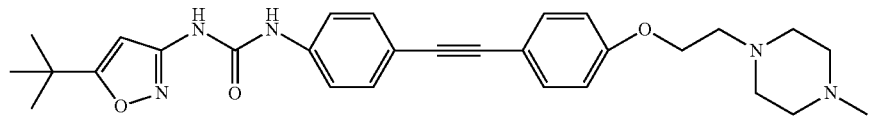

Step 1) 4-((4-(2-(4-methylpiperazin-1-yl)ethoxy)phenyl)ethynyl)aniline

The title compound was prepared as a claybank solid (296 mg, 63.1%) by the procedure described in step 2 of example 8, using 4-((4-aminophenyl)ethynyl)phenol (300.0 mg, 1.4 mmol), 1-(2-chloroethyl)-4-methylpiperazine (275.4 mg, 1.7 mmol), potassium carbonate (594.3 mg, 4.3 mmol) and potassium iodide (20 mg). The compound was characterized by the following spectroscopic data: MS-ESI: (ESI, pos.ion) m/z: 336.3 [M+1]$^+$.

Step 2) 1-(5-(tert-butyl)isoxazol-3-yl)-3-(4-((4-(2-(4-methylpiperazin-1-yl)ethoxy)phenyl) ethynyl) phenyl)urea The title compound was prepared as a white solid (25 mg, 42%) by the procedure described in step 3 of example 1, using 4-((4-(2-(4-methylpiperazin-1-yl)ethoxy)phenyl)ethynyl)aniline (200 mg, 0.26 mmol), dichloromethane (20 mL), phenyl (5-(tert-butyl)isoxazol-3-yl)carbamate (103.1 mg, 0.40 mmol), DMAP (20 mg) and triethylamine (13.1 mg, 0.13 mmol). The compound was characterized by the following spectroscopic data: MS-ESI: (ESI, pos.ion) m/z: 502.3 [M+1]$^+$; and $^1$H NMR (400 MHz, CDCl$_3$) δ: 9.47 (s, 1H), 8.64 (s, 1H), 7.56 (d, J=8.7 Hz, 2H), 7.47-7.43 (m, 4H), 6.83 (d, J=8.8 Hz, 2H), 6.19 (s, 1H), 4.14 (s, 2H), 3.00 (d, J=33.8 Hz, 10H), 2.77 (s, 3H), 1.36 (s, 9H).

Example 13

1-(5-(tert-Butyl)isoxazol-3-yl)-3-(4-((4-(3-(4-methylpiperazin-1-yl)propoxy)phenyl)ethynyl) phenyl) urea

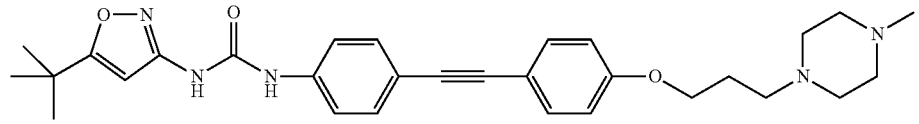

Step 1) 4-((4-(3-(4-methylpiperazin-1-yl)propoxy) phenyl)ethynyl)aniline

The title compound was prepared as a claybank solid (275 mg, 55%) by the procedure described in step 2 of example 8, using 4-((4-aminophenyl)ethynyl)phenol (300.0 mg, 1.4 mmol), 1-(3-chloropropyl)-4-methylpiperazine (303.2 mg, 1.7 mmol), potassium carbonate (594.3 mg, 4.3 mmol) and potassium iodide (20 mg). The compound was characterized by the following spectroscopic data: MS-ESI: (ESI, pos.ion) m/z: 350.3[M+1]$^+$.

Step 2) 1-(5-(tert-butyl)isoxazol-3-yl)-3-(4-((4-(3-(4-methylpiperazin-1-yl)propoxy)phenyl) ethynyl) phenyl)urea The title compound was prepared as a white solid (140 mg, 47%) by the procedure described in step 3 of example 1, using 4-((4-(3-(4-methylpiperazin-1-yl)propoxy)phenyl) ethynyl)aniline (200 mg, 0.57 mmol), phenyl (5-(tert-butyl) isoxazol-3-yl)carbamate (223.5 mg, 0.86 mmol), DMAP (20 mg) and triethylamine (28.8 mg, 0.28 mmol). The compound was characterized by the following spectroscopic data: MS-ESI: (ESI, pos.ion) m/z: 516.3 [M+1]$^+$; and $^1$H NMR (600 MHz, DMSO-d$_6$) δ 9.33 (s, 1H), 7.39 (d, J=8.6 Hz, 2H), 7.16 (d, J=8.5 Hz, 2H), 6.93 (d, J=8.7 Hz, 2H), 6.55 (d, J=8.5 Hz, 2H), 5.51 (s, 2H), 4.04 (t, J=5.8 Hz, 2H), 2.71 (m, 9H), 2.13-1.87 (m, 6H), 1.68-1.11 (s, 9H).

Example 14

1-(5-(tert-Butyl)isoxazol-3-yl)-3-(4-((4-(2-(4-(dimethylamino)piperidin-1-yl)ethoxy)phenyl) ethynyl) phenyl)urea

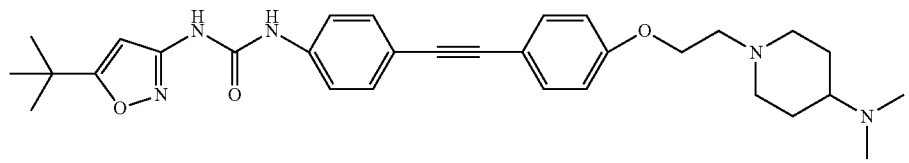 [SMILES: CN(C)C1CCN(CCOc2ccc(C#Cc3ccc(NC(=O)Nc4cc(C(C)(C)C)on4)cc3)cc2)CC1]

Step 1) 4-((4-(2-(4-dimethylaminopiperidin-1-yl) ethoxy)phenyl)ethynyl)aniline

The title compound was prepared as a claybank solid (263 mg, 52%) by the procedure described in step 2 of example 8, using 4-((4-aminophenyl)ethynyl)phenol (300.0 mg, 1.4 mmol), 1-(2-chloroethyl)-4-dimethylaminopiperidine (323.0 mg, 1.7 mmol), potassium carbonate (594.3 mg, 4.3 mmol) and potassium iodide (20 mg). The compound was characterized by the following spectroscopic data: MS-ESI: (ESI, pos.ion) m/z: 364.2[M+1]$^+$.

Step 2) 1-(5-(tert-butyl)isoxazol-3-yl)-3-(4-((4-(2-(4-(dimethylamino)piperidin-1-yl)ethoxy) phenyl) ethynyl)phenyl)urea The title compound was prepared as a white solid (27 mg, 18.6%) by the procedure described in step 3 of example 1, using 4-((4-(2-(4-dimethylaminopiperidin-1-yl)ethoxy)phenyl)ethynyl)aniline (100 mg, 0.28 mmol), phenyl (5-(tert-butyl)isoxazol-3-yl)carbamate (107.4 mg, 0.4 mmol), DMAP (10 mg) and triethylamine (14.4 mg, 0.14 mmol). The compound was characterized by the following spectroscopic data: MS-ESI: (ESI, pos.ion) m/z: 530.3 [M+1]$^+$; and $^1$H NMR (400 MHz, DMSO-d$_6$) δ: 9.47 (s, 1H), 7.60 (d, J=8.5 Hz, 2H), 7.45-7.39 (m, 4H), 7.21 (t, J=7.5 Hz, 2H), 6.97 (s, 1H), 6.50 (s, 1H), 4.09 (t, J=5.7 Hz, 2H), 2.95 (d, J=11.6 Hz, 2H), 2.67 (t, J=5.7 Hz, 2H), 2.15 (s, 5H), 2.00 (t, J=11.1 Hz, 2H), 1.70 (s, 6H), 1.29 (s, 9H).

Example 15

1-(5-(tert-Butyl)isoxazol-3-yl)-3-(4-((7-(3-morpholinopropoxy)pyrazolo[1,5-a]pyrimidin-3-yl)ethynyl)phenyl)urea

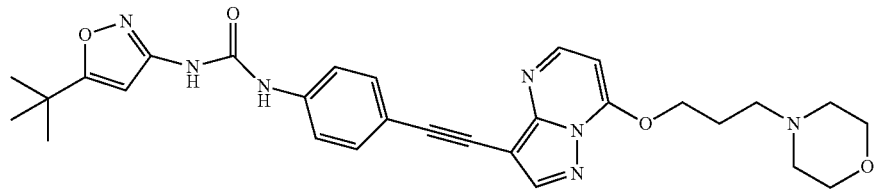 [SMILES: CC(C)(C)c1cc(NC(=O)Nc2ccc(C#Cc3cnn4c(OCCCN5CCOCC5)ccnc34)cc2)no1]

Step 1) 7-chloro-3-iodopyrazolo[1,5-a]pyrimidine

To a solution of 7-chloropyrazolo[1,5-a]pyrimidine (3.0 g, 19.5 mmol) in DMF (30 mL) was added NIS (5.3 g, 23 mmol). The reaction mixture was stirred at rt for 12 hours. To the mixture was added water (25 mL), and a lot of solid precipitated out. The resulting mixture was further stirred for 15 minutes, and then filtered. The filter cake was dried to give the title compound as an off-white solid (4.8 g, 88%). The compound was characterized by the following spectroscopic data: MS-ESI: (ESI, pos.ion) m/z: 279.9 [M+1]$^+$.

Step 2) 4-(3-((3-iodopyrazolo[1,5-a]pyrimidin-7-yl)oxy)propyl)morpholine

To a 50 mL one-neck flask were added t-BuOK (0.6 g, 5.0 mmol) and THF (50 mL). The mixture was cooled to 0° C., and N-hydroxypropyl morpholine (0.78 g, 5.4 mmol) was added dropwise slowly, then the resulting mixture was stirred at 0° C. for 30 minutes. Then 7-chloro-3-iodopyrazolo[1,5-a]pyrimidine (1.0 g, 3.6 mmol) was added to the mixture while keeping the temperature of the mixture at or below 10° C. After the addition, the reaction mixture was stirred at 0° C. for 2 hours. The resulting mixture was quenched with water (50 mL) and concentrated in vacuo. The residue was dissolved in dichloromethane (300 mL), and the mixture was washed with saturated aqueous sodium chloride (100 mL), dried over anhydrous sodium sulfate and concentrated in vacuo to give the title compound as a light yellow solid (1.3 g, 94%) which was used directly for the next step without further purification. The compound was characterized by the following spectroscopic data: MS-ESI: (ESI, pos.ion) m/z: 389.0 [M+1]$^+$.

Step 3) 4-((7-(3-morpholinopropoxy)pyrazolo[1,5-a]pyrimidin-3-yl)ethynyl)aniline The title compound was prepared as oil (0.31 g, 60%) by the procedure described in step 2 of example 1, using 4-(3-((3-iodopyrazolo[1,5-a]pyrimidin-7-yl)oxy)propyl) morpholine (0.5 g, 1.0 mmol), triethylamine (0.26 g, 2.6 mmol), 4-ethynylaniline (0.27 g, 2.3 mmol), CuI (0.019 g, 0.10 mmol) and PdCl$_2$(PPh$_3$)$_2$ (0.07 g, 0.1 mmol). The compound was characterized by the following spectroscopic data: MS-ESI: (ESI, pos.ion) m/z: 378.2[M+1]$^+$.

Step 4) 1-(5-(tert-butyl)isoxazol-3-yl)-3-(4-((7-(3-morpholinopropoxy)pyrazolo[1,5-a]pyrimidin-3-yl)ethynyl)phenyl) urea To a mixture of 4-((7-(3-morpholinopropoxy)pyrazolo[1,5-a]pyrimidin-3-yl) ethynyl)aniline (0.31 g, 0.82 mmol) in acetonitrile (10 mL) were added triethylamine (0.16 g, 1.6 mmol) and phenyl (5-(tert-butyl)isoxazol-3-yl)carbamate (0.26 g, 0.98 mmol). The reaction mixture was stirred at 80° C. for 16 hours and then concentrated in vacuo. The residue was dissolved in dichloromethane (300 mL), and the resulting mixture was washed with saturated aqueous sodium chloride solution (100 mL), dried with anhydrous sodium sulfate, concentrated in vacuo. The residue was purified by silica gel column chromatography (CH$_2$Cl$_2$/MeOH (v/v) =40/1) and further purified by preparative HPLC to give the title compound as a white solid (65 mg, 14.4%). The compound was characterized by the following spectroscopic data: MS-ESI: (ESI, pos.ion) m/z: 544.3 [M+1]$^+$; and $^1$H NMR (400 MHz, DMSO-d$_6$) δ 9.57 (s, 1H), 9.00 (s, 1H), 8.94 (d, J=7.5 Hz, 1H), 8.28 (s, 1H), 7.48 (dd, J=22.8, 8.8 Hz, 4H), 6.64 (d, J=7.5 Hz, 1H), 6.52 (s, 1H), 4.46 (s, 2H), 3.58-3.53 (m, 4H), 2.44 (t, J=6.9 Hz, 2H), 2.37 (s, 4H), 1.98-1.91 (m, 2H), 1.30 (s, 9H).

Example 16

1-(5-(tert-Butyl)isoxazol-3-yl)-3-(4-((7-(2-morpholinoethoxy)pyrazolo[1,5-a]pyrimidin-3-yl) ethynyl)phenyl)urea

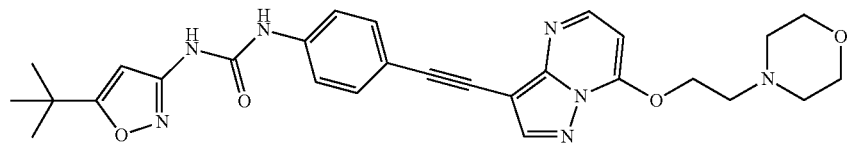 [SMILES: CC(C)(C)c1cc(NC(=O)Nc2ccc(C#Cc3cnn4c(OCCN5CCOCC5)ccnc34)cc2)no1]

Step 1) 4-(2-((3-iodopyrazolo[1,5-a]pyrimidin-7-yl)oxy)ethyl)morpholine

The title compound was prepared as a light yellow solid (0.98 g, 73%) by the procedure described in step 2 of example 15, using t-BuOK (0.6 g, 5.0 mmol), N-(2-hydroxyethyl)morpholine (0.71 g, 5.4 mmol) and 7-chloro-3-iodopyrazolo[1,5-a]pyrimidine (1.0 g, 3.6 mmol), which was used directly for the next step without further purification. The compound was characterized by the following spectroscopic data: MS-ESI: (ESI, pos.ion) m/z: 375.0 [M+1]$^+$.

Step 2) 4-((7-(2-morpholinoethoxy)pyrazolo[1,5-a]pyrimidin-3-yl)ethynyl)aniline The title compound was prepared as oil (0.22 g, 61%) by the procedure described in step 2 of example 1, using 4-(2-((3-iodopyrazolo[1,5-a]pyrimidin-7-yl)oxy)ethyl)morpholine (3.70 g, 1.0 mmol), triethylamine (0.26 g, 2.6 mmol), 4-ethynylaniline (0.27 g, 2.3 mmol), CuI (0.019 g, 0.10 mmol) and PdCl$_2$(PPh$_3$)$_2$ (0.07 g, 0.1 mmol). The compound was characterized by the following spectroscopic data: MS-ESI: (ESI, pos.ion) m/z: 364.2[M+1]$^+$.

Step 3) 1-(5-(tert-butyl)isoxazol-3-yl)-3-(4-((7-(2-morpholinoethoxy)pyrazolo[1,5-a]pyrimidin-3-yl)ethynyl)phenyl)urea The title compound was prepared as a light yellow solid (85 mg, 27%) by the procedure described in step 4 of example 15, using 4-((7-(2-morpholinoethoxy)pyrazolo[1,5-a]pyrimidin-3-yl)ethynyl)aniline (0.22 g, 0.6 mmol), triethylamine (0.16 g, 1.6 mmol), phenyl (5-(tert-butyl)isoxazol-3-yl)carbamate (0.26 g, 0.98 mmol). The compound was characterized by the following spectroscopic data: MS-ESI: (ESI, pos.ion) m/z: 530.3[M+1]$^+$; and $^1$H NMR (400 MHz, DMSO-d$_6$) δ: 10.16 (s, 1H), 9.97 (s, 1H), 8.95 (d, J=7.5 Hz, 1H), 8.28 (s, 1H), 7.53 (d, J=8.7 Hz, 2H), 7.43 (d, J=8.7 Hz, 2H), 6.66 (d, J=7.5 Hz, 1H), 6.53 (s, 1H), 4.58 (s, 2H), 3.57 (s, 4H), 3.04 (q, J=7.2 Hz, 4H), 1.30 (s, 9H).

Example 17

1-(5-(tert-Butyl)isoxazol-3-yl)-3-(4-((6-(3-morpholinopropoxy)pyridin-3-yl)ethynyl)phenyl) urea

Step 1) 4-(3-((5-iodopyridin-2-yl)oxy)propyl)morpholine

The title compound was prepared by the procedure described in step 1 of example 1, using 2-hydroxy-5-iodopyridine (5.0 g, 22.62 mmol), DMF (40 mL), cesium carbonate (11.06 g, 33.93 mmol) and 4-(3-chloropropyl)morpholine (4.42 g, 27 mmol). And the crude product was purified by silica gel column chromatography (CH$_2$Cl$_2$/MeOH (v/v)=50/1) to give the title compound as a light green solid (6.5 g, 83%). The compound was characterized by the following spectroscopic data: MS-ESI: (ESI, pos.ion) m/z: 349.1[M+1]$^+$.

Step 2) 4-((6-(3-morpholinopropoxy)pyridin-3-yl)ethynyl)aniline

The title compound was prepared as a brown ropy solid (0.35 g, 38%) by the procedure described in step 2 of example 1, using 4-(3-((5-iodopyridin-2-yl)oxy)propyl)morpholine (1.0 g, 2.87 mmol), 4-ethynylaniline (0.4 g, 3.44 mmol), CuI (0.05 g), PdCl$_2$(PPh$_3$)$_2$ (0.2 g) and triethylamine (0.35 g). The compound was characterized by the following spectroscopic data: MS-ESI: (ESI, pos.ion) m/z: 338.2 [M+1]$^+$.

Step 3) 1-(5-(tert-butyl)isoxazol-3-yl)-3-(4-((6-(3-morpholinopropoxy)pyridin-3-yl)ethynyl) phenyl) urea To a mixture of 4-((6-(3-morpholinopropoxy)pyridin-3-yl)ethynyl)aniline (0.20 g, 0.60 mmol) in acetonitrile (10 mL) were added phenyl (5-(tert-butyl)isoxazol-3-yl)carbamate (0.19 g, 0.71 mmol) and triethylamine (0.12 g, 1.2 mmol). The reaction mixture was stirred at rt for 30 minutes and then refluxed overnight. After the reaction monitored by TLC was completed, the resulting mixture was concentrated in vacuo to give a crude product (350 mg) which was purified by preparative HPLC to give the title compound as a light yellow solid (180 mg, 60%). The compound was characterized by the following spectroscopic data: MS-ESI: (ESI, pos.ion) m/z: 504.3 [M+1]$^+$; and $^1$H NMR (400 MHz, DMSO-d$_6$) δ 9.58 (s, 1H), 9.01 (s, 1H), 8.13 (d, J=2.4 Hz, 1H), 7.50 (d, J=8.8 Hz, 2H), 7.41 (d, J=8.7 Hz, 2H), 6.51 (s, 1H), 6.40 (d, J=9.4 Hz, 1H), 3.94 (t, J=7.0 Hz, 2H), 3.70-3.49 (m, 4H), 2.45-2.19 (m, 6H), 1.90-1.70 (m, 2H), 1.30 (s, 9H).

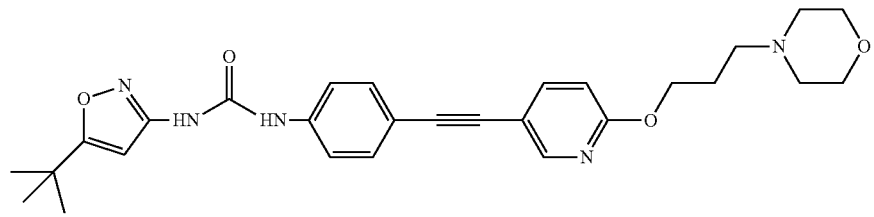 [SMILES: CC(C)(C)c1cc(NC(=O)Nc2ccc(C#Cc3ccc(OCCCN4CCOCC4)nc3)cc2)no1]

Example 18

1-(5-(tert-Butyl)isoxazol-3-yl)-3-(4-((4-chloro-3-(3-morpholinopropoxy)phenyl)ethynyl) phenyl) urea

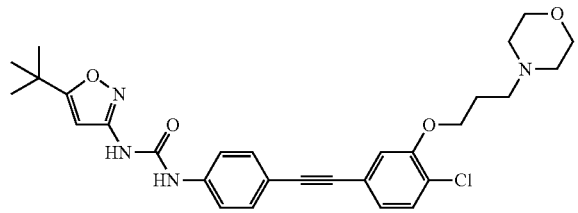 [SMILES: CC(C)(C)c1cc(NC(=O)Nc2ccc(C#Cc3ccc(Cl)c(OCCCN4CCOCC4)c3)cc2)no1]

Step 1) 5-((4-aminophenyl)ethynyl)-2-chlorophenol

To a 250 mL three-neck flask were added 2-chloro-5-iodophenol (2.54 g, 10.0 mmol), 4-ethynylaniline (2.34 g, 20.0 mmol), bis(triphenylphosphine)palladium(II) chloride (700 mg, 1.0 mmol) and CuI (190 mg, 1.0 mmol). THF (60 mL) and triethylamine (6 mL) were added to the mixture via syringe under a $N_2$ atmosphere and the mixture was stirred at 40° C. for 24 hours. The reaction mixture was poured into water (200 mL), and the resulting mixture was extracted with dichloromethane (500 mL). The organic phase was dried over anhydrous sodium sulfate, filtered, and the filtrate was concentrated in vacuo. The residue was purified by silica gel column chromatography ($CH_2Cl_2$/MeOH (v/v) =10/1) to give the title compound as a brown solid (1.2 g, 49.2%). The compound was characterized by the following spectroscopic data: MS-ESI: (ESI, pos.ion) m/z: 244.2 $[M+1]^+$.

Step 2) 4-((4-chloro-3-(3-morpholinopropoxy)phenyl)ethynyl)aniline

To a mixture of 5-((4-aminophenyl)ethynyl)-2-chlorophenol (500.0 mg, 2.1 mmol) and 1-(3-chloropropyl)morpholine (410.1 mg, 2.5 mmol) in acetonitrile (40 mL) were added potassium carbonate (869.4 mg, 6.3 mmol) and potassium iodide (50 mg). The reaction mixture was stirred at 85° C. for 12 hours, then filtered and the filtrate was concentrated in vacuo. The residue was purified by silica gel column chromatography ($CH_2Cl_2$/MeOH (v/v)=20/1) to give the title compound as a claybank solid (515 mg, 67.0%). The compound was characterized by the following spectroscopic data: MS-ESI: (ESI, pos.ion) m/z: 371.8$[M+1]^+$.

Step 3) 1-(5-(tert-butyl)isoxazol-3-yl)-3-(4-((4-chloro-3-(3-morpholinopropoxy)phenyl)ethynyl)phenyl)urea The title compound was prepared as a white solid (100 mg, 35%) by the procedure described in step 3 of example 1, using 4-((4-chloro-3-(3-morpholinopropoxy)phenyl)ethynyl)aniline (200 mg, 0.54 mmol), dichloromethane (20 mL), phenyl (5-(tert-butyl)isoxazol-3-yl)carbamate (210.6 mg, 0.81 mmol), DMAP (20 mg) and triethylamine (5 mL). The compound was characterized by the following spectroscopic data: MS-ESI: (ESI, pos.ion) m/z: 573.2$[M+1]^+$; and $^1$H NMR (400 MHz, $CDCl_3$) δ: 9.39 (s, 1H), 8.67 (s, 1H), 7.55 (d, J=8.6 Hz, 2H), 7.44 (d, J=8.6 Hz, 2H), 7.30 (s, 1H), 7.06 (d, J=9.8 Hz, 2H), 6.12 (s, 1H), 4.20 (t, J=5.8 Hz, 2H), 3.95 (s, 4H), 2.94 (m, 6H), 2.24 (d, J=5.8 Hz, 2H), 1.36 (s, 9H).

Example 19

1-(4-((4-(3-(2-Oxa-6-azaspiro[3.4]octan-6-yl)propoxy)phenyl)ethynyl)phenyl)-3-(5-(tert-butyl)isoxazol-3-yl)urea

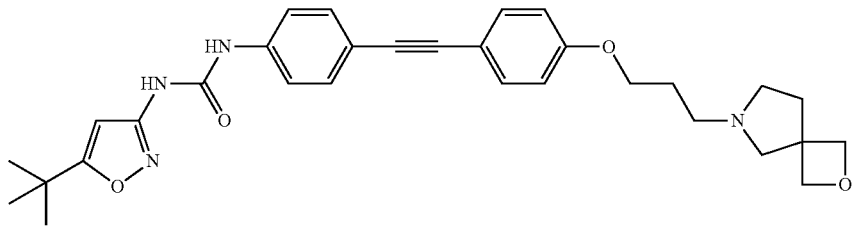 [SMILES: CC(C)(C)c1cc(NC(=O)Nc2ccc(C#Cc3ccc(OCCCN4CCC5(COC5)C4)cc3)cc2)no1]

Step 1) 4-((4-(3-(2-oxa-6-azaspiro[3.4]octan-6-yl)propoxy)phenyl)ethynyl)aniline To a mixture of 4-((4-aminophenyl)ethynyl)phenol (200.0 mg, 0.96 mmol), 6-(3-chloropropyl)-2-oxa-6-azaspiro[3.4]octane (217.0 mg, 1.14 mmol) in acetonitrile (40 mL) were added potassium carbonate (397.4 mg, 2.88 mmol) and potassium iodide (30 mg). The reaction mixture was stirred at 85° C. for 12 hours, then filtered. The filtrate was concentrated in vacuo and the residue was purified by silica gel column chromatography ($CH_2Cl_2$/MeOH (v/v)=20/1) to give the title compound as a claybank solid (185 mg, 53.5%). The compound was characterized by the following spectroscopic data: MS-ESI: (ESI, pos.ion) m/z: 363.3 $[M+1]^+$.

Step 2) 1-(4-((4-(3-(2-oxa-6-azaspiro[3.4]octan-6-yl)propoxy)phenyl)ethynyl)phenyl)-3-(5-(tert-butyl)isoxazol-3-yl)urea The title compound was prepared as a white solid (80 mg, 52.3%) by the procedure described in step 3 of example 1, using 4-((4-(3-(2-oxa-6-azaspiro[3.4]octan-6-yl)propoxy)phenyl)ethynyl)aniline (108 mg, 0.30 mmol), dichloromethane (20 mL), phenyl (5-(tert-butyl)isoxazol-3-yl)carbamate (116.4 mg, 0.45 mmol), DMAP (20 mg) and triethylamine (5 mL). The compound was characterized by the following spectroscopic data: MS-ESI: (ESI, pos.ion) m/z: 529.3 $[M+1]^+$; and $^1$H NMR (600 MHz, $CDCl_3$) δ: 9.38 (s, 1H), 8.65 (s, 1H), 7.54 (d, J=8.6 Hz, 2H), 7.45-7.38 (m, 4H), 6.84 (d, J=8.7 Hz, 1H), 6.06 (s, 1H), 4.06 (t, J=6.0 Hz, 2H), 3.88 (s, 4H), 2.76 (d, J=25.9 Hz, 6H), 2.16-2.10 (m, 2H), 1.37 (d, J=7.4 Hz, 9H).

Example 20

1-(5-(tert-Butyl)isoxazol-3-yl)-3-(4-((3-methoxy-4-(3-morpholinopropoxy)phenyl)ethynyl) phenyl)urea

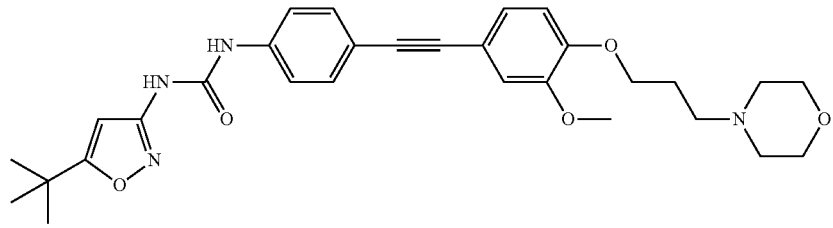 [SMILES: COc1cc(C#Cc2ccc(NC(=O)Nc3cc(C(C)(C)C)on3)cc2)ccc1OCCCN1CCOCC1]

Step 1)
4-((4-aminophenyl)ethynyl)-2-methoxyphenol

The title compound was prepared as a brown solid (1.63 g, 69.1%) by the procedure described in step 1 of example 18, using 2-methoxy-4-iodophenol (2.50 g, 10.0 mmol), 4-ethynylaniline (2.34 g, 20.0 mmol), bis(triphenylphosphine)palladium(II) chloride (700 mg, 1.0 mmol), CuI (190 mg, 1.0 mmol), THF (60 mL) and triethylamine (6 mL). The compound was characterized by the following spectroscopic data: MS-ESI: (ESI, pos.ion) m/z: 241.2 [M+1]$^+$.

Step 2) 4-((3-methoxy-4-(3-morpholinopropoxy)phenyl)ethynyl)aniline

The title compound was prepared as a claybank solid (215 mg, 47.0%) by the procedure described in step 2 of example 18, using 4-((4-aminophenyl)ethynyl)-2-methoxyphenol (0.3 g, 1.26 mmol), 1-(3-chloropropyl)morpholine (414.0 mg, 2.52 mmol), potassium carbonate (529.9 mg, 3.84 mmol) and potassium iodide (30 mg). The compound was characterized by the following spectroscopic data: MS-ESI: (ESI, pos.ion) m/z: 367.4[M+1]$^+$.

Step 3) 1-(5-(tert-butyl)isoxazol-3-yl)-3-(4-((3-methoxy-4-(3-morpholinopropoxy)phenyl) ethynyl) phenyl)urea The title compound was prepared as a white solid (50 mg, 16%) by the procedure described in step 3 of example 1, using 4-((3-methoxy-4-(3-morpholinopropoxy)phenyl)ethynyl)aniline (215 mg, 0.59 mmol), phenyl (5-(tert-butyl)isoxazol-3-yl)carbamate (231.4 mg, 0.89 mmol), DMAP (20 mg) and triethylamine (5 mL). The compound was characterized by the following spectroscopic data: MS-ESI: (ESI, pos.ion) m/z: 533.3[M+1]$^+$; and $^1$H NMR (400 MHz, CDCl$_3$) δ 9.40 (s, 1H), 8.60 (s, 1H), 7.51 (dd, J=20.8, 8.4 Hz, 4H), 7.10 (s, 1H), 7.04 (s, 1H), 6.84 (d, J=8.4 Hz, 1H), 6.06 (s, 1H), 4.14 (d, J=6.3 Hz, 2H), 3.89 (s, 3H), 3.86 (s, 4H), 2.80 (d, J=8.6 Hz, 6H), 2.21-2.15 (m, 2H), 1.36 (s, 9H).

Example 21

1-(5-(tert-Butyl)isoxazol-3-yl)-3-(4-((4-(3-morpholinopropoxy)phenyl)ethynyl)phenyl)urea

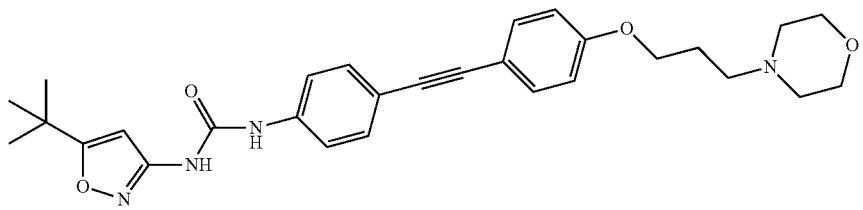 [SMILES: CC(C)(C)c1cc(NC(=O)Nc2ccc(C#Cc3ccc(OCCCN4CCOCC4)cc3)cc2)no1]

Step 1) 4-((4-nitrophenyl)ethynyl)phenol

To a two-neck flask were added 4-iodophenol (0.86 g, 3.9 mmol), 4-nitrophenylacetylene (0.85 g, 5.8 mmol), CuI (300 mg, 1.5 mmol), bis(triphenylphosphine)palladium(II) chloride (550 mg, 0.8 mmol). The mixture was degassed and refilled with N$_2$ for three times. Then toluene (20 mL) and triethylamine (0.3 mL) were added to the mixture under the N$_2$ atmosphere. The reaction mixture was stirred at 110° C. for 5 hours, then concentrated in vacuo. The residue was purified by silica gel column chromatography (EtOAc/PE (v/v)=1/1) to give the title compound as a light yellow solid (0.56 g, 60%). The compound was characterized by the following spectroscopic data: MS-ESI: (ESI, pos.ion) m/z: 240.1 [M+1]$^+$.

Step 2) 4-(3-(4-((4-nitrophenyl)ethynyl)phenoxy)propyl)morpholine

A mixture of 4-((4-nitrophenyl)ethynyl)phenol (0.71 g, 2.96 mmol), 4-(3-chloropropyl)morpholine (0.97 g, 5.92 mmol), potassium carbonate (1.23 g, 8.9 mmol) and tetrabutylammonium iodide (0.22 g, 0.6 mmol) in DMF (15 mL) was stirred at 90° C. for 6 hours. The reaction mixture was cooled to rt, and then water (200 mL) was added. Then the mixture was filtered. The filter cake was washed with water (20 mL) and dried to give the title compound as a brownish red solid (1.06 g, 98%). The compound was characterized by the following spectroscopic data: MS-ESI: (ESI, pos.ion) m/z: 367.3 [M+1]$^+$.

Step 3) 4-((4-(3-morpholinopropoxy)phenyl)ethynyl)aniline

A mixture of 4-(3-(4-((4-nitrophenyl)ethynyl)phenoxy)propyl)morpholine (1.06 g, 0.29 mmol), zinc powder (1.89 g, 2.9 mmol), ammonium chloride (0.62 g, 1.16 mmol) in a mixed solvent (EtOH/H$_2$O (v/v)=4/1, 25 mL) was refluxed for 3 hours and filtered to removed the solid. The filtrate was concentrated in vacuo, and to the residue was added a solution of dichloromethane (100 mL) and saturated aqueous sodium bicarbonate (100 mL). The mixture was partitioned. The organic layer was dried over anhydrous sodium sulfate and concentrated in vacuo to give the title compound as a light yellow solid (0.43 g, 44%). The compound was characterized by the following spectroscopic data: MS-ESI: (ESI, pos.ion) m/z: 337.3 [M+1]$^+$.

Step 4) 1-(5-(tert-butyl)isoxazol-3-yl)-3-(4-((4-(3-morpholinopropoxy)phenyl)ethynyl)phenyl) urea To a mixture of 4-((4-(3-morpholinopropoxy)phenyl)ethynyl)aniline (0.43 g, 1.27 mmol) in dichloromethane (10 mL) were added phenyl (5-(tert-butyl)isoxazol-3-yl)carbamate (0.36 g, 1.4 mmol) and DMAP (9 mg, 0.08 mmol) in turn at rt, and triethylamine (0.5 mL) was added dropwise with stirring. The reaction mixture was refluxed overnight and concentrated in vacuo. The residue was purified by silica gel column chromatography (CH$_2$Cl$_2$/MeOH (v/v)=20/1) to give the title compound as a white solid (315 mg, 49%). The compound was characterized by the following spectroscopic data: MS-ESI: (ESI, pos.ion) m/z: 503.4 [M+1]$^+$; and $^1$H NMR (400 MHz, DMSO-d$_6$): δ 9.57 (s, 1H), 9.00 (s, 1H), 7.50 (d, J=8.6 Hz, 2H), 7.46-7.44 (m, 4H), 6.96 (d, J=9.2 Hz, 2H), 6.51 (s, 1H), 4.03 (t, J=6.4 Hz, 2H), 3.57 (t, J=4.8 Hz, 4H), 2.43-2.36 (m, 6H), 1.89-1.84 (m, 2H), 1.30 (s, 9H).

Example 22

1-(4-((4-(3-(2-Oxa-5-azabicyclo[2.2.1]heptan-5-yl)propoxy)phenyl)ethynyl)phenyl)-3-(5-(tert-butyl)isoxazol-3-yl)urea

Step 1) 4-((4-(3-(2-oxa-5-azabicyclo[2.2.1]heptan-5-yl)propoxy)phenyl)ethynyl)aniline The title compound was prepared as a claybank solid (90 mg, 56%) by the procedure described in step 2 of example 8, using 4-((4-aminophenyl)ethynyl)phenol (100.0 mg, 0.47 mmol), 5-(3-chloropropyl)-2-oxa-5-azabicyclo[2.2.2]heptane (99.8 mg, 0.57 mmol), acetonitrile (40 mL), potassium carbonate (194.6 mg, 1.41 mmol) and potassium iodide (30 mg). The compound was characterized by the following spectroscopic data: MS-ESI: (ESI, pos.ion) m/z: 349.5 [M+1]$^+$.

Step 2) 1-(4-((4-(3-(2-oxa-5-azabicyclo[2.2.1]heptan-5-yl)propoxy)phenyl)ethynyl)phenyl)-3-(5-(tert-butyl)isoxazol-3-yl)urea The title compound was prepared as a white solid (22 mg, 17%) by the procedure described in step 3 of example 1, using 4-((4-(3-(2-oxa-5-azabicyclo[2.2.1]heptan-5-yl)propoxy)phenyl)ethynyl)aniline (90 mg, 0.26 mmol), dichloromethane (20 mL), phenyl (5-(tert-butyl)isoxazol-3-yl)carbamate (103.1 mg, 0.40 mmol), DMAP (20 mg) and triethylamine (5 mL). The compound was characterized by the following spectroscopic data: MS-ESI: (ESI, pos.ion) m/z: 515.4 [M+1]$^+$; and $^1$H NMR (400 MHz, CDCl$_3$) δ: 9.34 (s, 1H), 8.63 (s, 1H), 7.54-7.44 (m, 6H), 6.88 (d, J=8.8 Hz, 2H), 6.00 (s, 1H), 5.32 (s, 2H), 4.07 (s, 2H), 3.65 (dd, J=7.8, 1.4 Hz, 1H), 3.00-2.92 (m, 1H), 2.79 (ddd, J=19.2, 11.9, 4.6 Hz, 2H), 1.98-1.90 (m, 6H), 1.38 (s, 9H).

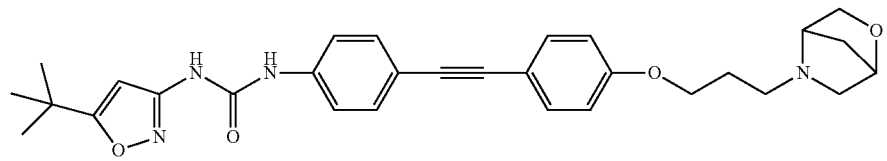 [SMILES: CC(C)(C)c1cc(NC(=O)Nc2ccc(C#Cc3ccc(OCCCN4CC5CC4CO5)cc3)cc2)no1]

Example 23

1-(4-((4-(3-(2-Oxa-6-azaspiro[3.3]heptan-6-yl)propoxy)-3-fluorophenyl)ethynyl)phenyl)-3-(5-(tert-butyl)isoxazol-3-yl)urea

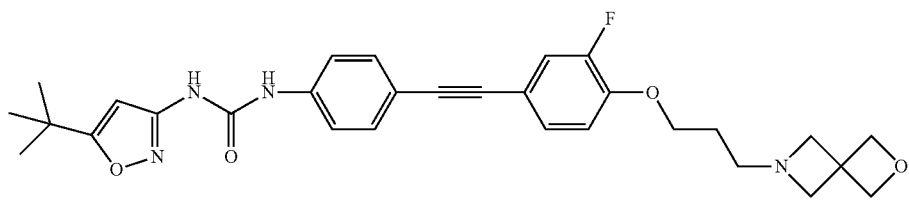 [SMILES: CC(C)(C)c1cc(NC(=O)Nc2ccc(C#Cc3ccc(OCCCN4CC5(COC5)C4)c(F)c3)cc2)no1]

Step 1) 3-(2-oxa-6-azaspiro[3.3]heptan-6-yl)propan-1-ol

To a mixture of 6-oxa-2-azaspiro[3.3]heptane (2 g, 10.6 mmol) in DMF (40 mL) was added potassium carbonate (4.15 g, 30 mmol). The reaction mixture was stirred at rt for 30 minutes, then 3-bromo-1-propanol (1.0 mL, 11 mmol) was added. The resulting mixture was stirred at 70° C. overnight, then concentrated in vacuo. The residue was purified by silica gel column chromatography (CH$_2$Cl$_2$/MeOH (v/v)=20/1) to give the title compound (1.1 g, 66%). The compound was characterized by the following spectroscopic data: MS-ESI: (ESI, pos.ion) m/z: 158.2 [M+1]$^+$.

Step 2) 6-(3-(2-fluoro-4-iodophenoxy)propyl)-2-oxa-6-azaspiro[3.3]heptane

To a 0° C. mixture of 3-(2-oxa-6-azaspiro[3.3]heptan-6-yl)propan-1-ol (2.5 g, 15.9 mmol), triphenylphosphine (4.17 g, 15.9 mmol), 2-fluoro-4-iodophenol (3.78 g, 15.9 mmol) in DMF (30 mL) was added diisopropyl azodicarboxylate (3.1 mL, 15.9 mmol). The reaction mixture was warmed to rt slowly and stirred overnight, then concentrated in vacuo. The residue was purified by silica gel column chromatography (CH$_2$Cl$_2$/MeOH (v/v)=10/1) to give the title compound (3.0 g, 50%). The compound was characterized by the following spectroscopic data: MS-ESI: (ESI, pos.ion) m/z: 378.1 [M+1]$^+$.

Step 3) 6-(3-(2-fluoro-4-((4-nitrophenyl)ethynyl)phenoxy)propyl)-2-oxa-6-azaspiro[3.3]heptane To a two-neck flask were added 6-(3-(2-fluoro-4-iodophenoxy)propyl)-2-oxa-6-azaspiro[3.3]heptane (146 mg, 0.39 mmol), 4-nitrophenylacetylene (85 mg, 0.58 mmol), CuI (30 mg, 0.15 mmol), and bis(triphenylphosphine)palladium(II) chloride (55 mg, 0.08 mmol). The mixture was degassed and refilled with N$_2$ for three times. Then toluene (20 mL) and triethylamine (0.3 mL) were added to the mixture under the N$_2$ atmosphere, and the mixture was stirred at 90° C. for 5 hours. The resulting mixture was concentrated in vacuo and the residue was purified by silica gel column chromatography (CH$_2$Cl$_2$/MeOH (v/v)=10/1) to give the title compound as a light yellow solid (100 mg, 65%). The compound was characterized by the following spectroscopic data: MS-ESI: (ESI, pos.ion) m/z: 397.2 [M+1]$^+$.

Step 4) 4-((4-(3-(2-oxa-6-azaspiro[3.3]heptan-6-yl)propoxy)-3-fluorophenyl)ethynyl)aniline To a mixture of 6-(3-(2-fluoro-4-((4-nitrophenyl)ethynyl)phenoxy)propyl)-2-oxa-6-azaspiro[3.3]heptane (113 mg, 0.29 mmol) in a mixed solvent ((MeOH/H$_2$O (v/v)=3/1, 20 mL) were added ammonium chloride (0.15 g, 2.9 mmol) and reduced iron power (80 mg, 1.43 mmol). The mixture was heated to 85° C. and refluxed for 3 hours, and then concentrated in vacuo. The residue was neutralized with saturated aqueous sodium bicarbonate solution (20 mL), and the resulting mixture was extracted with ethyl acetate (200 mL). The organic phase was washed with saturated aqueous sodium chloride solution (50 mL), dried over anhydrous sodium sulfate and concentrated in vacuo. The residue was purified by silica gel column chromatography (CH$_2$Cl$_2$/MeOH (v/v)=10/1) to give the title compound as oil (90 mg, 90%). The compound was characterized by the following spectroscopic data: MS-ESI: (ESI, pos.ion) m/z: 367.2 [M+1]$^+$.

Step 5) 1-(4-((4-(3-(2-oxa-6-azaspiro[3.3]heptan-6-yl)propoxy)-3-fluorophenyl)ethynyl)phenyl)-3-(5-(tert-butyl)isoxazol-3-yl)urea The title compound was prepared as a light yellow solid (200 mg, 40%) by the procedure described in step 3 of example 1, using 4-((4-(3-(2-oxa-6-azaspiro[3.3]heptan-6-yl)propoxy)-3-fluorophenyl)ethynyl)aniline (330 mg, 0.9 mmol), acetonitrile (50 mL), phenyl (5-(tert-butyl)isoxazol-3-yl)carbamate (1.2 g, 4.5 mmol) and DIPEA (1.5 mL, 9 mmol). The compound was characterized by the following spectroscopic data: MS-ESI: (ESI, pos.ion) m/z: 533.3 [M+1]$^+$; and $^1$H NMR (600 MHz, CD$_3$OD) δ 7.52 (d, J=8.6 Hz, 2H), 7.49-7.40 (m, 3H), 6.93-6.68 (m, 2H), 6.43 (s, 1H), 4.76 (s, 4H), 4.05 (t, J=6.1 Hz, 2H), 3.54 (s, 4H), 2.70 (t, J=7.3 Hz, 2H), 1.92-1.79 (m, 2H), 1.38 (s, 9H).

Example 24

1-(5-(tert-Butyl)isoxazol-3-yl)-3-(4-((4-(2-((4aR,7aS)-tetrahydro-2H-[1,4]dioxino[2,3-c]pyrro 1-6(3H)-yl)ethoxy)phenyl)ethynyl)phenyl)urea

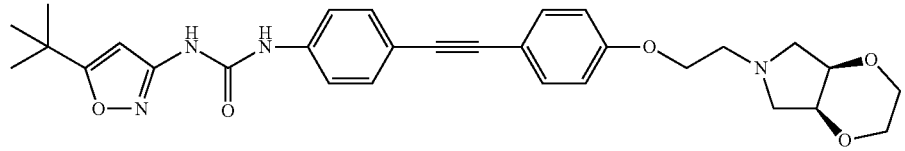 [SMILES: CC(C)(C)c1cc(NC(=O)Nc2ccc(C#Cc3ccc(OCCN4C[C@@H]5OCCO[C@@H]5C4)cc3)cc2)no1]

Step 1) (4aR,7aS)-6-(2-(4-((4-nitrophenyl)ethynyl)phenoxy)ethyl)hexahydro-2H-[1,4]dioxino[2,3-c]pyrrole The title compound was prepared as a claybank solid (0.43 g, 55%) by the procedure described in step 2 of example 18, using 4-((4-nitrophenyl)ethynyl)phenol (0.48 g, 2.0 mmol), (4aR,7aS)-6-(2-chloroethyl)-hexahydro-2H-[1,4]dioxino[2,3-c]pyrrole (0.57 g, 3.0 mmol), acetonitrile (40 mL), potassium carbonate (0.69 g, 5.0 mmol) and potassium iodide (50 mg). The compound was characterized by the following spectroscopic data: MS-ESI: (ESI, pos.ion) m/z: 395.2 [M+1]$^+$.

Step 2) 4-((4-(2-((4aR,7aS)-tetrahydro-2H-[1,4]dioxino[2,3-c]pyrrol-6(3H)-yl)ethoxy)phenyl) ethynyl)aniline The title compound was prepared as a light yellow solid (300 mg, 75%) by the procedure described in step 3 of example 21, using (4aR,7aS)-6-(2-(4-((4-nitrophenyl)ethynyl)phenoxy)ethyl)hexahydro-2H-[1,4]dioxino[2,3-c]pyrrole (0.43 g, 1.1 mmol), zinc powder (0.21 g, 3.3 mmol), ammonium chloride (0.32 g, 6.0 mmol) and a mixed solvent (EtOH/H$_2$O (v/v)=4/1, 25 mL). The compound was characterized by the following spectroscopic data: MS-ESI: (ESI, pos.ion) m/z: 365.2 [M+1]$^+$.

Step 3) 1-(5-(tert-butyl)isoxazol-3-yl)-3-(4-((4-(2-((4aR,7aS)-tetrahydro-2H-[1,4]dioxino[2,3-c]pyrrol-6(3H)-yl)ethoxy)phenyl)ethynyl)phenyl)urea The title compound was prepared as a white solid (0.22 g, 50%) by the procedure described in step 3 of example 1, using 4-((4-(2-((4aR,7aS)-tetrahydro-2H-[1,4]dioxino[2,3-c]pyrrol-6(3H)-yl)ethoxy)phenyl)ethynyl)aniline (300 mg, 0.82 mmol), acetonitrile (30 mL), phenyl (5-(tert-butyl)isoxazol-3-yl)carbamate (1.2 g, 4.5 mmol), DIPEA (1.5 mL, 9 mmol). The compound was characterized by the following spectroscopic data: MS-ESI: (ESI, pos.ion) m/z: 531.3 [M+1]$^+$; and $^1$H NMR (400 MHz, DMSO-d$_6$) δ 9.58 (s, 1H), 9.00 (s, 1H), 7.50 (d, J=8.8 Hz, 2H), 7.46-7.44 (m, 4H), 6.97 (d, J=8.9 Hz, 2H), 6.51 (s, 1H), 4.06 (t, J=5.7 Hz, 2H), 3.99 (p, J=4.4 Hz, 2H), 3.69 (ddd, J=10.2, 6.3, 3.9 Hz, 2H), 3.51-3.43 (m, 2H), 2.97-2.83 (m, 4H), 2.78 (dd, J=9.8, 4.3 Hz, 2H), 1.30 (s, 9H).

Example 25

1-(5-(tert-Butyl)isoxazol-3-yl)-3-(4-((4-(2-morpholinoethoxy)phenyl)ethynyl)phenyl)urea

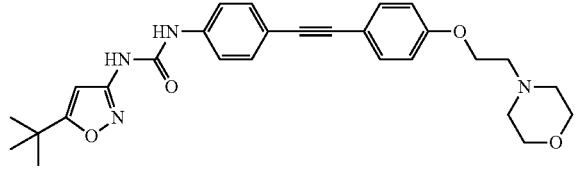 [SMILES: CC(C)(C)c1cc(NC(=O)Nc2ccc(C#Cc3ccc(OCCN4CCOCC4)cc3)cc2)no1]

Step 1) 4-(2-(4-((4-nitrophenyl)ethynyl)phenoxy)ethyl)morpholine

To a mixture of 4-((4-nitrophenyl)ethynyl)phenol (0.48 g, 2.0 mmol), 4-(2-chloroethyl)morpholine (0.45 g, 3.0 mmol) in acetonitrile (40 mL) were added potassium carbonate (0.69 g, 5.0 mmol) and potassium iodide (50 mg). The reaction mixture was stirred at 85° C. for 12 hours and filtered. The filtrate was concentrated in vacuo and the residue was purified by silica gel column chromatography (CH$_2$Cl$_2$/MeOH (v/v)=20/1) to give the title compound as a claybank solid (0.46 g, 65%). The compound was characterized by the following spectroscopic data: MS-ESI: (ESI, pos.ion) m/z: 353.1 [M+1]$^+$.

Step 2) 4-((4-(2-morpholinoethoxy)phenyl)ethynyl)aniline

A mixture of 4-(2-(4-((4-nitrophenyl)ethynyl)phenoxy)ethyl)morpholine (0.46 g, 1.3 mmol), zinc powder (0.25 g, 3.9 mmol) and ammonium chloride (0.32 g, 6.0 mmol) in a mixed solvent (EtOH/H$_2$O (v/v)=4/1, 25 mL) was refluxed for 3 hours. The resulting mixture was filtered to removed the solid, and the filtrate was concentrated in vacuo. To the residue were added dichloromethane (100 mL) and saturated aqueous sodium bicarbonate (100 mL). The resulting mixture was partitioned. The organic layer was dried over anhydrous sodium sulfate and concentrated in vacuo to give the title compound as a light yellow solid (335 mg, 80%). The compound was characterized by the following spectroscopic data: MS-ESI: (ESI, pos.ion) m/z: 323.2 [M+1]$^+$.

Step 3) 1-(5-(tert-butyl)isoxazol-3-yl)-3-(4-((4-(2-morpholinoethoxy)phenyl)ethynyl)phenyl) urea To a mixture of 4-((4-(2-morpholinoethoxy)phenyl)ethynyl)aniline (335 mg, 1.04 mmol) in acetonitrile (40 mL) were added phenyl (5-(tert-butyl)isoxazol-3-yl)carbamate (1.2 g, 4.5 mmol) and DIPEA (1.5 mL, 9 mmol) dropwise. The reaction mixture was refluxed for 40 hours, then concentrated in vacuo. The residue was purified by silica gel column chromatography (CH$_2$Cl$_2$/MeOH (v/v)=10/1) to give the title compound as a white solid (280 mg, 55%). The compound was characterized by the following spectroscopic data: MS-ESI: (ESI, pos.ion) m/z: 489.3 [M+1]$^+$; and $^1$H NMR (400 MHz, DMSO-d$_6$) δ 9.59 (s, 1H), 9.00 (s, 1H), 7.51-7.44 (m, 6H), 6.98 (d, J=8.9 Hz, 2H), 6.51 (s, 1H), 4.12 (t, J=5.7 Hz, 2H), 3.65-3.49 (m, 4H), 2.70 (t, J=5.7 Hz, 2H), 2.47 (m, 4H), 1.30 (s, 9H).

Example 26

1-(5-(tert-Butyl)isoxazol-3-yl)-3-(4-((4-(2-morpholinoethoxy)-3-(trifluoromethyl)phenyl) ethynyl)phenyl)urea (58 mg, 0.31 mmol), Pd (PPh$_3$)$_2$Cl$_2$ (108 mg, 0.15 mmol), THF (50 mL) and Et$_3$N (0.32 mL, 2.3 mmol). The crude product was purified by silica gel column chromatography (CH$_2$Cl$_2$/MeOH (v/v)=50/1) to give the title compound as a light yellow solid (315 mg, 70%). The compound was characterized by the following spectroscopic data: MS-ESI: (ESI, pos.ion) m/z: 420.9 [M+1]$^+$.

Step 3) 4-((4-(2-morpholinoethoxy)-3-(trifluoromethyl)phenyl)ethynyl)aniline

The title compound was prepared as a light yellow solid (135 mg, 75%) by the procedure described in step 4 of example 23, using 4-(2-(4-((4-nitrophenyl)ethynyl)-2-(trifluoromethyl)phenoxy)ethyl)morpholine (210 mg, 0.5 mmol), a mixed solvent (MeOH/H$_2$O (v/v)=3/1, 16 mL), ammonium chloride (0.24 g, 4.5 mmol) and reduced iron power (0.13 g, 2.3 mmol). The compound was characterized by the following spectroscopic data: MS-ESI: (ESI, pos.ion) m/z: 391.3[M+1]$^+$.

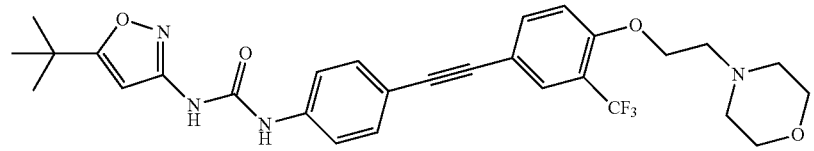 [SMILES: CC(C)(C)c1cc(NC(=O)Nc2ccc(C#Cc3ccc(OCCN4CCOCC4)c(C(F)(F)F)c3)cc2)no1]

Step 1) 4-(2-(4-iodo-2-(trifluoromethyl)phenoxy)ethyl)morpholine

The title compound was prepared as an oil (681 mg, 85%) by the procedure described in step 1 of example 1, using 2-trifluoromethyl-4-iodophenol (576 mg, 2.00 mmol), acetonitrile (70 mL), chloroethylmorpholine (360 mg, 2.40 mmol) and potassium carbonate (552 mg, 4.00 mmol). The compound was characterized by the following spectroscopic data: MS-ESI: (ESI, pos.ion) m/z: 402.8 [M+1]$^+$.

Step 2) 4-(2-(4-((4-nitrophenyl)ethynyl)-2-(trifluoromethyl)phenoxy)ethyl)morpholine The title compound was prepared by the procedure described in step 2 of example 1, using 4-(2-(4-iodo-2-(trifluoromethyl)phenoxy)ethyl)morpholine (400 mg, 0.99 mmol), 4-nitrophenylacetylene (294 mg, 1.99 mmol), CuI Step 4) 1-(5-(tert-butyl)isoxazol-3-yl)-3-(4-((4-(2-morpholinoethoxy)-3-(trifluoromethyl) phenyl)ethynyl)phenyl)urea The title compound was prepared as a light yellow solid (100 mg, 38.9%) by the procedure described in step 3 of example 1, using 4-((4-(2-morpholinoethoxy)-3-(trifluoromethyl)phenyl)ethynyl)aniline (180 mg, 0.35 mmol), acetonitrile (30 mL), triethylamine (0.3 mL, 2.2 mmol) and phenyl (5-(tert-butyl)isoxazol-3-yl)carbamate (0.29 g, 1.1 mmol). The compound was characterized by the following spectroscopic data: MS-ESI: (ESI, pos.ion) m/z: 557.1[M+1]$^+$; and $^1$H NMR (600 MHz, DMSO-d$_6$) δ 9.62 (s, 1H), 9.11 (s, 1H), 7.78 (d, J=8.7 Hz, 1H), 7.74 (d, J=1.6 Hz, 1H), 7.53-7.48 (m, 4H), 7.34 (d, J=8.8 Hz, 1H), 6.52 (s, 1H), 4.28 (t, J=5.3 Hz, 2H), 3.56 (d, J=3.9 Hz, 4H), 2.74 (s, 2H), 2.52-2.50 (m, 4H), 1.30 (s, 9H).

Example 27

1-(4-((4-(3-(2-Oxa-6-azaspiro[3.3]heptan-6-yl)propoxy)-3-(trifluoromethyl)phenyl)ethynyl)phenyl)-3-(5-(tert-butyl)isoxazol-3-yl)urea

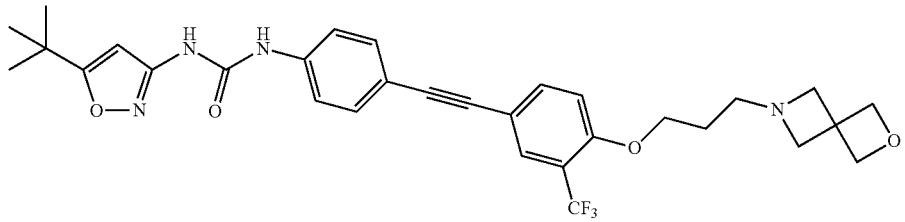 [SMILES: CC(C)(C)c1cc(NC(=O)Nc2ccc(C#Cc3ccc(OCCCN4CC5(COC5)C4)c(C(F)(F)F)c3)cc2)no1]

Step 1) 1-(3-chloropropoxy)-4-iodo-2-(trifluoromethyl)benzene

To a mixture of 2-trifluoromethyl-4-iodophenol (300 mg, 1.04 mmol) in acetonitrile (30 mL) were added 1-bromo-3-chloropropane (190 mg, 1.18 mmol) and potassium carbonate (430 mg, 3.12 mmol). The reaction mixture was refluxed with stirring. After the reaction was completed, the mixture was concentrated in vacuo. To the residue was added water (50 mL) and the mixture was extracted with dichloromethane (500 mL). The organic phase was washed with saturated aqueous sodium chloride solution (100 mL), dried over anhydrous sodium sulfate and concentrated in vacuo. The residue was purified by silica gel column chromatography (EtOAc/PE (v/v)=1/5) to give the title compound as an oil (276 mg, 75.7%). The compound was characterized by the following spectroscopic data: MS-ESI: (ESI, pos.ion) m/z: 365.2 [M+1]$^+$.

Step 2) 1-(3-chloropropoxy)-4-((4-nitrophenyl)ethynyl)-2-(trifluoromethyl)benzene The title compound was prepared as a light yellow solid (635 mg, 82.8%) by the procedure described in step 3 of example 23, using 1-(3-chloropropoxy)-4-iodo-2-(trifluoromethyl)benzene (730 mg, 2.0 mmol), 4-nitrophenylacetylene (590 mg, 4.0 mmol), CuI (58 mg, 0.31 mmol), Pd(PPh$_3$)$_2$Cl$_2$ (108 mg, 0.15 mmol), THF (100 mL) and Et$_3$N (0.32 mL, 2.3 mmol). The compound was characterized by the following spectroscopic data: MS-ESI: (ESI, pos.ion) m/z: 384.3 [M+1]$^+$.

Step 3) 4-((4-(3-chloropropoxy)-3-(trifluoromethyl)phenyl)ethynyl)aniline

The title compound was prepared as oil (275 mg, 74.3%) by the procedure described in step 4 of example 23, using 1-(3-chloropropoxy)-4-((4-nitrophenyl)ethynyl)-2-(trifluoromethyl)benzene (400 mg, 1.05 mmol), a mixed solvent (MeOH/H$_2$O (v/v)=3/1, 120 mL), ammonium chloride (830 g, 15.65 mmol) and reduced iron power (438 g, 7.83 mmol). The compound was characterized by the following spectroscopic data: MS-ESI: (ESI, pos.ion) m/z: 354.1[M+1]$^+$.

Step 4) 1-(5-(tert-butyl)isoxazol-3-yl)-3-(4-((4-(3-chloropropoxy)-3-(trifluoromethyl)phenyl) ethynyl)phenyl)urea The title compound was prepared as oil (262 mg, 50.6%) by the procedure described in step 3 of example 1, using 4-((4-(3-chloropropoxy)-3-(trifluoromethyl)phenyl)ethynyl)aniline (350 mg, 0.99 mmol), acetonitrile (70 mL), Et$_3$N (0.3 mL, 2.2 mmol) and phenyl (5-(tert-butyl)isoxazol-3-yl) carbamate (0.55 g, 2.1 mmol). The compound was characterized by the following spectroscopic data: MS-ESI: (ESI, pos.ion) m/z: 520.5[M+1]$^+$.

Step 5) 1-(4-((4-(3-(2-oxa-6-azaspiro[3.3]heptan-6-yl)propoxy)-3-(trifluoromethyl)phenyl) ethynyl)phenyl)-3-(5-(tert-butyl)isoxazol-3-yl)urea To a mixture of 1-(5-(tert-butyl)isoxazol-3-yl)-3-(4-((4-(3-chloropropoxy)-3-(trifluoromethyl)phenyl)ethynyl)phenyl)urea (100 mg, 0.19 mmol) in acetonitrile (30 mL) were added potassium carbonate (430 mg, 3.12 mmol) and 2-oxa-6-azaspiro[3.3]heptane (20 mg, 0.2 mmol). The reaction mixture was refluxed. After the reaction was completed, the mixture was concentrated in vacuo. To the residue was added water (50 mL) and the resulting mixture was extracted with dichloromethane (500 mL). The organic phase was washed with saturated aqueous sodium chloride solution (100 mL), dried over anhydrous sodium sulfate, and concentrated in vacuo. The residue was purified by silica gel column chromatography (CH$_2$Cl$_2$/MeOH (v/v)=10/1) to give the title compound as a light yellow solid (77 mg, 70%). The compound was characterized by the following spectroscopic data: MS-ESI: (ESI, pos.ion) m/z: 583.1 [M+1]$^+$; and $^1$H NMR (400 MHz, CDCl$_3$) δ 7.74 (s, 1H), 7.60 (d, J=9.2 Hz, 1H), 7.56 (d, J=8.6 Hz, 2H), 7.49 (d, J=8.6 Hz, 2H), 6.93 (d, J=8.4 Hz, 1H), 5.98 (s, 1H), 4.12 (t, J=5.8 Hz, 2H), 3.65 (s, 4H), 2.84-2.76 (m, 2H), 1.99-1.95 (m, 2H), 1.38 (s, 9H), 1.28 (s, 4H).

Example 28

1-(5-(tert-Butyl)isoxazol-3-yl)-3-(4-((4-(3-(4-methylpiperazin-1-yl)propoxy)-3-(trifluoromethyl)phenyl)ethynyl)phenyl)urea

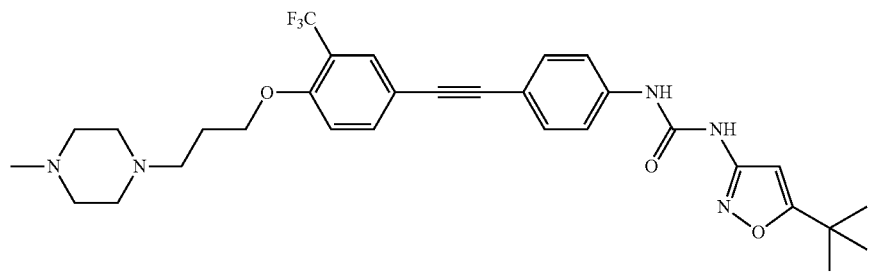 [SMILES: CN1CCN(CCCOc2ccc(C#Cc3ccc(NC(=O)Nc4cc(C(C)(C)C)on4)cc3)cc2C(F)(F)F)CC1]

Step 1) 1-(3-(4-iodo-2-(trifluoromethyl)phenoxy)propyl)-4-methylpiperazine

The title compound was prepared as an oil (320 mg, 71.7%) by the procedure described in step 1 of example 1, using 2-trifluoromethyl-4-iodophenol (300 mg, 1.04 mmol), acetonitrile (30 mL), 1-(3-chloropropyl)-4-methylpiperazine (200 mg, 1.14 mmol) and potassium carbonate (430 mg, 3.12 mmol). The compound was characterized by the following spectroscopic data: MS-ESI: (ESI, pos.ion) m/z: 428.9 [M+1]$^+$.

Step 2) 1-methyl-4-(3-(4-((4-nitrophenyl)ethynyl)-2-(trifluoromethyl)phenoxy)propyl) piperazine The title compound was prepared as a light yellow solid (650 mg, 88.8%) by the procedure described in step 2 of example 1, using 1-(3-(4-iodo-2-(trifluoromethyl)phenoxy)propyl)-4-methylpiperazine (700 mg, 1.63 mmol), nitrophenylacetylene (480 mg, 3.27 mmol), CuI (58 mg, 0.31 mmol), Pd(PPh$_3$)$_2$Cl$_2$ (108 mg, 0.15 mmol), THF (70 mL) and Et$_3$N (0.32 mL, 2.3 mmol). The compound was characterized by the following spectroscopic data: MS-ESI: (ESI, pos.ion) m/z: 449.3 [M+1]$^+$.

Step 3) 4-((4-(3-(4-methylpiperazin-1-yl)propoxy)-3-(trifluoromethyl)phenyl)ethynyl)aniline The title compound was prepared as an oil (420 mg, 64.3%) by the procedure described in step 4 of example 23, using 1-methyl-4-(3-(4-((4-nitrophenyl)ethynyl)-2-(trifluoromethyl)phenoxy)propyl)piperazine (700 mg, 0.5 mmol), a mixed solvent ((MeOH/H$_2$O (v/v)=3/1, 160 mL), ammonium chloride (830 g, 15.65 mmol) and reduced iron power (438 g, 7.83 mmol). The compound was characterized by the following spectroscopic data: MS-ESI: (ESI, pos.ion) m/z: 418.3[M+1]$^+$.

Step 4) 1-(5-(tert-butyl)isoxazol-3-yl)-3-(4-((4-(3-(4-methylpiperazin-1-yl)propoxy)-3-(trifluoromethyl)phenyl)ethynyl)phenyl)urea The title compound was prepared as a light yellow solid (40 mg, 28.6%) by the procedure described in step 3 of example 1, using 4-((4-(3-(4-methylpiperazin-1-yl)propoxy)-3-(trifluoromethyl)phenyl)ethynyl)aniline (100 mg, 0.35 mmol), acetonitrile (30 mL), triethylamine (0.3 mL, 2.2 mmol) and phenyl (5-(tert-butyl)isoxazol-3-yl)carbamate (0.29 g, 1.1 mmol). The compound was characterized by the following spectroscopic data: MS-ESI: (ESI, pos.ion) m/z: 584.5[M+1]$^+$; and $^1$H NMR (600 MHz, CD$_3$OD) δ 7.70 (d, J=8.8 Hz, 1H), 7.68 (s, 1H), 7.55 (d, J=8.4 Hz, 2H), 7.47 (d, J=8.4 Hz, 2H), 7.22 (d, J=8.6 Hz, 1H), 6.40 (s, 1H), 4.22 (t, J=5.8 Hz, 2H), 3.33 (s, 4H), 2.74-2.71 (m, 2H), 2.69 (s, 4H), 2.66 (s, 3H), 2.07 (s, 2H), 1.37 (s, 9H).

Examples 29-44

The following compounds of examples 29-44 can be prepared by using appropriate starting materials according to Scheme 2:

| Example | Structure | MS [M + 1]+ |
|---|---|---|
| 29 | 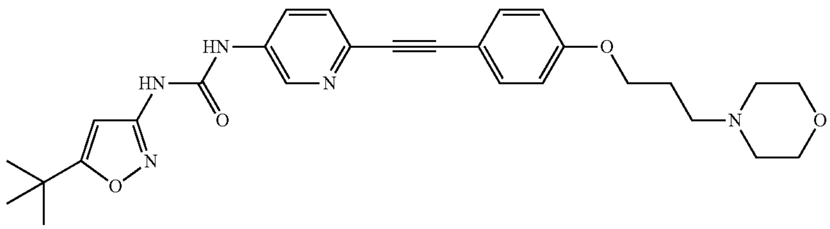 | 504.25 |
| 30 | 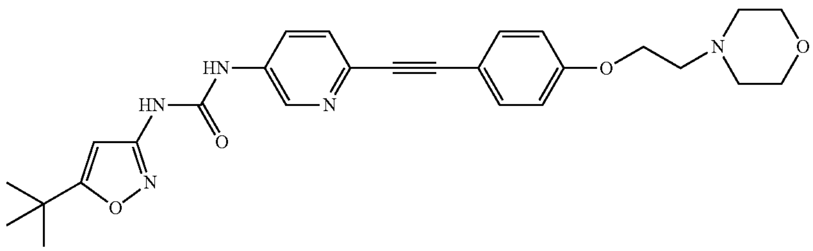 | 490.24 |
| 31 | 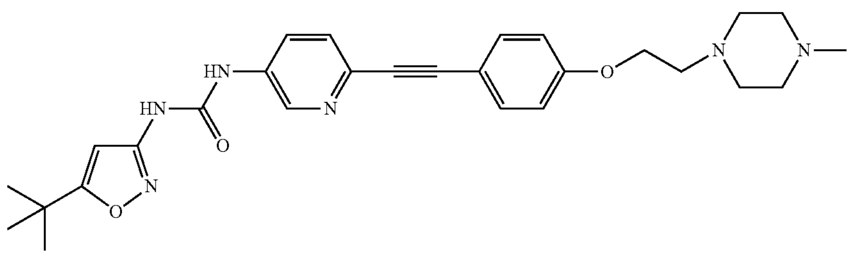 [SMILES: CN1CCN(CCOc2ccc(C#Cc3ccc(NC(=O)Nc4cc(C(C)(C)C)on4)cn3)cc2)CC1] | 503.27 |
| 32 | 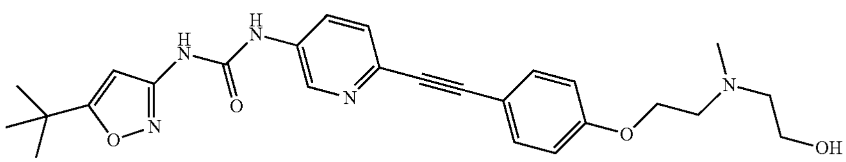 [SMILES: CN(CCO)CCOc1ccc(C#Cc2ccc(NC(=O)Nc3cc(C(C)(C)C)on3)cn2)cc1] | 478.24 |
| 33 | 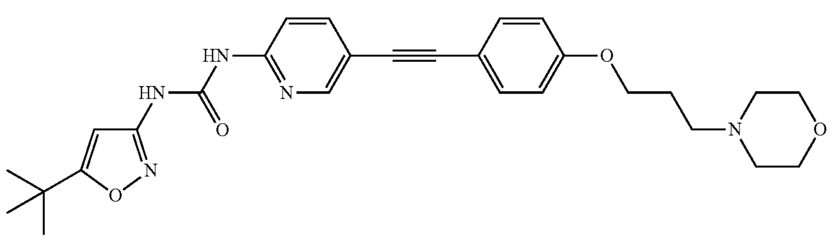 [SMILES: CC(C)(C)c1cc(NC(=O)Nc2ccc(C#Cc3ccc(OCCCN4CCOCC4)cc3)cn2)no1] | 504.25 |
| 34 | 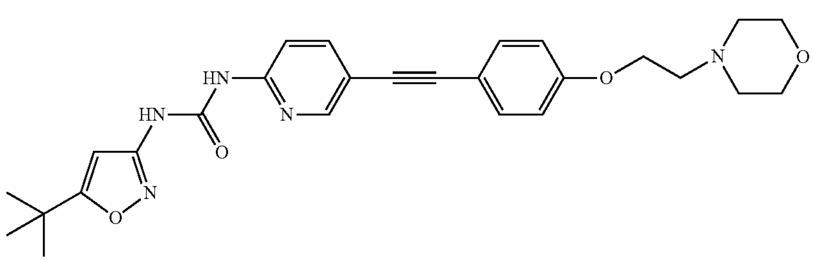 | 490.24 |

| Example | Structure | MS [M + 1]+ |
|---|---|---|
| 35 | 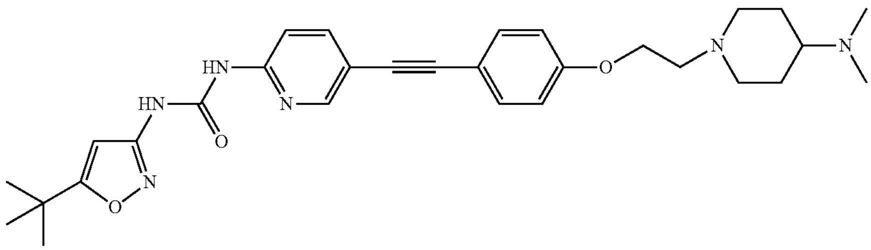 [SMILES: CN(C)C1CCN(CCOc2ccc(C#Cc3ccc(NC(=O)Nc4cc(C(C)(C)C)on4)nc3)cc2)CC1] | 531.30 |
| 36 | 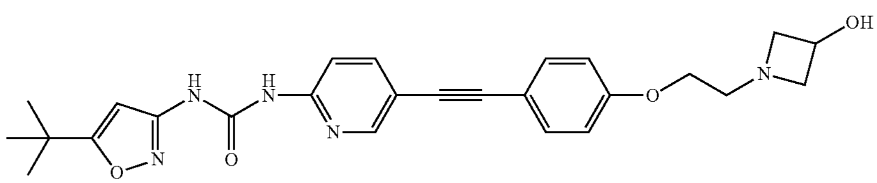 [SMILES: CC(C)(C)c1cc(NC(=O)Nc2ccc(C#Cc3ccc(OCCN4CC(O)C4)cc3)cn2)no1] | 476.22 |
| 37 | 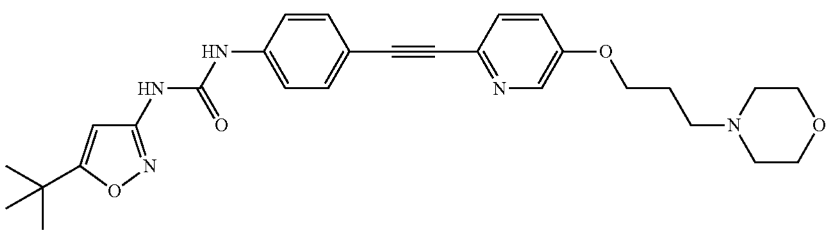 | 504.25 |
| 38 | 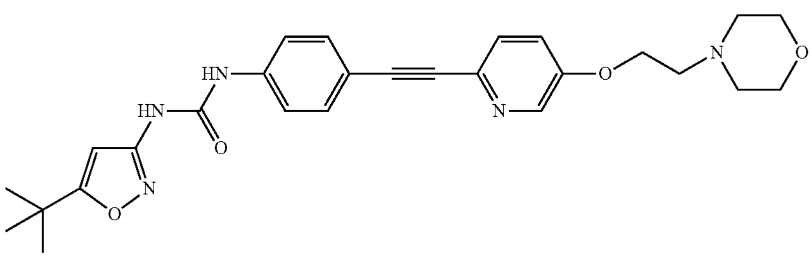 | 490.24 |
| 39 | 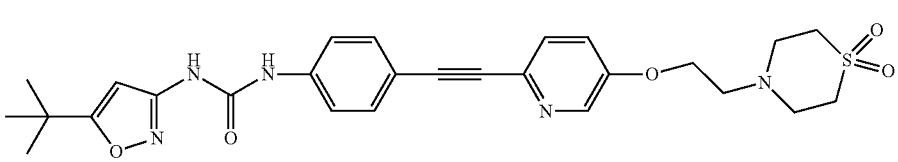 [SMILES: CC(C)(C)c1cc(NC(=O)Nc2ccc(C#Cc3ccc(OCCN4CCS(=O)(=O)CC4)cn3)cc2)no1] | 538.20 |
| 40 | — | — |
| 41 | 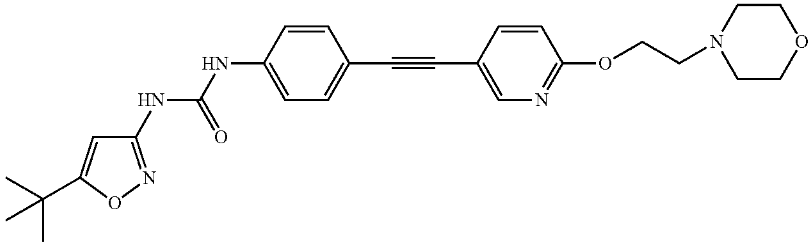 [SMILES: CC(C)(C)c1cc(NC(=O)Nc2ccc(C#Cc3ccc(OCCN4CCOCC4)nc3)cc2)no1] | 490.24 |

-continued

| Example | Structure | MS [M + 1]+ |
|---------|-----------|-------------|
| 42 | 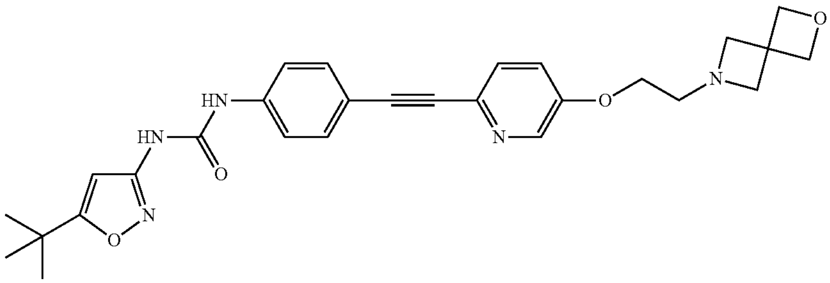 [SMILES: CC(C)(C)c1cc(NC(=O)Nc2ccc(C#Cc3ccc(OCCN4CC5(COC5)C4)cn3)cc2)no1] | 502.24 |
| 43 | 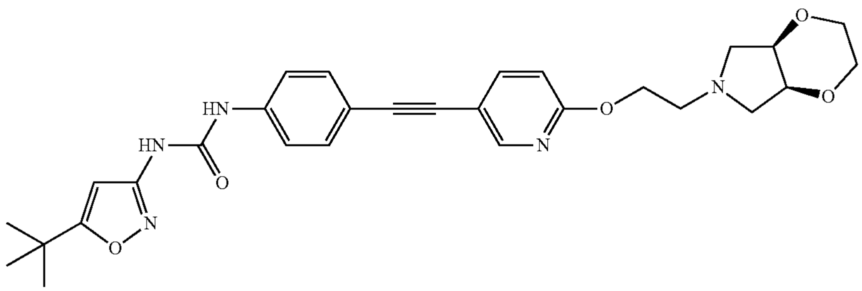 [SMILES: CC(C)(C)c1cc(NC(=O)Nc2ccc(C#Cc3ccc(OCCN4C[C@@H]5OCCO[C@@H]5C4)nc3)cc2)no1] | 532.25 |
| 44 | 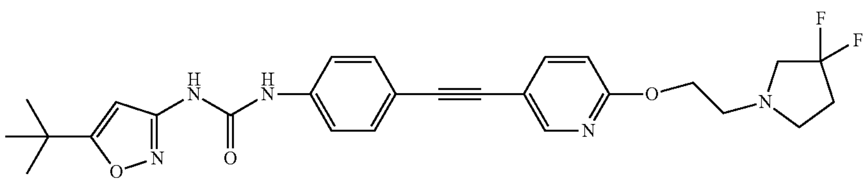 [SMILES: CC(C)(C)c1cc(NC(=O)Nc2ccc(C#Cc3ccc(OCCN4CCC(F)(F)C4)nc3)cc2)no1] | 510.22 |

Examples 45-72

The following compounds of examples 45-72 can be prepared by using appropriate starting materials according to Scheme 11:

| Example | Structure | MS [M + 1]+ |
|---------|-----------|-------------|
| 45 | 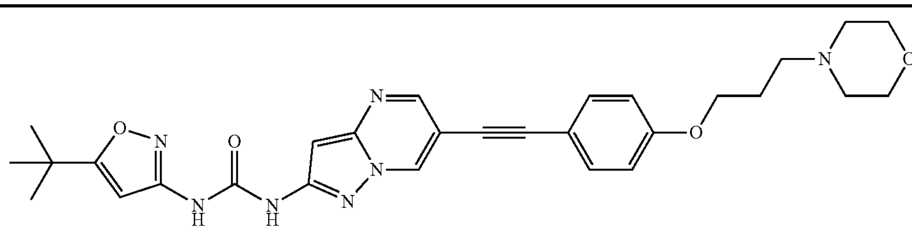 | 544.26 |
| 46 | 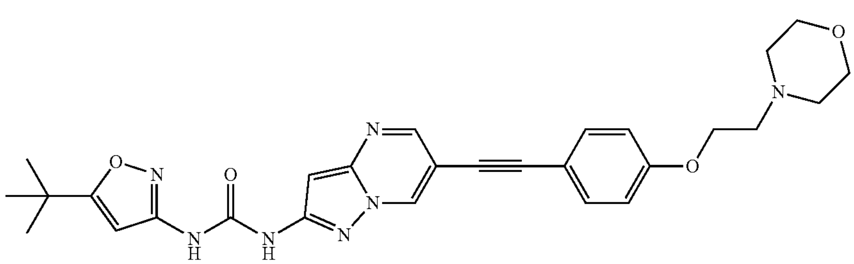 | 530.24 |

-continued

| Example | Structure | MS [M + 1]+ |
|---|---|---|
| 47 | 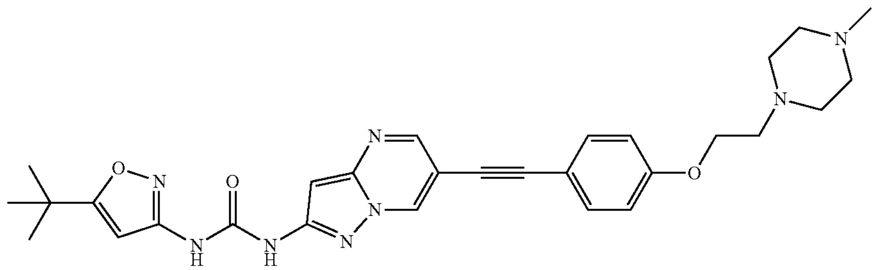 [SMILES: CN1CCN(CCOc2ccc(C#Cc3cnc4cc(NC(=O)Nc5cc(C(C)(C)C)on5)nn4c3)cc2)CC1] | 543.28 |
| 48 | 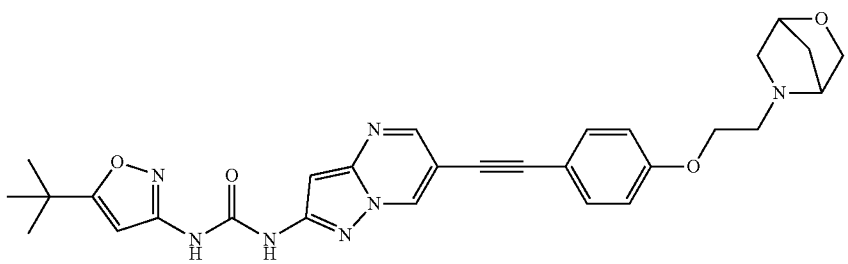 [SMILES: CC(C)(C)c1cc(NC(=O)Nc2cc3ncc(C#Cc4ccc(OCCN5CC6CC5CO6)cc4)cn3n2)no1] | 542.24 |
| 49 | 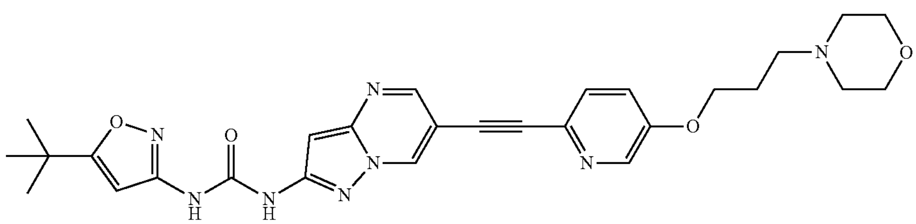 [SMILES: CC(C)(C)c1cc(NC(=O)Nc2cc3ncc(C#Cc4ccc(OCCCN5CCOCC5)cn4)cn3n2)no1] | 545.25 |
| 50 | 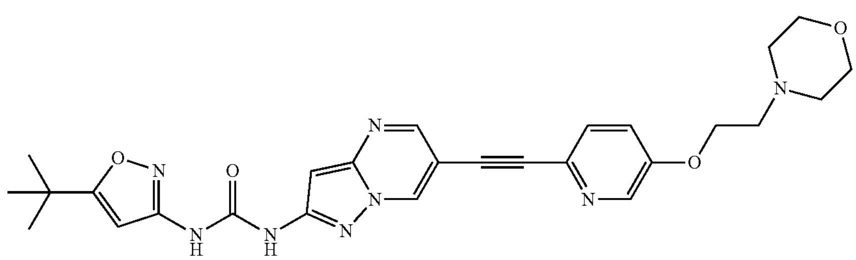 [SMILES: CC(C)(C)c1cc(NC(=O)Nc2cc3ncc(C#Cc4ccc(OCCN5CCOCC5)cn4)cn3n2)no1] | 531.24 |
| 51 | 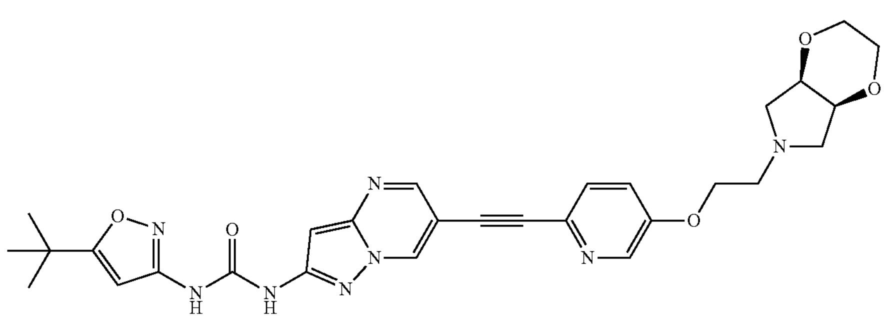 [SMILES: CC(C)(C)c1cc(NC(=O)Nc2cc3ncc(C#Cc4ccc(OCCN5C[C@@H]6OCCO[C@@H]6C5)cn4)cn3n2)no1] | 573.25 |
| 52 | 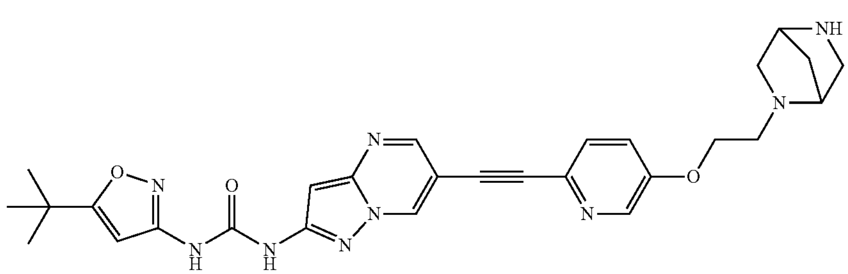 [SMILES: CC(C)(C)c1cc(NC(=O)Nc2cc3ncc(C#Cc4ccc(OCCN5CC6CC5CN6)cn4)cn3n2)no1] | 542.25 |

-continued

| Example | Structure | MS [M + 1]+ |
|---|---|---|
| 53 | 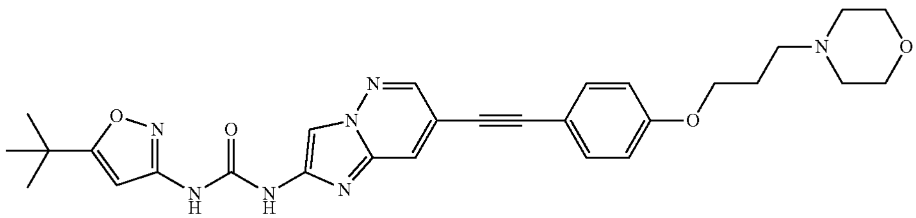 [SMILES: CC(C)(C)c1cc(NC(=O)Nc2cn3ncc(C#Cc4ccc(OCCCN5CCOCC5)cc4)cc3n2)no1] | 544.26 |
| 54 | 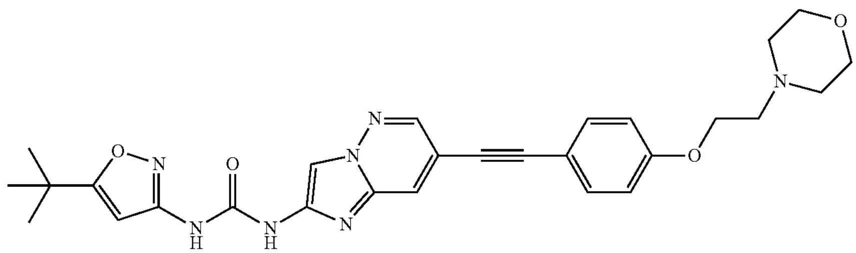 [SMILES: CC(C)(C)c1cc(NC(=O)Nc2cn3ncc(C#Cc4ccc(OCCN5CCOCC5)cc4)cc3n2)no1] | 530.24 |
| 55 | 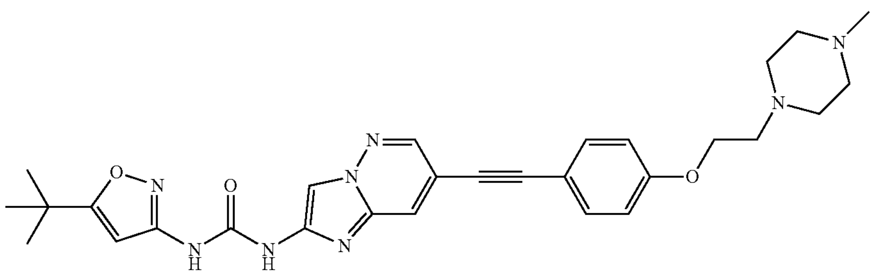 [SMILES: CN1CCN(CCOc2ccc(C#Cc3cnn4cc(NC(=O)Nc5cc(C(C)(C)C)on5)nc4c3)cc2)CC1] | 543.28 |
| 56 | 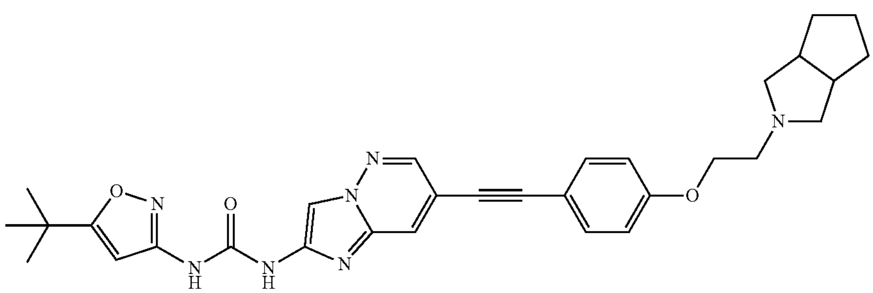 [SMILES: CC(C)(C)c1cc(NC(=O)Nc2cn3ncc(C#Cc4ccc(OCCN5CC6CCCC6C5)cc4)cc3n2)no1] | 554.28 |
| 57 | 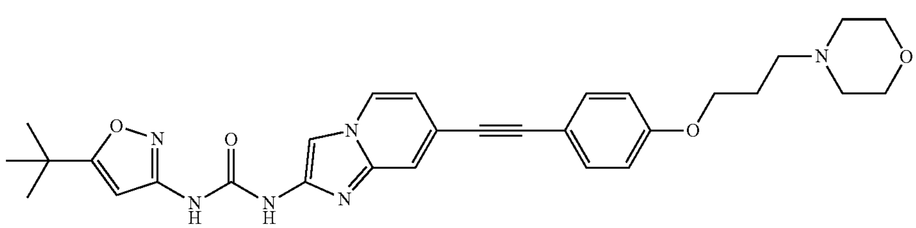 [SMILES: CC(C)(C)c1cc(NC(=O)Nc2cn3ccc(C#Cc4ccc(OCCCN5CCOCC5)cc4)cc3n2)no1] | 543.26 |
| 58 | 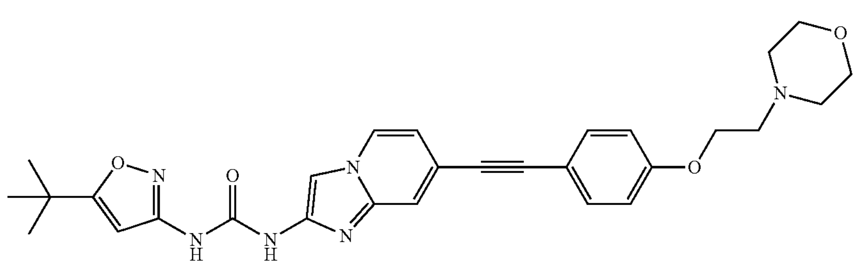 [SMILES: CC(C)(C)c1cc(NC(=O)Nc2cn3ccc(C#Cc4ccc(OCCN5CCOCC5)cc4)cc3n2)no1] | 529.25 |

-continued

| Example | Structure | MS [M + 1]+ |
|---|---|---|
| 59 | 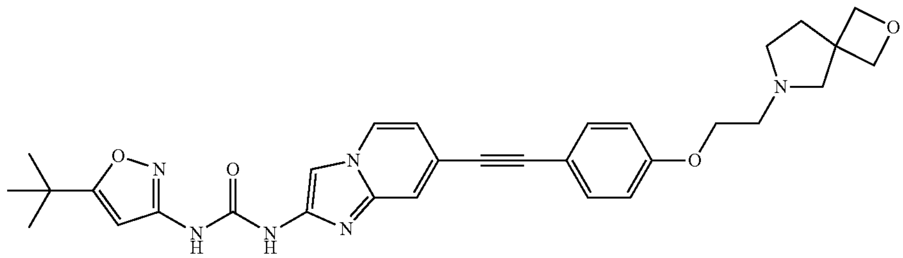 [SMILES: CC(C)(C)c1cc(NC(=O)Nc2cn3ccc(C#Cc4ccc(OCCN5CCC6(COC6)C5)cc4)cc3n2)no1] | 555.26 |
| 60 | 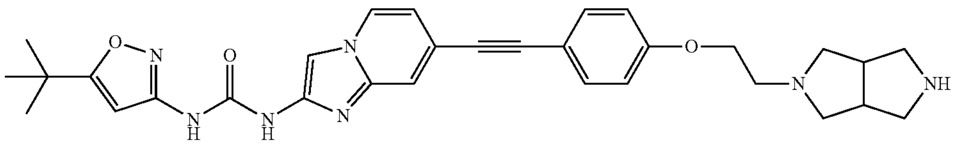 [SMILES: CC(C)(C)c1cc(NC(=O)Nc2cn3ccc(C#Cc4ccc(OCCN5CC6CNCC6C5)cc4)cc3n2)no1] | 554.28 |
| 61 | 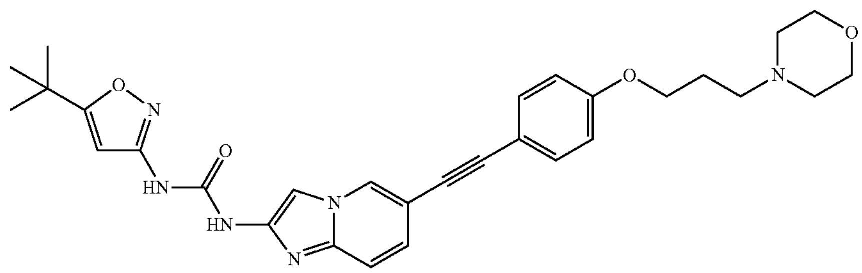 [SMILES: CC(C)(C)c1cc(NC(=O)Nc2cn3cc(C#Cc4ccc(OCCCN5CCOCC5)cc4)ccc3n2)no1] | 543.26 |
| 62 | 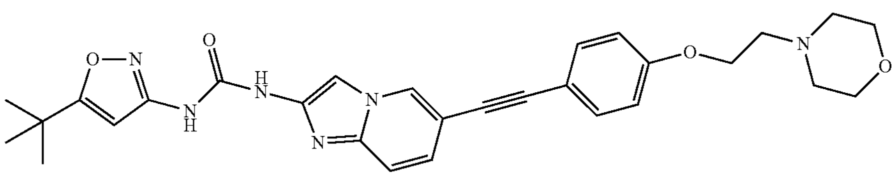 [SMILES: CC(C)(C)c1cc(NC(=O)Nc2cn3cc(C#Cc4ccc(OCCN5CCOCC5)cc4)ccc3n2)no1] | 529.25 |
| 63 | 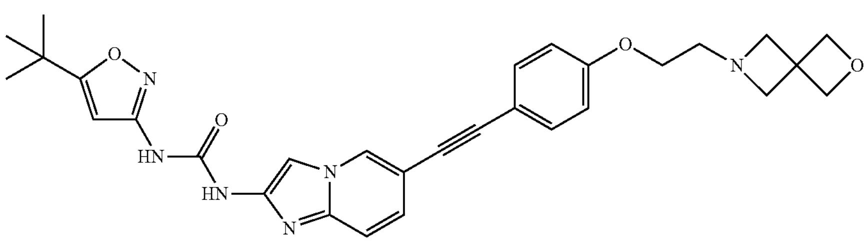 [SMILES: CC(C)(C)c1cc(NC(=O)Nc2cn3cc(C#Cc4ccc(OCCN5CC6(COC6)C5)cc4)ccc3n2)no1] | 541.25 |
| 64 | 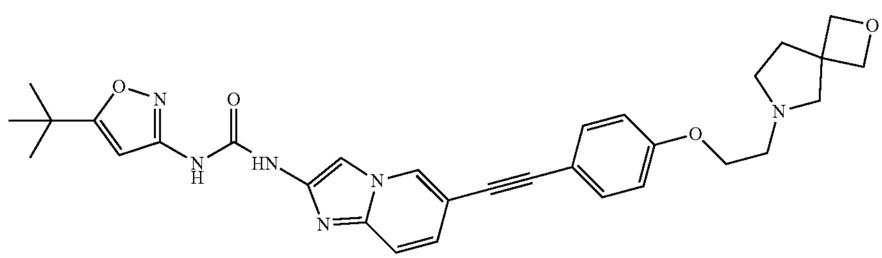 [SMILES: CC(C)(C)c1cc(NC(=O)Nc2cn3cc(C#Cc4ccc(OCCN5CCC6(COC6)C5)cc4)ccc3n2)no1] | 555.26 |
| 65 | 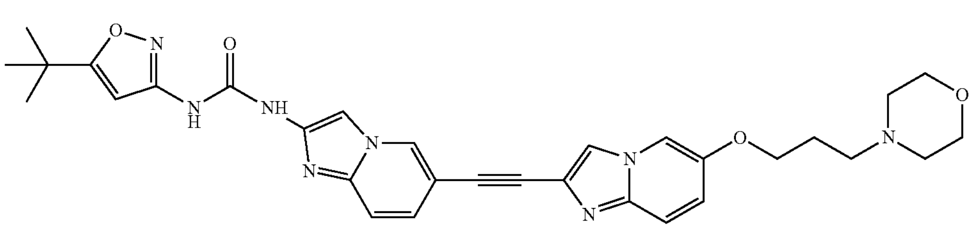 [SMILES: CC(C)(C)c1cc(NC(=O)Nc2cn3cc(C#Cc4cn5cc(OCCCN6CCOCC6)ccc5n4)ccc3n2)no1] | 583.27 |

-continued
| Example | Structure | MS [M + 1]+ |
|---|---|---|
| 66 | 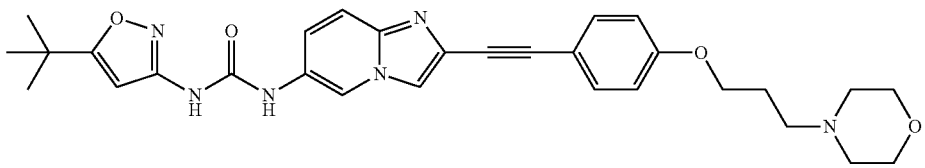 [SMILES: CC(C)(C)c1cc(NC(=O)Nc2ccc3nc(C#Cc4ccc(OCCCN5CCOCC5)cc4)cn3c2)no1] | 543.26 |
| 67 | 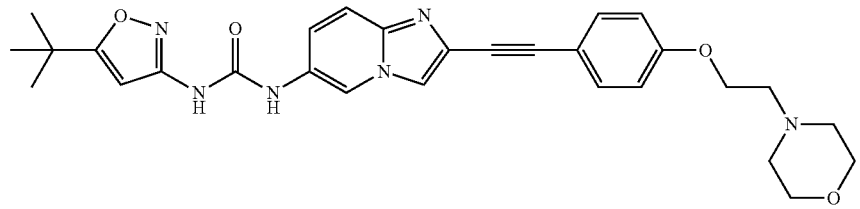 [SMILES: CC(C)(C)c1cc(NC(=O)Nc2ccc3nc(C#Cc4ccc(OCCN5CCOCC5)cc4)cn3c2)no1] | 529.25 |
| 68 | 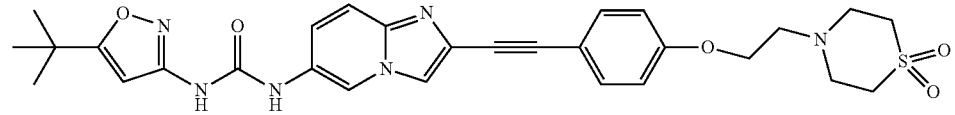 [SMILES: CC(C)(C)c1cc(NC(=O)Nc2ccc3nc(C#Cc4ccc(OCCN5CCS(=O)(=O)CC5)cc4)cn3c2)no1] | 577.22 |
| 69 | 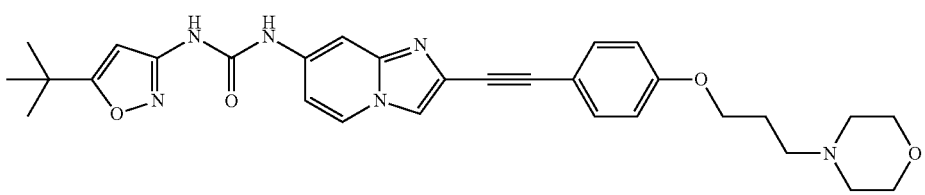 [SMILES: CC(C)(C)c1cc(NC(=O)Nc2ccn3cc(C#Cc4ccc(OCCCN5CCOCC5)cc4)nc3c2)no1] | 543.26 |
| 70 | 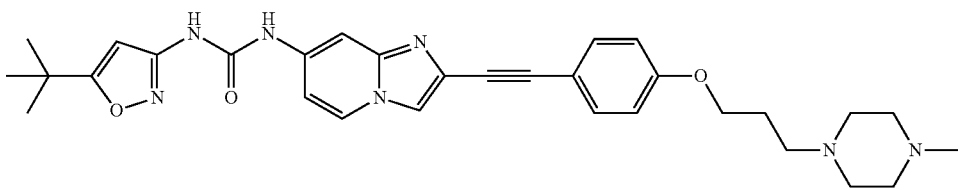 [SMILES: CN1CCN(CCCOc2ccc(C#Cc3cn4ccc(NC(=O)Nc5cc(C(C)(C)C)on5)cc4n3)cc2)CC1] | 556.30 |
| 71 | 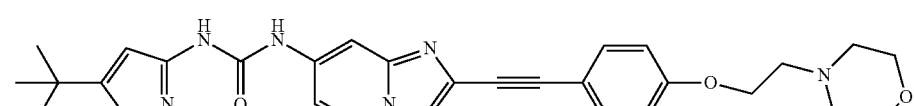 | 529.25 |
| 72 | 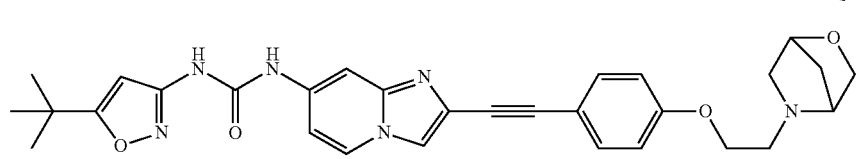 | 541.25 |

Examples 73 to 78

The following compounds of examples 73-78 can be prepared by using appropriate starting materials according to Scheme 2:

| Example | structure | MS [M + 1]+ |
|---|---|---|
| 73 | 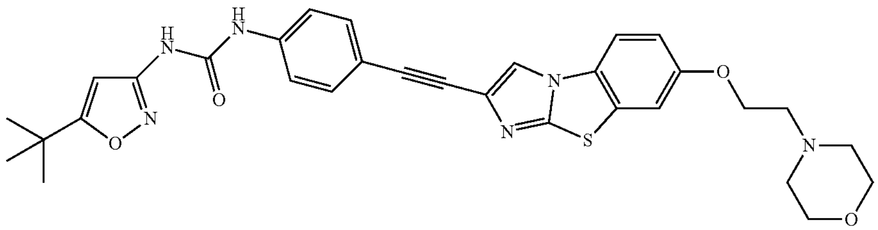 [SMILES: CC(C)(C)c1cc(NC(=O)Nc2ccc(C#Cc3cn4c(n3)sc3cc(OCCN5CCOCC5)ccc34)cc2)no1] | 585.22 |
| 74 | 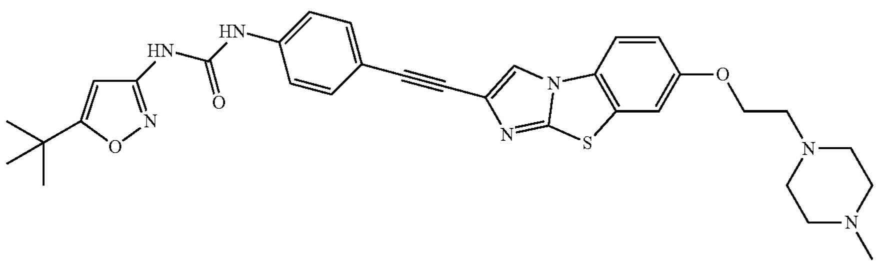 [SMILES: CN1CCN(CCOc2ccc3c(c2)sc2nc(C#Cc4ccc(NC(=O)Nc5cc(C(C)(C)C)on5)cc4)cn23)CC1] | 598.25 |
| 75 | 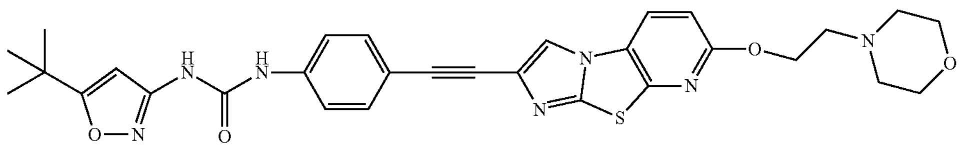 [SMILES: CC(C)(C)c1cc(NC(=O)Nc2ccc(C#Cc3cn4c(n3)sc3nc(OCCN5CCOCC5)ccc34)cc2)no1] | 586.22 |
| 76 | 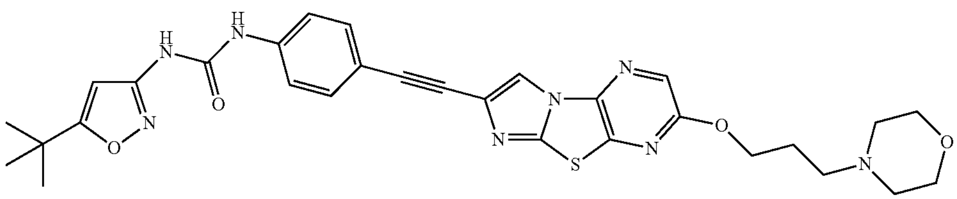 [SMILES: CC(C)(C)c1cc(NC(=O)Nc2ccc(C#Cc3cn4c(n3)sc3nc(OCCCN5CCOCC5)cnc34)cc2)no1] | 601.23 |
| 77 | 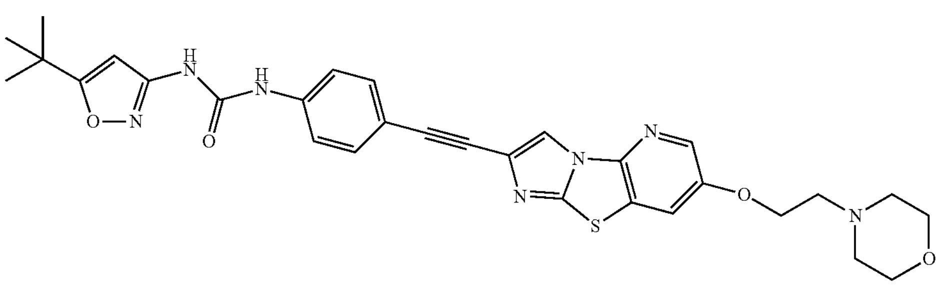 [SMILES: CC(C)(C)c1cc(NC(=O)Nc2ccc(C#Cc3cn4c(n3)sc3cc(OCCN5CCOCC5)cnc34)cc2)no1] | 586.22 |
| 78 | 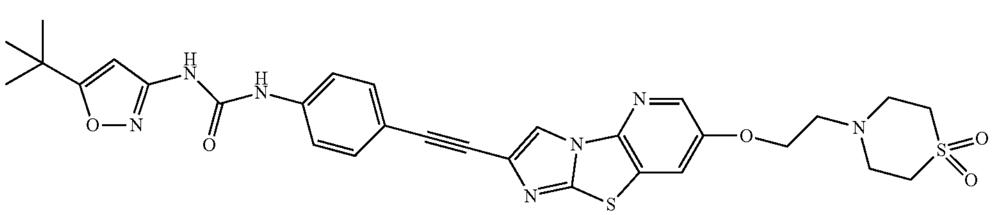 [SMILES: CC(C)(C)c1cc(NC(=O)Nc2ccc(C#Cc3cn4c(n3)sc3cc(OCCN5CCS(=O)(=O)CC5)cnc34)cc2)no1] | 634.18 |

Example 79

1-(5-(tert-Butyl)isoxazol-3-yl)-3-(2-methoxy-4-((4-(3-morpholinopropoxy)phenyl)ethynyl) phenyl)urea

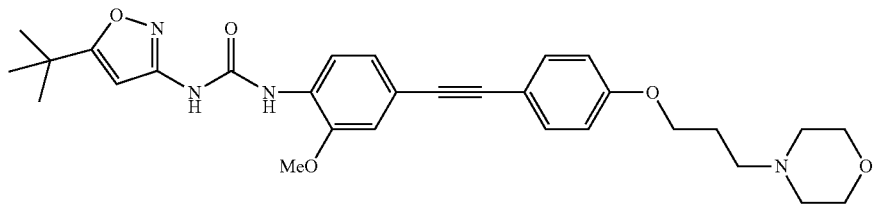 [SMILES: CC(C)(C)c1cc(NC(=O)Nc2ccc(C#Cc3ccc(OCCCN4CCOCC4)cc3)cc2C#N)no1]

Step 1) 4-(3-(4-iodophenoxy)propyl)morpholine

The title compound was prepared by the procedure described in step 1 of example 1, using 4-iodophenol (20 g, 91 mmol), DMF (100 mL), potassium carbonate (42 g, 300 mmol) and 4-(3-chloropropyl)morpholine (14.9 g, 91 mmol), and the reaction mixture was concentrated in vacuo to give the title compound (30 g, 95%) which was used directly for the next step.

Step 2) 4-(3-(4-ethynylphenoxy)propyl)morpholine

To a 250 mL two-neck flask were added 4-(3-(4-iodophenoxy)propyl)morpholine (15.0 g, 43.20 mmol), CuI (1.7 g, 8.9 mmol) and Pd(PPh$_3$)$_2$Cl$_2$ (3.0 g, 4.3 mmol). The mixture was degassed and refilled with N$_2$ for three times. Then acetonitrile (500 mL), trimethylsilylacetylene (10 mL) and triethylamine (30 mL) were added via syringe under the N$_2$ atmosphere. The reaction mixture was stirred at 90° C. for 8 hours and concentrated in vacuo. The residue was dissolved in anhydrous methanol (500 mL), and to the mixture was added potassium carbonate (25 g). The resulting mixture was stirred overnight at rt. The mixture was concentrated in vacuo, and the residue was diluted with water (300 mL). The resulting mixture was extracted with ethyl acetate (1000 mL), dried over anhydrous sodium sulfate, filtered, and the filtrate was concentrated in vacuo. The residue was purified by silica gel column chromatography (CH$_2$Cl$_2$/MeOH (v/v)=25/1) to give the title compound as a white solid (7.1 g, 67%). The compound was characterized by the following spectroscopic data: MS-ESI: (ESI, pos.ion) m/z: 246.2 [M+1]$^+$.

Step 3) 1-(5-(tert-butyl)isoxazol-3-yl)-3-(2-methoxy-4-((4-(3-morpholinopropoxy)phenyl) ethynyl)phenyl)urea To a two-neck flask were added 4-iodo-2-methoxyaniline (130 mg, 0.52 mmol), CuI (0.02 g, 0.1 mmol), Pd(PPh$_3$)$_2$Cl$_2$ (38 mg, 0.054 mmol) and 4-(3-(4-ethynylphenoxy)propyl)morpholine (0.19 g, 0.77 mmol). The mixture was degassed and refilled with N$_2$ for three times. Then THF (20 mL) and triethylamine (0.4 mL) were added under the N$_2$ atmosphere.

The reaction mixture was stirred at rt for 2 hours under the N$_2$ atmosphere, then phenyl (5-(tert-butyl)isoxazol-3-yl)carbamate (0.14 g, 0.54 mmol) and DMAP (20 mg) were added. The resulting mixture was refluxed for 5 hours and then concentrated in vacuo. The residue was purified by silica gel column chromatography (CH$_2$Cl$_2$/MeOH (v/v)=25/1) to give the title compound as a white solid (0.16 g, 58%). The compound was characterized by the following spectroscopic data: MS-ESI: (ESI, pos.ion) m/z: 533.3 [M+1]$^+$; and $^1$H NMR (600 MHz, DMSO-d$_6$) δ 10.13 (s, 1H), 8.80 (s, 1H), 8.17 (d, J=8.4 Hz, 1H), 7.46 (d, J=8.7 Hz, 2H), 7.16 (d, J=1.6 Hz, 1H), 7.10 (dd, J=8.3, 1.6 Hz, 1H), 6.98 (d, J=8.8 Hz, 2H), 6.48 (s, 1H), 4.05 (s, 2H), 3.92 (s, 3H), 3.59 (m, 4H), 2.42 (m, 6H), 1.95-1.86 (m, 2H), 1.30 (s, 9H).

Example 80

1-(5-(tert-Butyl)isoxazol-3-yl)-3-(2-cyano-4-((4-(3-morpholinopropoxy)phenyl)ethynyl) phenyl)urea

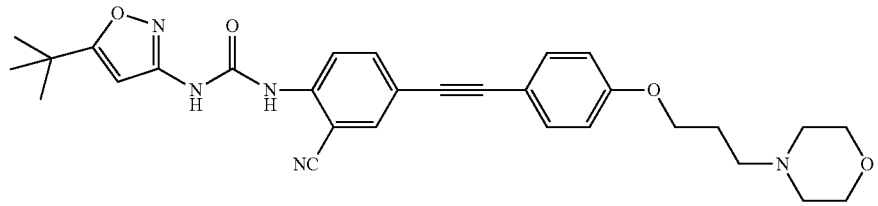 [SMILES: CC(C)(C)c1cc(NC(=O)Nc2ccc(C#Cc3ccc(OCCCN4CCOCC4)cc3)cc2F)no1]

The title compound was prepared as a white solid (90 mg, 70%) by the procedure described in step 3 of example 79, using 2-amino-5-iodo-benzonitrile (59.2 mg, 0.24 mmol), CuI (9 mg, 0.047 mmol), Pd(PPh$_3$)$_2$Cl$_2$ (17 mg, 0.024 mmol), 4-(3-(4-ethynylphenoxy)propyl)morpholine (0.12 g, 0.49 mmol), THF (20 mL), triethylamine (0.2 mL), phenyl (5-(tert-butyl)isoxazol-3-yl)carbamate (0.13 g, 0.5 mmol) and DMAP (14 mg, 0.11 mmol). The compound was characterized by the following spectroscopic data: MS-ESI: (ESI, pos.ion) m/z: 528.3 [M+1]$^+$; and $^1$H NMR (400 MHz, DMSO-d$_6$) δ 11.48 (s, 1H), 10.65 (s, 1H), 8.25 (s, 1H), 7.74 (d, J=8.4 Hz, 1H), 7.50 (d, J=8.5 Hz, 2H), 7.19 (d, J=8.5 Hz, 1H), 6.99 (d, J=8.6 Hz, 2H), 6.28 (s, 1H), 4.06 (t, J=6.3 Hz, 2H), 3.64-3.49 (m, 4H), 2.41 (dd, J=17.8, 10.7 Hz, 6H), 1.94-1.79 (m, 2H), 1.34 (s, 9H).

Example 81

1-(5-(tert-Butyl)isoxazol-3-yl)-3-(2-fluoro-4-((4-(3-morpholinopropoxy)phenyl)ethynyl) phenyl)urea

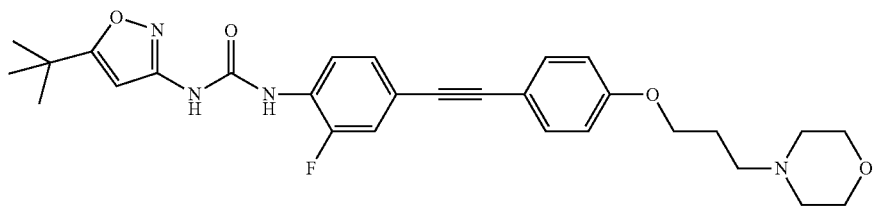

The title compound was prepared as a white solid (130 mg, 59%) by the procedure described in step 3 of example 79, using 2-fluoro-4-iodoaniline (100 mg, 0.42 mmol), 4-(3-(4-ethynylphenoxy)propyl)morpholine (210 mg, 0.86 mmol), CuI (0.02 g, 0.1 mmol, 100 mass %), Pd(PPh$_3$)$_2$Cl$_2$ (38 mg, 0.054 mmol), THF (20 mL), triethylamine (0.4 mL), phenyl (5-(tert-butyl)isoxazol-3-yl)carbamate (220 mg, 0.85 mmol) and DMAP (25 mg, 0.20 mmol). The compound was characterized by the following spectroscopic data: MS-ESI: (ESI, pos.ion) m/z: 521.3 [M+1]$^+$; and $^1$H NMR (400 MHz, DMSO-d$_6$) δ 9.90 (s, 1H), 8.96 (s, 1H), 8.20 (t, J=8.5 Hz, 1H), 7.45 (dd, J=17.1, 5.2 Hz, 3H), 7.33 (d, J=8.8 Hz, 1H), 6.98 (d, J=8.8 Hz, 2H), 6.50 (s, 1H), 4.06 (t, J=6.3 Hz, 2H), 3.61 (s, 4H), 2.50 (m, 6H), 2.00-1.82 (m, 2H), 1.30 (s, 9H).

Example 82

4-(3-(4-((4-(3-(5-(tert-Butyl)isoxazol-3-yl)ureido)phenyl)ethynyl)phenoxy)propyl)morpholine 4-oxide

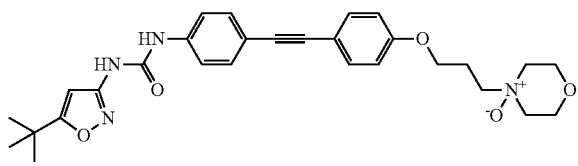

To a mixture of 1-(5-(tert-butyl)isoxazol-3-yl)-3-(4-((4-(3-morpholinopropoxy)phenyl) ethynyl)phenyl)urea (560 mg, 1.11 mmol) in dichloromethane (50 mL) was added MCPBA (0.25 g, 1.4 mmol). The reaction mixture was refluxed for 3 hours and diluted with dichloromethane (300 mL). The organic phase was washed with saturated aqueous sodium bicarbonate (100 mL) twice, dried over anhydrous sodium sulfate and filtered. The filtrate was concentrated in vacuo and the residue was purified by silica gel column chromatography (CH$_2$Cl$_2$/MeOH (v/v)=5/1) to give the title compound as a white solid (0.3 g, 50%). The compound was characterized by the following spectroscopic data: MS-ESI: (ESI, pos.ion) m/z: 519.3 [M+1]$^+$; and $^1$H NMR (400 MHz, CD$_3$OD) δ 7.46 (dd, J=21.2, 9.4 Hz, 3H), 7.18 (ddd, J=14.2, 10.8, 6.4 Hz, 1H), 6.94 (d, J=8.7 Hz, 1H), 6.83 (d, J=6.1 Hz, 1H), 6.40 (s, 1H), 5.88-5.74 (m, 1H), 4.96 (dd, J=24.5, 13.7 Hz, 2H), 4.20 (dt, J=11.7, 8.5 Hz, 2H), 3.92-3.75 (m, 1H), 3.64-3.39 (m, 2H), 3.17 (d, J=11.9 Hz, 1H), 2.47-2.35 (m, 1H), 2.11-1.88 (m, 2H), 1.39 (s, 9H).

Example 83

4-(3-(4-((4-(3-(5-(tert-Butyl)isoxazol-3-yl)ureido) phenyl)ethynyl)-3-fluorophenoxy)propyl) morpholine 4-oxide

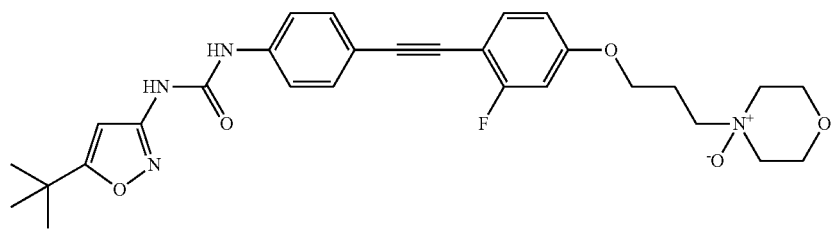

The title compound was prepared as a white solid (0.13 g, 70%) by the procedure described in example 82, using 1-(5-(tert-butyl)isoxazol-3-yl)-3-(4-((2-fluoro-4-(3-morpholinopropoxy)phenyl)ethynyl)phenyl)urea (181 mg, 0.35 mmol), dichloromethane (40 mL) and MCPBA (75 mg, 0.43 mmol). The compound was characterized by the following spectroscopic data: MS-ESI: (ESI, pos.ion) m/z: 537.3 [M+1]$^+$; and $^1$H NMR (400 MHz, DMSO-d$_6$) δ 9.82 (s, 1H), 9.64 (s, 1H), 7.49 (dd, J=28.2, 8.5 Hz, 4H), 7.09-6.86 (m, 2H), 6.85 (d, J=9.3 Hz, 1H), 6.52 (s, 1H), 4.29-3.92 (m, 6H), 3.79 (d, J=13.1 Hz, 2H), 3.58 (m, 2H), 2.33 (s, 2H), 1.99 (s, 2H), 1.30 (s, 9H).

Example 84

1-(5-(1-Hydroxy-2-methylpropan-2-yl)isoxazol-3-yl)-3-(4-((4-(3-morpholinopropoxy)phenyl) ethynyl) phenyl)urea Step 1) phenyl (5-(1-hydroxy-2-methylpropan-2-yl) isoxazol-3-yl)carbamate To a mixture of 2-(3-aminisoxazol-5-yl)-2-methylpropan-1-ol (200 mg, 1.28 mmol) in THF (40 mL) was added potassium carbonate (2.0 g, 14 mmol), and then phenyl chloroformate (1 mL, 7.97 mmol) was added under a N$_2$ atmosphere. The reaction mixture was stirred at rt for 10 hours, and quenched with saturated aqueous sodium bicarbonate solution (50 mL). The mixture was extracted with ethyl acetate (300 mL), and the organic phase was dried over anhydrous sodium sulfate, concentrated in vacuo. The residue was purified by silica gel column chromatography eluted with ethyl acetate to give the title compound as a white solid (0.2 g, 60%). The compound was characterized by the following spectroscopic data: MS-ESI: (ESI, pos.ion) m/z: 277.2 [M+1]$^+$.

Step 2) 1-(5-(1-hydroxy-2-methylpropan-2-yl)isoxazol-3-yl)-3-(4-((4-(3-morpholinopropoxy) phenyl) ethynyl)phenyl)urea The title compound was prepared as a white solid (0.1 g, 33%) by the procedure described in step 4 of example 21, using phenyl (5-(1-hydroxy-2-methylpropan-2-yl)isoxazol-3-yl)carbamate (160 mg, 0.58 mmol), dichloromethane (20 mL), 4-((4-(3-morpholinopropoxy)phenyl)ethynyl)aniline

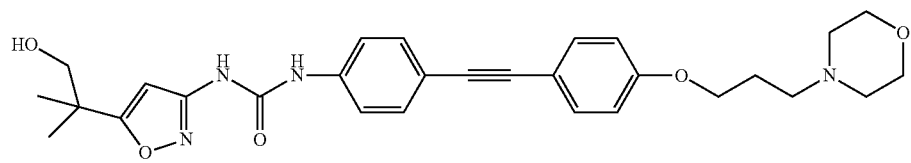 [SMILES: CC(C)(CO)c1cc(NC(=O)Nc2ccc(C#Cc3ccc(OCCCN4CCOCC4)cc3)cc2)no1]

(0.15 g, 0.45 mmol), Et₃N (0.5 mL, 4 mmol) and DMAP (35 mg, 0.29 mmol). The compound was characterized by the following spectroscopic data: MS-ESI: (ESI, pos.ion) m/z: 519.3 [M+1]⁺; and ¹H NMR (400 MHz, DMSO-d₆) δ 9.56 (s, 1H), 9.00 (s, 1H), 7.47 (dd, J=19.6, 8.4 Hz, 6H), 6.97 (d, J=8.6 Hz, 2H), 6.53 (s, 1H), 4.96 (t, J=5.5 Hz, 1H), 4.05 (t, J=6.3 Hz, 2H), 3.58 (s, 4H), 3.44 (t, J=9.1 Hz, 3H), 2.47-2.29 (m, 6H), 1.95-1.77 (m, 2H), 1.23 (s, 6H).

Example 85

1-(4-((2-Fluoro-4-(3-morpholinopropoxy)phenyl) ethynyl)phenyl)-3-(5-(1-hydroxy-2-methyl propan-2-yl)isoxazol-3-yl)urea

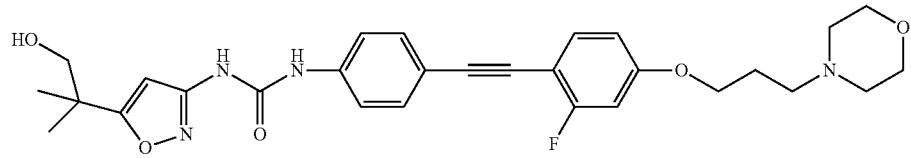 [SMILES: CC(C)(CO)c1cc(NC(=O)Nc2ccc(C#Cc3ccc(OCCCN4CCOCC4)cc3F)cc2)no1]

The title compound was prepared as a white solid (0.17 g, 45%) by the procedure described in step 4 of example 21, using 4-((2-fluoro-4-(3-morpholinopropoxy)phenyl)ethynyl)aniline (252 mg, 0.71 mmol), phenyl (5-(1-hydroxy-2-methylpropan-2-yl)isoxazol-3-yl)carbamate (0.26 g, 0.94 mmol), dichloromethane (30 mL), DMAP (45 mg, 0.39 mmol) and Et₃N (1 mL, 7.19 mmol). The compound was characterized by the following spectroscopic data: MS-ESI: (ESI, pos.ion) m/z: 537.3 [M+1]⁺; and ¹H NMR (400 MHz, DMSO-d₆) δ 9.57 (s, 1H), 9.02 (s, 1H), 7.49 (dt, J=17.9, 6.2 Hz, 5H), 6.96 (dd, J=11.7, 2.3 Hz, 1H), 6.83 (dd, J=8.7, 2.2 Hz, 1H), 6.53 (s, 1H), 4.96 (t, J=5.5 Hz, 1H), 4.07 (t, J=6.3 Hz, 2H), 3.65-3.50 (m, 4H), 3.45 (d, J=5.4 Hz, 2H), 2.40 (dd, J=16.3, 9.2 Hz, 6H), 1.89 (dd, J=13.4, 6.5 Hz, 2H), 1.23 (s, 6H).

Example 86

1-(5-(tert-Butyl)isoxazol-3-yl)-3-(4-((3-hydroxy-4-(3-morpholinopropoxy)phenyl)ethynyl) phenyl)urea

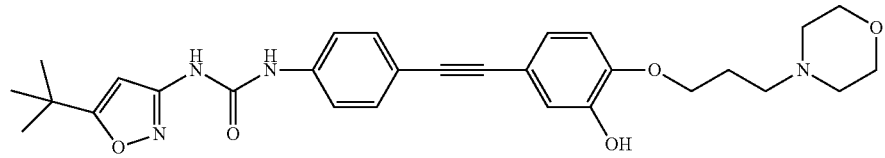 [SMILES: CC(C)(C)c1cc(NC(=O)Nc2ccc(C#Cc3ccc(OCCCN4CCOCC4)c(O)c3)cc2)no1]

Step 1) 4-iodo-2-methoxyphenyl 4-methylbenzenesulfonate

To a mixture of 4-iodo-2-methoxyphenol (513 mg, 2.05 mmol) in dichloromethane (30 mL) were added Et₃N (1.5 mL, 11 mmol) and tosyl chloride (0.40 g, 2.1 mmol) in turn. The reaction mixture was stirred at rt overnight and quenched with diluted hydrochloric acid (20 mL, 1M). The resulting mixture was extracted with dichloromethane (200 mL), and the organic phase was dried over anhydrous sodium sulfate and concentrated in vacuo. The residue was fully dried to give the title compound as oil (0.78 g, 94%).

Step 2) 2-hydroxy-4-iodophenyl 4-methylbenzenesulfonate

To a −70° C. solution of 4-iodo-2-methoxyphenyl 4-methylbenzenesulfonate (300 mg, 0.74 mmol) in dichloromethane (30 mL) was added BBr₃ (2 mL, 20.8 mmol) dropwise. The reaction mixture was stirred at −70° C. for 3 hours and quenched with water (30 mL). The mixture was extracted with dichloromethane (300 mL), dried over anhydrous sodium sulfate, and concentrated in vacuo to give the title compound as oil (0.24 g, 83%). The compound was characterized by the following spectroscopic data: ¹H NMR (400 MHz, CDCl₃) δ 7.78 (d, J=8.3 Hz, 2H), 7.38 (dd, J=5.1, 3.0 Hz, 3H), 7.10 (dd, J=8.5, 2.0 Hz, 1H), 6.51 (d, J=8.5 Hz, 1H), 2.49 (s, 3H).

Step 3) 4-iodo-2-((2-(trimethylsilyl)ethoxy) methoxy)phenyl 4-methylbenzenesulfonate To a mixture of 2-hydroxy-4-iodophenyl 4-methylbenzenesulfonate (158 mg, 0.40 mmol) in dichloromethane (20 mL) were added Et₃N (0.3 mL, 2 mmol) and SEMCl (0.15 mL, 0.85 mmol). The reaction mixture was stirred at rt for 2 hours. The resulting mixture was quenched with saturated aqueous sodium bicarbonate solution (50 mL), then the mixture was extracted with dichloromethane (300 mL). The organic phase was was dried over anhydrous sodium sulfate and concentrated in vacuo to give the title compound as oil (0.19 g, 90%).

Step 4) 4-iodo-2-((2-(trimethylsilyl)ethoxy) methoxy)phenol

To a mixture of 4-iodo-2-((2-(trimethylsilyl)ethoxy) methoxy)phenyl 4-methylbenzenesulfonate (226 mg, 0.43 mmol) in a mixed solvent (ethanol/water (v/v)=1/1, 20 mL) was added potassium hydroxide (0.26 g, 4.6 mmol). The reaction mixture was stirred at 100° C. for 3 hours, then quenched with saturated aqueous ammonium chloride solution (100 mL). The resulting mixture was extracted with ethyl acetate (500 mL), then the organic phase was dried over anhydrous sodium sulfate and concentrated in vacuo. The residue was purified by silica gel column chromatography (EtOAc/PE (v/v)=1/10) to give the title compound as a white solid (0.1 g, 60%). The compound was characterized by the following spectroscopic data: ¹H NMR (400 MHz, DMSO-d₆) δ 9.38 (s, 1H), 7.29 (d, J=2.0 Hz, 1H), 7.13 (dd, J=8.3, 2.0 Hz, 1H), 6.64 (d, J=8.4 Hz, 1H), 5.18 (s, 2H), 3.77-3.66 (m, 2H), 0.92-0.86 (m, 2H), −0.01 (s, 9H).

Step 5) 4-(3-(4-iodo-2-((2-(trimethylsilyl)ethoxy)methoxy)phenoxy)propyl)morpholine The title compound was prepared as a white solid (47 mg, 82%) by the procedure described in step 1 of example 1, using 4-iodo-2-((2-(trimethylsilyl)ethoxy)methoxy)phenol (42.8 mg, 0.117 mmol), N-(3-chloropropyl) morpholine (21 mg, 0.13 mmol), DMF (10 mL) and potassium carbonate (0.1 g, 0.7 mmol). The compound was characterized by the following spectroscopic data: MS-ESI: (ESI, pos.ion) m/z: 494.2 [M+1]$^+$.

Step 6) 4-(3-(4-((4-nitrophenyl)ethynyl)-2-((2-(trimethylsilyl)ethoxy)methoxy)phenoxy)propyl) morpholine The title compound was prepared as a white solid (800 mg, 77%) by the procedure described in step 3 of example 23, using 4-(3-(4-iodo-2-((2-(trimethylsilyl)ethoxy)methoxy)phenoxy)propyl)morpholine (1.0 g, 2.03 mmol), 4-nitrophenylacetylene (1.0 g, 6.8 mmol), CuI (80 mg, 0.42 mmol), Pd(PPh$_3$)$_2$Cl$_2$ (0.15 g, 0.21 mmol), THF (200 mL) and Et$_3$N (1.5 mL, 11 mmol). The compound was characterized by the following spectroscopic data: MS-ESI: (ESI, pos.ion) m/z: 513.3 [M+1]$^+$.

Step 7) 4-((4-(3-morpholinopropoxy)-3-((2-(trimethylsilyl)ethoxy)methoxy)phenyl)ethynyl) aniline The title compound was prepared as oil (392 mg, 80%) by the procedure described in step 4 of example 23, using 4-(3-(4-((4-nitrophenyl)ethynyl)-2-((2-(trimethylsilyl)ethoxy)methoxy)phenoxy)propyl)morpholine (520 mg, 1.014 mmol), a mixed solvent of MeOH and H$_2$O (v/v=3/1, 80 mL), ammonium chloride (0.6 g, 10.0 mmol) and iron power (0.3 g, 5.0 mmol). The compound was characterized by the following spectroscopic data: MS-ESI: (ESI, pos.ion) m/z: 483.3 [M+1]$^+$.

Step 8) 5-((4-aminophenyl)ethynyl)-2-(3-morpholinopropoxy)phenol 4-((4-(3-Morpholinopropoxy)-3-((2-(trimethylsilyl)ethoxy)methoxy)phenyl)ethynyl)aniline (40 mg, 0.083 mmol) was dissolved in a mixed solvent of TFA/DCM/MeOH (v/v/v=1/1/1, 15 mL) in an ice-water bath. The mixture was stirred for 30 minutes in the ice-water bath, then warmed slowly to rt and stirred for 1 hour. The mixture was concentrated in vacuo and and the residue was fully dried to give the title compound as oil (16.4 mg, 90%). The compound was characterized by the following spectroscopic data: MS-ESI: (ESI, pos.ion) m/z: 353.2 [M+1]$^+$.

Step 9) 1-(5-(tert-butyl)isoxazol-3-yl)-3-(4-((3-hydroxy-4-(3-morpholinopropoxy)phenyl) ethynyl) phenyl)urea The title compound was prepared as a white solid (28 mg, 66%) by the procedure described in step 4 of example 21, using 5-((4-aminophenyl)ethynyl)-2-(3-morpholinopropoxy)phenol (29 mg, 0.082 mmol), THF (20 mL), phenyl (5-(tert-butyl)isoxazol-3-yl)carbamate (50 mg, 0.192 mmol), DMAP (10 mg, 0.08 mmol) and Et$_3$N (0.5 mL, 4 mmol). The compound was characterized by the following spectroscopic data: MS-ESI: (ESI, pos.ion) m/z: 519.3 [M+1]$^+$; and $^1$H NMR (400 MHz, DMSO-d$_6$) δ 9.57 (s, 1H), 8.99 (s, 1H), 7.47 (dd, J=21.7, 7.6 Hz, 3H), 6.92 (d, J=6.6 Hz, 2H), 6.51 (s, 1H), 4.02 (t, 2H), 3.58 (m, 4H), 2.46 (m, 2H), 2.38 (m, 4H), 1.89 (m, 2H), 1.30 (s, 8H).

Example 87

1-(5-(tert-butyl)isoxazol-3-yl)-3-(2-hydroxy-4-((4-(3-morpholinopropoxy)phenyl)ethynyl) phenyl)urea

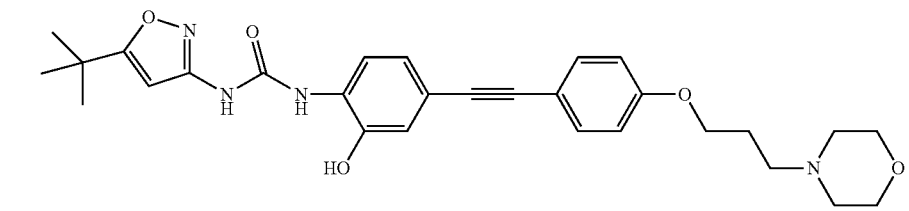

The title compound was prepared as a white solid (135 mg, 50%) by the procedure described in step 3 of example 79, using 2-amino-5-iodophenol (122 mg, 0.52 mmol), CuI (0.02 g, 0.1 mmol), Pd(PPh$_3$)$_2$Cl$_2$ (0.04 g, 0.054 mmol), 4-(3-(4-ethynylphenoxy)propyl)morpholine (0.20 g, 0.77 mmol), THF (20 mL), triethylamine (0.4 mL), phenyl (5-(tert-butyl)isoxazol-3-yl)carbamate (0.14 g, 0.54 mmol) and DMAP (20 mg). The compound was characterized by the following spectroscopic data: MS-ESI: (ESI, pos.ion) m/z: 519.3 [M+1]$^+$; and $^1$H NMR (400 MHz, DMSO-d$_6$) δ 10.32 (s, 1H), 10.07 (s, 1H), 8.75 (s, 1H), 8.09 (d, J=8.8 Hz, 1H), 7.44 (d, J=8.7 Hz, 2H), 6.96 (d, J=8.5 Hz, 4H), 6.47 (s, 1H), 4.05 (t, J=6.4 Hz, 2H), 3.63-3.49 (m, 4H), 2.41 (dd, J=17.8, 10.6 Hz, 6H), 1.94-1.79 (m, 2H), 1.30 (s, 9H).

Example 88

4-(3-(4-((4-(3-(5-(1-Hydroxy-2-methylpropan-2-yl) isoxazol-3-yl)ureido)phenyl)ethynyl) phenoxy)propyl)morpholine 4-oxide

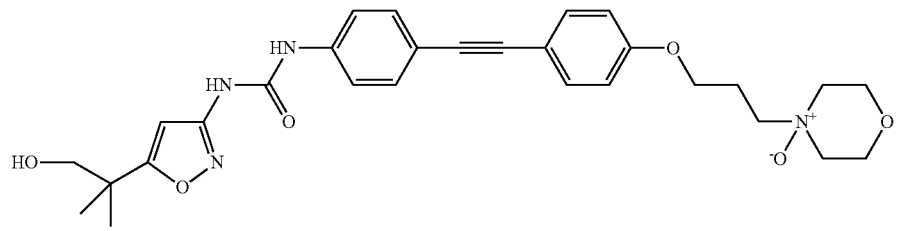

The title compound was prepared by the procedure described in example 82, using 1-(5-(1-hydroxy-2-methylpropan-2-yl)isoxazol-3-yl)-3-(4-((4-(3-morpholinopropoxy)phenyl) ethynyl)phenyl)urea (200 mg, 0.39 mmol), dichloromethane (30 mL) and MCPBA (86 mg, 0.5 mmol). And the crude product was purified by silica gel column chromatography (CH$_2$Cl$_2$/MeOH (v/v)=50/7) to give the title compound as a white solid (125 mg, 60%). The compound was characterized by the following spectroscopic data: MS-ESI: (ESI, pos.ion) m/z: 535.3 [M+1]$^+$; and $^1$H NMR (400 MHz, DMSO-d$_6$) δ 9.82 (s, 1H), 9.58 (s, 1H), 7.47 (dt, J=11.7, 8.7 Hz, 6H), 6.97 (d, J=8.7 Hz, 2H), 6.54 (s, 1H), 5.33 (s, 1H), 4.97 (t, J=5.5 Hz, 1H), 4.13 (t, J=9.6 Hz, 4H), 3.70 (d, J=10.3 Hz, 2H), 3.44 (s, 2H), 3.41 (s, 2H), 2.97 (d, J=11.0 Hz, 2H), 2.30 (dd, J=14.8, 7.1 Hz, 2H), 2.00 (dd, J=14.5, 6.9 Hz, 2H), 1.23 (d, J=4.9 Hz, 6H).

Example 89

4-(3-(3-Fluoro-4-((4-(3-(5-(1-hydroxy-2-methylpropan-2-yl)isoxazol-3-yl)ureido)phenyl) ethynyl)phenoxy)propyl)morpholine 4-oxide The title compound was prepared by the procedure described in example 82, using 1-(4-((2-fluoro-4-(3-morpholinopropoxy)phenyl)ethynyl)phenyl)-3-(5-(1-hydroxy-2-methylprop an-2-yl)isoxazol-3-yl)urea (300 mg, 0.56 mmol), dichloromethane (30 mL) and MCPBA (138 mg, 0.8 mmol), and the crude product was purified by silica gel column chromatography (CH$_2$Cl$_2$/MeOH (v/v)=50/7) to give the title compound as a white solid (192 mg, 62%). The compound was characterized by the following spectroscopic data: MS-ESI: (ESI, pos.ion) m/z: 553.3 [M+1]$^+$; and $^1$H NMR (600 MHz, DMSO-d$_6$) δ 9.87 (s, 1H), 9.72 (s, 1H), 7.52 (t, J=8.7 Hz, 2H), 7.45 (d, J=8.6 Hz, 2H), 6.98 (dd, J=11.6, 2.2 Hz, 1H), 6.84 (dd, J=8.6, 2.1 Hz, 1H), 6.55 (s, 1H), 5.33 (s, 1H), 5.05-4.93 (m, 1H), 4.23-4.03 (m, 3H), 3.71 (d, J=10.4 Hz, 2H), 3.55-3.37 (m, 6H), 3.00 (d, J=9.1 Hz, 2H), 2.34-2.22 (m, 2H), 2.07-1.94 (m, 2H), 1.23 (d, J=6.7 Hz, 6H).

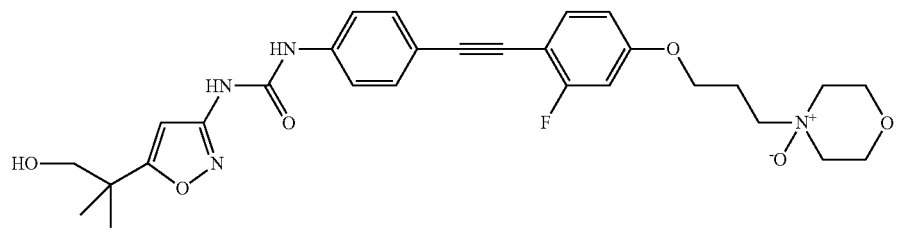

Example 90

1-(4-((4-(3-Morpholinopropoxy)phenyl)ethynyl)phenyl)-3-(5-(1,1,1-trifluoro-2-methylpropan-2-yl)isoxazol-3-yl)urea

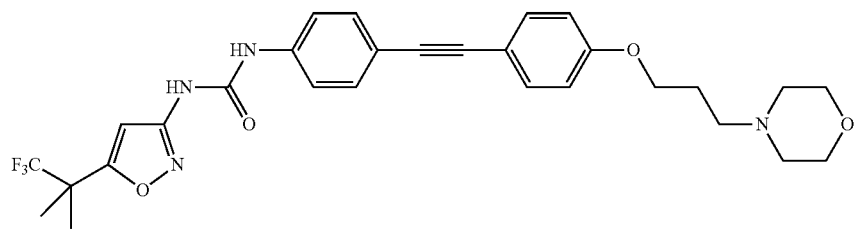 [SMILES: CC(C)(c1cc(NC(=O)Nc2ccc(C#Cc3ccc(OCCCN4CCOCC4)cc3)cc2)no1)C(F)(F)F]

Step 1) 5,5,5-trifluoro-4,4-dimethyl-3-oxopentanenitrile

To a −78° C. solution of diisopropylamine (15 mL, 107 mmol) in THF (150 mL) was added n-BuLi (2.4 mol/L, 8 mL) dropwise. The reaction mixture was stirred for 30 minutes and a solution of methyl 3,3,3-trifluoro-2,2-dimethylpropanoate (3 g, 17.63 mmol) in acetonitrile (10 mL, 239 mmol) was added dropwise slowly. One hour later, the mixture was warmed slowly to rt and stirred for 2 hours. The mixture was quenched with saturated aqueous ammonium chloride solution (50 mL), and the resulting mixture was extracted with ethyl acetate (300 mL), dried over anhydrous sodium sulfate and filtered. The filtrate was concentrated in vacuo and the residue was purified by silica gel column chromatography (EtOAc/PE (v/v)=1/1) to give the title compound as a white solid (1.53 g, 48%). The compound was characterized by the following spectroscopic data: MS-ESI: (ESI, pos.ion) m/z: 180.1 [M+1]$^+$; and $^1$H NMR (600 MHz, CDCl$_3$) δ 3.77 (s, 2H), 1.43 (s, 6H).

Step 2) 5-(1,1,1-trifluoro-2-methylpropan-2-yl)isoxazol-3-amine

To a mixture of MeOH in H$_2$O (10%, 20 mL) were added 5,5,5-trifluoro-4,4-dimethyl-3-oxopentanenitrile (0.2 g, 1.12 mmol), hydroxylamine hydrochloride (0.11 g, 1.6 mmol) and sodium bicarbonate (0.30 g, 3.6 mmol). The reaction mixture was stirred at 60° C. for 12 hours and concentrated hydrochloric acid (3 mL) was added dropwise. The mixture was heated to 80° C. and stirred for 1 hour. Then the reaction mixture was cooled to 0° C., and adjusted with aqueous sodium hydroxide to pH 10. The resulting mixture was extracted with dichloromethane (300 mL), and the organic phase was dried over anhydrous sodium sulfate, concentrated in vacuo. The residue was purified by silica gel column chromatography (EtOAc/PE (v/v)=1/2) to give the title compound as a white solid (80 mg, 37%). The compound was characterized by the following spectroscopic data: MS-ESI: (ESI, pos.ion) m/z: 195.1 [M+1]$^+$; and $^1$H NMR (400 MHz, CDCl$_3$) δ 5.81 (s, 1H), 3.96 (s, 2H), 1.55 (s, 6H).

Step 3) phenyl (5-(1,1,1-trifluoro-2-methylpropan-2-yl)isoxazol-3-yl)carbamate The title compound was prepared by the procedure described in step 1 of example 84, using 5-(1,1,1-trifluoro-2-methylpropan-2-yl)isoxazol-3-amine (0.3 g, 1.55 mmol) in THF (50 mL), potassium carbonate (2.2 g, 16 mmol) and phenyl chloroformate (1 mL, 7.97 mmol) under a N$_2$ atmosphere. The crude product was purified by silica gel column chromatography (EtOAc/PE (v/v)=1/10) to give the title compound as a white solid (0.45 g, 93%). The compound was characterized by the following spectroscopic data: MS-ESI: (ESI, pos.ion) m/z: 315.1 [M+1]$^+$.

Step 4) 1-(4-((4-(3-morpholinopropoxy)phenyl)ethynyl)phenyl)-3-(5-(1,1,1-trifluoro-2-methyl propan-2-yl) isoxazol-3-yl)urea The title compound was prepared as a white solid by the procedure described in step 4 of example 21, using phenyl (5-(1,1,1-trifluoro-2-methylpropan-2-yl)isoxazol-3-yl)carbamate (0.45 g, 1.43 mmol), 4-((4-(3-morpholinopropoxy)phenyl)ethynyl)aniline (0.36 g, 1.1 mmol), DMAP (30 mg, 0.25 mmol), dichloromethane (20 mL) and DIPEA (2.5 mL, 15 mmol). The compound was characterized by the following spectroscopic data: MS-ESI: (ESI, pos.ion) m/z: 557.3 [M+1]$^+$; and $^1$H NMR (400 MHz, DMSO-d$_6$) δ 9.74 (s, 1H), 9.02 (s, 1H), 7.48 (dd, J=21.3, 9.1 Hz, 6H), 6.97 (d, J=8.8 Hz, 2H), 6.91 (s, 1H), 4.05 (t, J=6.4 Hz, 2H), 3.66-3.50 (m, 4H), 2.47-2.26 (m, 6H), 1.97-1.79 (m, 2H), 1.56 (s, 6H).

In Vitro Anti-Tumor Activity Assay

Example A: Evaluation of In Vitro Enzymatic Inhibitory Activity

Test Method

Materials used herein include HEPES (2-(4-(2-Hydroxyethyl)-1-piperazinyl)ethanesulfonic acid), Brij-35 (dodecyl polyglycol ether), DTT (dithiothreitol), EDTA (ethylenediamine tetraacetic acid), EGFR (human epidermal growth factor receptor), HER2 (human epidermal growth factor receptor 2), EGFR T790M (human epidermal growth factor receptor T790M mutation), Peptide FAM-P22 (fluorescein-labeled peptide 22), ATP (adenosine triphosphate), DMSO (dimethyl sulfoxide), 96-well plate, 384-well plate, staurosporine, Coating Reagent #3 and so on, all of which are commercially available.

1. Preparation of 1× Kinase Base Buffer and Stop Buffer (1) 1× Kinase buffer without MnCl$_2$ consisted of 50 mM HEPES, pH 7.5, 0.0015% Brij-35, 10 mM MgCl$_2$ and 2 mM DTT. (2) Stop buffer consisted of 100 mM HEPES, pH 7.5, 0.015% Brij-35, 0.2% Coating Reagent #3 and 50 mM EDTA.

2. Preparation of the Compounds for Testing Kinases: The Compounds were Diluted by Serial Dilution.

(1) The compound to be tested was diluted to a concentration with 100% DMSO which is 50 times the highest final concentration, and 100 μL of the diluted compound solution was transferred to a well in a 96-well plate. (2) The compound was serially diluted by transferring 20 μL original solution to 60 μL of 100% DMSO in the next well and so forth to obtain 10 different concentrations. (3) DMSO (100 μL, 100%) was added to two empty wells as a control without compound and a control without enzyme in the same 96-well plate. (4) Intermediate plate was prepared by transferring 10 μL of each compound solution from source plate to a new 96-well plate, and to each well of the intermediate plate was added 90 μL of 1× Kinase base buffer, then the mixture on the intermediate plate was mixed for 10 minutes on shaker. (5) Assay plate was prepared by transferring 5 μL of compound solution from well of the 96-well intermediate plate to a 384-well plate in duplicates.

3. Kinase Reaction

Kinase reaction was performed according to the following procedures: (1) 2.5× kinase solution was prepared by adding kinase into 1× kinase base buffer; (2) 2.5× peptide solution was prepared by adding FAM-labeled peptide and ATP into 1× kinase base buffer; (3) 2.5× kinase solution (10 μL) was added to each well of the 384-well assay plate containing 5 μL of compound in 10% DMSO and then the assay plate was incubated at room temperature for 10 minutes; (4) 2.5× peptide solution (10 μL) was added to each well of the 384-well assay plate. (5) stop buffer (25 μL) was added to stop the kinase reaction after incubation at 28° C. for a specified period of time.

4. Data Measurement: The Data were Read and Collected.

5. Curve Fitting (1) Conversion data were collected and converted to inhibition values with the following formula: percent inhibition=(max-conversion)/(max-min)*100, in which "max" means the value of control without compound, "conversion" stands for the sample value, and "min" means the value of control without enzyme. (2) The data were fitted in XLfit to obtain $IC_{50}$ values.

The $IC_{50}$ values of the compounds disclosed herein in inhibiting FLT3 kinase were shown in Table 2.

TABLE 2

In vitro enzymatic inhibitory activity of the compounds of the invention

| Example No. | FLT3 ($IC_{50}$, nM) |
|---|---|
| 1 | 115 |
| 2 | 75 |
| 3 | 62 |
| 4 | 39 |
| 5 | 189 |
| 6 | 94 |
| 8 | 61 |
| 11 | 169 |
| 12 | 28 |
| 13 | 23 |
| 14 | 72 |
| 15 | 102 |
| 20 | 110 |
| 21 | 41 |
| 24 | 160 |
| 25 | 84 |

Conclusion: It was shown from Table 2 that, the compounds of the invention exhibited good in vitro enzymatic inhibitory activities.

Example B: Evaluation of In Vitrocytology Inhibitory Activity

Test Method

Cell assay condition was shown below:

| Cell name | Cells/per well | Incubation time (h) | Complete medium |
|---|---|---|---|
| MV-4-11 | 15000 | 72 | IMDM + 10% FBS |

1. Plating Cells:

a. A complete medium was prepared and mixed well. b. Cell was recovered, and cell lines of between about two generations in good condition of growth were selected. c. The cell culture flasks were removed from the incubator, and the labeled cell name on the bottles, culture medium type and cell algebra were checked. d. The cell suspension was pipette into a centrifuge tube, and centrifuged at 800-1000 rpm for 3-5 minutes. e. Cell supernatant of the centrifuge tube was aspirated. f. Appropriate volume of culture medium was added into the centrifuge tube, and the cells were resuspended by gentle pipetting uniform. g. Vi-Cell XR cytometer was used for count. h. The cell suspension was adjusted to the appropriate concentration. i. The cell suspension was added to the bottom wall of the white 96-well plate, 100 microliters/well. Cells name, kind of board density and date were detailed labeled, and the culture plate was placed in $CO_2$ incubator overnight.

2. Preparation and Addition of the Test Compounds i) Preparation of test compound plates by diluting to 10 concentrations with DMSO: first, the test compound stock solution was prepared by dissolving a weighed compound in DMSO to a concentration of 10 mM, and then diluted to the concentration of 4 mM, which was then diluted to the concentration of 0.4 mM used as the highest concentration for testing with DMSO. The highest concentration was sequentially followed by 3-fold dilution for a total of 10 concentrations. Staurosporine was the positive control drug. ii) Addition of test compounds: a. 0.5 μL of test compound prepared above in compound plate was added into the cell culture plate that had been incubated overnight. Then the culture plate was incubated in an incubator at 37° C. for 72 hours.

3. Detection and Analysis a. 72 hours after the compound treatment, cells was observed under an inverted microscope morphology, and cell growth state in DMSO control well was normal, there was no contamination. b. The cell culture plate was placed in equilibrium at room temperature for 30 minutes. c. The cell viability detection reagent at 100 μL/well was placed into culture plate. d. The mixture in culture plate was mixed two minutes in the vibration plate machine to induce cell lysis. e. 96-well plate was placed for 10 minutes at room temperature, making it stable luminescent signal. f. White base film was pasted on the bottom of the culture plate, and the plate was tested by using Flexstation3 (related to: light, integration time 500 ms). g. Experimental results were recorded and analyzed.

TABLE 3

In vitro cytology inhibitory activity of the compounds of the invention

| Example No. | MV4-11 (IC50, nM) |
|---|---|
| 4 | 5.2 |
| 6 | 3.1 |

TABLE 3-continued

In vitro cytology inhibitory activity of the compounds of the invention

| Example No. | MV4-11 (IC50, nM) |
|---|---|
| 7 | 3.2 |
| 8 | 3.4 |
| 12 | 1.6 |
| 13 | 2.4 |
| 14 | 11.43 |
| 17 | 11.65 |
| 19 | 13.8 |
| 21 | 2.8 |
| 81 | 4.7 |
| 82 | 3.0 |
| 83 | 2.3 |
| 84 | 2.1 |
| 85 | 1.6 |
| 86 | 0.9 |
| 87 | 25.5 |
| 88 | 1.8 |
| 89 | 4.8 |

Conclusion: It was shown from Table 3 that, the compounds of the invention exhibited good inhibitory activities on MV-4-11 cell proliferation.

Example B: Evaluation of Pharmacokinetic Activity

Test Method
1. Preparation of the Test Compound Solutions

The test compound solutions were prepared using appropriate amounts of 5% DMSO, 5% KolliphorHS15 and 90% Saline to dissolve each compound completely.

2. Animal Experiment 140-190 g male SD rats were randomly divided into two groups. One group was administered through intravenous drug delivery with the dosage of 1.0 or 2.0 mg/kg, and the other group was administered by oral with the dosage of 5.0 mg/kg. For intravenous administration, caudal vein blood samples at the time points of 0.0833, 0.25, 0.5, 1.0, 2.0, 4.0, 6.0, 8.0 and 24 h were collected after drug administration (the time point of drug administration was set as 0 h); and for oral administration, caudal vein blood samples at the time points of 0.25, 0.5, 1.0, 2.0, 4.0, 6.0, 8.0 and 24 h were collected after drug administration (the time point of drug administration was set as 0 h). Appropriate range of standard curve was established according to the sample concentration, and the test compound concentrations in plasma sample were measured by LC-MS/MS analysis. Pharmacokinetic parameters were calculated by non-compartmental method using WinNonLin 6.3 software based on drug concentration-time curves.

3. Results

TABLE 4

Pharmacokinetic parameters of the compounds of the invention

| Example No. | Route | Dosage (mg/kg) | $T_{1/2}$ (h) | $T_{max}$ (h) | $V_{ss}$ (l/kg) | $C_{max}$ (ng/ml) | $AUC_{last}$ (h * ng/ml) | $AUC_{INF}$ (h * ng/ml) | F (%) |
|---|---|---|---|---|---|---|---|---|---|
| 4 | iv | 2 | 6.23 | 0.08 | 1.83 | 2693.33 | 6566.69 | 6936.01 | 69.29 |
|   | po | 5 | 5.86 | 2.67 | / | 1366.67 | 11345.94 | 12015.34 |  |
| 9 | iv | 1 | 1.7 | 0.083 | 1.62 | 793 | 1330 | 1390 | 115.78 |
|   | po | 5 | 2.85 | 2.67 | / | 1090 | 8010 | 8030 |  |
| 24 | iv | 1 | 4.51 | 0.083 | 1.69 | 1340 | 2130 | 2160 | 63.61 |
|   | po | 5 | 3.9 | 4 | / | 862 | 6770 | 6870 |  |

Note:
"/" refers the value wasn't determined.

Conclusion: It was shown from table 4 that, the compounds of the invention had good pharmacokinetic activities, such as having good absorptions, high exposure levels, and high bioavailabilities.

Having thus described the invention in detail with general description, specific embodiments and experiments, it will be obvious to those skilled in the art that various changes or modifications may be made therein without departing from the spirit of the invention and defined in the appended claims.

What is claimed is:

1. A compound having Formula (I), or a stereoisomer, a geometric isomer, a tautomer, an N-oxide, a hydrate, a solvate, a metabolite, an ester, a pharmaceutically acceptable salt or a prodrug thereof,

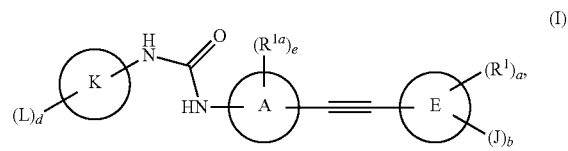

(I)

wherein
each of ring A and ring E is independently $C_{6-10}$ aryl or $C_{1-12}$ heteroaryl;
each J is -G-$(CH_2)_n$—$R^2$;
each G is independently —O—, —S(=O)$_t$—, —S—, —C(=O)—, —OC(=O)—, —C(=S)—, —C(=S)—N($R^4$)— or —$(CH_2)_n$—C(=O)—;
each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{1-4}$ alkylamino, $C_{1-4}$ alkyl-C(=O)—NH—, $C_{1-4}$ alkylthio, $C_{3-10}$ cycloalkyl, $C_{2-10}$ heterocyclyl, $C_{1-6}$ alkoxy-$C_{1-6}$-alkyl or $C_{1-4}$ hydroxyalkyl;
each $R^2$ is independently —$NR^3R^{3a}$, cycloalkyl, cycloalkylalkyl, heterocyclylalkyl, heterocyclyl, alkyl-S(=O)$_t$—, hydroxyalkyl, hydroxyalkoxy, aminoalkoxy, haloalkoxy, alkoxyalkyl, alkyl, alkoxy, alkylaminohaloalkoxy, alkylaminoalkoxy, arylalkoxy, arylalkylamino, heteroarylalkoxy, heteroarylalkylamino, heterocyclylalkylamino, heterocyclylalkylaryl, heterocylylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, aryl, arylalkyl, heteroarylalkyl, heteroaryl, bridged heterobicyclyl, spiro heterobicyclyl or fused heterobicyclyl;

each $R^3$ and $R^{3a}$ is independently $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

each $R^4$ is independently H, $C_{1-4}$ alkyl, $C_{3-10}$ cycloalkyl, $C_{2-10}$ heterocyclyl, $C_{1-6}$ alkoxy-$C_{1-6}$-alkyl or $C_{1-4}$ hydroxyalkyl;

ring K is 5- to 6-membered heteroaryl;

each L is independently amino, nitro, $C_{1-4}$ alkylthio, $C_{1-6}$ alkyl, $C_{3-10}$ cycloalkyl, $C_{2-10}$ heterocyclyl, $C_{1-4}$ haloalkyl, $C_{1-4}$ alkylamino, hydroxy, F, Cl, Br, I, $C_{1-4}$ alkyl-C(=O)—NH—, $C_{1-4}$ alkoxy, $C_{1-4}$ hydroxyalkyl or cyano;

each a and e is independently 0, 1, 2, 3 or 4;

each n, d and b is independently 1, 2, 3 or 4; and each t is independently 0, 1 or 2;

wherein optionally each aryl, —(CH$_2$)$_n$—C(=O)—, alkyl-S(=O)$_t$—, hydroxyalkyl, arylalkyl, heteroarylalkyl, heteroaryl, heterocyclyl, bridged heterobicyclyl, spiro heterobicyclyl, fused heterobicyclyl, alkyl, alkoxy, alkoxyalkyl, haloalkyl, alkylamino, hydroxyalkoxy, aminoalkoxy, haloalkoxy, cycloalkylalkyl, heterocyclylalkyl, alkylaminohaloalkoxy, alkylaminoalkoxy, arylalkoxy, arylalkylamino, heteroarylalkoxy, heteroarylalkylamino, heterocyclylalkylamino, heterocyclylalkylaryl, heterocyclylalkylheteroaryl, cycloalkyloxy, cycloalkylamino, heterocyclylalkoxy, carbocyclylalkoxy, carbocyclylalkylamino, aryloxyalkoxy, aryloxy, heteroaryloxy, heteroaryloxyalkoxy, heterocyclyloxyalkoxy, carbocyclyloxyalkoxy, heterocyclyloxy, fused bicyclyloxy, fused bicyclylalkyl, fused heterobicyclylalkyl, fused heterobicyclyloxy, fused heterobicyclylamino, fused heterobicyclylalkoxy, fused heterobicyclylalkylamino, fused heterobicyclyloxyalkoxy, fused heterobicyclyloxyalkylamino, spiro heterobicyclylalkyl, spiro heterobicyclylalkoxy, bridged heterobicyclylalkyl, bridged heterobicyclyloxy, bridged heterobicyclylalkoxy, bridged heterobicyclylalkylamino, alkyl-C(=O)—NH—, alkylthio and cycloalkyl described in $R^1$, $R^{1a}$, $R^2$, $R^3$, $R^{3a}$, A, E, J, G, L and/or K is independently substituted with one or more $R^{2a}$ which are the same or different, and wherein each $R^{2a}$ is independently H, F, Cl, Br, I, $C_{1-4}$ haloalkyl, $C_{1-4}$ alkyl, $C_{1-4}$ alkylamino, di-$C_{1-4}$ alkylamino, di($C_{1-4}$ alkyl)amino, hydroxy, cyano, nitro, —C(=O)—NH$_2$, carboxy, —S(=O)$_t$O—H, —OS(=O)$_t$—H, —S(=O)$_t$NH$_2$, triazolyl, tetrazolyl, —(CR$^{3b}$R$^{3c}$)$_n$—NH$_2$, amino, oxo (=O), $C_{1-4}$ alkyl-C(=O)—, benzyl, phenyl, $C_{1-6}$ alkyl-S(=O)$_t$—, $C_{1-6}$ alkoxy-$C_{1-6}$-alkyl, $C_{1-4}$ alkyl-C(=O)—NH—, $C_{1-4}$ alkoxy, $C_{1-4}$ hydroxyalkyl or $C_{1-4}$ alkylthio; and each $R^{3b}$ and $R^{3c}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{2-10}$ heterocyclyl, $C_{1-6}$ alkoxy-$C_{1-6}$-alkyl or $C_{1-4}$ hydroxyalkyl.

2. The compound according to claim 1 having Formula (II) or Formula (IIa), or a stereoisomer, a geometric isomer, a tautomer, an N-oxide, a hydrate, a solvate, a metabolite, an ester, a pharmaceutically acceptable salt or a prodrug thereof,

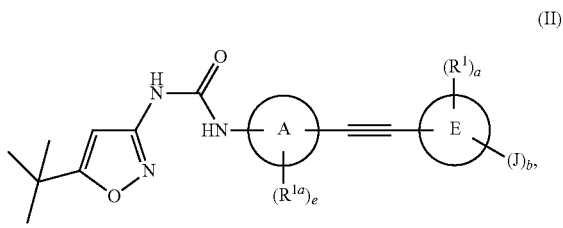

(II)

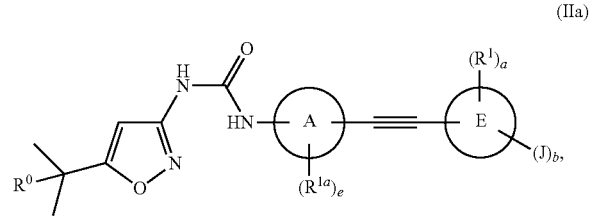

(IIa)

wherein $R^0$ is $C_{2-3}$ alkyl, trifluoromethyl, fluoromethyl, difluoromethyl or hydroxymethyl.

3. The compound according to claim 1, wherein each ring A and ring E is independently one of the following subformulae:

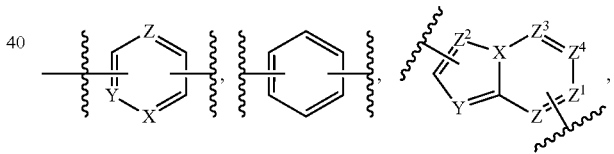

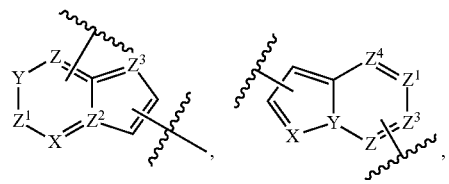

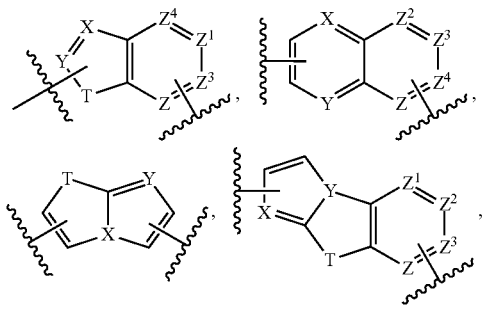

-continued

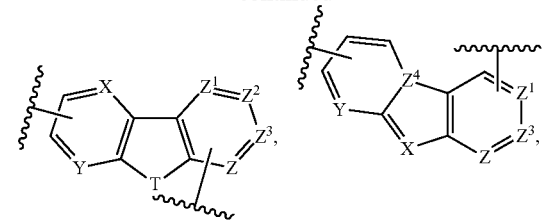

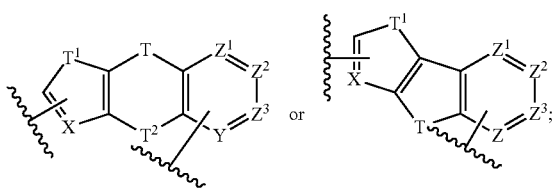

wherein each X, Y, Z, $Z^1$, $Z^2$, $Z^3$ and $Z^4$ is independently N or CH;

each T, $T^1$ and $T^2$ is independently —O—, —S—, —N($R^4$)— or —CH$_2$—; and each $R^1$ and $R^{1a}$ is independently H, F, Cl, Br, cyano, nitro, hydroxy, mercapto, amino, carboxy, $C_{1-4}$ alkyl, $C_{1-4}$ haloalkyl, $C_{1-6}$ alkoxy, $C_{3-10}$ cycloalkyl, $C_{1-4}$ alkylamino, $C_{2-10}$ heterocyclyl, $C_{1-6}$ alkoxy-$C_{1-6}$-alkyl or $C_{1-4}$ hydroxyalkyl; or each ring A and ring E is independently one of the following sub-formulae:

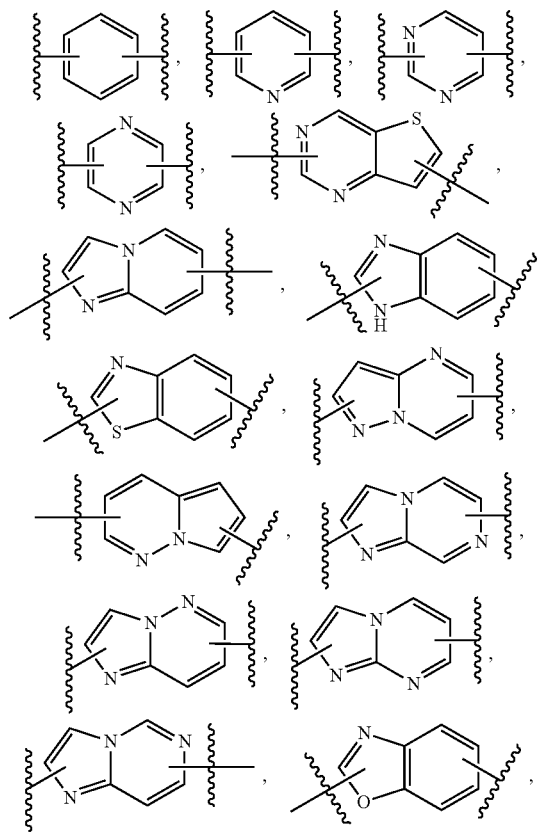

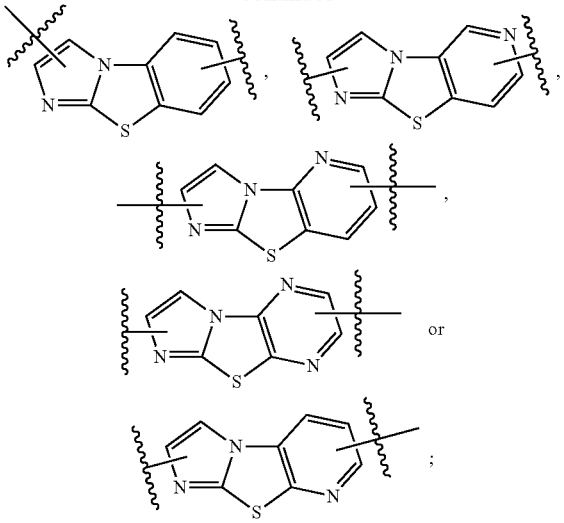

each $R^1$ and $R^{1a}$ is independently H, F, Cl, Br, trifluoromethyl, chloroethyl, trifluoroethyl, methyl, ethyl, propyl, isopropyl, dimethylamino, methylamino, diethylamino, ethylamino, hydroxy, cyano, nitro, methoxy, ethoxy, propoxy, cyclopropyl, cyclobutyl, cyclohexyl, cyclopentyl, $C_{2-10}$ heterocyclyl, $C_{1-6}$ alkoxy-$C_{1-6}$-alkyl or $C_{1-4}$ hydroxyalkyl.

4. The compound according to claim 1, wherein, each $R^2$ is independently —NR$^3$R$^{3a}$, $C_{3-10}$ cycloalkyl, $C_{3-10}$ cycloalkyl-$C_{1-4}$-alkyl, $C_{2-10}$ heterocyclyl-$C_{1-4}$-alkyl, $C_{1-6}$ alkyl-S(=O)$_t$—, $C_{1-4}$ hydroxyalkyl, $C_{1-4}$ hydroxyalkoxy, $C_{1-4}$ aminoalkoxy, $C_{1-4}$ haloalkoxy, $C_{1-4}$ alkylamino-$C_{1-4}$-haloalkoxy, $C_{1-4}$ alkylamino-$C_{1-4}$-alkoxy, $C_{1-6}$ alkoxy-$C_{1-6}$-alkyl, $C_{1-6}$ alkyl, $C_{1-6}$ alkoxy, $C_{6-10}$ aryl-$C_{1-4}$-alkoxy, $C_{6-10}$ aryl-$C_{1-4}$-alkylamino, $C_{1-9}$ heteroaryl-$C_{1-4}$-alkoxy, $C_{1-9}$ heteroaryl-$C_{1-4}$-alkylamino, $C_{2-10}$ heterocyclyl-$C_{1-4}$-alkylamino, $C_{2-10}$ heterocyclyl-$C_{1-4}$-alkyl-$C_{6-10}$-aryl, $C_{2-10}$ heterocyclyl-$C_{1-4}$-alkyl-$C_{1-9}$-heteroaryl, $C_{3-10}$ cycloalkyloxy, $C_{3-10}$ cycloalkylamino, $C_{2-10}$ heterocyclyl-$C_{1-4}$-alkoxy, $C_{3-10}$ carbocyclyl-$C_{1-4}$-alkoxy, $C_{3-10}$ carbocyclyl-$C_{1-4}$-alkylamino, $C_{6-10}$ aryloxy-$C_{1-4}$-alkoxy, $C_{6-10}$ aryloxy, $C_{1-9}$ heteroaryloxy, $C_{1-9}$ heteroaryloxy-$C_{1-4}$-alkoxy, $C_{2-10}$ heterocyclyloxy-$C_{1-4}$-alkoxy, $C_{3-10}$ carbocyclyloxy-$C_{1-4}$-alkoxy, $C_{2-10}$ heterocyclyloxy, $C_{6-10}$ aryl, $C_{6-10}$ aryl-$C_{1-6}$-alkyl, $C_{1-9}$ heteroaryl-$C_{1-6}$-alkyl, $C_{1-9}$ heteroaryl, $C_{2-10}$ heterocyclyl, $C_{6-12}$ fused bicyclyloxy, $C_{6-12}$ fused bicyclyl-$C_{1-6}$-alkyl, $C_{5-12}$ fused heterobicyclyl-$C_{1-6}$-alkyl, $C_{5-12}$ fused heterobicyclyloxy, $C_{5-12}$ fused heterobicyclylamino, $C_{5-12}$ fused heterobicyclyl-$C_{1-6}$-alkoxy, $C_{5-12}$ fused heterobicyclyl-$C_{1-6}$-alkylamino, $C_{5-12}$ fused heterobicyclyloxy-$C_{1-6}$-alkoxy, $C_{5-12}$ fused heterobicyclyloxy-$C_{1-6}$-alkylamino, $C_{5-12}$ spiro heterobicyclyl-$C_{1-6}$-alkyl, $C_{5-12}$ spiro heterobicyclyl-$C_{1-6}$-alkoxy, $C_{5-12}$ bridged heterobicyclyl-$C_{1-6}$-alkyl, $C_{5-12}$ bridged heterobicyclyloxy, $C_{5-12}$ bridged heterobicyclyl-$C_{1-6}$-alkoxy, $C_{5-12}$ bridgedheterobicyclyl-$C_{1-6}$-alkylamino, $C_{5-12}$ bridged heterobicyclyl, $C_{5-12}$ spiro heterobicyclyl or $C_{5-12}$ fused heterobicyclyl; and wherein each $R^2$ is independently substituted with one or more $R^{2a}$ which are the same or different; and each $R^3$ and $R^{3a}$ is independently $C_{1-4}$ alkyl, $C_{3-10}$ cycloalkyl, $C_{2-10}$ heterocycloalkyl, $C_{1-6}$ alkoxy-$C_{1-6}$-alkyl or $C_{1-4}$ hydroxyalkyl; or each R² is independently —NR³R³ᵃ, C₁₋₄ alkoxy-C₁₋₄-alkyl, C₁₋₄ alkyl or C₁₋₄ hydroxyalkyl, or each R² is independently one of the following sub-formulae:

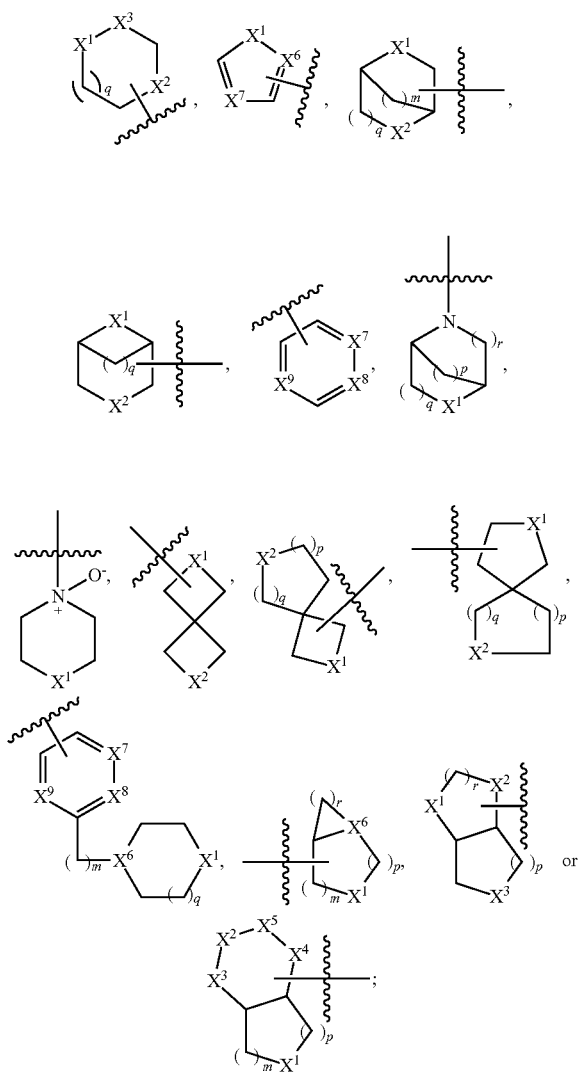

wherein each X⁶, X⁷, X⁸ and X⁹ is independently N or CH;

each X¹, X², X³, X⁴ and X⁵ is independently —(C(R⁴ᵇ)₂)ₘ—, —C(=O)—, —O—, —N(R⁴ᵃ)— or —S(=O)ₜ—;

each q, m, p and r is independently 0, 1, 2, 3 or 4;

each t is independently 0, 1 or 2;

wherein each R² is independently substituted with one or more R²ᵃ which are the same or different;

each R⁴ᵃ is independently H, C₁₋₄ alkyl, C₃₋₁₀ cycloalkyl, C₂₋₁₀ heterocycloalkyl, C₁₋₆ alkoxy-C₁₋₆-alkyl, or C₁₋₄ hydroxyalkyl; and each R⁴ᵇ is independently H, F, Cl, Br, cyano, nitro, hydroxy, mercapto, amino, carboxy, C₁₋₄ alkyl, C₃₋₁₀ cycloalkyl, C₁₋₄ haloalkyl, C₁₋₄ alkoxy, C₁₋₄ alkylamino, —(CR³ᵇR³ᶜ)ₙ—NH₂, —C(=O)—NH₂, C₂₋₁₀ heterocycloalkyl, C₁₋₆ alkoxy-C₁₋₆-alkyl or C₁₋₄ hydroxyalkyl.

5. The compound according to claim 1, wherein, each R² is independently one of the following sub-formulae:

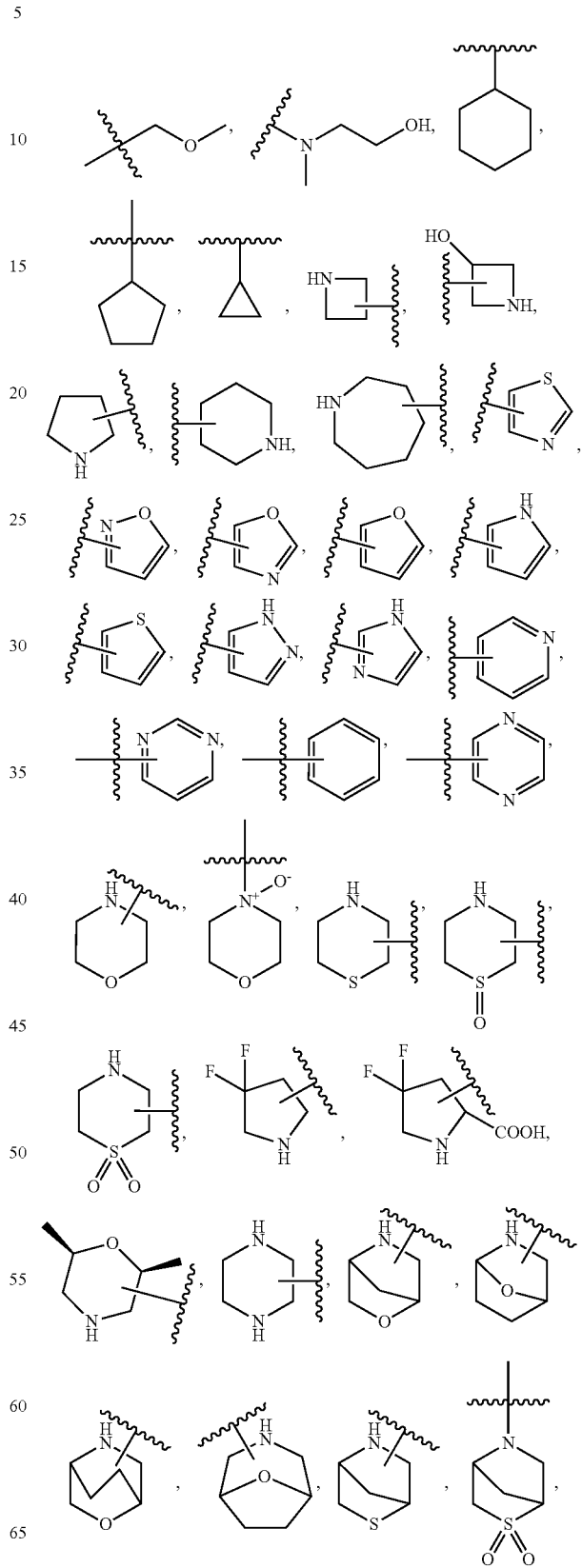

-continued

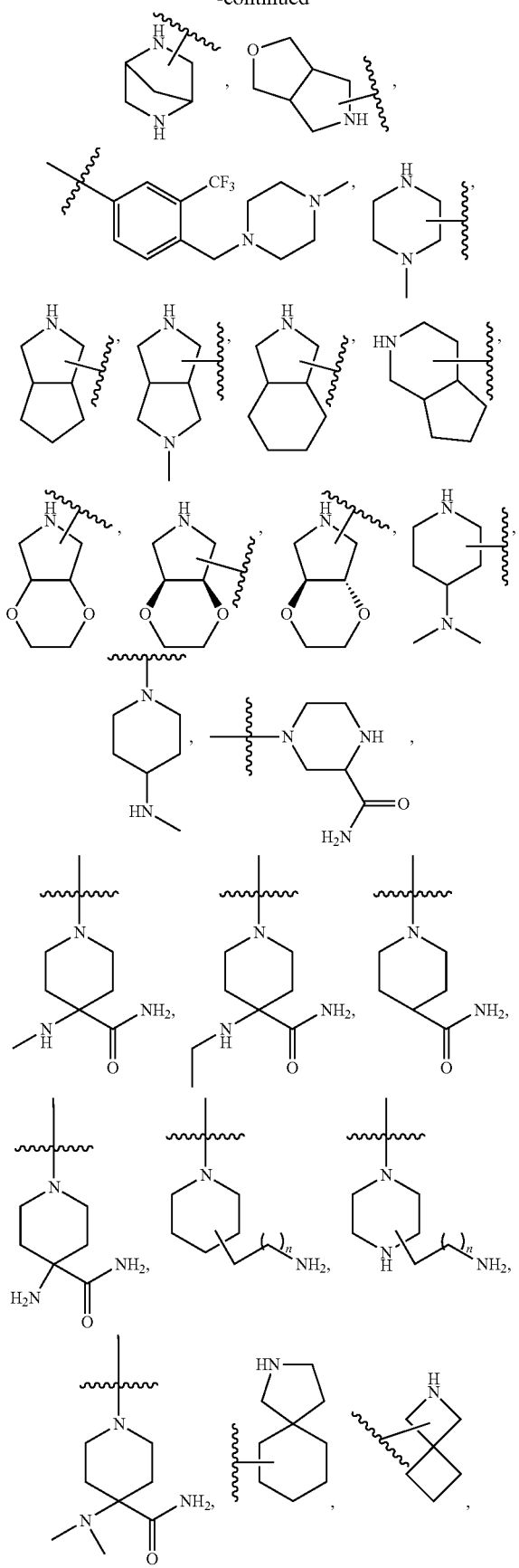

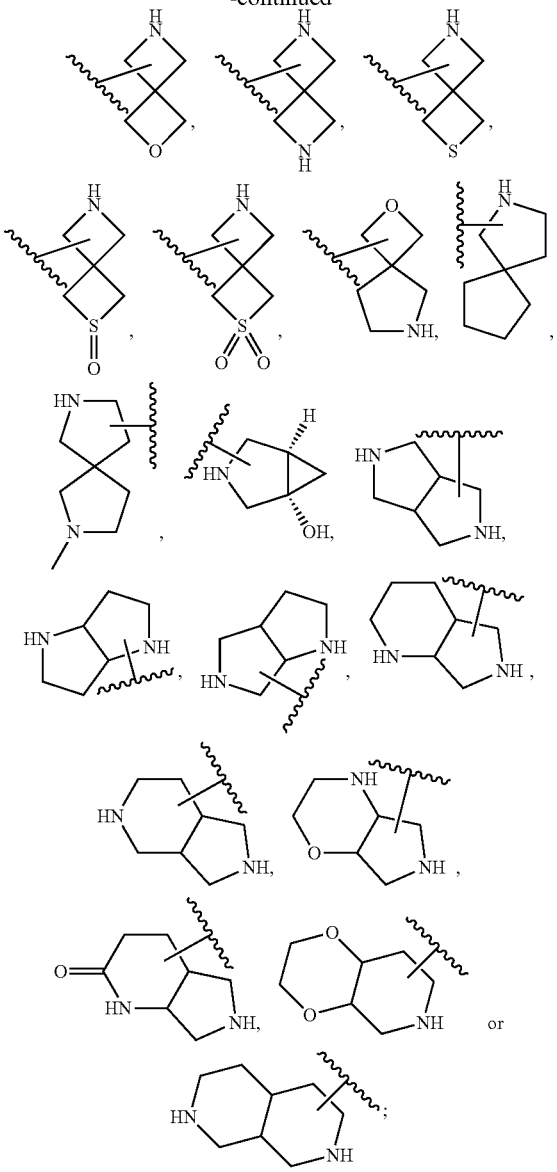

each $R^3$ and $R^{3a}$ is independently methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl;

each $R^4$ and $R^{4a}$ is independently H, methyl, ethyl, propyl, isopropyl, tert-butyl, cyclopropyl, cyclopentyl, cyclohexyl, $C_{2-10}$ heterocycloalkyl, $C_{1-6}$ alkoxy-$C_{1-6}$-alkyl or $C_{1-4}$ hydroxyalkyl;

each $R^{4b}$ is independently H, F, Cl, Br, cyano, nitro, hydroxy, mercapto, amino, carboxy, methyl, ethyl, propyl, isopropyl, tert-butyl, cyclopropyl, cyclopentyl, cyclohexyl, trifluoromethyl, methoxy, $C_{1-4}$ alkylamino, —$(CR^{3b}R^{3c})_n$—$NH_2$, —$C(=O)$—$NH_2$, $C_{2-10}$ heterocycloalkyl, $C_{1-6}$ alkoxy-$C_{1-6}$-alkyl or $C_{1-4}$ hydroxyalkyl;

wherein each sub-formula represented by $R^2$ is independently substituted with one or more $R^{2a}$ which are the same or different; and each $R^{2a}$ is independently H, F, Cl, Br, I, trifluoromethyl, chloroethyl, trifluoroethyl, methyl, ethyl, propyl, isopropyl, dimethylamino, methylamino, diethylamino, ethylamino, hydroxy, cyano, nitro, —C(=O)—NH$_2$, carboxy, —S(=O)$_t$O—H, —OS(=O)$_t$—H, —S(=O)$_t$NH$_2$, triazolyl, tetrazolyl, —(CH$_2$)—NH$_2$, —(CH$_2$)$_3$—NH$_2$, —(CH(CF$_3$))—NH$_2$, —(CH$_2$)$_2$—NH$_2$, oxo (=O), methyl-C(=O)—, ethyl-C(=O)—, propyl-C(=O)—, benzyl or phenyl.

6. The compound according to claim 1, wherein, ring K is

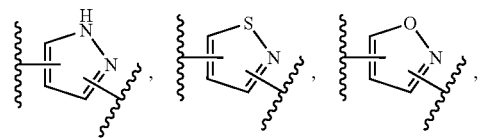

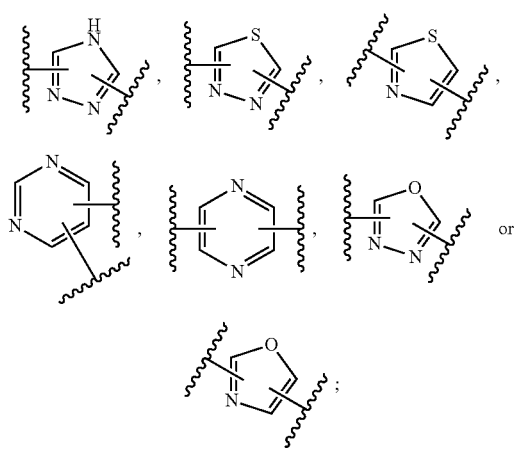

and each L is independently cyclopropyl, cyclobutyl, cyclopentyl, cyclohexyl, C$_{3-6}$ heterocycloalkyl, amino, cyano, nitro, F, Cl, Br, I, trifluoromethyl, 1,1,1-trifluoro-2-methylprop-2-yl, methyl, ethyl, butyl, propyl, isopropyl, tert-butyl, C$_{1-4}$ alkylamino, hydroxy, cyano, nitro, C$_{1-4}$ alkyl-C(=O)—NH—, C$_{1-4}$ alkoxy, hydroxymethyl, hydroxyethyl, 1-hydroxy-n-butyl, 2-hydroxy-n-propyl, hydroxy-tert-butyl or C$_{1-4}$ alkylthio.

7. The compound according to claim 1 having Formula (III) or (IIIa), or a stereoisomer, a geometric isomer, a tautomer, an N-oxide, a hydrate, a solvate, a metabolite, an ester, a pharmaceutically acceptable salt or a prodrug thereof,

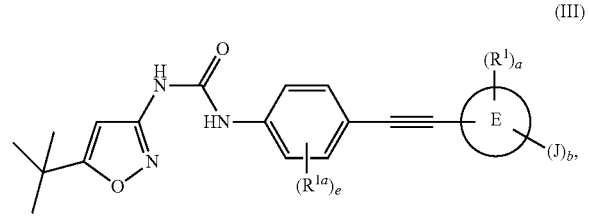

(III)

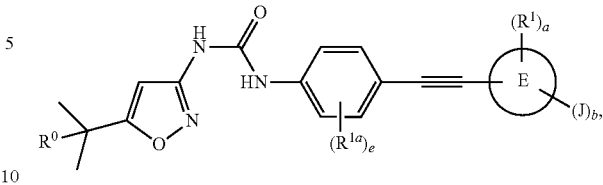

(IIIa)

wherein R$^0$ is C$_{2-3}$ alkyl, trifluoromethyl, fluoromethyl, difluoromethyl or hydroxymethyl.

8. The compound according to claim 1 having Formula (VIIa), or a stereoisomer, a geometric isomer, a tautomer, an N-oxide, a hydrate, a solvate, a metabolite, an ester, a pharmaceutically acceptable salt or a prodrug thereof,

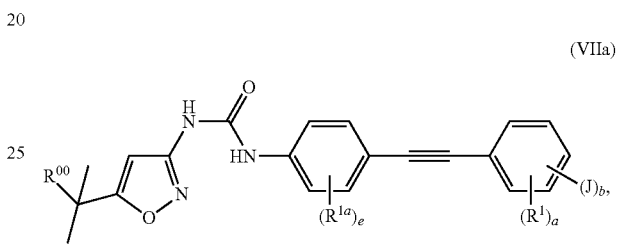

(VIIa)

wherein R$^{00}$ is C$_{1-3}$ alkyl, trifluoromethyl, fluoromethyl, difluoromethyl or hydroxymethyl.

9. The compound according to claim 1 having Formula (IV) or (V), or a stereoisomer, a geometric isomer, a tautomer, an N-oxide, a hydrate, a solvate, a metabolite, an ester, a pharmaceutically acceptable salt or a prodrumg thereof,

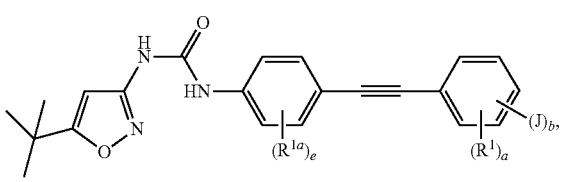

(IV)

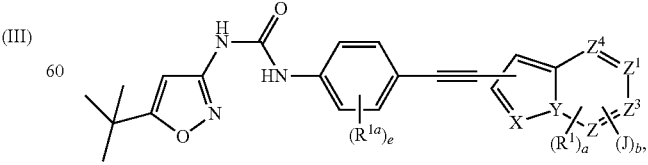

(V)

wherein each of X, Y, Z, Z$^1$, Z$^3$ and Z$^4$ is independently N or CH.

10. The compound according to claim 1 having Formula (IIIb), or a stereoisomer, a geometric isomer, a tautomer, an N-oxide, a hydrate, a solvate, a metabolite, an ester, a pharmaceutically acceptable salt or a prodrug thereof,

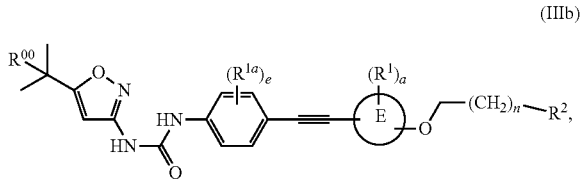

wherein $R^{00}$ is $C_{1-3}$ alkyl, trifluoromethyl, fluoromethyl, difluoromethyl or hydroxymethyl.

11. A compound having one of the following structures, or a stereoisomer, a geometric isomer, a tautomer, an N-oxide, a hydrate, a solvate, a metabolite, an ester, a pharmaceutically acceptable salt or a prodrug thereof,

1

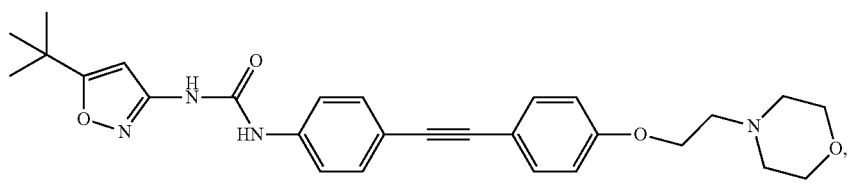

2

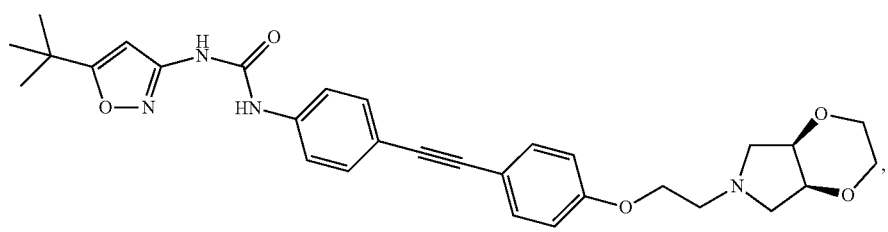

3

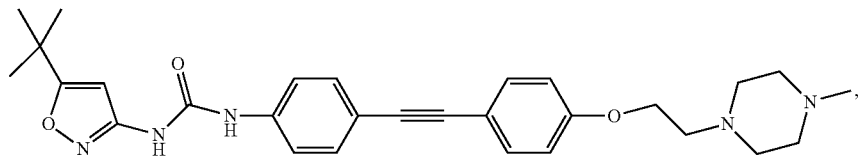

4

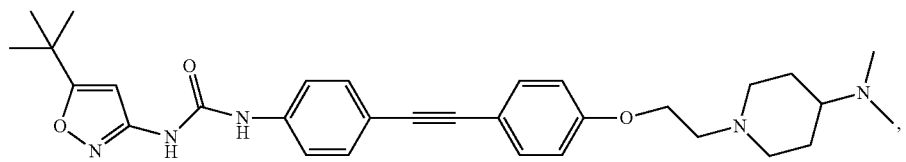

5

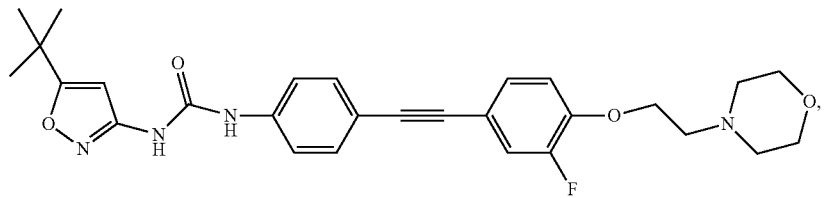

6

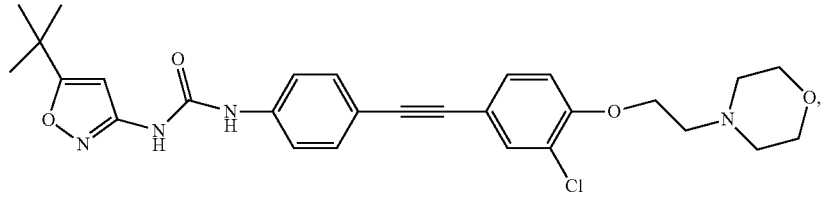

7
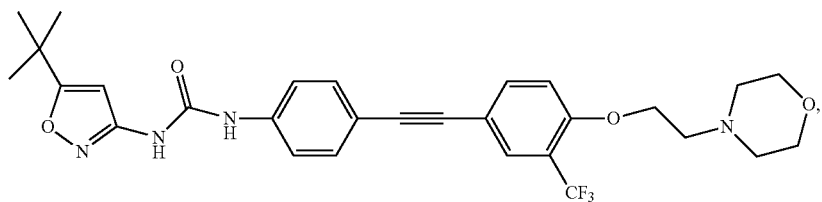
8
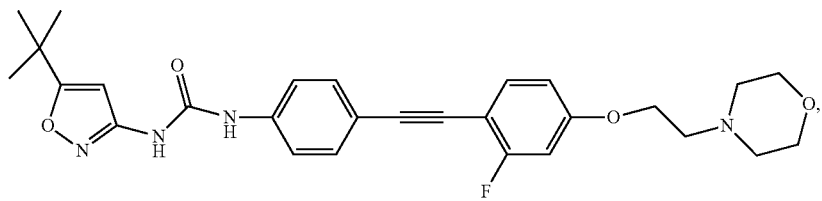
9
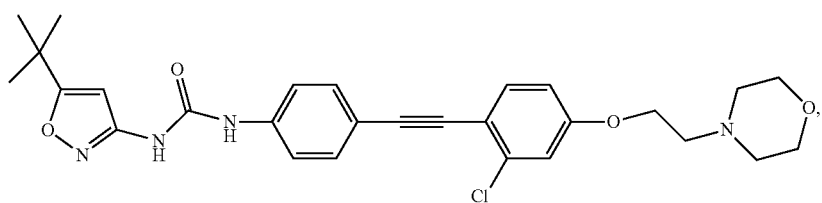
10
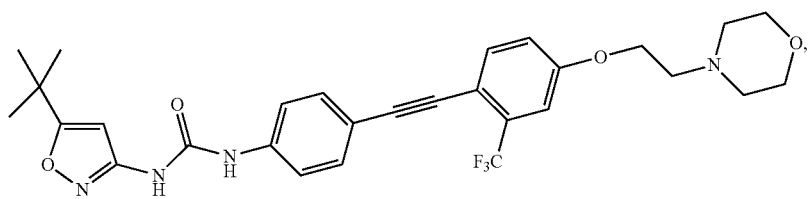
11
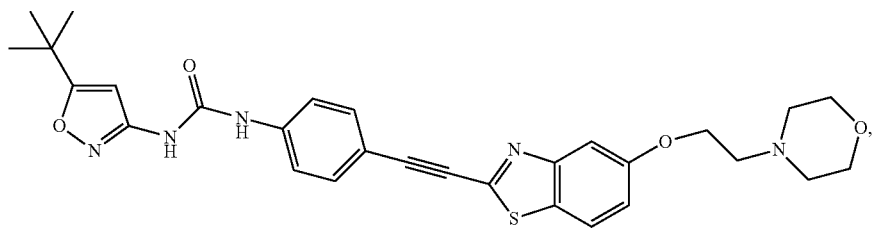
12
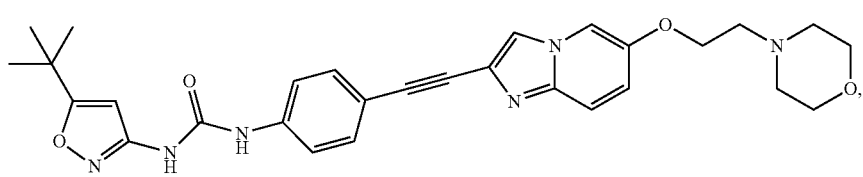
13
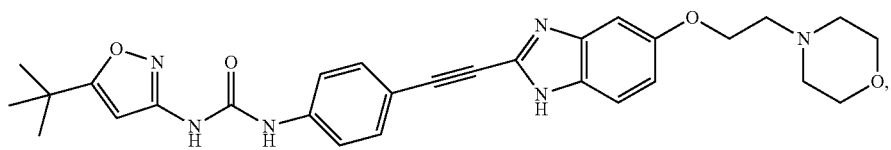

14
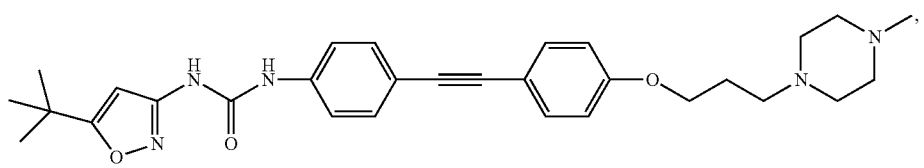
15
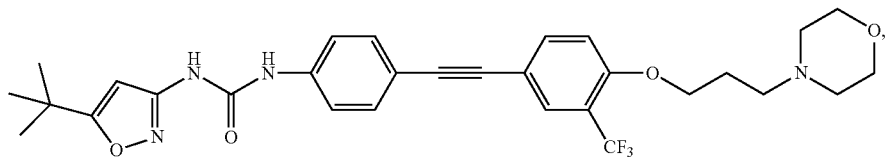
16
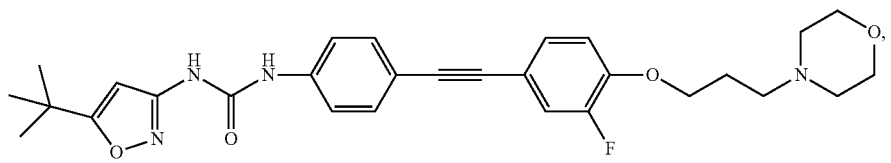
17
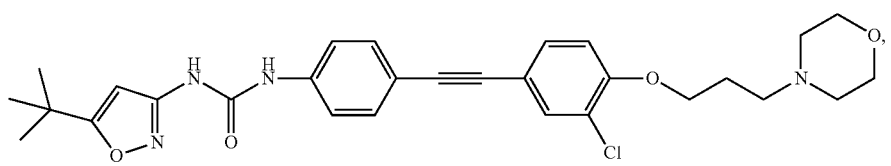
18
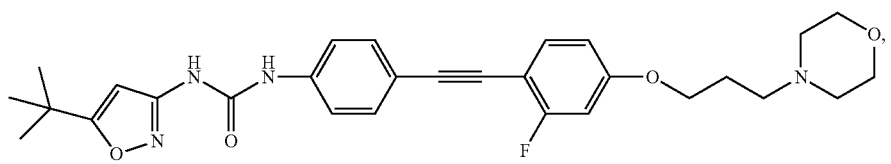
19
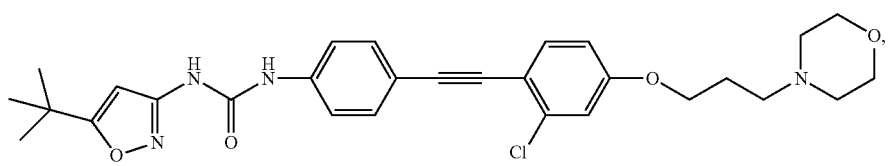
20
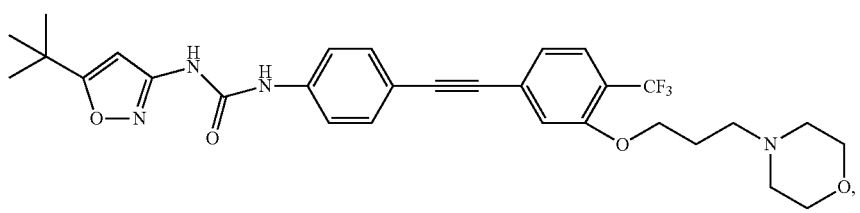
21
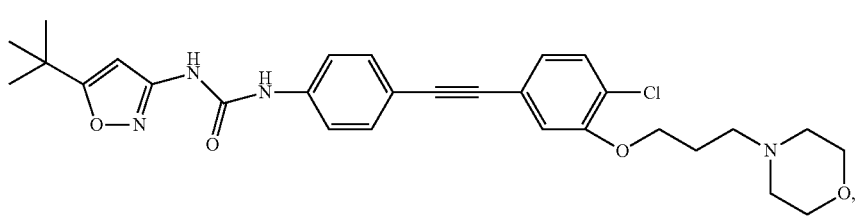

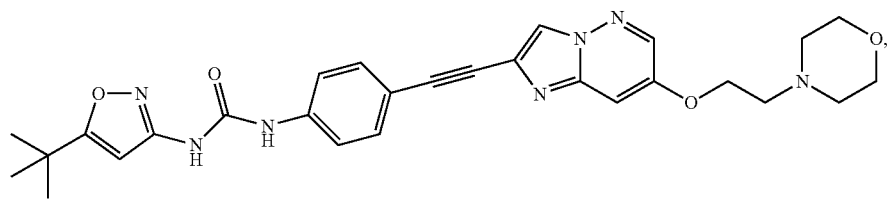
22
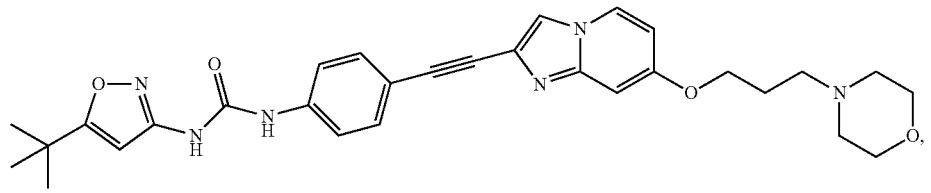
23
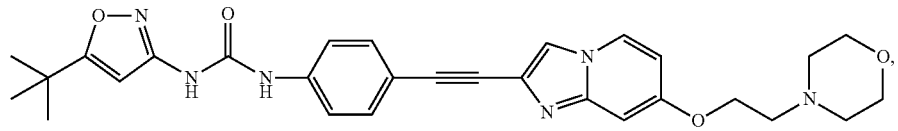
24
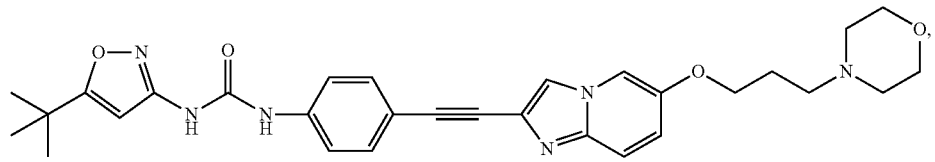
25
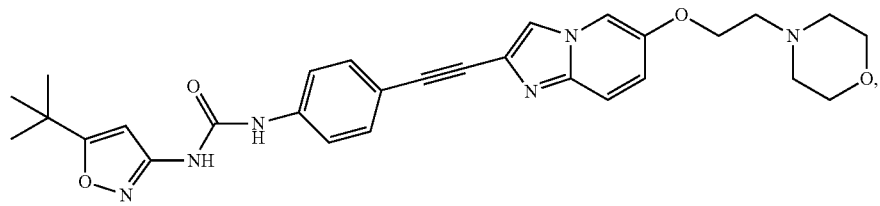
26
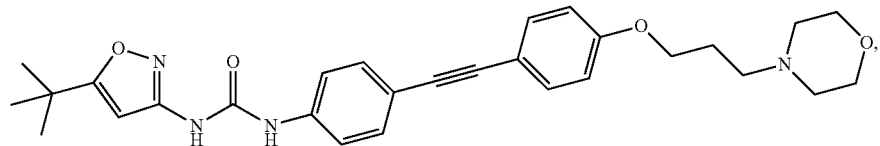
27
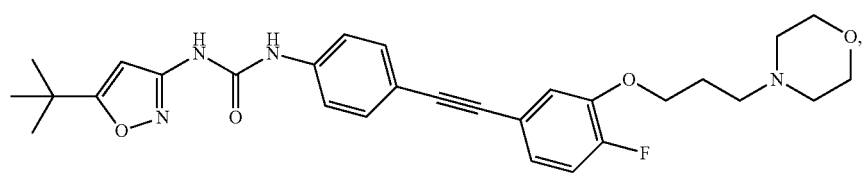
28
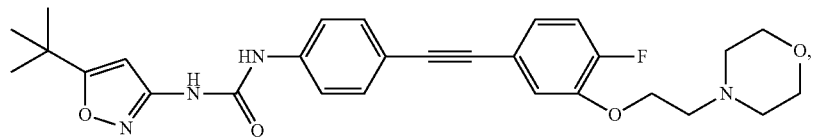
29

30
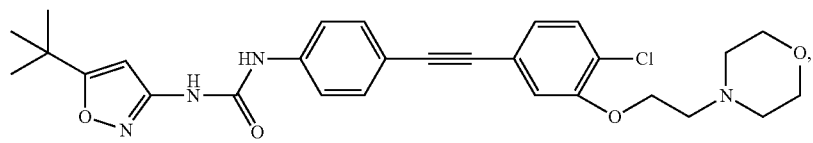
31
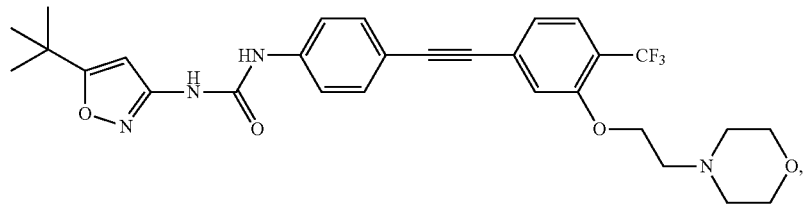
32
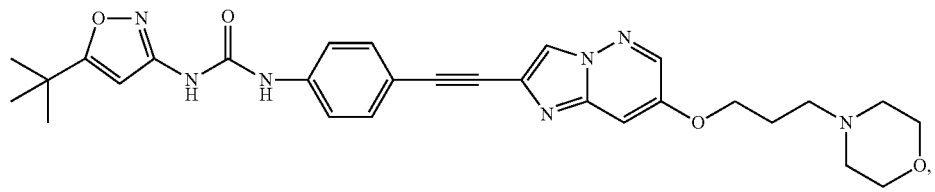
33
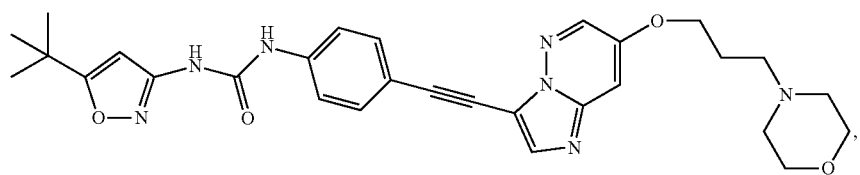
34
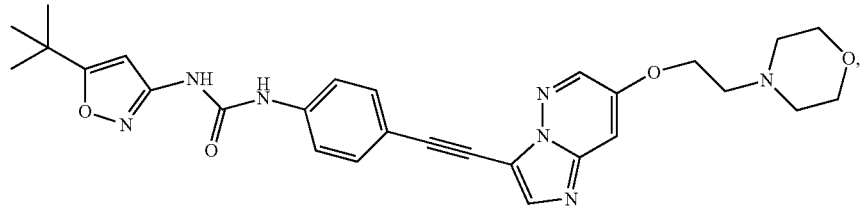
35
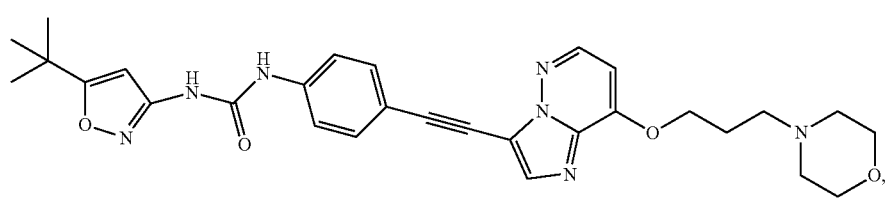
36
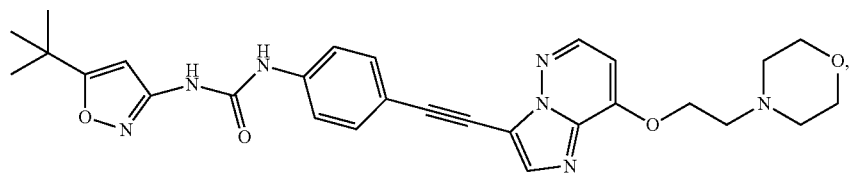
37
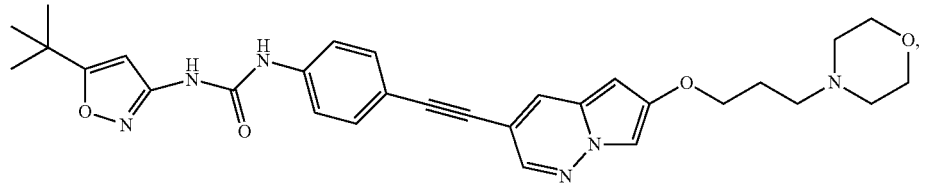

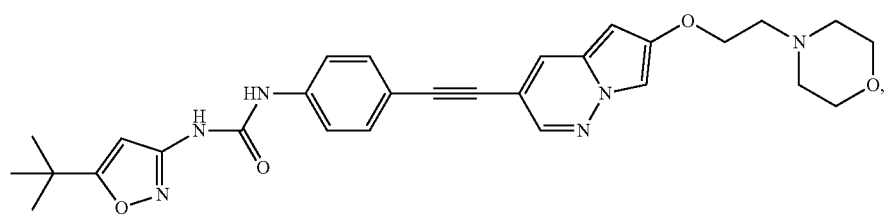
38
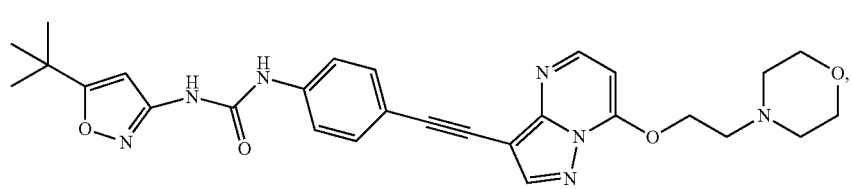
39
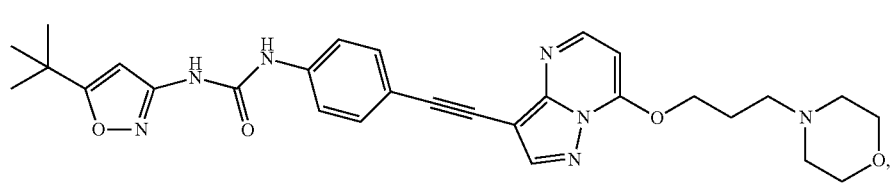
40
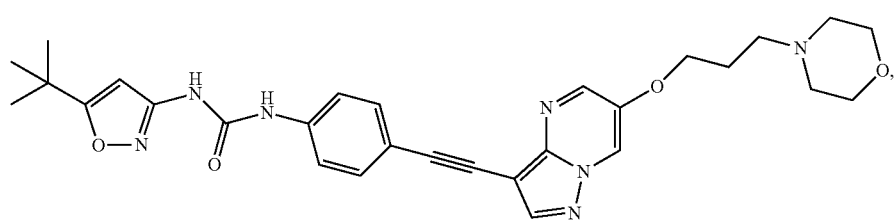
41
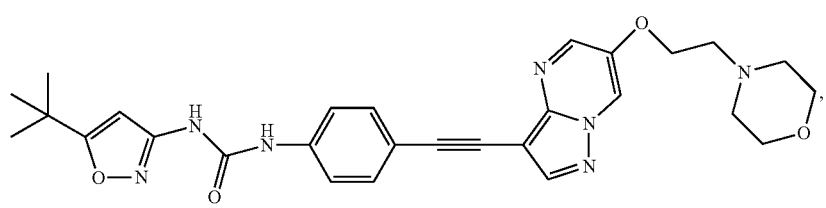
42
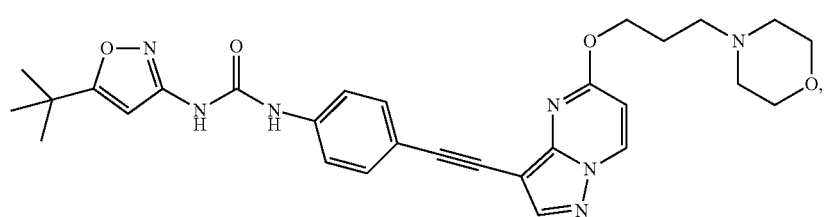
43
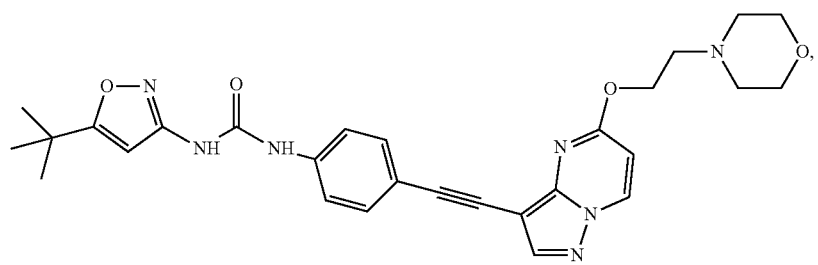
44

45
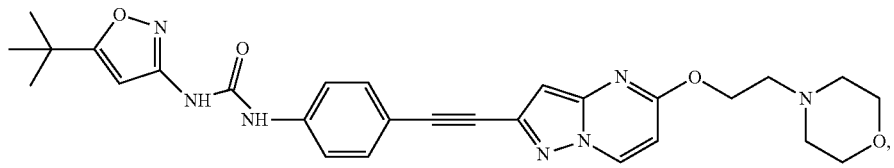
46
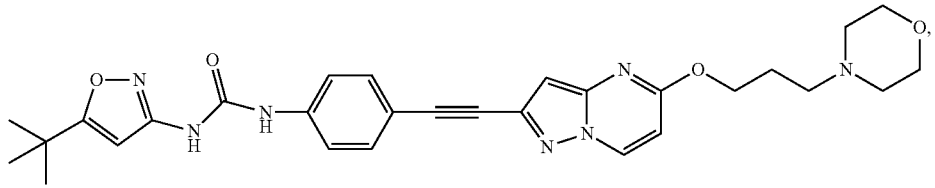
47
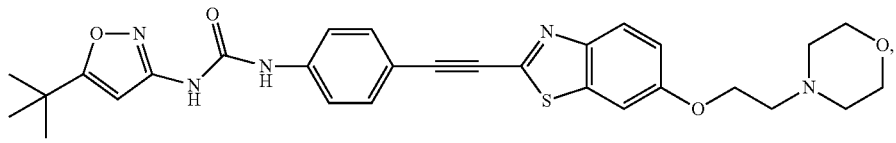
48
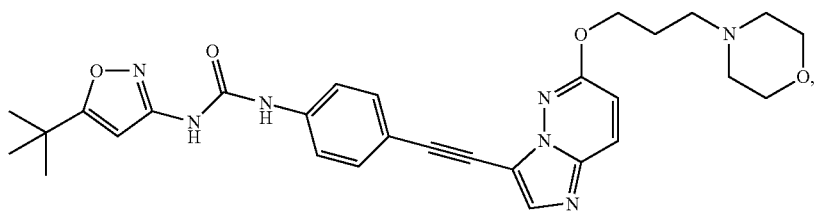
49
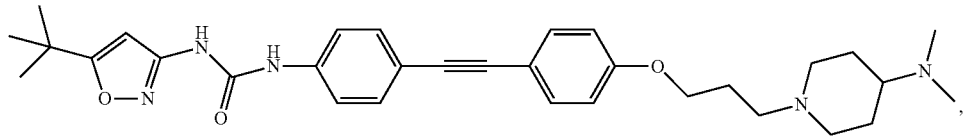
50
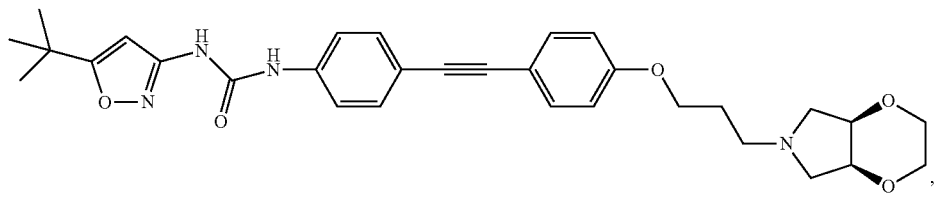
51
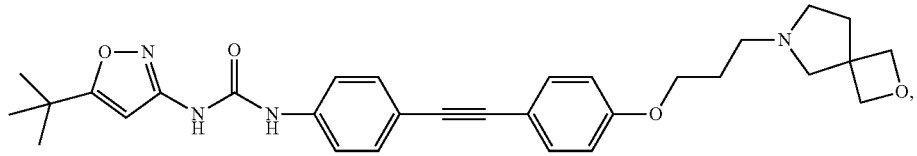
52
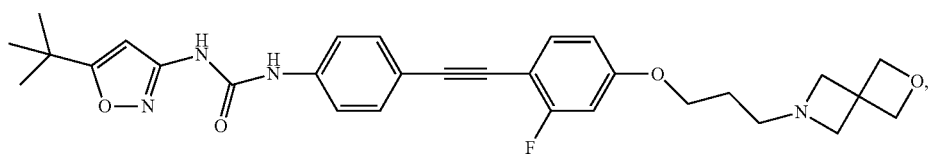
53
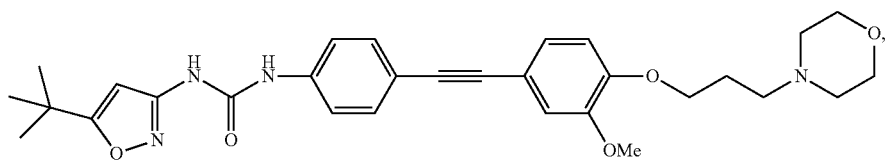

54
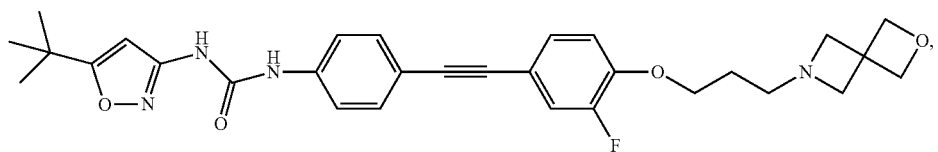
58
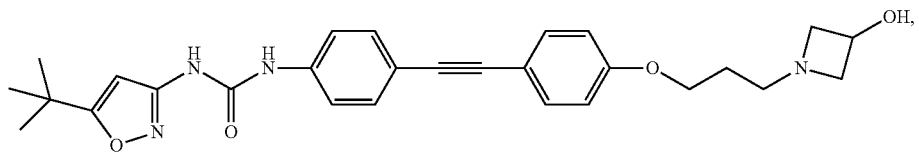
59
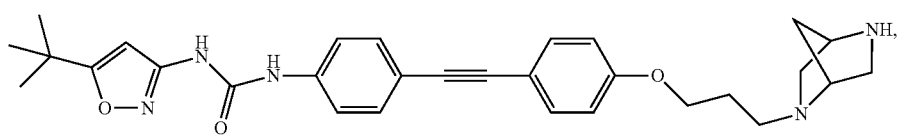
60
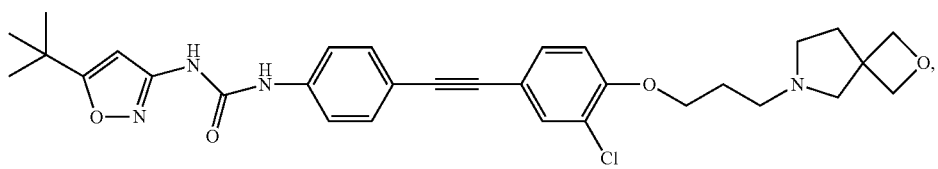
61
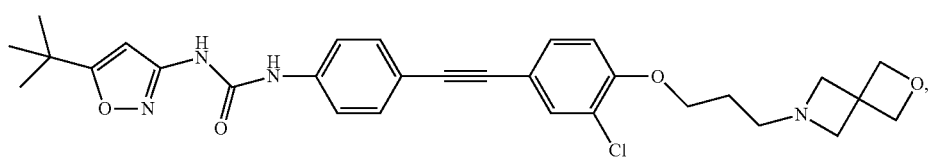
62
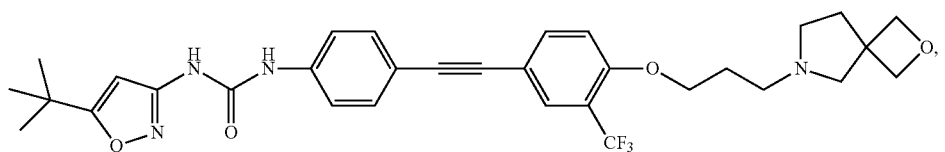
63
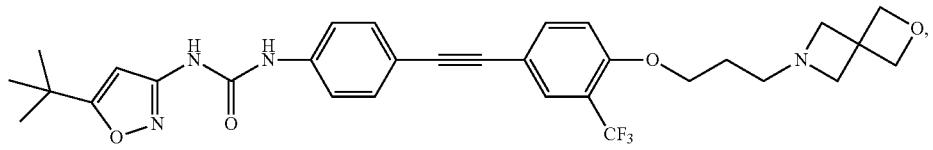
64
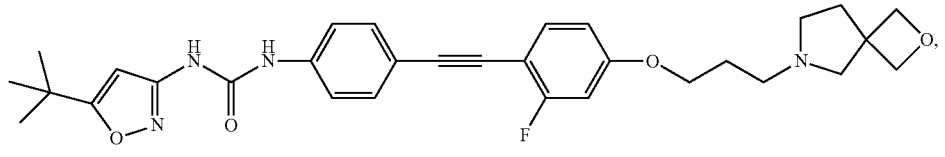
65
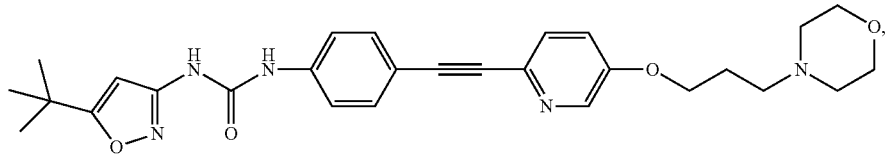

66
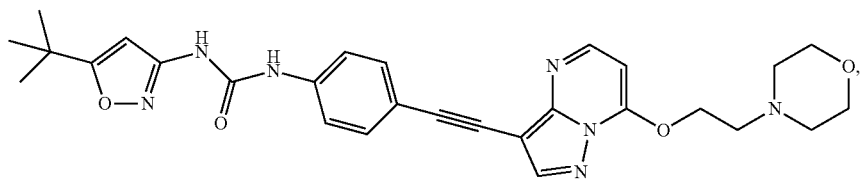
67
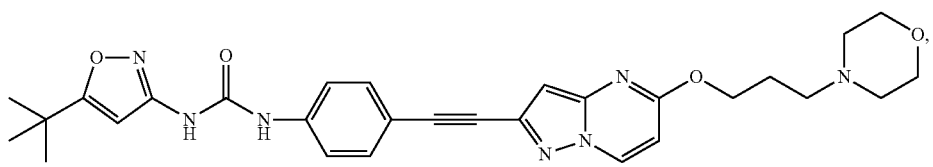
68
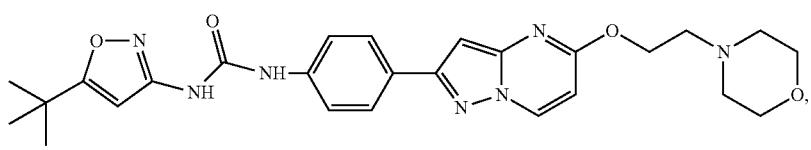
69
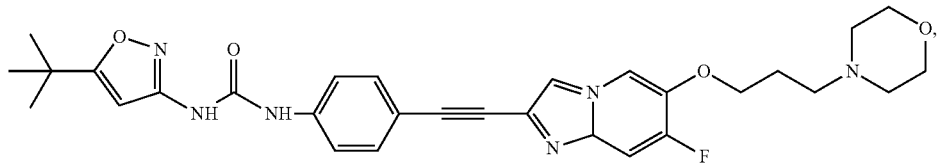
70
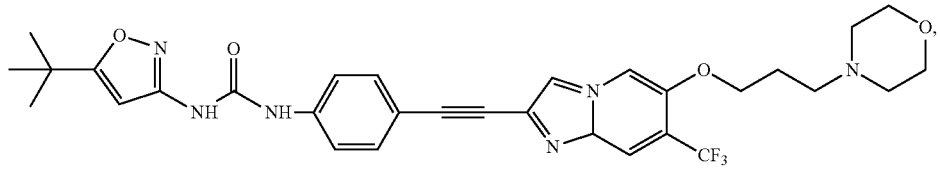
71
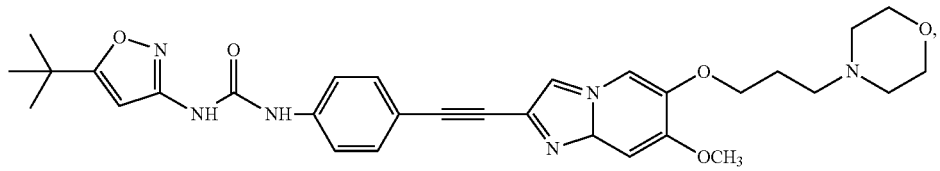
72
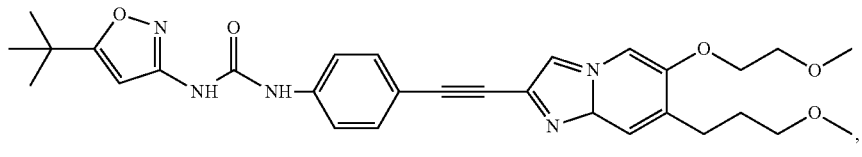
73
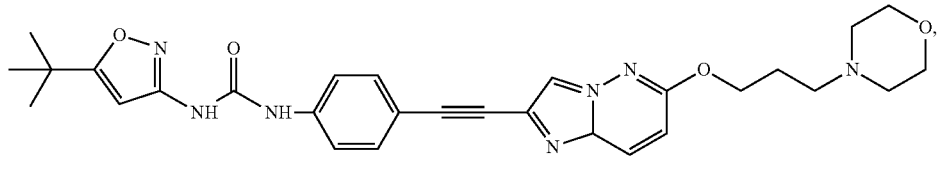

-continued
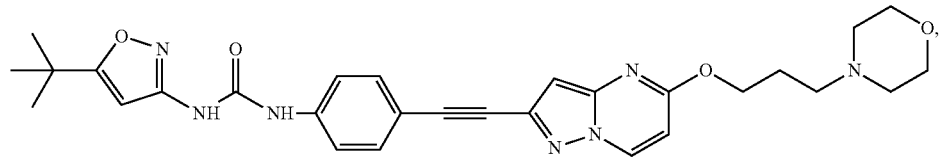
74
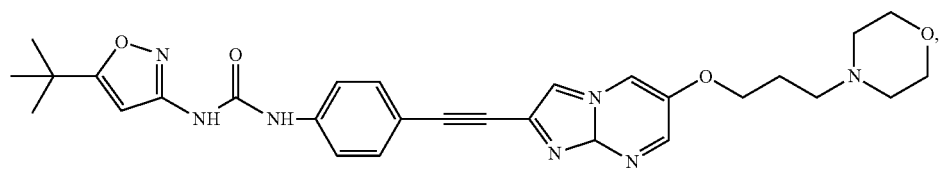
75
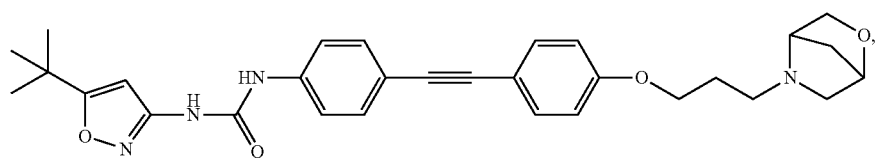
76
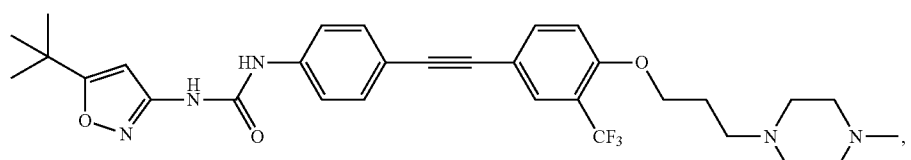
77
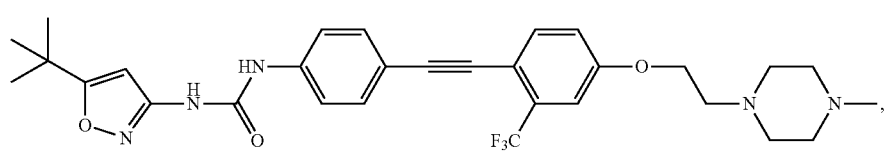
78
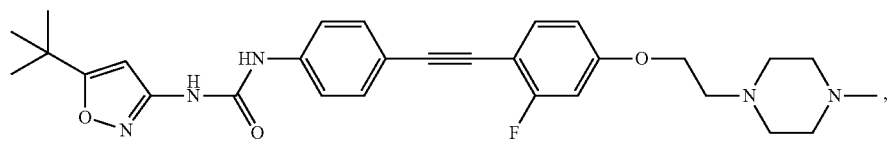
79
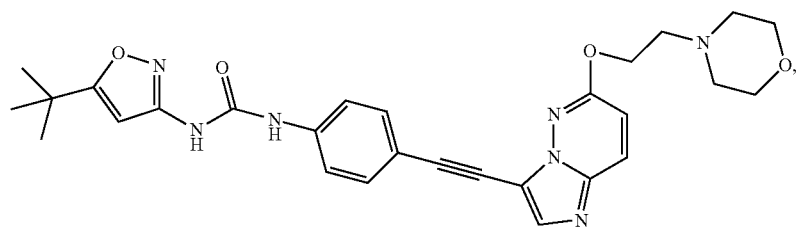
80
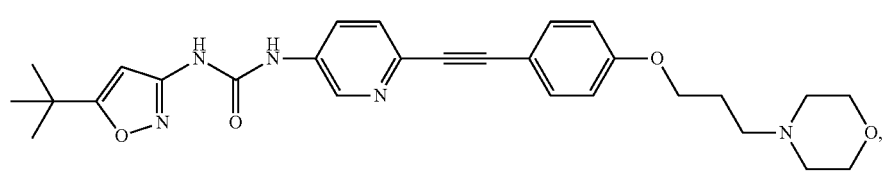
81

82
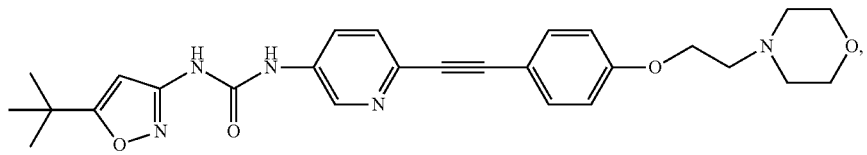
83
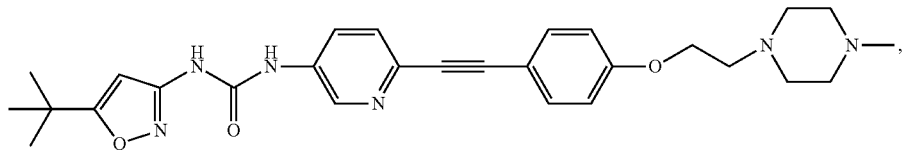
84
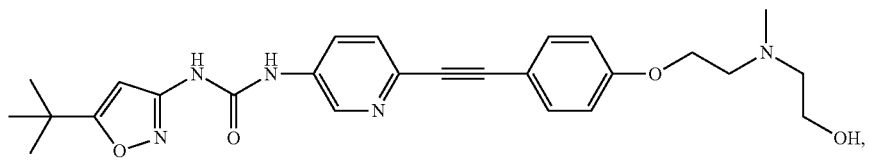
85
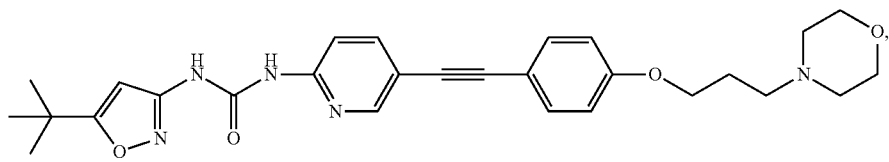
86
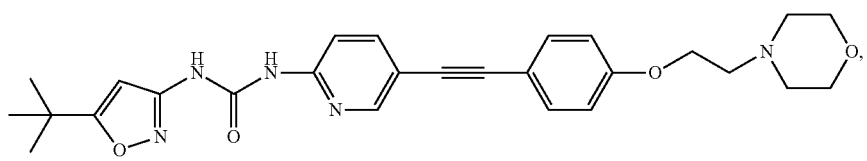
87
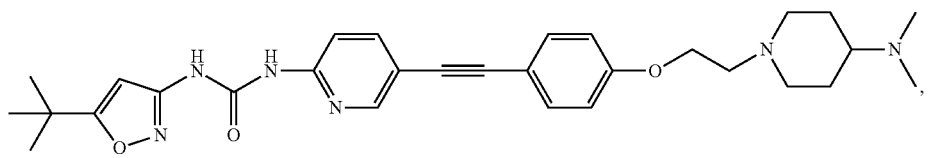
88
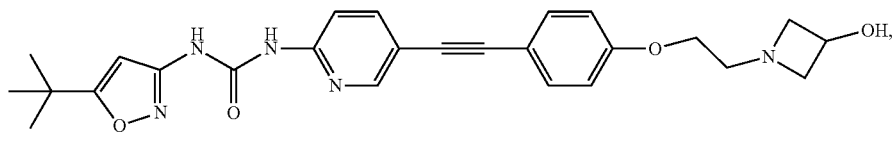
89
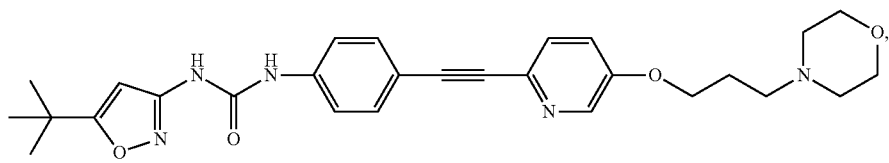
90
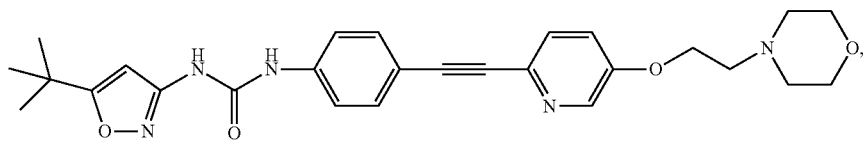

91
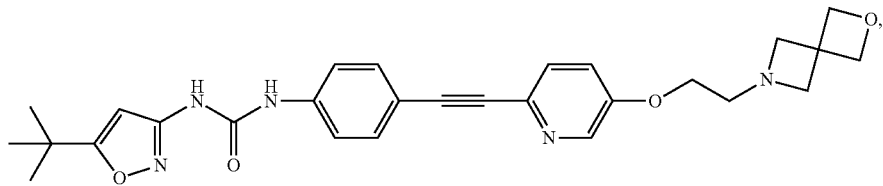
92
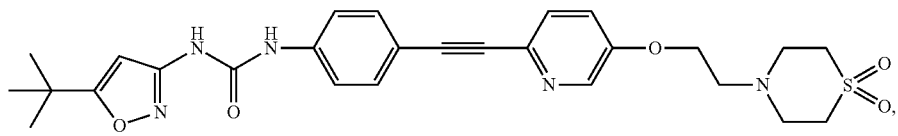
93
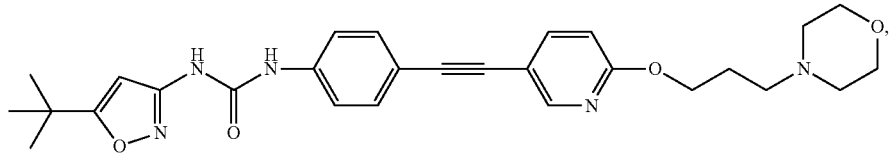
94
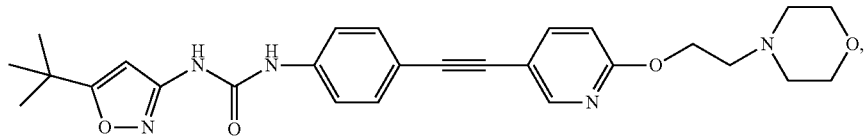
95
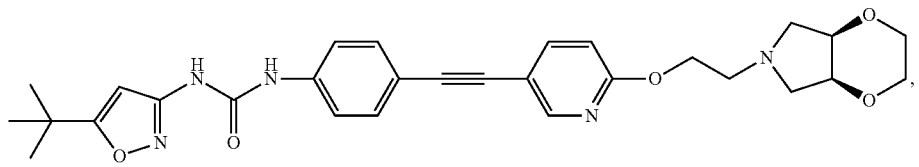
96
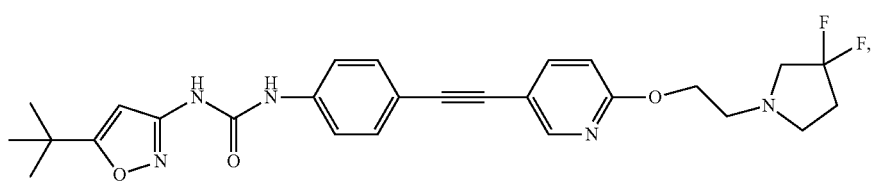
97
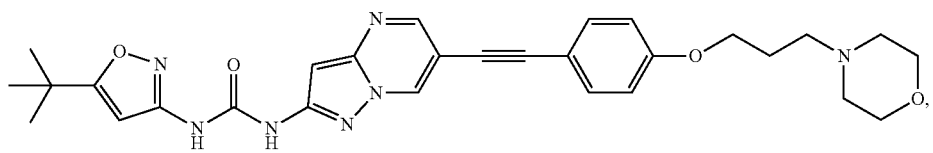
98
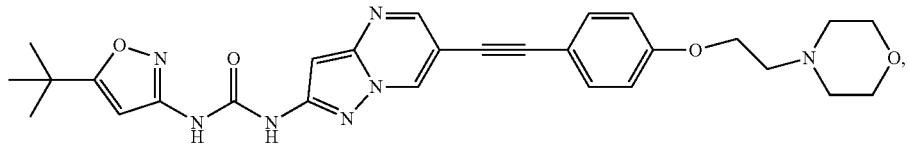
99
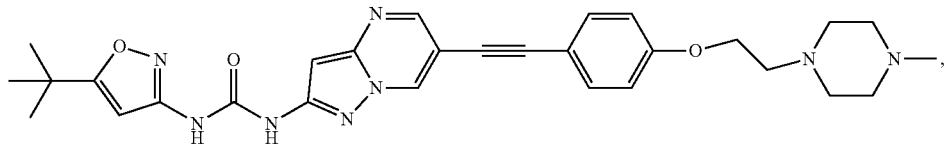

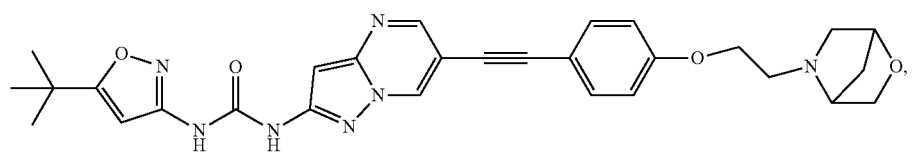
100
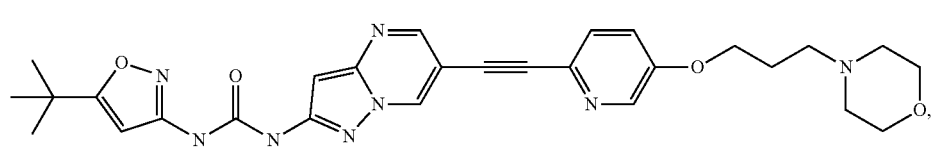
101
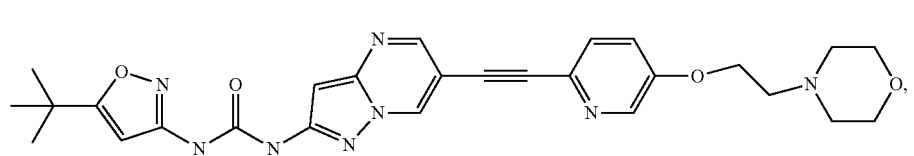
102
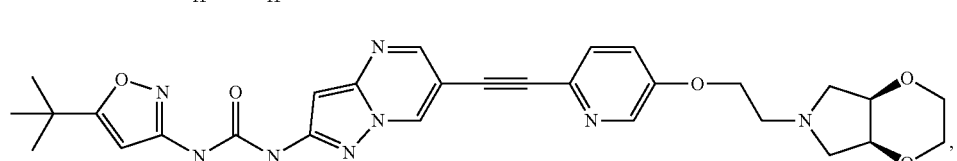
103
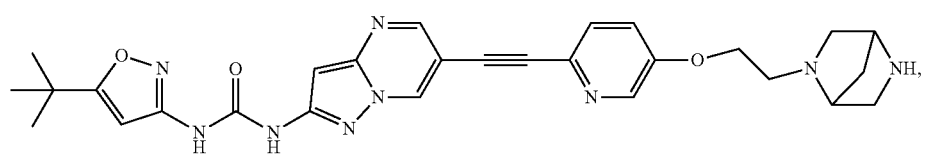
104
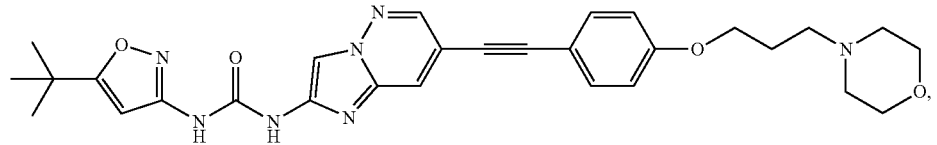
105
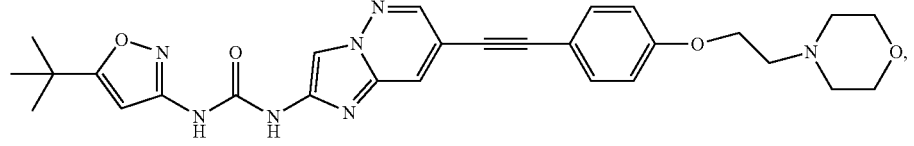
106
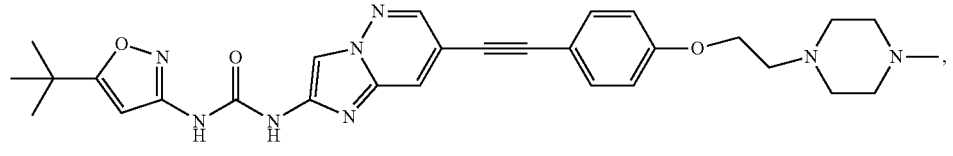
107
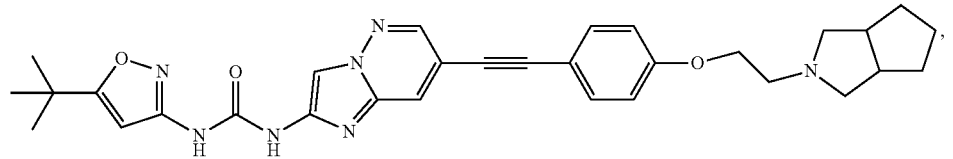
108

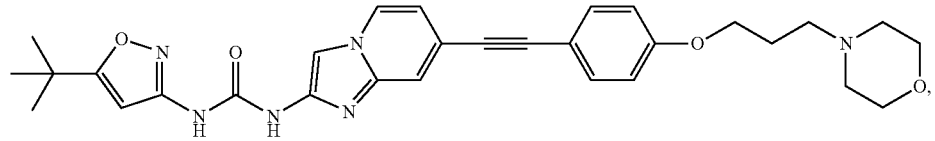
109
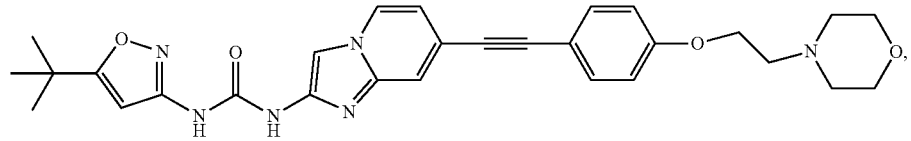
110
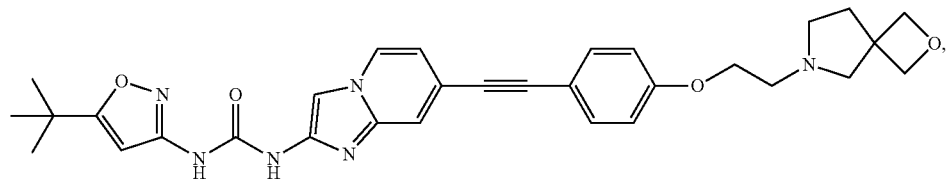
111
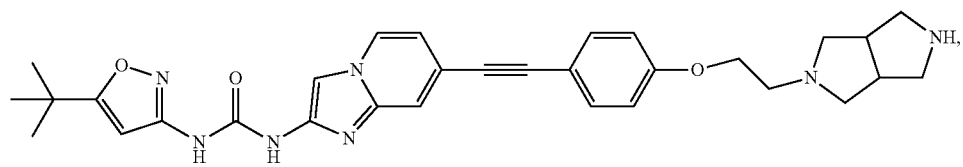
112
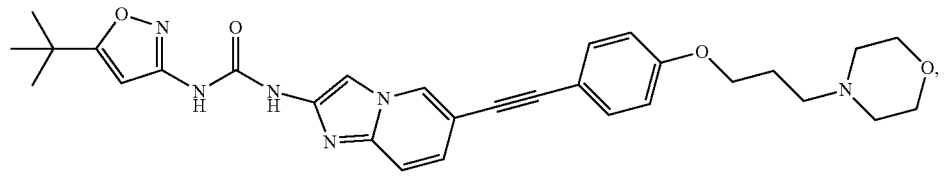
113
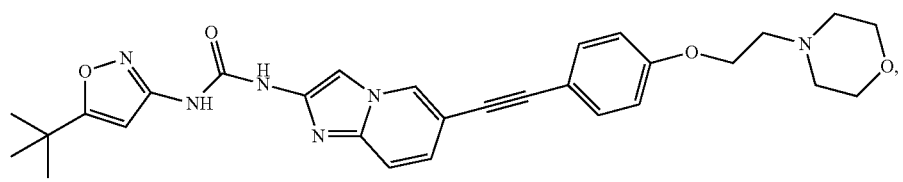
114
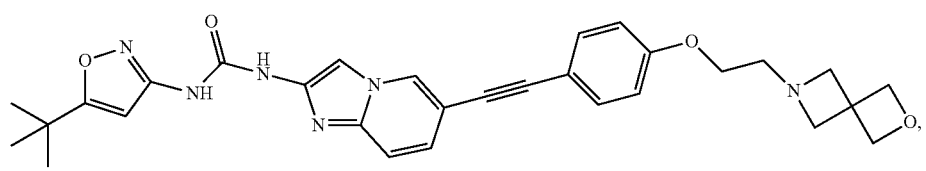
115
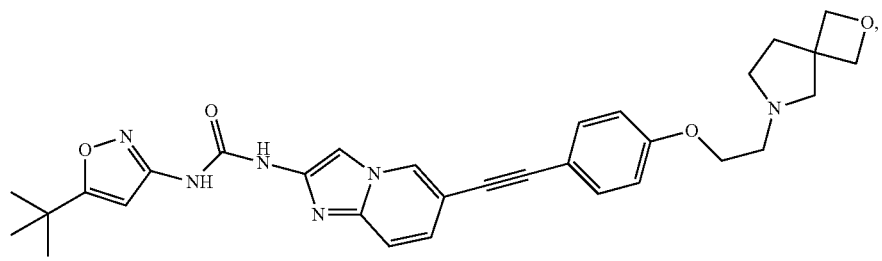
116

117
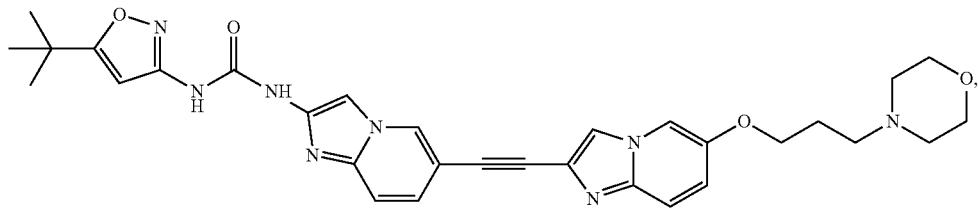
118
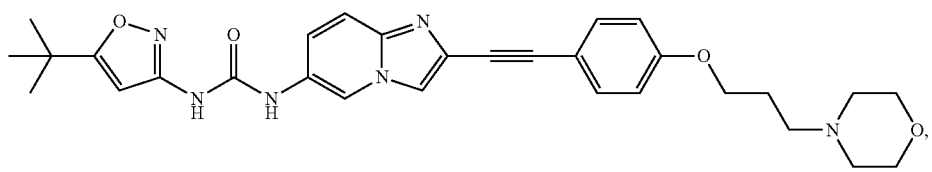
119
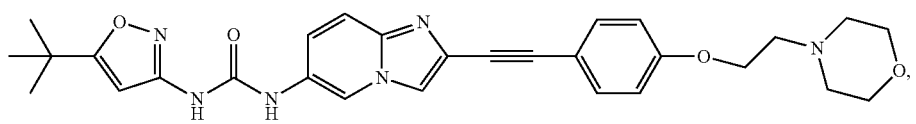
120
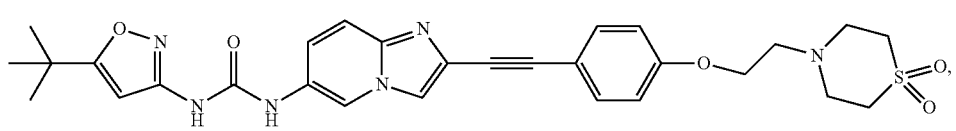
121
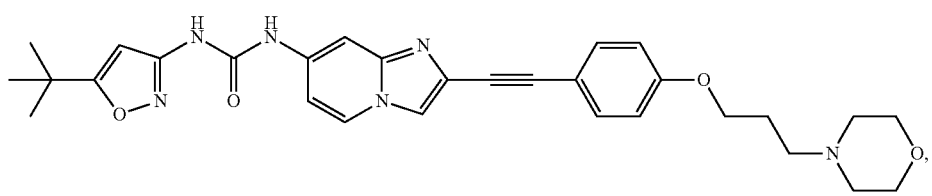
122
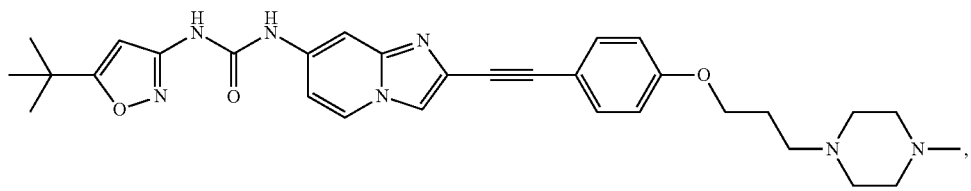
123
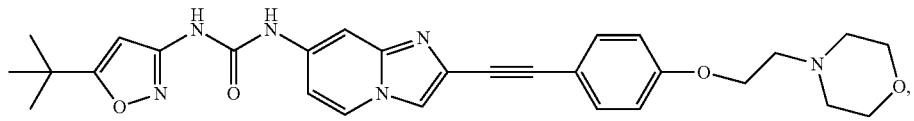
124
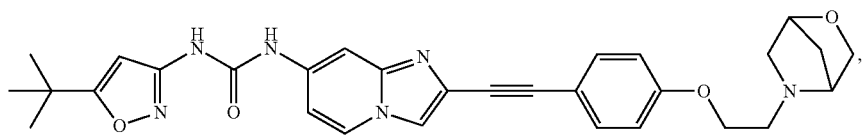
125
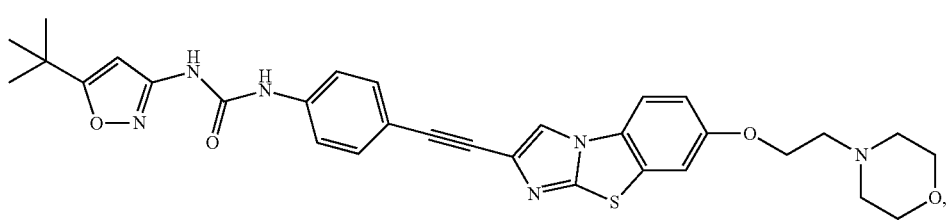

-continued
126
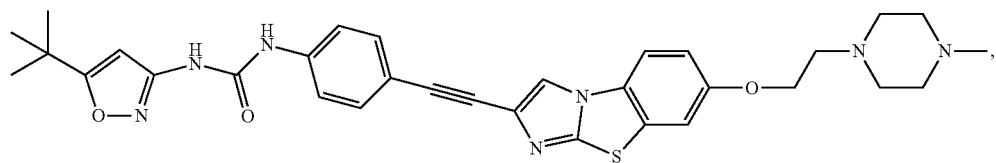
127
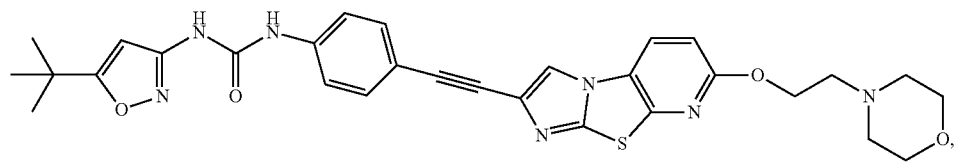
128
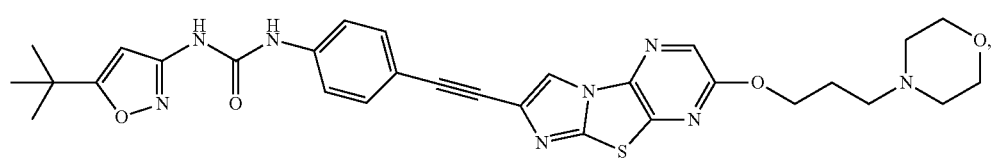
129
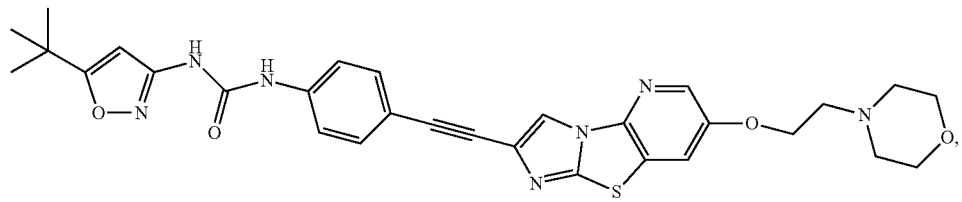
130
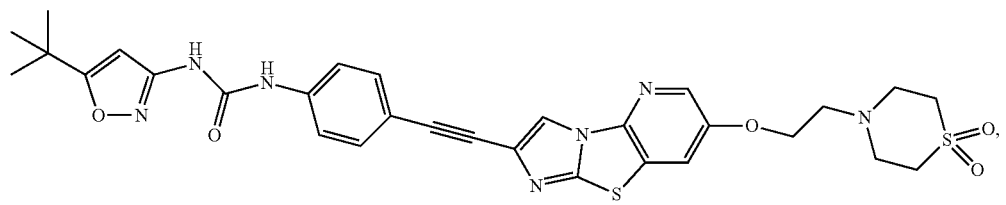
131
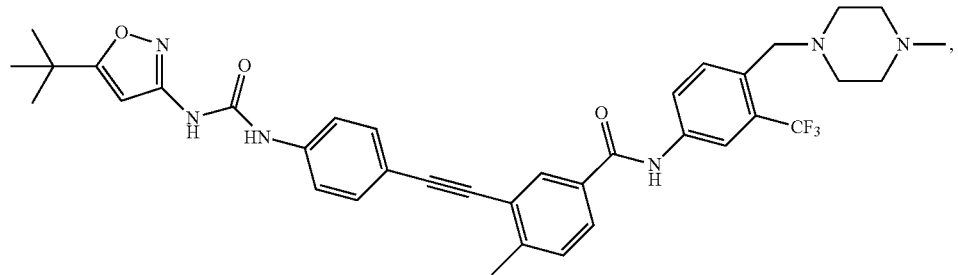
132
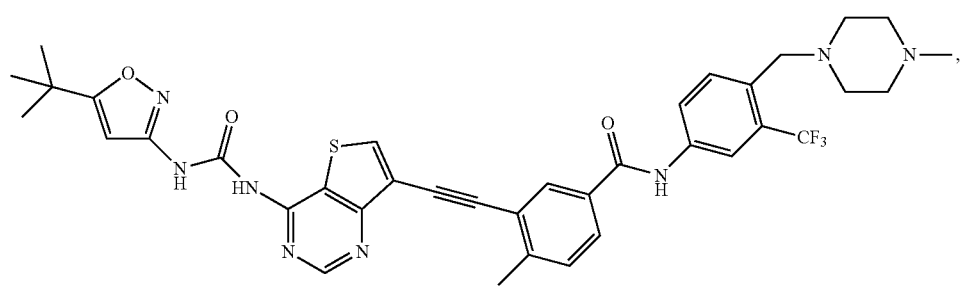

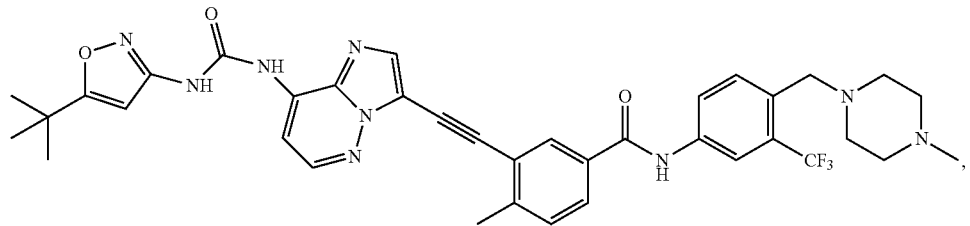
133
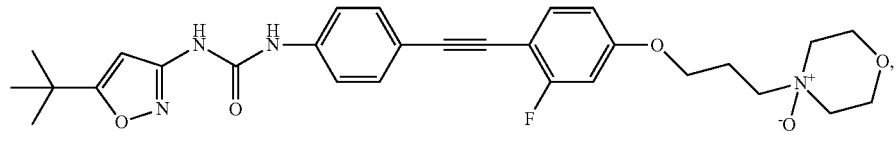
134
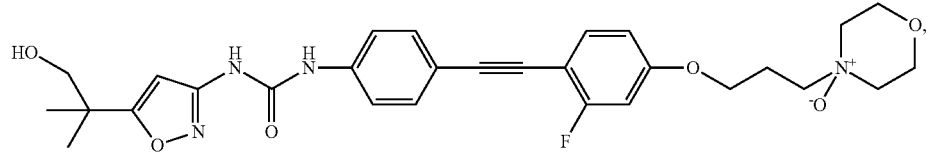
135
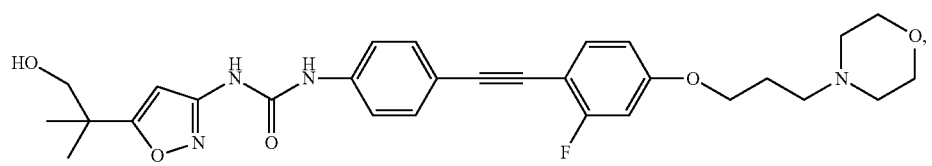
136
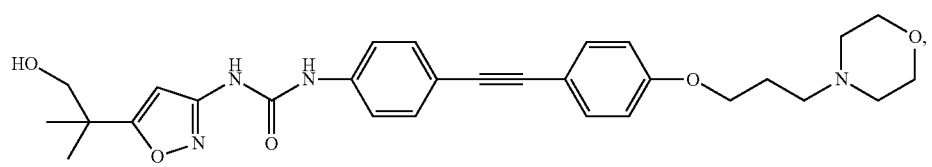
137
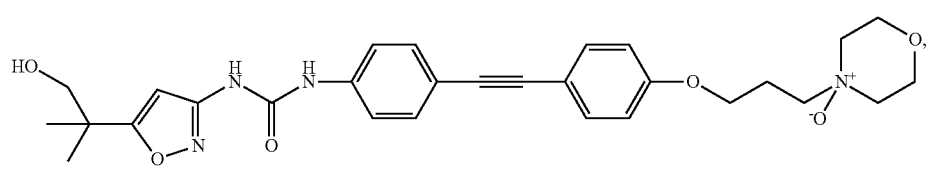
138
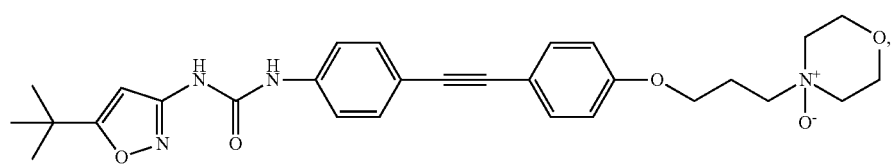
139
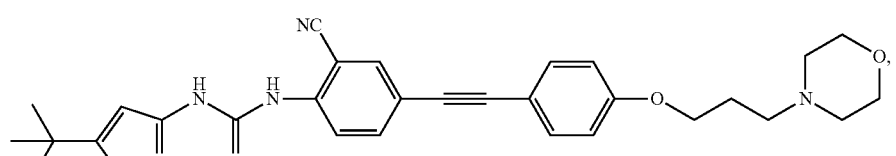
140
141

-continued

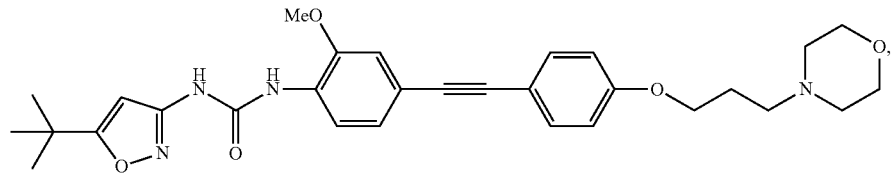

142

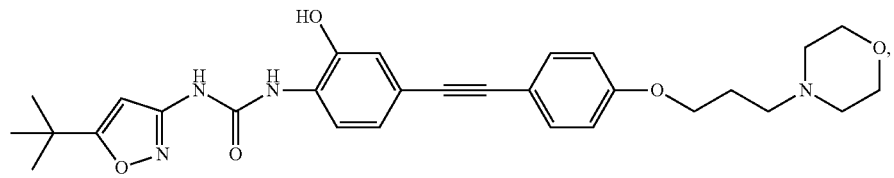

143

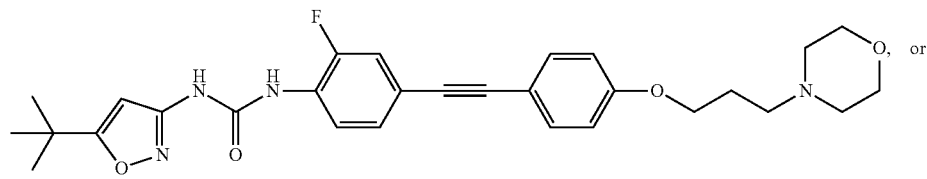

144

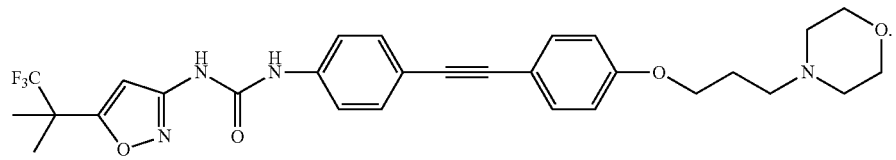

145

12. A pharmaceutical composition comprising the compound according to claim 1; and at least one of pharmaceutically acceptable carriers, excipients, diluents, adjuvants or vehicles.

13. The pharmaceutical composition according to claim 12 further comprising other active agent used for treating a proliferative disease, an autoimmune disease or an inflammatory disease, wherein the other active agent is a chemotherapeutic agent, antiproliferative agent, immunosuppressive agent, immunostimulatory agent, antiinflammatory agent, an agent for treating atherosclerosis, an agent for treating pulmonary fibrosis, CDK4/6-kinase inhibitor, ABL inhibitor, ABL/Scr inhibitor, aurora kinase inhibitor, non-ATP-competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

14. The pharmaceutical composition according to claim 13, wherein the other active agent is chlorambucil, melphalan, cyclophosphamide, ifosfamide, busulfan, carmustine, lomustine, streptozotocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin C, ixabepilone, tamoxifen, flutamide, gonadorelin analogue, megestrol, prednisone, dexamethasone, methylprednisolone, thalidomide, interferon-α, leucovorin calcium, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, rituximab, tositumomab, trastuzumab, cabozantinib, ponatinib, midostaurin, pacritinib, quizartinib, gilteritinib, AKN-028, AT-9283, crenolanib, ENMD-2076, famitinib, dovitinib, PLX-3397, palbociclib, abemaciclib, ribociclib, rigosertib sodium, selinexor, roniciclib, AT-7519, seliciclib, alvocidib or a combination thereof.

15. A method of managing, treating or lessening a proliferative disease in a patient comprising administering to the patient a therapeutically effective amount of the compound according to claim 1, wherein the proliferative disease is chronic myelogenous leukemia, gastrointestinal stromal tumor, acute myelogenous leukemia (AML), mutant chronic myelogenous leukemia (CML), acute lymphocytic leukemia (ALL), leukemia, colorectal cancer, stomach cancer, breast cancer, lung cancer, prostate cancer, pancreatic cancer, thyroid cancer, ovarian cancer, lymphoma, multiple myeloma, or non-small cell lung cancer.

16. A drug combination comprising the compound according to claim 1 and one or more other active agents used for the treatment of a proliferative disease, an autoimmune disease or an inflammatory disease; wherein the other active agent is chemotherapeutic agent, antiproliferative agent, immunosuppressive agent, immunostimulatory agent, antiinflammatory agent, CDK4/6-kinase inhibitor, ABL inhibitor, ABL/Scr inhibitor, aurora kinase inhibitor, non- ATP-competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

17. A method of managing, treating or lessening a proliferative disease in a patient comprising administering to the patient a therapeutically effective amount of the pharmaceutical composition according to claim 12, wherein the proliferative disease is chronic myelogenous leukemia, gastrointestinal stromal tumor, acute myelogenous leukemia (AML), mutant chronic myelogenous leukemia (CML), acute lymphocytic leukemia (ALL), leukemia, colorectal cancer, stomach cancer, breast cancer, lung cancer, prostate cancer, pancreatic cancer, thyroid cancer, ovarian cancer, lymphoma, multiple myeloma, or non-small cell lung cancer.

18. A drug combination comprising the pharmaceutical composition according to claim 12 one or more other active agents used for the treatment of a proliferative disease, an autoimmune disease or an inflammatory disease; wherein the other active agent is chemotherapeutic agent, antiproliferative agent, immunosuppressive agent, immunostimulatory agent, antiinflammatory agent, CDK4/6-kinase inhibitor, ABL inhibitor, ABL/Scr inhibitor, aurora kinase inhibitor, non-ATP-competitive inhibitor of BCR-ABL, c-KIT mutation inhibitor, RET inhibitor, PDGFR inhibitor, VEGFR inhibitor, FLT3 inhibitor, FLT3-ITD inhibitor or a combination thereof.

* * * * *